(12) United States Patent
Lam et al.

(10) Patent No.: US 7,381,732 B2
(45) Date of Patent: Jun. 3, 2008

(54) PYRAZOLOBENZAMIDES AND DERIVATIVES AS FACTOR XA INHIBITORS

(75) Inventors: Patrick Y. Lam, Chadds Ford, PA (US); Charles G. Clark, Cherry Hill, PA (US); Renhua Li, Noblesville, IN (US); Tasir S. Haque, Yardley, PA (US); Karen A. Rossi, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 277 days.

(21) Appl. No.: 11/256,893

(22) Filed: Oct. 24, 2005

(65) Prior Publication Data

US 2006/0089496 A1    Apr. 27, 2006

Related U.S. Application Data

(60) Provisional application No. 60/622,236, filed on Oct. 26, 2004.

(51) Int. Cl.
*C07D 471/16*  (2006.01)
*A61K 31/437* (2006.01)
*A61P 7/02*   (2006.01)

(52) U.S. Cl. .................................. 514/303; 546/119
(58) Field of Classification Search ................ 546/119; 514/303

See application file for complete search history.

(56) References Cited

U.S. PATENT DOCUMENTS

| | | | |
|---|---|---|---|
| 6,413,980 B1 | 7/2002 | Fevig et al. | |
| 6,492,384 B1 | 12/2002 | Mederski et al. | |
| 6,506,771 B2 | 1/2003 | Pinto et al. | |
| 2002/0091116 A1 | 7/2002 | Zhu | |
| 2003/0018023 A1 | 1/2003 | Pinto et al. | |
| 2003/0191115 A1 | 10/2003 | Pinto et al. | |

FOREIGN PATENT DOCUMENTS

| | | |
|---|---|---|
| EP | 1078917 A | 2/2001 |
| EP | 1 426 364 | 6/2004 |
| EP | 1 433 788 | 6/2004 |
| WO | WO99/64044 A | 12/1999 |
| WO | WO 00/39131 | 7/2000 |
| WO | WO 01/19798 | 3/2001 |
| WO | WO 02/094197 | 11/2002 |
| WO | WO03/024222 | 3/2003 |
| WO | WO 03/026652 | 4/2003 |
| WO | WO 2004/056815 | 7/2004 |

OTHER PUBLICATIONS

Tummino, P.J. et al., "The Human Immunodeficiency Virus Type 1 (HIV-1) Nucleocapsid Protein Zinc Ejection Activity of Disulfide Benzamides and Benzisothiazolones: Correlation with Anti-HIV and Virucidal Activities" Feb. 1997, Antimicrobial Agents and Chemotherapy, American Society for Microbiology, pp. 394-400.

Penglie, Zhang et al., "Design, Synthesis and SAR of Monobenzamidines and Aminoisoquinolines as Factor Xa Inhibitors", Biorganic & Medicinal Chemistry Letters, vol. 12, 2002, pp. 1657-1661.

Akio, Kakefuda et al., "N-Nethylbenzanilide Derivatives as a Novel Class of Selective Vla Receptor Antagonists" Biorganic & Medicinal Chemistry Letters, vol. 12, 2002, pp. 229-232.

Collington, D.M et al., "Internuclear Cyclisation, Part XXV, Aromatisation of Some Spirocyclohexadiene Dimers" J.Chem. Soc, vol. 1968, pp. 1026-1028.

Vasileva et al., "Synthesis and biological activity of acyl derivatives of 4-aminoantipyrine", Pharm. Chem. J. vol. 17, No. 9, 1983, pp. 633-635.

Wilputte-Steinert, L.P. et al., "Contribution a l'etude de l'action des bases sur les sels d'ammonium quaternaries", Bull. Soc. Chim. Belges, vol. 78, 1969, pp. 77-88.

Hamuro et al., "Oligoanthranilamdes, Non-Peptide Subunits that Show Formation of Specific Secondary Structure", J. Am. Chem. Soc., vol. 118, 1996, pp. 7529-7541.

Database Crossfire Beilstein, Database accession No. 3178824 (BRN) & Krasowitzkii; Kotschergina; DANKAS Dokl. Akad, Nauk SSSR; 86; 1952; pp. 1121-1123; Chem. Abstr. 1953, 12319 abstract.

Database Crossfire Beilstein; Database accession No. 8398405 (BRN) & Supuran, Claudiu; Manole, Gheorghe; Schiketanz, Ana; Gheorghiu, Mircea D.; Puscas, Ioan; RRCHAX Rev. Roum. Chim. 36; 1-3; 1991- 251-255 abstract.

Elodi, S. et al., "Optimization of Conditions for the Catalytic Effect of The Factor IXa—Factor VIII Complex: Probable role of the complex in the amplification of blood coagulation", Thrombosis Research, vol. 15, pp. 617-629 (1979).

*Primary Examiner*—Bruck Kifle
(74) *Attorney, Agent, or Firm*—Jing G. Sun

(57) ABSTRACT

The present application describes pyrazolobenzamides and derivatives thereof of Formula I:

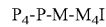

$P_4$-P-M-$M_4$I or pharmaceutically acceptable salt forms thereof. Compounds of the present invention are useful as inhibitors of trypsin-like serine proteases, specifically factor Xa.

5 Claims, No Drawings

PYRAZOLOBENZAMIDES AND DERIVATIVES AS FACTOR XA INHIBITORS

CROSS REFERENCE TO RELATED APPLICATIONS

The present application claims the priority benefit of U.S. Provisional Application No. 60/622,236, filed Oct. 26, 2004, which is expressly incorporated fully herein by reference

FIELD OF THE INVENTION

This invention relates generally to pyrazolobenzamides and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617-629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

Accordingly, the present invention provides novel pyrazolobenzamides and derivatives thereof that are useful as factor Xa inhibitors or pharmaceutically acceptable salts, solvates, or prodrugs thereof.

The present invention also provides processes and intermediates for making the compounds of the present invention or a stereoisomer or a pharmaceutically acceptable salt, solvate, or prodrug form thereof.

The present invention provides pharmaceutical compositions comprising a pharmaceutically acceptable carrier and a therapeutically effective amount of at least one of the compounds of the present invention or a pharmaceutically acceptable salt, solvate, or prodrug form thereof.

The present invention provides a method for treating thromboembolic disorders comprising administering to a mammal in need of such treatment a therapeutically effective amount of at least one of the compounds of the present invention or a pharmaceutically acceptable salt, solvate, or prodrug form thereof.

The present invention provides a novel method of treating a patient in need of thromboembolic disorder treatment, comprising: administering a compound of the present invention or a pharmaceutically acceptable salt, solvate, or prodrug form thereof in an amount effective to treat a thromboembolic disorder.

The present invention provides a novel method, comprising: administering a compound of the present invention or a pharmaceutically acceptable salt, solvate, or prodrug form thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that pyrazolobenzamide compounds of Formula I:

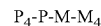

wherein P, $P_4$, M, and $M_4$ are defined below, or pharmaceutically acceptable salt or prodrug forms thereof, are effective factor Xa inhibitors.

DETAILED DESCRIPTION OF PREFERRED EMBODIMENTS

In a first embodiment, the present invention provides a novel compound of Formula I:

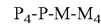

or a stereoisomer or pharmaceutically acceptable salt, solvate, or prodrug form thereof wherein:

M is a 3-10 membered carbocycle or a 4-10 membered heterocycle, consisting of: carbon atoms and 1-3 heteroatoms selected from O, $S(O)_p$, N, and $NZ^2$;

ring M is substituted with 0-3 $R^{1a}$ and 0-2 carbonyl groups, and there are 0-3 ring double bonds;

P is fused onto ring M and is a 5, 6, or 7 membered carbocycle or a 5, 6, or 7 membered heterocycle, consisting of: carbon atoms and 1-3 heteroatoms selected from O, $S(O)_p$, and N;

ring P is substituted with 0-3 $R^{1a}$ and 0-2 carbonyl groups, and there are 0-3 ring double bonds;

alternatively, ring P is absent and $P_4$ is directly attached to ring M, provided that when ring P is absent, $P_4$ and $M_4$ are attached to the 1,2, 1,3, or 1,4 positions of ring M;

one of $P_4$ and $M_4$ is -Z-A-B and the other -$G_1$-G;

G is a group of Formula IIa or IIb:

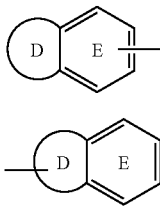

in formula IIa, ring E is substituted with 1-2 $R^a$, provided that at least one $R^a$ is ortho to the point of attachment of ring E;

in formula IIb, ring D is substituted with 1-2 $R^a$, provided that at least one $R^a$ is ortho to the point of attachment of ring D;

ring D, including the two atoms of Ring E to which it is attached, is a 5-6 membered ring consisting of: carbon atoms and 0-2 heteroatoms selected from the group consisting of N, O, and $S(O)_p$;

ring D is substituted with 0-2 R and there are 0-3 ring double bonds;

E is selected from phenyl, pyridyl, pyrimidyl, pyrazinyl, and pyridazinyl, and is substituted with 0-2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 0-2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 0-1 R and with a 5-6 membered heterocycle consisting of: carbon atoms and 1-4 heteroatoms selected from the group consisting of N, O, and $S(O)_p$, wherein the 5-6 membered heterocycle is substituted with 0-2 carbonyl and 1-2 R and there are 0-3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

alternatively, when 2 R groups are attached to adjacent atoms, they combine to form methylenedioxy or ethylenedioxy;

$R^a$ is $(CR^8R^9)_{0-3}R^b(CR^8R^{2b})_{0-4}R^b_{0-1}(CR^8R^9)_{0-4}R^c$;

$R^b$ is selected from O, C(O), $C(O)NR^3$, $C(O)N((CH_2)_{1-3}R^3)$, S(O), $S(O)_2$, $S(O)_2NR^3$, $NR^3$, $NR^3C(O)$, $NR^3S(O)_2$, $OC(O)NR^3$, $NR^3C(O)NR^3$, and $SC(O)NR^3$;

$R^c$ is selected from H, $OR^3$, $NR^3C(O)R^3$, $C(O)R^3$, $CO_2R^3$, $C(O)NR^3R^{3a}$, $S(O)_2NR^3R^{3a}$, —CN, $C_{3-10}$ carbocycle substituted with 0-2 $R^4$, and 5-12 membered heterocycle substituted with 0-2 $R^4$ and consisting of: carbon atoms and 1-4 heteroatoms selected from the group consisting of N, O, and $S(O)_p$;

provided that when the $(CR^8R^{2b})_{0-4}R^b_{0-1}(CR^8R^9)_{0-4}$ portion of $R^a$ is absent, then $R^c$ is selected from $NR^3C(O)R^3$, $S(O)_2NR^3R^{3a}$, $C_{3-10}$ carbocycle substituted with 0-2 $R^4$, and 5-12 membered heterocycle substituted with 0-2 $R^4$ and consisting of: carbon atoms and 1-4 heteroatoms selected from the group consisting of N, O, and $S(O)_p$;

further provided that when the $R^a$ is C(O)—NR*R* and NR*R* is a heterocyclic ring, then the heterocyclic ring is substituted with 1-2 $R^4$;

further provided that the $(CR^8R^{2b})_{0-4}R^b_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

A is selected from: $C_{3-10}$ carbocycle substituted with 0-2 $R^4$, and 5-12 membered heterocycle consisting of: carbon atoms and 1-4 heteroatoms selected from the group consisting of N, O, and $S(O)_p$ and substituted with 0-2 $R^4$;

B is selected from Y, X—Y, $N(B^1)C(O)C(R^3R^{3g})_{1-4}NB^2B^3$, $C(B^5)=NB^4$, and

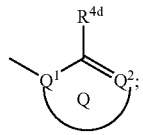

provided that Z and B are attached to different atoms on A and that the $R^{4d}$ shown is other than OH;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0-2 $R^{4b}$, and —$(CH_2)_{0-2}$-5-6 membered heterocycle consisting of: carbon atoms and 1-4 heteroatoms selected from the group consisting of N, O, and $S(O)_p$ and substituted with 0-2 $R^{4b}$;

$B^2$ is selected from H, $C_{1-6}$ alkyl substituted with 0-2 $R^{4c}$, $C(O)R^{2e}$, $C(O)OR^{2d}$, $C(O)NR^{2d}R^{2d}$, $C(O)NH(CH_2)_2NR^{2d}R^{2d}$, $SO_2NR^{2d}R^{2d}$, $C(O)NHSO_2$—$C_{1-4}$ alkyl, and $S(O)_pR^{5a}$;

$B^3$ is selected from H, $C_{1-6}$ alkyl substituted with 0-2 $R^{4c}$, —$(CH_2)_{0-2}$-3-6 membered carbocycle substituted with 0-2 $R^5$, and a —$(CH_2)_{0-2}$-4-6 membered heterocycle consisting of: carbon atoms and 1-4 heteroatoms selected from the group consisting of N, O, and $S(O)_p$ and substituted with 0-2 $R^5$;

$B^4$ is selected from H, $SO_2R^{3b}$, $C(O)R^{3b}$, $SO_2NR^3R^{3b}$, $C(O)NR^3R^{3b}$, $OR^2$, $SR^2$, —CN, and $NO_2$;

$B^5$ is $NR^2R^{2f}$ or $CR^3R^2R^{2f}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5-6 membered ring consisting of, in addition to the C—C—N shown, carbon atoms and from 0-1 additional heteroatoms selected from N, O, and $S(O)_p$, and this ring is substituted with 0-1 $R^5$;

ring Q is a 5-8 membered ring consisting of, in addition to the $Q^1$-$CR^{4d}$=$Q^2$ group shown, carbon atoms and 0-2 heteroatoms selected from N, O, and $S(O)_p$, and the ring is substituted with an additional 0-2 $R^{4d}$;

Y is selected from: $CY^1Y^2R^{4a}$, $NR^3R^{3a}$, $C(O)NR^3R^{3a}$, $C_{3-10}$ carbocycle substituted 0-2 $R^4$ and 0-1 $R^{4a}$, and, 3-10 membered heterocycle consisting of: carbon atoms and 1-4 heteroatoms selected from the group consisting of N, O, and $S(O)_p$ and substituted with 0-2 $R^4$ and 0-1 $R^{4a}$;

$Y^1$ and $Y^2$ are independently $C_{1-4}$ alkyl substituted with 0-2 $R^4$;

X is absent or is selected from $-(CR^2R^{2a})_{1-4}-$, $-CR^2(CR^{2b})(CH_2)_t-$, $-C(O)-$, $-C(=NR^{1b})-$, $-CR^2(NR^{1b}R^2)-$, $-CR^2(OR^2)-$, $-CR^2(SR^2)-$, $-C(O)CR^2R^{2a}-$, $-CR^2R^{2a}C(O)$, $-S(O)-$, $-S(O)_2-$, $-SCR^2R^{2a}-$, $-S(O)CR^2R^{2a}-$, $-S(O)_2CR^2R^{2a}-$, $-CR^2R^{2a}S(O)-$, $-CR^2R^{2a}S(O)_2-$, $-S(O)_2NR^2CR^2R^{2a}-$, $-NR^2S(O)_2-$, $-CR^2R^{2a}NR^2S(O)_2-$, $-NR^2S(O)_2CR^2R^{2a}-$, $-NR^2C(O)-$, $-C(O)NR^2CR^2R^{2a}-$, $-NR^2C(O)CR^2R^{2a}-$, $-CR^2R^{2a}NR^2C(O)-$, $-NR^2CR^2R^{2a}-$, and $-OCR^2R^{2a}-$;

$G_1$ is absent or is selected from $(CR^3R^{3a})_{1-5}$, $(CR^3R^{3a})_{0-2}CR^3=CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uOC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2 NR^{3b}(CR^3R^{3a})_w$, $(CR^3R^{3a})_uNR^{3e}(CR^3R^{3a})_w$, $(CR^3R^{3a})_uC(O)(CR^3R^{3a})_uC(O)(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(O)_2 NR^{3b}C(O)(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}CR^3R^{3a})_w$, wherein u+w total 0, 1, 2, 3, or 4 and the right side of $G_1$ is attached to ring G, provided that $G_1$ does not form an N—S, $NCH_2N$, $NCH_2O$, or $NCH_2S$ bond with either group to which it is attached;

Z is selected from a bond, $-CR^3R^{3e})_{1-4}-$, $(CR^3R^{3e})_qO(CR^3R^{3e})_{q1}$, $(CR^3R^{3e})_qNR^{3b}(CR^3R^{3e})_{q1}$, $(CR^3R^{3e})_qC(O)(CR^3R^{3e})_{q1}$, $(CR^3R^{3e})_qC(O)(CR^3R^{3e})_{q1}$, $(CR^3R^{3e})_qC(O)(CR^3R^{3e})_{q1}$, $(CR^3R^{3e})_qOC(O)(CR^3R^{3e})_{q1}$, $(CR^3R^{3e})_qC(O)NR^{3b}(CR^3R^{3e})_{q1}$, $(CR^3R^{3e})_qNR^{3b}C(O)(CR^3R^{3e})_{q1}$, $(CR^3R^{3e})_qOC(O)O(CR^3R^{3e})_{q1}$, $(CR^3R^{3e})_qOC(O)NR^{3b}(CR^3R^{3e})_{q1}$, $(CR^3R^{3e})_qNR^{3b}C(O)O(CR^3R^{3e})_{q1}$, $(CR^3R^{3e})_qNR^{3b}C(O)NR^{3b}(CR^3R^{3e})_{q1}$, $(CR^3R^{3e})_qC(O)(CR^3R^{3e})_qC(O)(CR^3R^{3e})_{q1}$, $(CR^3R^{3e})_qNR^{3b}(CR^3R^{3e})_qC(O)NR^{3b}(CR^3R^{3e})_{q1}$, $(CR^3R^{3e})_qNR^{3b}C(O)(CR^3R^{3e})_qC(O)(CR^3R^{3e})_{q1}$, $(CR^3R^{3e})_qC(O)(CR^3R^{3e})_qC(O)NR^{3b}(CR^3R^{3e})_{q1}$, $(CR^3R^{3e})_qNR^{3b}C(O)(CR^3R^{3e})_qC(O)NR^{3b}(CR^3R^{3e})_{q1}$, $(CR^3R^{3e})_qS(CR^3R^{3e})_{q1}$, $(CR^3R^{3e})_qS(O)(CR^3R^{3e})_{q1}$, $(CR^3R^{3e})_qS(O)_2(CR^3R^{3e})_{q1}$, $(CR^3R^{3e})_qSO_2NR^{3b}(CR^3R^{3e})_{q1}$, $(CR^3R^{3e})_qNR^{3b}SO_2(CR^3R^{3e})_{q1}$, $(CR^3R^{3e})_qS(O)_2NR^{3b}C(O)(CR^3R^{3e})_{q1}$, $(CR^3R^{3e})_qC(O)NR^{3b}S(O)_2(CR^3R^{3e})_{q1}$, and $(CR^3R^{3e})_qNR^{3b}SO_2NR^{3b}(CR^3R^{3e})_{q1}$, wherein q+q1 total 0, 1, 2, 3, or 4 and the right side of Z is attached to ring A, provided that Z does not form a N—S, $NCH_2N$, $NCH_2O$, or $NCH_2S$ bond with either group to which it is attached;

$Z^2$ is selected from H, $S(O)_2NHR^{3b}$, $C(O)R^{3b}$, $C(O)NHR^{3b}$, $C(O)OR^{3f}$, $S(O)R^{3f}$, $S(O)_2R^{3f}$, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, $-(C_{0-4}$ alkyl)-$C_{3-10}$ carbocycle substituted with 0-3 $R^{1a}$, and $-(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{1a}$, at each occurrence, is selected from H, $-(CR^3R^{3a})_r-R^{1b}$, $-(CR^3R^{3a})_r-CR^3R^{1b}R^{1b}$, $-(CR^3R^{3a})_r-O-(CR^3R^{3a})_r-R^{1b}$, $-(CR^3R^{3a})_r-NR^2-(CR^3R^{3a})_r-R^{1b}$, $-(CR^3R^{3a})_r-S(O)_p-(CR^3R^{3a})_r-R^{1b}$, $-(CR^3R^{3a})_r-CO_2-(CR^3R^{3a})_r-R^{1b}$, $-(CR^3R^{3a})_r-C(O)NR^2-(CR^3R^{3a})_r-R^{1b}$, $-(CR^3R^{3a})_r-C(O)-(CR^3R^{3a})_r-R^{1b}$, $-C_{2-6}$ alkenylene-$R^{1b}$, $-C_{2-6}$ alkynylene-$R^{1b}$, and $-(CR^3R^{3a})_r-C(=NR^{1b})NR^3R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $C_{1-3}$ alkyl, F, Cl, Br, I, —CN, $-NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0-2 $R^{4b}$, and 5-10 membered heterocycle substituted with 0-2 $R^{4b}$ and consisting of carbon atoms and from 1-4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, $-(CH_2)_r-C_{3-10}$ carbocycle substituted with 0-2 $R^{4b}$, and $-(CH_2)_r-$5-10 membered heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $C_{1-6}$ alkyl, $-(CH_2)_r-C_{3-10}$ carbocycle substituted with 0-2 $R^{4b}$, and $-(CH_2)_r-$5-10 membered heterocycle consisting of: carbon atoms and 1-4 heteroatoms selected from the group consisting of N, O, and $S(O)_p$, and substituted with 0-2 $R^{4b}$;

alternatively, $NR^2R^{2a}$ forms a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy substituted with 0-2 $R^{4b}$, $C_{1-6}$ alkyl substituted with 0-2 $R^{4b}$, $-(CH_2)_r-C_{3-10}$ carbocycle substituted with 0-2 $R^{4b}$, and $-(CH_2)_r-$5-10 membered heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $C_{1-4}$ alkoxy, $C_{1-6}$ alkyl, $-(CH_2)_r-C_{3-10}$ carbocycle substituted with 0-2 $R^{4b}$, and $-(CH_2)_r-$5-10 membered heterocycle containing from 1-4 heteroatoms selected from the group consisting of N, O, and $S(O)_p$, and substituted with 0-2 $R^{4b}$;

$R^{2d}$, at each occurrence, is selected from H, $R^{4c}$, $C_{1-6}$ alkyl substituted with 0-2 $R^{4c}$, $-(CR^3R^{3a})_r-C_{3-10}$ carbocycle substituted with 0-2 $R^{4c}$, and $-(CR^3R^{3a})_r-$5-

10 membered heterocycle substituted with 0-2 $R^{4c}$ and consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5-10 membered saturated, partially saturated or unsaturated ring substituted with 0-2 $R^{4b}$ and consisting of: 0-1 additional heteroatoms selected from the group consisting of N, O, and $S(O)_p$;

$R^{2e}$, at each occurrence, is selected from H, $R^{4c}$, $C_{1-6}$ alkyl substituted with 0-2 $R^{4c}$, —$(CR^3R^{3a})_r$—$C_{3-10}$ carbocycle substituted with 0-2 $R^{4c}$, and —$(CR^3R^{3a})_r$-5-10 membered heterocycle substituted with 0-2 $R^{4c}$ and consisting of: carbon atoms and 1-4 heteroatoms selected from the group consisting of N, O, and $S(O)_p$, provided that $R^{2e}$ forms other than a C(O)-halo or C(O)—$S(O)_p$ moiety;

$R^{2f}$ at each occurrence, is selected from H, $CF_3$, $C_{1-4}$ alkoxy substituted with 0-2 $R^{4b}$, $C_{1-6}$ alkyl substituted with 0-2 $R^{4b}$, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and $S(O)_p$ and substituted with 0-2 $R^{4b}$;

alternatively, $CR^2R^{2f}$ forms a 5-8 membered ring consisting of: carbon atoms and 0-2 heteroatoms selected from N, O, and $S(O)_p$, and this ring is substituted with 0-2 $R^{4b}$;

alternatively, $NR^2R^{2f}$ forms a 5-8 membered ring consisting of: carbon atoms and 0-2 additional heteroatoms selected from N, O, and $S(O)_p$, and this ring is substituted with 0-2 $R^{4b}$;

alternatively, when $B^4$ is $SO_2R^{3b}$ and $B^5$ is $NR^2R^{2f}$, $R^{3b}$ and $R^{2f}$ combine to form a 5-8 membered ring consisting of: carbon atoms and 0-2 additional heteroatoms selected from N, O, and $S(O)_p$, and this ring is substituted with 0-2 $R^{4b}$;

alternatively, when $B^4$ is $C(O)R^{3b}$ and $B^5$ is $NR^2R^2$, $R^{3b}$ and $R^{2f}$ combine to form a 5-8 membered ring consisting of: carbon atoms and 0-2 additional heteroatoms selected from N, O, and $S(O)_p$, and this ring is substituted with 0-2 $R^{4b}$;

alternatively, when $B^5$ is $NR^2R^{2f}$, $B^4$ and $R^{2f}$ combine to form a 5-8 membered ring consisting of: carbon atoms and 0-2 additional heteroatoms selected from N, O, and $S(O)_p$, and this ring is substituted with 0-2 $R^{4b}$ and the $R^2$ group of $NR^2R^{2f}$, in addition to the groups recited below, is selected from $SO_2R^{3b}$, $C(O)R^{3b}$, and —CN;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0-1 additional heteroatoms selected from the group consisting of N, O, and $S(O)_p$;

$R^{3b}$, at each occurrence, is selected from H, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-5-10 membered carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-5-10 membered carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{3f}$, at each occurrence, is selected from: $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-5-10 membered carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3-6 membered carbocycle, and —$(CH_2)_r$-5-6 membered heterocycle consisting of: carbon atoms and 1-4 heteroatoms selected from the group consisting of N, O, and $S(O)_p$;

alternatively, $CR^3R^{3g}$ forms a cyclopropyl group;

$R^4$, at each occurrence, is selected from =O, CHO, $(CR^3R^{3a})_rOR^2$, $(CR^3R^{3a})_rF$, $(CR^3R^{3a})_rCl$, $(CR^3R^{3a})_rBr$, $(CR^3R^{3a})_rI$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_r$ $NR^2C(O)R^{2b}$, $(CR^3R^{3a})_rC(O)NR^2R^{2a}$, $(CR^3R^{3a})_r$ $NR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_r$ $NR^2C(=NR^2)NR^2R^{2a}$, $(CR^3R^{3a})_rC(O)NR^2C(=NR^2)NR^2R^{2a}$, $(CR^3R^{3a})_rSO_2NR^2R^{2a}$, $(CR^3R^{3a})_r$ $NR^2SO_2NR^2R^{2a}$, $(CR^3R^{3a})_rNR^2SO_2$—$C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $NH(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5-6 membered carbocycle substituted with 0-1 $R^5$, and a $(CR^3R^{3a})_r$-5-6 membered heterocycle consisting of: carbon atoms and 1-4 heteroatoms selected from the group consisting of N, O, and $S(O)_p$ and substituted with 0-1 $R^5$;

$R^{4a}$ is selected from $C_{1-6}$ alkyl substituted with 0-2 $R^{4c}$, $C_{2-6}$ alkenyl substituted with 0-2 $R^{4c}$, $C_{2-6}$ alkynyl substituted with 0-2 $R^{4c}$, —$(CR^3R^{3g})_r$—$C_{5-10}$ membered carbocycle substituted with 0-3 $R^{4c}$, —$(CR^3R^{3g})_r$-5-10 membered heterocycle substituted with 0-3 $R^{4c}$ and consisting of: carbon atoms and 1-4 heteroatoms selected from the group consisting of N, O, and $S(O)_p$, $(CR^3R^{3g})_rCN$, $(CR^3R^{3g})_rC(=NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C(R^{2e})(=NR^{2d})$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—C(O)R$^{2e}$, $(CR^3R^{3g})_r$—OC(O)R$^{2e}$, $(CR^3R^{3g})_r$—C(O)NR$^{2d}$R$^{2d}$, $(CR^3R^{3g})_r$—C(O)OR$^{2d}$, $(CR^3R^{3g})_r$—NR$^{2d}$C(O)NR$^{2d}$R$^{2d}$, $(CR^3R^{3g})_r$—OC(O)NR$^{2d}$R$^{2d}$, $(CR^3R^{3g})_r$—NR$^{2d}$C(O)OR$^{2d}$, $(CR^3R^{3g})_r$—SO$_2$NR$^{2d}$R$^{2d}$, $(CR^3R^{3g})_r$—NR$^{2d}$SO$_2$NR$^{2d}$R$^{2d}$, $(CR^3R^{3g})_r$—C(O)NR$^{2d}$SO$_2$R$^{2d}$, $(CR^3R^{3g})_r$—NR$^{2d}$SO$_2$R$^{2d}$, and $(CR^3R^{3g})_r$—S(O)$_p$R$^{2d}$, provided that S(O)$_p$R$^{2d}$ forms other than S(O)$_2$H or S(O)H and further provided that R$^{4a}$ is other than a hydroxamic acid;

R$^{4b}$, at each occurrence, is selected from H, =O, (CH$_2$)$_r$OR$^3$, (CH$_2$)$_r$F, (CH$_2$)$_r$Cl, (CH$_2$)$_r$Br, (CH$_2$)$_r$I, C$_{1-4}$ alkyl, (CH$_2$)$_r$CN, (CH$_2$)$_r$NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$—C(O)NR$^3$R$^{3a}$, (CH$_2$)$_r$NR$^3$C(O)NR$^3$R$^{3a}$, (CH$_2$)$_r$—C(=NR$^3$)NR$^3$R$^{3a}$, (CH$_2$)$_r$NR$^3$C(=NR$^3$)NR$^3$R$^{3a}$, (CH$_2$)$_r$ SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, and (CH$_2$)$_r$(CF$_2$)$_r$CF$_3$;

R$^{4c}$, at each occurrence, is selected from =O, (CR$^3$R$^{3a}$)$_r$ OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, C$_{2-6}$ alkenyl, C$_{2-6}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$N=CHOR$^3$, (CR$^3$R$^{3a}$)$_r$C(O)NR$^2$(CH$_2$)$_2$NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$NR$^2$C(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$C(O)NR$^2$SO$_2$—C$_{1-4}$ alkyl, (CR$^3$R$^{3a}$)$_r$NR$^2$SO$_2$R$^{5a}$, (CR$^3$R$^{3a}$)$_r$C(O)NR$^2$SO$_2$R$^{5a}$, (CR$^3$R$^{3a}$)$_r$S(O)$_p$R$^{5a}$, (CF$_2$)$_r$CF$_3$, (CR$^3$R$^{3a}$)$_r$C$_{3-10}$ carbocycle substituted with 0-2 R$^{4b}$, and (CR$^3$R$^{3a}$)$_r$4-10 membered heterocycle substituted with 0-2 R$^{4b}$ and consisting of carbon atoms and from 1-4 heteroatoms selected from the group consisting of N, O, and S(O)$_p$;

R$^{4d}$, at each occurrence, is selected from H, (CR$^3$R$^{3a}$)$_r$ OR$^2$, (CR$^3$R$^{3a}$)$_r$F, (CR$^3$R$^{3a}$)$_r$Br, (CR$^3$R$^{3a}$)$_r$Cl, C$_{1-4}$ alkyl, (CR$^3$R$^{3a}$)$_r$CN, (CR$^3$R$^{3a}$)$_r$NO$_2$, (CR$^3$R$^{3a}$)$_r$ NR$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$N=CHOR$^3$, (CR$^3$R$^{3a}$)$_r$C(O)NH(CH$_2$)$_2$NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$NHC(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$—C$_{1-4}$ alkyl, (CR$^3$R$^{3a}$)$_r$C(O)NHSO$_2$—C$_{1-4}$ alkyl, (CR$^3$R$^{3a}$)$_r$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, (CR$^3$R$^{3a}$)$_r$-5-6 membered carbocycle substituted with 0-1 R$^5$, and a (CR$^3$R$^{3a}$)$_r$-5-6 membered heterocycle consisting of: carbon atoms and 1-4 heteroatoms selected from the group consisting of N, O, and S(O)$_p$ and substituted with 0-1 R$^5$;

R$^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CH$_2$)$_r$NR$^3$C(O)NR$^3$R$^{3a}$, (CH$_2$)$_r$CH(=NOR$^{3d}$), (CH$_2$)$_r$C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, (CF$_2$)$_r$CF$_3$, phenyl substituted with 0-2 R$^6$, naphthyl substituted with 0-2 R$^6$, and benzyl substituted with 0-2 R$^6$;

R$^{5a}$, at each occurrence, is selected from C$_{1-6}$ alkyl, (CH$_2$)$_r$OR$^3$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CF$_2$)$_r$CF$_3$, phenyl substituted with 0-2 R$^6$, naphthyl substituted with 0-2 R$^6$, and benzyl substituted with 0-2 R$^6$, provided that R$^{5a}$ does not form a S—N or S(O)$_p$—C(O) bond;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkyl-C(O)—, C$_{1-6}$ alkyl-O—, (CH$_2$)$_n$-phenyl, C$_{1-4}$ alkyl-OC(O)—, C$_{6-10}$ aryl-O—, C$_{6-10}$ aryl-OC(O)—, C$_{6-10}$ aryl-CH$_2$—C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl-C$_{1-4}$ alkyl-C(O)—;

R$^8$, at each occurrence, is selected from H, C$_{1-6}$ alkyl, and (CH$_2$)$_n$-phenyl;

alternatively, R$^7$ and R$^8$, when attached to the same nitrogen, combine to form a 5-10 membered heterocyclic ring consisting of carbon atoms and 0-2 additional heteroatoms selected from the group consisting of N, O, and S(O)$_p$;

R$^9$, at each occurrence, is selected from H, C$_{1-6}$ alkyl, and (CH$_2$)$_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

In a second embodiment, the present invention provides a novel compound of Formula II:

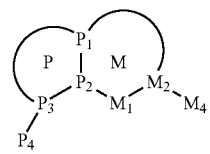

II or a stereoisomer or pharmaceutically acceptable salt, solvate, or prodrug form thereof, wherein:

ring M, including P$_1$, P$_2$, M$_1$, and M$_2$, is a 5, 6, or 7 membered carbocycle or a 5, 6, or 7 membered heterocycle, consisting of: carbon atoms and 1-3 heteroatoms selected from O, S(O)$_p$, N, and NZ$^2$;

ring M is substituted with 0-2 R$^{1a}$ and 0-2 carbonyl groups, and there are 0-3 ring double bonds;

ring P, including P$_1$, P$_2$, and P$_3$, is a 5 or 6 membered aromatic heterocycle, consisting of: carbon atoms and 1-3 heteroatoms selected from O, S(O)$_p$, and N;

alternatively, ring P, including P$_1$, P$_2$, and P$_3$, is a 5 or 6 membered dihydro-aromatic heterocycle, consisting of: carbon atoms and 1-3 heteroatoms selected from O, S(O)$_p$, and N;

ring P is substituted with 0-2 R$^{1a}$;

one of P$_4$ and M$_4$ is -Z-A-B and the other -G$_1$-G;

G is a group of Formula IIa or IIb:

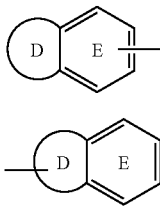

IIa

IIb in formula IIa, ring E is substituted with 1-2 $R^a$, provided that at least one $R^a$ is ortho to the point of attachment of ring E;

in formula IIb, ring D is substituted with 1-2 $R^a$, provided that at least one $R^a$ is ortho to the point of attachment of ring D;

ring D, including the two atoms of Ring E to which it is attached, is a 5-6 membered ring consisting of: carbon atoms and 0-2 heteroatoms selected from the group consisting of N, O, and $S(O)_p$;

ring D is substituted with 0-2 R and there are 0-3 ring double bonds;

E is selected from phenyl, pyridyl, pyrimidyl, pyrazinyl, and pyridazinyl, and is substituted with 0-2 R;

alternatively, ring D is absent, and ring E is selected from phenyl, pyridyl, pyrimidyl, and thienyl, and ring E is substituted with 0-2 R;

alternatively, ring D is absent, ring E is selected from phenyl, pyridyl, and thienyl, and ring E is substituted with 0-2 R and a 5-6 membered heterocycle consisting of: carbon atoms and 1-4 heteroatoms selected from the group consisting of N, O, and $S(O)_p$, wherein the 5-6 membered heterocycle is substituted with 0-2 carbonyl and 1-2 R and there are 0-3 ring double bonds;

R is selected from H, $C_{1-4}$ alkyl, F, Cl, OH, $OCH_3$, $OCH_2CH_3$, $OCH(CH_3)_2$, CN, C(=NH)$NH_2$, C(=NH)NHOH, C(=NH)$NHOCH_3$, $NH_2$, $NH(C_{1-3}$ alkyl), $N(C_{1-3}$ alkyl$)_2$, C(=NH)$NH_2$, $CH_2NH_2$, $CH_2NH(C_{1-3}$ alkyl), $CH_2N(C_{1-3}$ alkyl$)_2$, $(CR^8R^9)_t NR^7R^8$, $C(O)NR^7R^8$, $CH_2C(O)NR^7R^8$, $S(O)_p NR^7R^8$, $CH_2S(O)_p NR^7R^8$, $SO_2R^3$, and $OCF_3$;

alternatively, when 2 R groups are attached to adjacent atoms, they combine to form methylenedioxy or ethylenedioxy;

$R^a$ is $(CR^8R^9)_{0-1}R^b(CR^8R^{2b})_{0-4}R^b_{0-1}(CR^8R^9)_{0-1}R^c$;

$R^b$ is selected from O, C(O), $C(O)NR^3$, $C(O)N((CH_2)_{2-3}R^3)$, S(O), $S(O)_2$, $S(O)_2NR^3$, $NR^3$, $NR^3C(O)$, and $NR^3S(O)_2$;

$R^c$ is selected from H, $OR^3$, $NR^3C(O)R^3$, $C(O)R^3$, $CO_2R^3$, $C(O)NR^3R^{3a}$, $S(O)_2NR^3R^{3a}$, —CN, $C_{3-10}$ carbocycle substituted with 0-2 $R^4$, and 5-12 membered heterocycle substituted with 0-2 $R^4$ and consisting of: carbon atoms and 1-4 heteroatoms selected from the group consisting of N, O, and $S(O)_p$;

$R^c$ is selected from H, $OR^3$, $NR^3C(O)R^3$, $C(O)R^3$, $CO_2R^3$, $C(O)NR^3R^{3a}$, $S(O)_2NR^3R^{3a}$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;

provided that when the $(CR^8R^{2b})_{0-4}R^b_{0-1}(CR^8R^9)_{0-1}$ portion of $R^a$ is absent, then $R^c$ is selected from $NR^3C(O)R^3$, $S(O)_2NR^3R^{3a}$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;

further provided that when the $R^a$ is C(O)—NR*R* and NR*R* is a heterocyclic ring, then the heterocyclic ring is substituted with 1-2 $R^4$;

further provided that the $(CR^8R^{2b})_{0-4}R^b_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

A is selected from: $C_{5-10}$ carbocycle substituted with 0-2 $R^4$, and 5-10 membered heterocycle consisting of: carbon atoms and 1-4 heteroatoms selected from the group consisting of N, O, and $S(O)_p$ and substituted with 0-2 $R^4$;

B is selected from Y, X—Y, $N(B^1)C(O)C(R^3R^{3g})NB^2B^3$, $N(B^1)C(O)C(R^3R^{3g})C(R^3R^{3g})NB^2B^3$,

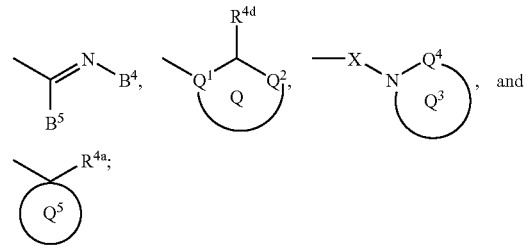

provided that Z and B are attached to different atoms on A, the $R^{4d}$ shown is other than OH, and that the A-X—N moiety forms other than a N—N—N group;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0-2 $R^{4b}$, and —$(CH_2)_{0-1}$-5-6 membered heterocycle consisting of: carbon atoms and 1-4 heteroatoms selected from the group consisting of N, O, and $S(O)_p$ and substituted with 0-2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0-1 $R^{4c}$, —$(CH_2)_{0-1}$-3-6 membered carbocycle substituted with 0-1 $R^5$, and a —$(CH_2)_{0-1}$-5-6 membered heterocycle consisting of: carbon atoms and 1-4 heteroatoms selected from the group consisting of N, O, and $S(O)_p$ and substituted with 0-1 $R^5$;

$B^4$ is selected from H, $SO_2R^{3b}$, $C(O)R^{3b}$, $SO_2NR^3R^{3b}$, $C(O)NR^3R^{3b}$, $OR^2$, and —CN;

$B^5$ is $NR^2R^{2f}$ or $CR^3R^2R^{2f}$;

ring Q is a 5-6 membered ring consisting of, in addition to the $Q^1$-$CR^{4d}$=$Q^2$ group shown, carbon atoms and 0-2 heteroatoms selected from N, O, and $S(O)_p$, and the ring is substituted with an additional 0-2 $R^{4d}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5-6 membered ring consisting of, in addition to the C—C—N shown, carbon atoms and from 0-1 additional heteroatoms selected from N, O, and $S(O)_p$, and this ring is substituted with 0-1 $R^5$;

$Q^4$ is selected from C=O and $SO_2$;

ring $Q^3$ is a 4-7 membered monocyclic or tricyclic ring consisting of, in addition to the N-$Q^4$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^4$;

alternatively, ring $Q^3$ is a 4-7 membered ring to which another ring is fused, wherein: the 4-7 membered ring consists of, in addition to the shown amide group, carbon atoms and 0-2 heteroatoms selected from $NR^{4c}$, O, S, S(O), and $S(O)_2$ and 0-1 double bonds are present within the ring; the fusion ring is phenyl or a 5-6 membered heteroaromatic consisting of carbon atoms and 1-2 heteroatoms selected from $NR^{4c}$, O, and S;

ring $Q^3$, which includes the 4-7 membered ring and the fusion ring, is substituted with 0-3 $R^4$;

ring $Q^5$ is a $C_{3-7}$ monocyclic carbocycle or 3-7 membered monocyclic heterocycle, wherein the carbocycle or heterocycle consists of: carbon atoms and 0-2 heteroatoms selected from N, O, and $S(O)_p$, the carbocycle or heterocycle further comprises 0-2 double bonds and 0-2 carbonyl groups, and the carbocycle or heterocycle is substituted with 0-2 $R^4$;

X is selected from —$(CR^2R^{2a})_{1-4}$—, —C(O)—, —C(=$NR^{1c}$)—, —$CR^2(NR^{1b}R^2)$—, —C(O) $CR^2R^{2a}$—, —$CR^2R^{2a}$C(O)—, —C(O)$NR^2$—, —$NR^2C$ (O)—, —C(O)$NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, —$S(O)_2$—, —$NR^2S(O)_2$—, O, —$CR^2R^{2a}O$—, and —$OCR^2R^{2a}$—;

Y is selected from: $CY^1Y^2R^{4a}$, $NR^3R^{3a}$, and C(O) $NR^3R^{3a}$;

$Y^1$ and $Y^2$ are independently $C_{1-3}$ alkyl substituted with 0-2 $R^4$;

alternatively, Y is selected from one of the following carbocyclic and heterocycles that are substituted with 1 $R^{4a}$ and 0-2 $R^4$: cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

Z is selected from a bond, $CH_2$, $CH_2CH_2$, $CH_2O$, $OCH_2$, C(O), NH, $CH_2NH$, $NHCH_2$, $CH_2C(O)$, C(O)$CH_2$, C(O)NH, NHC(O), NHC(O)$CH_2C(O)$NH, $S(O)_2$, $CH_2S(O)_2$, $S(O)_2(CH_2)$, $SO_2NH$, and $NHSO_2$, wherein the right side of Z is attached to ring A, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, C(O) $R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_p$ $R^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, C(O) $NR^2(CH_2)_rOR^2$, $SO_2NR^2R^{2a}$, $NR^2SO_2R^2$, $C_{5-6}$ carbocycle substituted with 0-2 $R^{4b}$, and 5-6 membered heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0-2 $R^{4b}$, $C_{5-6}$ carbocycle substituted with 0-2 $R^{4b}$, a $C_{5-6}$ carbocyclic-$CH_2$-group substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0-2 $R^{4b}$, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

alternatively, $NR^2R^{2a}$ forms a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0-2 $R^{4b}$, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0-2 $R^{4b}$, $C_{5-6}$ carbocycle substituted with 0-2 $R^{4b}$, and 5-6 membered heterocycle containing from 1-4 heteroatoms selected from the group consisting of N, O, and $S(O)_p$, and substituted with 0-2 $R^{4b}$;

$R^{2d}$, at each occurrence, is selected from H, $R^{4c}$, $C_{1-4}$ alkyl substituted with 0-2 $R^{4c}$, —$(CR^3R^{3a})_r$—$C_{3-6}$ carbocycle substituted with 0-2 $R^{4c}$, and —$(CR^3R^{3a})_r$-5-6 membered heterocycle substituted with 0-2 $R^{4c}$ and consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2e}$, at each occurrence, is selected from H, $R^{4c}$, $C_{1-4}$ alkyl substituted with 0-2 $R^{4c}$, —$(CR^3R^{3a})_r$—$C_{3-6}$ carbocycle substituted with 0-2 $R^{4c}$, and —$(CR^3R^{3a})_r$-5-6 membered heterocycle substituted with 0-2 $R^{4c}$ and consisting of: carbon atoms and 1-4 heteroatoms selected from the group consisting of N, O, and $S(O)_p$, provided that $R^{2e}$ forms other than a C(O)-halo or C(O)—S(O)$_p$ moiety;

$R^{2f}$ at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0-1 $R^{4b}$, $C_{5-6}$ carbocycle substituted with 0-2 $R^{4b}$, and 5-6 membered heterocycle containing from 1-4 heteroatoms selected from the group consisting of N, O, and $S(O)_p$ and substituted with 0-2 $R^{4b}$;

alternatively, $CR^2R^{2f}$ forms a 5-6 membered ring consisting of: carbon atoms and 0-2 heteroatoms selected from N, O, and $S(O)_p$, and this ring is substituted with 0-2 $R^{4b}$;

alternatively, $NR^2R^{2f}$ forms a 5-6 membered ring consisting of: carbon atoms and 0-2 additional heteroatoms selected from N, O, and $S(O)_p$, and this ring is substituted with 0-2 $R^{4b}$;

alternatively, when $B^5$ is $NR^2R^{2f}$, $B^4$ and $R^{2f}$ combine to form a 5-6 membered ring consisting of: carbon atoms and 0-2 additional heteroatoms selected from N, O, and $S(O)_p$, and this ring is substituted with 0-2 $R^{4b}$ and the $R^2$ group of $NR^2R^{2f}$, in addition to the groups recited below, is selected from $SO_2R^{3b}$ and $C(O)R^{3b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3b}$, at each occurrence, is selected from H, $CF_3$, $CH_3$, $CH_2CH_3$, $CH_2CH_2CH_3$, $CH(CH_3)_2$, —$(C_{0-1}$ alkyl)-5-6 membered carbocycle substituted with 0-1 $R^{1a}$, and —$(C_{0-1}$ alkyl)-5-6 membered heterocycle substituted with 0-1 $R^{1a}$ and consisting of: carbon atoms and 1-4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $NR^2SO_2NR^2R^{2a}$, $S(O)_pR^{5a}$, $NR_3SO_2$—$C_{1-4}$ alkyl, $NR^2SO_2R^5$, $CF_3$, $CF_2CF_3$, 5-6 membered carbocycle substituted with 0-1 $R^5$, and a 5-6 membered heterocycle consisting of: carbon atoms and 1-4 heteroatoms selected from the group consisting of N, O, and $S(O)_p$, and substituted with 0-1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR_3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4c}$, at each occurrence, is selected from =O, $(CR^3R^{3a})_r OR^2$, $(CR^3R^{3a})_r F$, $(CR^3R^{3a})_r Br$, $(CR^3R^{3a})_r Cl$, $(CR^3R^{3a})_r CF_3$, $C_{1-4}$ alkyl, $C_{2-3}$ alkenyl, $C_{2-3}$ alkynyl, $(CR^3R^{3a})_r CN$, $(CR^3R^{3a})_r NO_2$, $(CR^3R^{3a})_r NR^2R^{2a}$, $(CR^3R^{3a})_r N(\rightarrow O)R^2R^{2a}$, $(CR^3R^{3a})_r C(O)R^{2c}$, $(CR^3R^{3a})_r NR^2C(O)R^{2b}$, $(CR^3R^{3a})_r C(O)NR^2R^{2a}$, $(CR^3R^{3a})_r NR^2C(O)NR^2R^{2a}$, $(CR^3R^{3a})_r SO_2NR^2R^{2a}$, $(CR^3R^{3a})_r NR^2SO_2NR^2R^{2a}$, $(CR^3R^{3a})_r NR^2SO_2R^{5a}$, $(CR^3R^{3a})_r C(O)NR^2SO_2R^{5a}$, $(CR^3R^{3a})_r S(O)_p R^{5a}$, $(CF_2)_r CF_3$, $(CR^3R^{3a})_r C_{3-10}$ carbocycle substituted with 0-2 $R^{4b}$, and $(CR^3R^{3a})_r$ 5-10 membered heterocycle consisting of carbon atoms and from 1-4 heteroatoms selected from the group consisting of N, O, and $S(O)_p$ and substituted with 0-2 $R^{4b}$;

$R^{4d}$, at each occurrence, is selected from H, $CH_2OR^2$, $OR^2$, $C_{1-4}$ alkyl, $CH_2$—CN, —CN, $CH_2NO_2$, $NO_2$, $CH_2NR^2R^{2a}$, $NR^2R^{2a}$, $CH_2$—$C(O)R^{2c}$, $C(O)R^{2c}$, $NR^2C(O)R^{2b}$, $(CH_2)_r C(O)NR^2R^{2a}$, $NR^2C(O)NR^2R^{2a}$, $(CH_2)_r SO_2NR^2R^{2a}$, $NR^2SO_2NR^2R^{2a}$, $NR^2SO_2R^5$, $(CH_2)_r S(O)_p R^{5a}$, $CH_2CF_3$, $CF_3$, $CH_2$-5-6 membered carbocycle substituted with 0-1 $R^5$, 5-6 membered carbocycle substituted with 0-1 $R^5$, a $CH_2$-5-6 membered heterocycle consisting of: carbon atoms and 1-4 heteroatoms selected from the group consisting of N, O, and $S(O)_p$ and substituted with 0-1 $R^5$, and a 5-6 membered heterocycle consisting of: carbon atoms and 1-4 heteroatoms selected from the group consisting of N, O, and $S(O)_p$ and substituted with 0-1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR_3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$;

$R^{5a}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $CF_3$, $CF_2CF_3$, phenyl substituted with 0-2 $R^6$, naphthyl substituted with 0-2 $R^6$, and benzyl substituted with 0-2 $R^6$, provided that $R^{5a}$ does not form a S—N or $S(O)_p$—C(O) bond; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

In a third embodiment, the present invention provides a novel compound or a stereoisomer or pharmaceutically acceptable salt, solvate, or prodrug form thereof, wherein the compound is selected from:
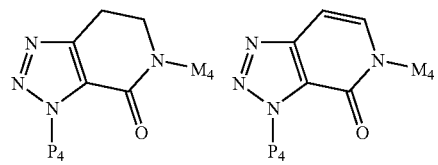
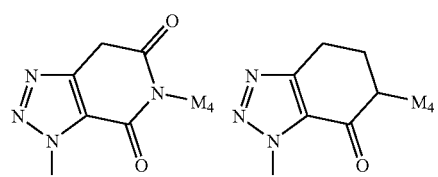
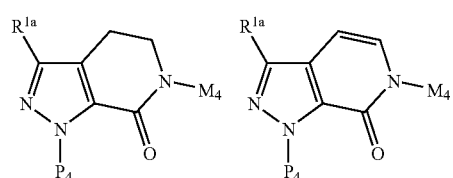
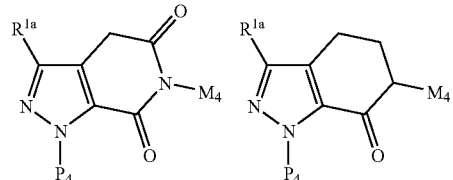
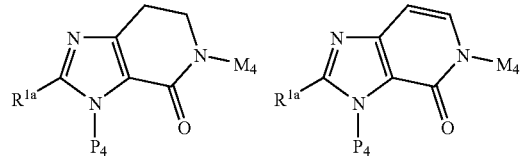
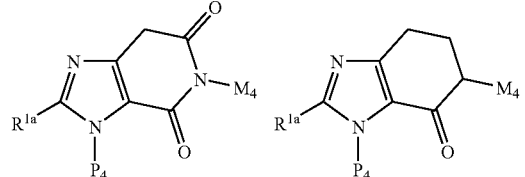
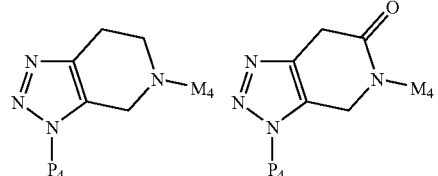
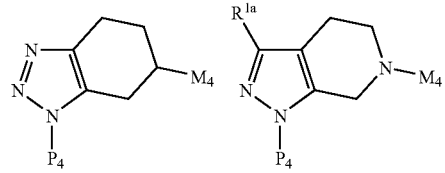
-continued
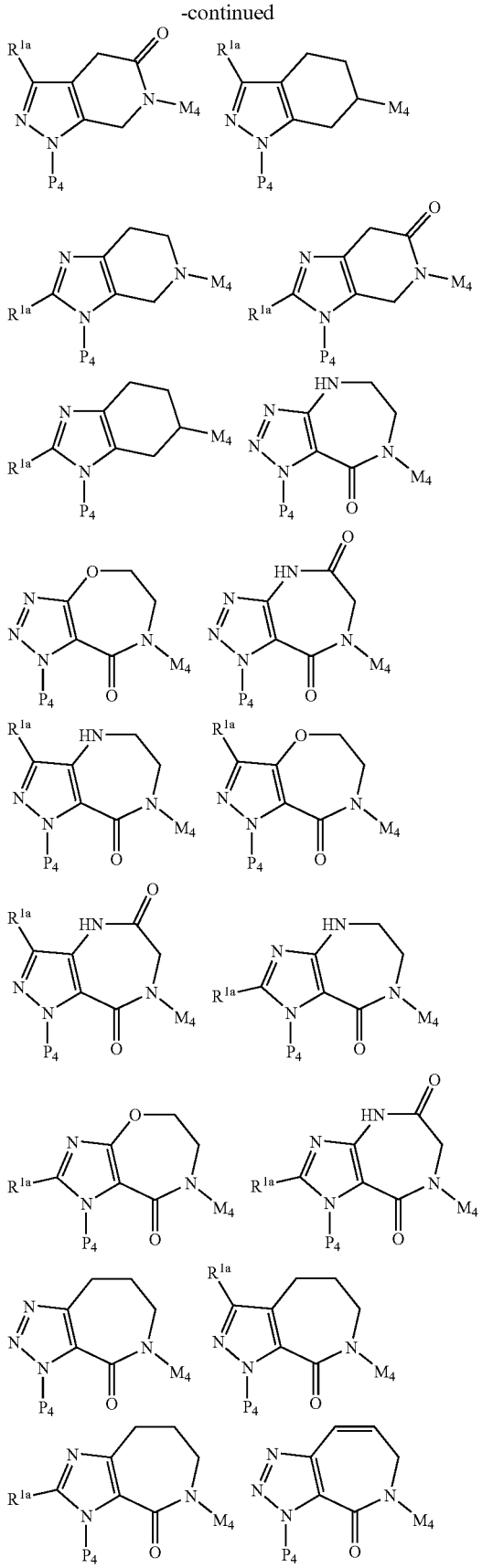

-continued
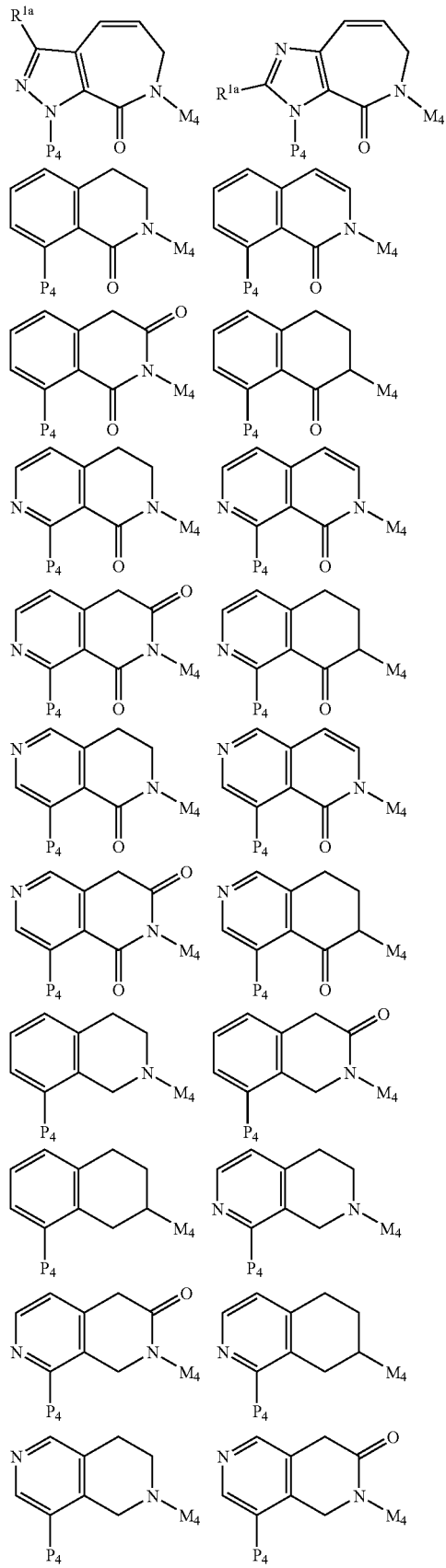
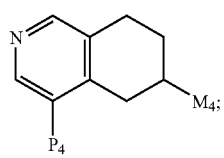
$P_4$ is -G;
$M_4$ is -A-B;
G is substituted with 1 $R^a$ and is selected from the following group, wherein $R^a$ is attached adjacent to the point of attachment of G:
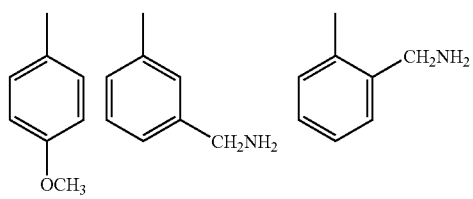
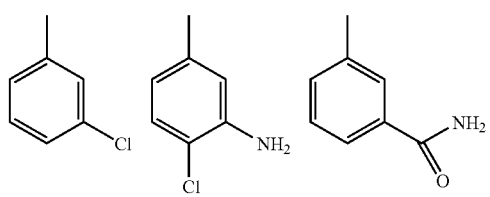
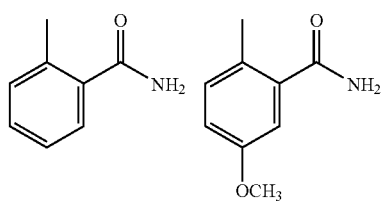
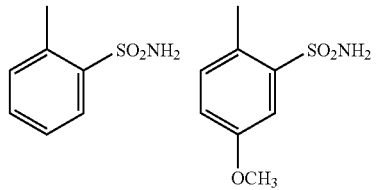
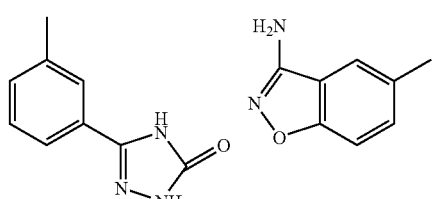
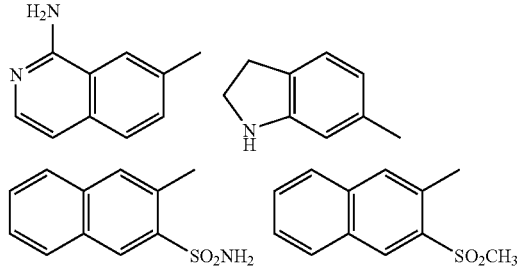

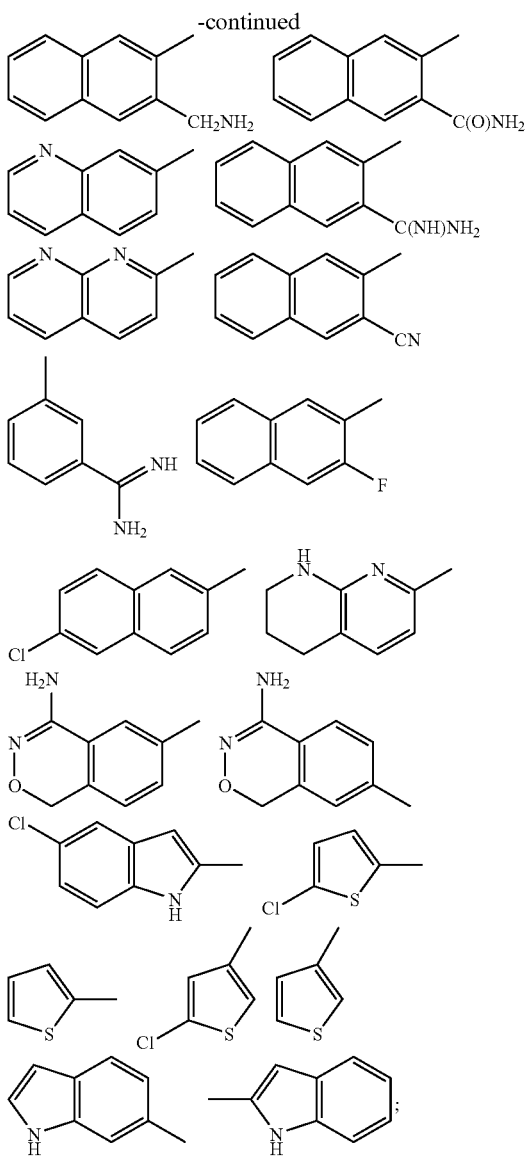

$R^a$ is $R^b(CR^8R^{2b})_{0-4}R^b_{0-1}(CR^8R^9)_{0-1}R^c$;

$R^b$ is selected from $C(O)NR^3$, $S(O)_2NR^3$, $NR^3C(O)$, and $NR^3S(O)_2$;

$R^c$ is selected from H, $OR^3$, $NR^3C(O)R^3$, $C(O)NR^3R^{3a}$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;

provided that when the $(CR^8R^{2b})_{0-4}R^b_{0-1}(CR^8R^9)_{0-1}$ portion of $R^a$ is absent, then $R^c$ is selected from $NR^3C(O)R^3$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;

further provided that the $(CR^8R^{2b})_{0-4}R^b_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

$G_1$ is absent or is selected from $(CR^3R^{3a})_{1-3}$, $CR^3$=$CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, and $(CR^3R^{3a})_uS(O)_2NR^{3b}(CR^3R^{3a})_w$, wherein u+w total 0, 1, or 2, wherein the right side of $G_1$ is attached to ring G, provided that $G_1$ does not form a N—S, $NCH_2N$, $NCH_2O$, or $NCH_2S$ bond with either group to which it is attached;

A is selected from one of the following carbocyclic and heterocyclic groups which are substituted with 0-2 $R^4$; cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, $CH_2CH_3$, $CH_2CH_2CH_3$, $CH(CH_3)_2$, —$(CH_2)_{0-1}$—$C_{5-6}$ carbocycle substituted with 0-2 $R^{4b}$, and —$(CH_2)_{0-1}$-5-6 membered heterocycle consisting of: carbon atoms and 1-4 heteroatoms selected from the group consisting of N, O, and $S(O)_p$ and substituted with 0-2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0-1 $R^{4c}$, —$(CH_2)_{0-1}$-3-6 membered carbocycle substituted with 0-1 $R^5$, and a —$(CH_2)_{0-1}$-5-6 membered heterocycle consisting of: carbon atoms and 1-4 heteroatoms selected from the group consisting of N, O, and $S(O)_p$ and substituted with 0-1 $R^5$;

$B^4$ is selected from H, $SO_2R^{3b}$ and $OR^2$;

$B^5$ is $NR^2R^{2f}$;

ring Q is a 5-6 membered ring consisting of, in addition to the N—$CR^{4d}$=N group shown, carbon atoms and 0-2 heteroatoms selected from N, O, and $S(O)_p$, and the ring is substituted with an additional 0-2 $R^{4d}$;

$Q^4$ is selected from C=O and $SO_2$;

ring $Q^3$ is a 5-7 membered ring consisting of, in addition to the N-$Q^4$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^{4a}$;

alternatively, ring $Q^3$ is a 5-7 membered ring to which another ring is fused, wherein: the 5-7 membered ring consists of, in addition to the shown amide group, carbon atoms and 0-2 heteroatoms selected from $NR^{4c}$, O, S, S(O), and $S(O)_2$, and 0-1 double bonds are present within the ring; the fusion ring is phenyl or a 5-6 membered heteroaromatic consisting of carbon atoms and 1-2 heteroatoms selected from $NR^{4c}$, O, and S;

ring $Q^3$, which includes the 5-7 membered ring and the fusion ring, is substituted with 0-3 $R^{4a}$;

ring $Q^5$, is a $C_{3-6}$ monocyclic carbocycle or 5-6 membered monocyclic heterocycle, wherein the carobocycle or heterocycle consists of carbon atoms and 0-2 heteroatoms selected from N, O, and S(O)p, the carbocycle or heterocycle further comprises 0-1 double bonds and 0-1 carbonyl groups, and the carbocycle or heterocycle is substituted with 0-2 $R^4$;

X is selected from $-(CR^2R^{2a})_{1-2}-$, $-C(=NR^{1b})-$, $-C(O)-$, $-S(O)_2-$, $-NR^2S(O)_2-$, $-NR^2S(O)_2-$, $-NR^2C(O)-$, $-C(O)NR^2-$, $-NR^2C(O)CR^2R^{2a}-$, $-NR^2C(O)NR^2-$, $NR^2$, $-NR^2CR^2R^{2a}-$, $-CR^2R^{2a}NR^2-$, O, $-OCR^2R^{2a}-$, and $-CR^2R^{2a}O-$;

Y is selected from: $CY^1Y^2R^{4a}$, $NR^3R^{3a}$, and $C(O)NR^3R^{3a}$;

$Y^1$ and y are independently $C_{1-2}$ alkyl substituted with 0-2 $R^4$;

alternatively, Y is selected from one of the following carbocyclic and heterocycles that are substituted with 1 $R^{4a}$ and 0-1 $R^4$: cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5-6 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, F, Cl, Br, $-CN$, $-CHO$, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0-2 $R^{4b}$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0-2 $R^{4b}$, a benzyl substituted with 0-2 $R^{4b}$, and a 5-6 membered aromatic heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl substituted with 0-2 $R^{4b}$, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

alternatively, $NR^2R^{2a}$ forms a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0-2 $R^{4b}$, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0-2 $R^{4b}$, phenyl substituted with 0-2 $R^{4b}$, and 5-6 membered aromatic heterocycle containing from 1-4 heteroatoms selected from the group consisting of N, O, and $S(O)_p$, and substituted with 0-2 $R^{4b}$;

$R^{2d}$, at each occurrence, is selected from H, $R^{4c}$, $C_{1-4}$ alkyl substituted with 0-2 $R^{4c}$, $C_{3-6}$ carbocycle substituted with 0-2 $R^{4c}$, $-(CR^3R^{3a})-C_{3-6}$ carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and $-(CR^3R^{3a})$-5-6 membered heterocycle substituted with 0-2 $R^{4c}$ and consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0-2 $R^{4c}$, $C_{3-6}$ carbocycle substituted with 0-2 $R^{4c}$, $-(CR^3R^{3a})-C_{3-6}$ carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and $-(CR^3R^{3a})$-5-6 membered heterocycle substituted with 0-2 $R^{4c}$ and consisting of: carbon atoms and 1-4 heteroatoms selected from the group consisting of N, O, and $S(O)_p$, provided that $R^{2e}$ forms other than a C(O)-halo or C(O)—$S(O)_p$ moiety;

$R^{2f}$ at each occurrence, is selected from H, $CF_3$, $CH_3$, $CH_2CH_3$, $CH_2CH_2CH_3$, $CH(CH_3)_2$, $OCH_3$, and benzyl;

alternatively, $NR^2R^{2f}$ forms a 5-6 membered ring consisting of: carbon atoms and 0-2 additional heteroatoms selected from N, O, and $S(O)_p$, and this ring is substituted with 0-2 $R^{4b}$;

alternatively, $B^4$ and $R^{2f}$ combine to form a 5-6 membered ring consisting of: carbon atoms and 0-1 additional heteroatoms selected from N, O, and $S(O)_p$, and this ring is substituted with 0-2 $R^{4b}$ and the $R^2$ group of $NR^2R^{2f}$, in addition to the groups recited below, can be $SO_2R^{3b}$;

$R^{3b}$, at each occurrence, is selected from H, $CF_3$, $CH_3$, $CH_2CH_3$, $CH_2CH_2CH_3$, and $CH(CH_3)_2$;

$R^4$, at each occurrence, is selected from H, $=O$, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $-CN$, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from $-(CR^3R^{3g})_r$-5-6 membered carbocycle substituted with 0-3 $R^{4c}$, $-(CR^3R^{3g})_r$-5-6 membered heterocycle substituted with 0-3 $R^{4c}$ and consisting of: carbon atoms and 1-4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r-NR^{2d}C(O)R^{2e}$, $(CR^3R^{3g})_r-C(O)R^{2e}$, $(CR^3R^{3g})_r-OC(O)R^{2e}$, $(CR^3R^{3g})_r-C(O)NR^{2d}R^{2d}$, $(CR^3R^{3g})_r-C(O)OR^{2d}$, $(CR^3R^{3g})_r-NR^{2d}C(O)NR^{2d}R^{2d}$, $(CR^3R^{3g})_r-NR^{2d}C(O)OR^{2d}$, $(CR^3R^{3g})_r-SO_2NR^{2d}R^{2d}$, $(CR^3R^{3g})_r-$ $NR^{2d}SO_2R^{2d}$, and $(CR^3R^{3g})_r-S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2-C(O)R^3$, $C(O)OR^{3c}$, $CH_2-C(O)OR^{3c}$, $NR^3C(O)R^{3a}$, $CH_2NR^3C(O)R^{3a}$, $C(O)NR^3R^{3a}$, $CH_2-C(O)NR^3R^{3a}$, $SO_2NR^3R^{3a}$, $CH_2SO_2NR^3R^{3a}$, $NR_3SO_2-C_{1-4}$ alkyl, $CH_2NR^3SO_2-C_{1-4}$ alkyl, $NR^3SO_2$-phenyl, $CH_2NR^3SO_2$-phenyl, $S(O)_pCF_3$, $CH_2S(O)_pCF_3$, $S(O)_p-C_{1-4}$ alkyl, $CH_2S(O)_p-C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{2-3}$ alkenyl, $C_{2-3}$ alkynyl, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0-2 $R^{4b}$, $(CR^3R^{3a})C_{3-10}$ carbocycle substituted with 0-2 $R^{4b}$, 5-10 membered heterocycle consisting of carbon atoms and from 1-4 heteroatoms selected from the group consisting of N, O, and $S(O)_p$ and substituted with 0-2 $R^{4b}$, and $(CR^3R^{3a})$-5-10 membered heterocycle consisting of carbon atoms and from 1-4 heteroatoms selected from the group consisting of N, O, and $S(O)_p$ and substituted with 0-2 $R^{4b}$;

$R^{4d}$, at each occurrence, is selected from H, $CH_2OR^2$, $OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $CH_2NR^2R^{2a}$, $NR^2R^{2a}$, $C(O)R^{2c}$, $NR^2C(O)R^{2b}$, $C(O)NR^2R^{2a}$, $NR^2C(O)NR^2R^{2a}$, $NR^2SO_2R^5$, $SO_2NR^2R^{2a}$, 6-membered carbocycle substituted with 0-1 $R^5$, and a 5-6 membered heterocycle consisting of: carbon atoms and 1-2 heteroatoms selected from the group consisting of N, O, and $S(O)_p$ and substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

In a fourth embodiment, the present invention provides a novel compound or a stereoisomer or pharmaceutically acceptable salt, solvate, or prodrug form thereof, within the scope of the third embodiment, wherein:

G is substituted with 1 $R^a$, wherein $R^a$ is attached adjacent to the point of attachment of G:

$R^a$ is $R^b(CR^8R^{2b})_{0-3}R^b_{0-1}R^c$;

$R^b$ is $C(O)NR^3$;

$R^c$ is selected from H, $OR^3$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;

provided that when the $(CR^8R^{2b})_{0-4}R^b_{0-1}(CR^8R^9)_{0-1}$ portion of $R^a$ is absent, then $R^c$ is selected from $C_{5-10}$ carbocycle substituted with 0-2 $R^4$ and 5-11 membered heterocycle substituted with 0-2 $R^4$ and consisting of: carbon atoms and 1-4 heteroatoms selected from the group consisting of N, O, and $S(O)_p$;

further provided that the $(CR^8R^{2b})_{0-4}R^b_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, NHC(O), $CH_2S(O)_2$, $S(O)_2(CH_2)$, $SO_2NH$, and $NHSO_2$, wherein the right side of $G_1$ is attached to ring G, provided that $G_1$ does not form a N—S, $NCH_2N$, $NCH_2O$, or $NCH_2S$ bond with either group to which it is attached;

A is selected from cyclohexyl, piperidinyl, piperazinyl, phenyl, pyridyl, and pyrimidyl, and is substituted with 0-2 $R^4$;

B is selected from Y, $N(B^1)C(O)C(R^3R^{3g})NB^2B^3$,

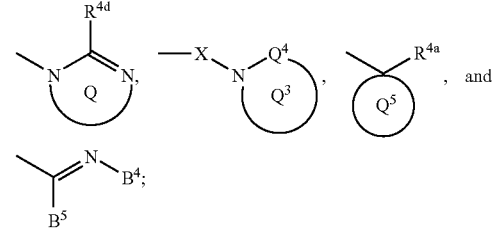

, and provided that Z and B are attached to different atoms on A, the $R^{4d}$ shown is other than OH, and that the A-X—N moiety forms other than a N—N—N group;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3-6 membered carbocycle substituted with 0-1 $R^5$, and a —$(CH_2)_{0-1}$-5-6 membered heterocycle consisting of: carbon atoms and 1-4 heteroatoms selected from the group consisting of N, O, and $S(O)_p$ and substituted with 0-1 $R^5$;

$B^4$ is selected from H, $SO_2R^{3b}$, and $OR^2$;

$B^5$ is $NR^2R^{2f}$;

ring Q is a 5-6 membered ring consisting of, in addition to the N—$CR^{4d}$=N group shown, carbon atoms and 0-1 heteroatoms selected from N, O, and $S(O)_p$, and the ring is substituted with an additional 0-2 $R^{4d}$;

$Q^4$ is selected from C=O and $SO_2$;

ring $Q^3$ is a 6-7 membered ring consisting of, in addition to the N-$Q^4$ group shown, carbon atoms and 0-1 heteroatoms selected from $NR^{4c}$, O, S, S(O), and $S(O)_2$, wherein: 0-2 double bonds are present within the ring and the ring is substituted with 0-2 $R^4$;

alternatively, ring $Q^3$ is a 5-7 membered ring to which another ring is fused, wherein: the 5-7 membered ring consists of, in addition to the shown amide group, carbon atoms and 0-1 heteroatoms selected from $NR^{4c}$, O, S, S(O), and S(O)$_2$, and 0-1 double bonds are present within the ring; the fusion ring is phenyl;

ring Q$^3$, which includes the 5-7 membered ring and the fusion ring, is substituted with 0-2 R$^4$;

ring Q$^5$ is substituted with 0-1 R$^4$ and is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl;

X is selected from CH$_2$, C(O), —S(O)$_2$—, —NHC(O)—, —C(O)NH—, —CH$_2$NH—, O, and —CH$_2$O—;

Y is selected from N(CH$_3$)$_2$, C(O)(CH$_3$)$_2$, C(CH$_3$)$_2$R$^{4a}$ and C(CH$_2$CH$_3$)$_2$R$^{4a}$;

alternatively, Y is selected from phenyl, pyridyl, pyrrolidino, N-pyrrolidino-carbonyl, morpholino, N-morpholino-carbonyl, 1,2,3-triazolyl, imidazolyl, and benzimidazolyl, and is substituted with 1 R$^{4a}$ and 0-1 R$^4$;

R$^{1a}$, at each occurrence, is selected from H, R$^{1b}$, CH(CH$_3$)R$^{1b}$, C(CH$_3$)$_2$R$^{1b}$, and CH$_2$R$^{1b}$, provided that R$^{1a}$ forms other than an N-halo, N—S, or N—CN bond;

R$^{1b}$ is selected from CH$_3$, CH$_2$CH$_3$, F, Cl, Br, —CN, CF$_3$, OR$^2$, NR$^2$R$^{2a}$, C(O)R$^{2b}$, CO$_2$R$^{2b}$, CO$_2$R$^{2a}$, S(O)$_p$R$^2$, C(O)NR$^2$R$^{2a}$, SO$_2$NR$^2$R$^{2a}$, NR$^2$SO$_2$R$^2$, and 5-6 membered aromatic heterocycle consisting of carbon atoms and from 1-4 heteroatoms selected from the group consisting of N, O, and S(O)$_p$, and substituted with 0-2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0-1 R$^{4b}$, benzyl substituted with 0-1 R$^{4b}$, and 5-6 membered aromatic heterocycle consisting of: carbon atoms and 1-4 heteroatoms selected from the group consisting of N, O, and S(O)$_p$, and substituted with 0-1 R$^{4b}$;

R$^{2a}$, at each occurrence, is selected from H, CH$_3$, CH$_2$CH$_3$, CH$_2$CH$_2$CH$_3$, CH(CH$_3$)$_2$, benzyl substituted with 0-1 R$^{4b}$, phenyl substituted with 0-1 R$^{4b}$, and 5-6 membered aromatic heterocycle consisting of: carbon atoms and 1-4 heteroatoms selected from the group consisting of N, O, and S(O)$_p$, and substituted with 0-1 R$^{4b}$;

alternatively, NR$^2$R$^{2a}$ forms a 5 or 6 membered saturated, partially saturated or unsaturated ring substituted with 0-1 R$^{4b}$ and consisting of: 0-1 additional heteroatoms selected from the group consisting of N, O, and S(O)$_p$;

R$^{2b}$, at each occurrence, is selected from OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0-1 R$^{4b}$, phenyl substituted with 0-1 R$^{4b}$, and 5-6 membered aromatic heterocycle consisting of: carbon atoms and 1-4 heteroatoms selected from the group consisting of N, O, and S(O)$_p$, and substituted with 0-1 R$^{4b}$;

R$^{2c}$, at each occurrence, is selected from OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0-1 R$^{4b}$, phenyl substituted with 0-1 R$^{4b}$, and 5-6 membered aromatic heterocycle containing from 1-4 heteroatoms selected from the group consisting of N, O, and S(O)$_p$, and substituted with 0-1 R$^{4b}$;

R$^{2d}$, at each occurrence, is selected from H, R$^{4c}$, C$_{1-4}$ alkyl substituted with 0-2 R$^{4c}$, C$_{3-6}$ carbocycle substituted with 0-2 R$^{4c}$, —(CH$_2$)—C$_{3-6}$ carbocycle substituted with 0-2 R$^{4c}$, 5-6 membered heterocycle substituted with 0-2 R$^{4c}$ and consisting of: carbon atoms and 1-4 heteroatoms selected from the group consisting of N, O, and S(O)$_p$, and —(CH$_2$)-5-6 membered heterocycle substituted with 0-2 R$^{4c}$ and consisting of: carbon atoms and 1-4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0-2 R$^{4c}$, C$_{3-6}$ carbocycle substituted with 0-2 R$^{4c}$, —(CH$_2$)—C$_{3-6}$ carbocycle substituted with 0-2 R$^{4c}$, 5-6 membered heterocycle substituted with 0-2 R$^{4c}$ and consisting of: carbon atoms and 1-4 heteroatoms selected from the group consisting of N, O, and S(O)$_p$, and —(CH$_2$)-5-6 membered heterocycle and consisting of: carbon atoms and 1-4 heteroatoms selected from the group consisting of N, O, and S(O)$_p$, provided that R$^{2e}$ forms other than a C(O)-halo or C(O)—S(O) moiety;

R$^{2f}$, at each occurrence, is selected from H, CH$_3$, CH$_2$CH$_3$, OCH$_3$, and benzyl;

alternatively, NR$^2$R$^{2f}$ forms a 5-6 membered ring consisting of: carbon atoms and 0-1 additional heteroatoms selected from N, O, and S(O)$_p$, and this ring is substituted with 0-1 R$^{4b}$;

alternatively, B$^4$ and R$^{2f}$ combine to form a 5 membered ring consisting of: carbon atoms and 0-1 additional heteroatoms selected from N, O, and S(O)$_p$, and this ring is substituted with 0-2 R and the R$^2$ group of NR$^2$R$^{2f}$, in addition to the groups recited below, can be SO$_2$R$^{3b}$;

R$^{3b}$, at each occurrence, is selected from H and CH$_3$;

R$^4$, at each occurrence, is selected from H, =O, OH, OR$^2$, CH$_2$OR$^2$, (CH$_2$)$_2$OR$^2$, F, Br, Cl, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, CF$_3$, and CF$_2$CF$_3$;

R$^{4a}$ is selected from —(CR$^3$R$^{3g}$)$_r$-5-6 membered carbocycle substituted with 0-3 R$^{4c}$, —(CR$^3$R$^{3g}$)$_r$-5-6 membered heterocycle substituted with 0-3 R$^{4c}$ and consisting of: carbon atoms and 1-4 heteroatoms selected from the group consisting of N, O, and S(O)$_p$, (CR$^3$R$^{3g}$)$_r$NR$^{2d}$R$^{2d}$, (CR$^3$R$^{3g}$)$_r$N(→O)R$^{2d}$R$^{2d}$, (CR$^3$R$^{3g}$)$_r$OR$^{2d}$, (CR$^3$R$^{3g}$)$_r$—C(O)NR$^{2d}$R$^{2d}$, (CR$^3$R$^{3g}$)$_r$—NR$^{2d}$C(O)R$^{2e}$, (CR$^3$R$^{3g}$)$_r$—C(O)R$^{2e}$, (CR$^3$R$^{3g}$)$_r$—NR$^{2d}$C(O)NR$^{2d}$R$^{2d}$, (CR$^3$R$^{3g}$)$_r$—NR$^{2d}$C(O)OR$^{2d}$, (CR$^3$R$^{3g}$)$_r$—NR$^{2d}$SO$_2$R$^{2d}$, and (CR$^3$R$^{3g}$)$_r$—S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)—C$_{1-4}$ alkyl, S(O)$_p$-phenyl, and CF$_3$;

R$^{4c}$, at each occurrence, is selected from =O, OR$^2$, CH$_2$OR$^2$, F, Br, Cl, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-3}$ alkenyl, C$_{2-3}$ alkynyl, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0-2 R$^{4b}$, (CH$_2$)C$_{3-6}$ carbocycle substituted with 0-2 R$^{4b}$, 5-6 membered heterocycle consisting of carbon atoms and from 1-4 heteroatoms selected from the group consisting of N, O, and $S(O)_p$ and substituted with 0-2 $R^{4b}$, and $(CH_2)$-5-6 membered heterocycle consisting of carbon atoms and from 1-4 heteroatoms selected from the group consisting of N, O, and $S(O)_p$ and substituted with 0-2 $R^{4b}$;

$R^{4d}$, at each occurrence, is selected from H, $CH_2OR^2$, $OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2NR^2R^{2a}$, $NR^2R^{2a}$, $C(O)R^{2c}$, $NR^2C(O)R^{2b}$, $C(O)NR^2R^{2a}$, $SO_2NR^2R^{2a}$, $NR^2SO_2R^5$, phenyl substituted with 0-1 $R^5$, and a 5-6 membered heterocycle consisting of: carbon atoms and 1 heteroatom selected from the group consisting of N, O, and $S(O)_p$ and substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR_3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In a fifth embodiment, the present invention provides a novel compound or a stereoisomer or pharmaceutically acceptable salt, solvate, or prodrug form thereof, within the scope of the fourth embodiment, wherein:

A is selected from the group: cyclohexyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from Y, $N(B^1)C(O)C(R^3R^{3g})NB^2B^3$,

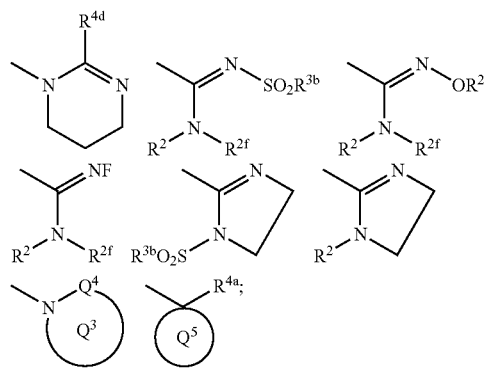

provided that Z and B are attached to different atoms on A and that the $R^{4d}$ shown is other than OH;

$B^1$ is selected from H, $CH_3$, $CH_2CH_3$, and $CH_2CH_2CH_3$;
$B^2$ is selected from H, $CH_3$, and $CH_2CH_3$;
$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, cyclohexyl, and $CH_2$-cyclopropyl;

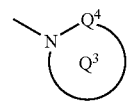

is attached to a different atom on A than M and is selected from the group:

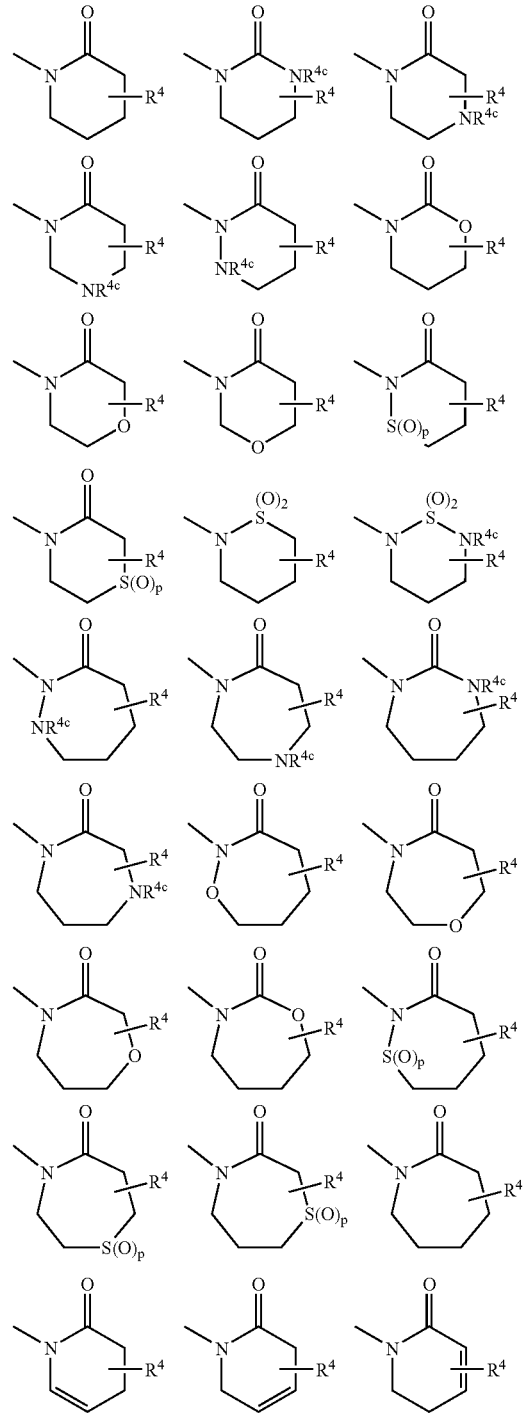

-continued

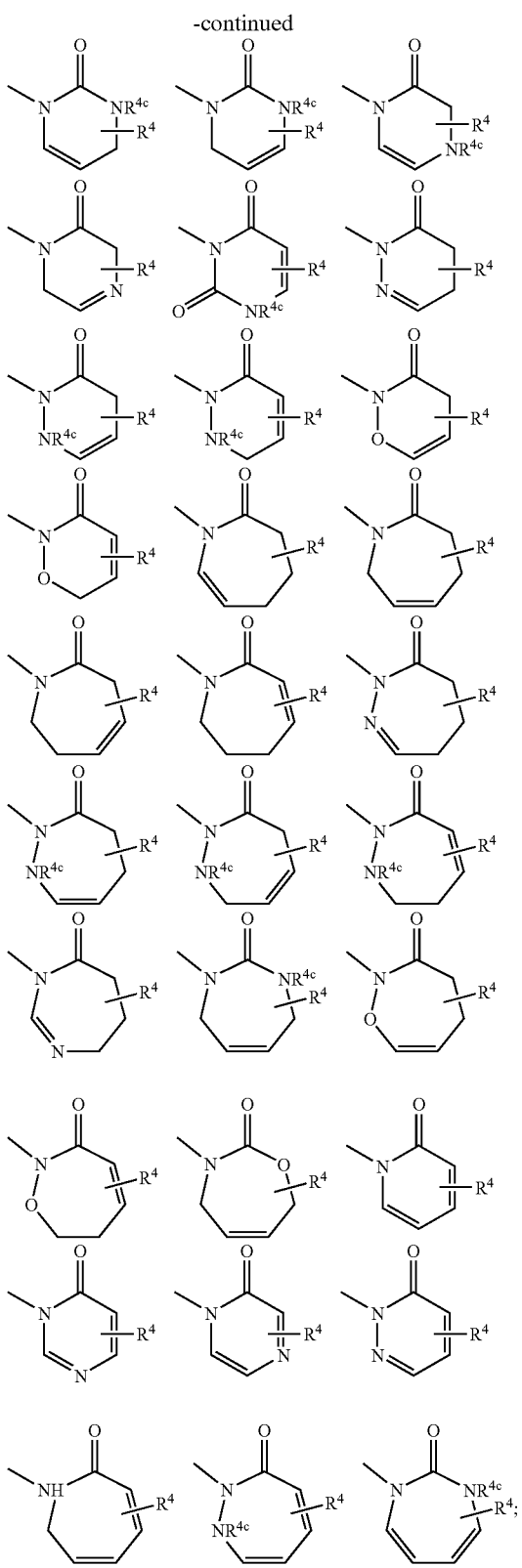

ring Q⁵ is selected from cyclopropyl, cyclobutyl, cyclopentyl, 2-cyclopentanonyl, cyclohexyl, 2-cyclohexanonyl, pyrrolidinyl (attached to A and R⁴ᵃ at the 2-position), pyrrolidinyl (attached to A and R⁴ᵃ at the 3-position), 2-pyrrolidinonyl (attached to A and R⁴ᵃ at the 3-position), piperidinyl (attached to A and R⁴ᵃ at the 4-position), 4-piperdinonyl (attached to A and R⁴ᵃ at the 3-position), tetrahydrofuranyl, and tetrahydropyranyl (attached to A and R⁴ᵃ at the 4-position);

Y is selected from $N(CH_3)_2$, $C(O)(CH_3)_2$, $C(CH_3)_2R^{4a}$ and $C(CH_2CH_3)_2R^{4a}$;

alternatively, Y is selected from phenyl, pyridyl, 1,2,3-triazolyl, imidazolyl, and benzimidazolyl, and is substituted with 1 R⁴ᵃ;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0-2 $R^{4c}$, $C_{3-6}$ cycloalkyl substituted with 0-2 $R^{4c}$, phenyl substituted with 0-2 $R^{4c}$, and 5-6 membered aromatic heterocycle substituted with 0-2 $R^{4c}$ and consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0-2 $R^{4c}$, $C_{3-6}$ cycloalkyl substituted with 0-2 $R^{4c}$, phenyl substituted with 0-2 $R^{4c}$, and 5-6 membered aromatic heterocycle substituted with 0-2 $R^{4c}$ and consisting of: carbon atoms and 1-4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, and $OCH_3$;

alternatively, $NR^2R^{2f}$ forms a ring selected from morpholine, piperazine, piperidine, and pyrrolidine;

R⁴, at each occurrence, is selected from H, =O, CH₃, CH₂CH₃, CH₂CH₂CH₃, CH(CH₃)₂, CH₂CH₂CH₂CH₃, CH₂CH(CH₃)₂, CH(CH₃)CH₂CH₃, and C(CH₃)₃;

R⁴ᵃ is selected from —(CH₂)ᵣ-5-6 membered carbocycle substituted with 0-3 R⁴ᶜ, —(CH₂)ᵣ-5-6 membered heterocycle substituted with 0-3 R⁴ᶜ and consisting of: carbon atoms and 1-4 heteroatoms selected from the group consisting of N, O, and S(O)ₚ, (CH₂)ᵣNR²ᵈR²ᵈ, (CH₂)ᵣN(→O)R²ᵈR²ᵈ, (CH₂)ᵣOR²ᵈ, (CH₂)ᵣ—C(O)NR²ᵈR²ᵈ, (CH₂)ᵣ—NR²ᵈC(O)R²ᵉ, (CH₂)ᵣ—C(O)R²ᵉ, (CH₂)ᵣ—NR²ᵈC(O)NR²ᵈR²ᵈ, (CH₂)ᵣ—NR²ᵈC(O)OR²ᵈ, (CH₂)ᵣ—NR²ᵈSO₂R²ᵈ, and (CH₂)ᵣ—S(O)ₚR²ᵈ, provided that S(O)ₚR²ᵈ forms other than S(O)₂H or S(O)H;

R⁴ᵇ, at each occurrence, is selected from H, =O, OR³, CH₂OR³, F, Cl, CH₃, CH₂CH₃, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂-phenyl, S(O)₂CH₃, S(O)₂-phenyl, and CF₃;

R⁴ᶜ, at each occurrence, is selected from =O, OH, OCH₃, OCH₂CH₃, OCH₂CH₂CH₃, OCH(CH₃)₂, CH₃, CH₂CH₃, CH₂CH₂CH₃, CH(CH₃)₂, C₂₋₃ alkenyl, C₂₋₃ alkynyl, CH₂OH, CH₂OCH₃, CH₂OCH₂CH₃, CH₂OCH₂CH₂CH₃, CH₂OCH(CH₃)₂, F, Br, Cl, CF₃, NR²R²ᵃ, CH₂NR²R²ᵃ, N(→O)R²R²ᵃ, CH₂N(→O)R²R²ᵃ, C(O)R²ᶜ, CH₂C(O)R²ᶜ, NR²C(O)R²ᵇ, CH₂NR²C(O)R²ᵇ, C(O)NR²R²ᵃ, CH₂C(O)NR²R²ᵃ, SO₂NR²R²ᵃ, CH₂SO₂NR²R²ᵃ, NR²SO₂R⁵ᵃ, CH₂NR²SO₂R⁵ᵃ, S(O)ₚR⁵ᵃ, CH₂S(O)ₚR⁵ᵃ, CF₃, cyclopropyl substituted with 0-1 R⁴ᵇ, cyclobutyl substituted with 0-1 R⁴ᵇ, cyclopentyl substituted with 0-1 R⁴ᵇ, phenyl substituted with 0-1 R⁴ᵇ, —CH₂-cyclopropyl substituted with 0-1 R⁴ᵇ, —CH₂-cyclobutyl substituted with 0-1 R⁴ᵇ, —CH₂-cyclopentyl substituted with 0-1 R⁴ᵇ, benzyl substituted with 0-2 R⁴ᵇ, 5-6 membered aromatic heterocycle consisting of carbon atoms and from 1-4 heteroatoms selected from the group consisting of N, O, and S(O)ₚ and substituted with 0-2 R⁴ᵇ, and (CH₂)-5-6 membered aromatic heterocycle consisting of carbon atoms and from 1-4 heteroatoms selected from the group consisting of N, O, and S(O)ₚ and substituted with 0-2 R⁴ᵇ;

R⁴ᵈ, at each occurrence, is selected from H, OCH₃, CH₃, CH₂CH₃, CH₂CH₂CH₃, CH(CH₃)₂, NR²R²ᵃ, NR²C(O)R²ᵇ, NR²SO₂R⁵, phenyl, 2-oxo-pyrrolidinyl, and 2-oxo-piperidinyl;

R⁵, at each occurrence, is selected from H, =O, CH₃, CH₂CH₃, OR³, CH₂OR³, F, Cl, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)₂—CH₃, S(O)₂-phenyl, CF₃, phenyl substituted with 0-2 R⁶, naphthyl substituted with 0-2 R⁶, and benzyl substituted with 0-2 R⁶; and R⁶, at each occurrence, is selected from H, OH, OR², F, Cl, CH₃, CH₂CH₃, NR²R²ᵃ, CH₂NR²R²ᵃ, C(O)R²ᵇ, CH₂C(O)R²ᵇ, NR²C(O)R²ᵇ, and SO₂NR²R²ᵃ.

In a sixth embodiment, the present invention provides a novel compound or a stereoisomer or pharmaceutically acceptable salt, solvate, or prodrug form thereof, within the scope of the fourth embodiment, wherein:

A is selected from the group: phenyl, 2-pyridyl, 2-pyrimidyl, and 2-F-phenyl, wherein B is substituted at the 4-position of A;

B is selected from:

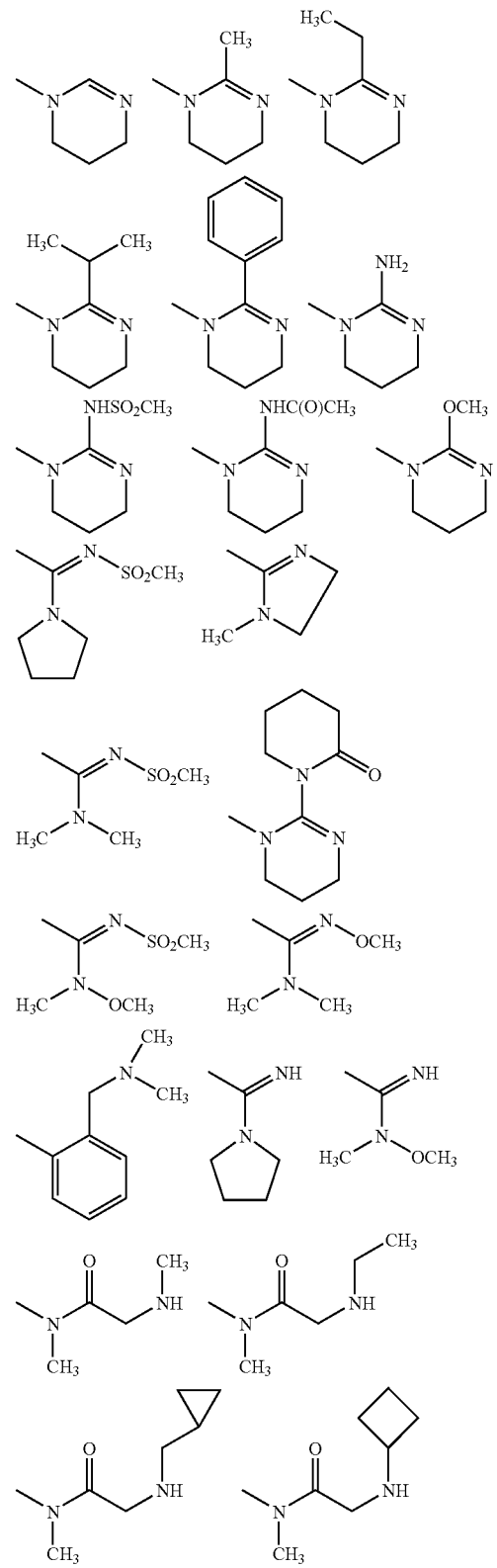

-continued

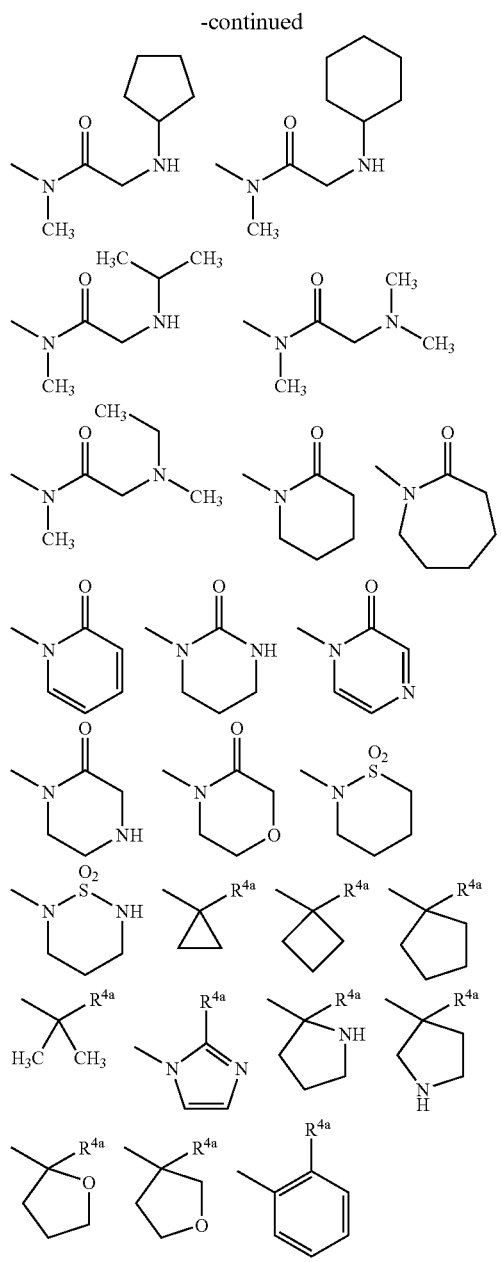

R$^{2d}$, at each occurrence, is selected from H, C$_{1-4}$ alkyl substituted with 0-1 R$^{4c}$, C$_{3-6}$ cycloalkyl substituted with 0-2 R$^{4c}$, phenyl substituted with 0-2 R$^{4c}$, and a 5-6 membered aromatic heterocycle consisting of: carbon atoms and 1-4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, C$_{1-4}$ alkyl substituted with 0-1 R$^{4c}$, C$_{3-6}$ cycloalkyl substituted with 0-2 R$^{4c}$, phenyl, substituted with 0-2 R$^{4c}$, and 5-6 membered aromatic heterocycle consisting of: carbon atoms and 1-4 heteroatoms selected from the group consisting of N, O, and S(O)$_p$, provided that R$^{2e}$ forms other than a C(O)-halo or C(O)—S(O)$_p$ moiety;

R$^{4a}$ is selected from NR$^{2d}$R$^{2d}$, CH$_2$NR$^{2d}$R$^{2d}$, CH$_2$CH$_2$NR$^{2d}$R$^{2d}$, N(→O)R$^{2d}$R$^{2d}$, CH$_2$N(→O) R$^{2d}$R$^{2d}$, CH$_2$OR$^{2d}$, C(O)R$^{2e}$, C(O)NR$^{2d}$R$^{2d}$, CH$_2$C(O) NR$^{2d}$R$^{2d}$, NR$^{2d}$C(O)R$^{2e}$, CH$_2$NR$^{2d}$C(O)R$^{2e}$, NR$^{2d}$C (O)NR$^{2d}$R$^{2d}$, CH$_2$NR$^{2d}$C(O)NR$^{2d}$R$^{2d}$, NR$^{2d}$C(O) OR$^{2d}$, CH$_2$NR$^{2d}$C(O)OR$^{2d}$, NR$^{2d}$SO$_2$R$^{2d}$, CH$_2$NR$^{2d}$SO$_2$R$^{2d}$, S(O)$_p$R$^{2d}$, CH$_2$S(O)$_p$R$^{2d}$, 5-6 membered carbocycle substituted with 0-2 R$^{4c}$, —(CH$_2$)-5-6 membered carbocycle substituted with 0-2 R$^{4c}$, 5-6 membered heterocycle substituted with 0-2 R$^{4c}$ and consisting of: carbon atoms and 1-4 heteroatoms selected from the group consisting of N, O, and S(O)$_p$, and —(CH$_2$)-5-6 membered heterocycle substituted with 0-2 R$^{4c}$ and consisting of: carbon atoms and 1-4 heteroatoms selected from the group consisting of N, O, and S(O)$_p$ provided that S(O)$_p$R$^{2d}$ forms other than S(O)$_2$H or S(O)H; and R$^{4c}$ is selected from =O, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, CH=CH$_2$, CH≡CH, CH$_2$OH, CH$_2$OCH$_3$, CH$_2$OCH$_2$CH$_3$, CH$_2$OCH$_2$CH$_2$CH$_3$, CH$_2$OCH(CH$_3$)$_2$, F, Br, Cl, CF$_3$, NR$^2$R$^{2a}$, CH$_2$NR$^2$R$^{2a}$, C(O)R$^{2c}$, CH$_2$C(O)R$^{2c}$, NR$^2$C (O)R$^{2b}$, CH$_2$NR$^2$C(O)R$^{2b}$, C(O)NR$^2$R$^{2a}$, CH$_2$C(O) NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, and CH$_2$S(O)$_p$R$^{5a}$.

In a seventh embodiment, the present invention provides a novel compound of

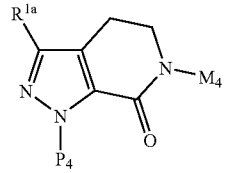

or a stereoisomer or pharmaceutically acceptable salt, solvate, or prodrug form thereof, wherein:

P$_4$ is -G;

M$_4$ is -A-B;

A-B is selected from:

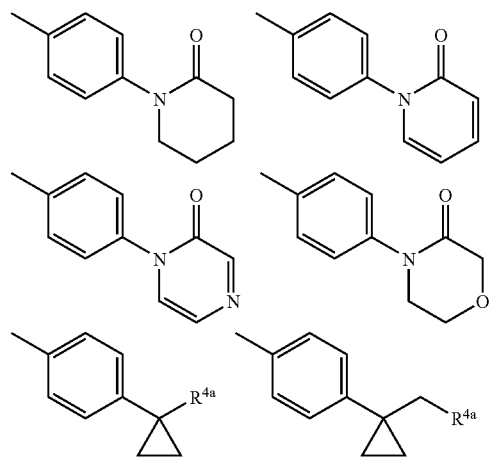

-continued
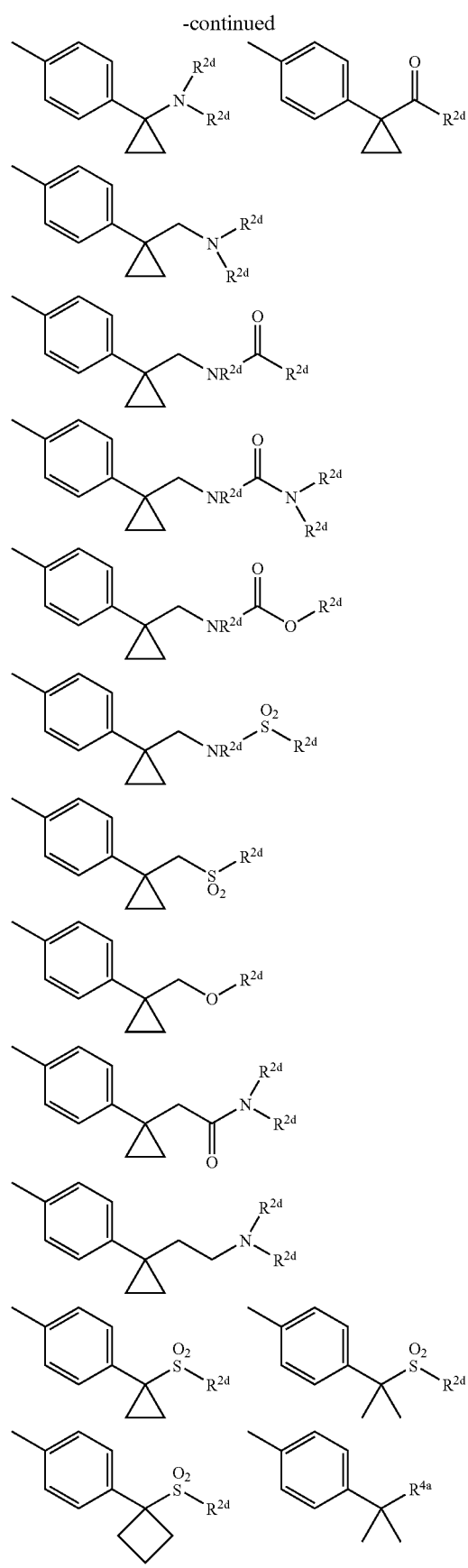
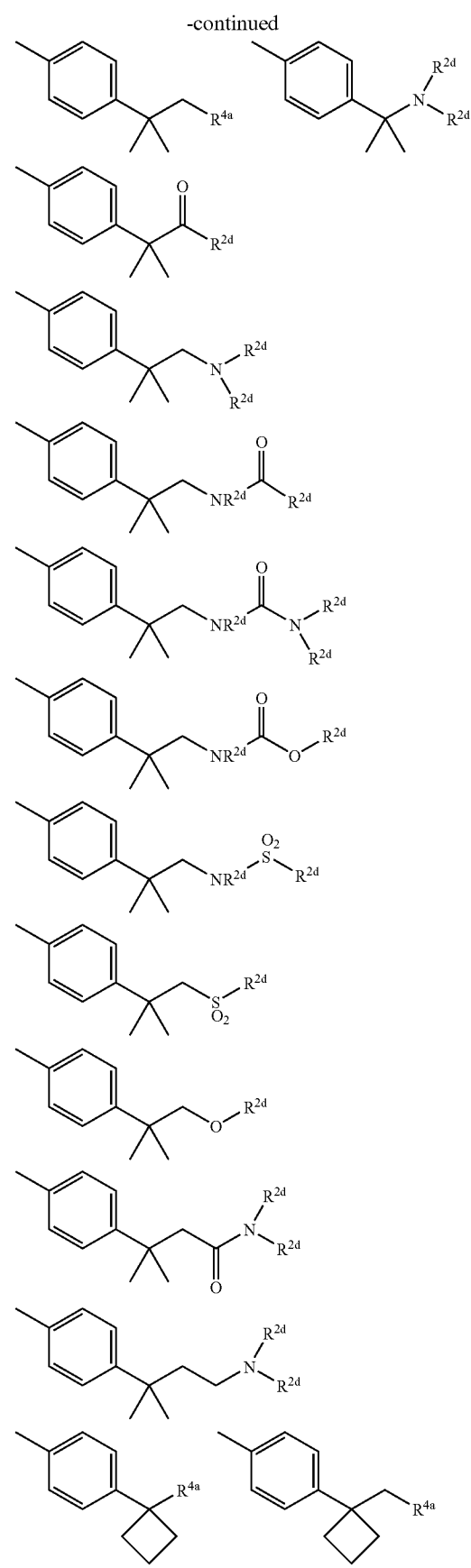

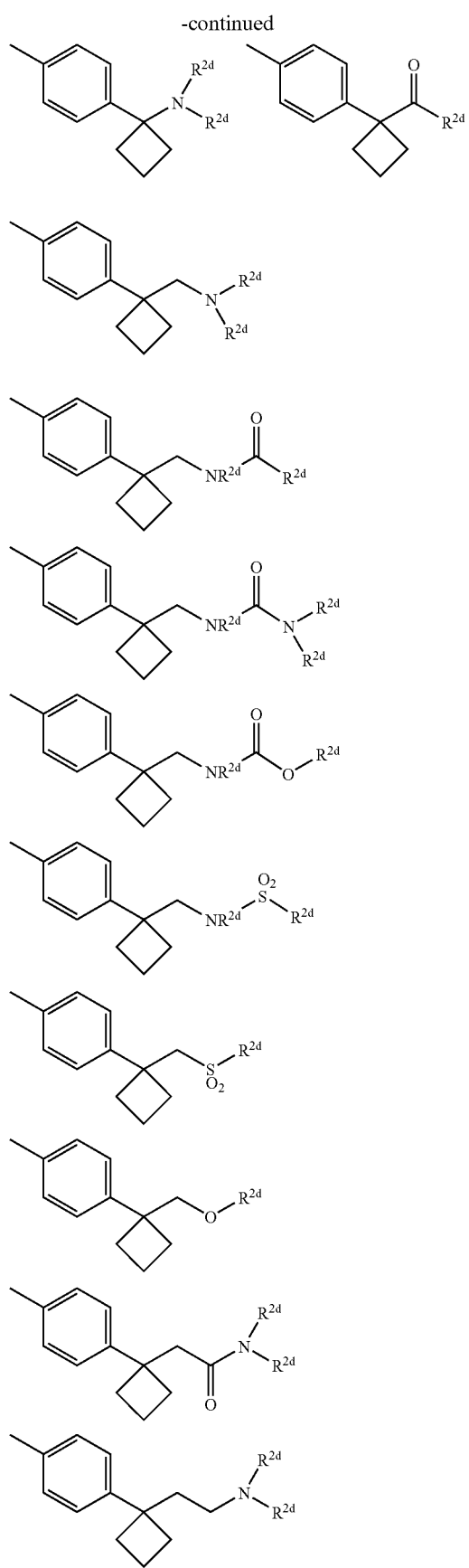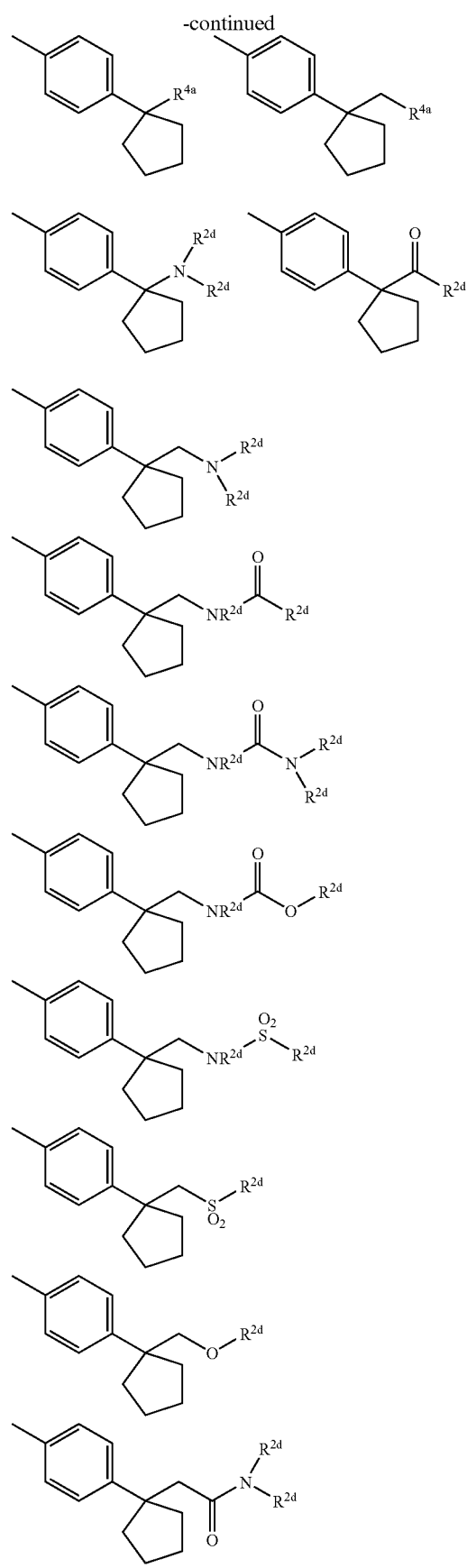

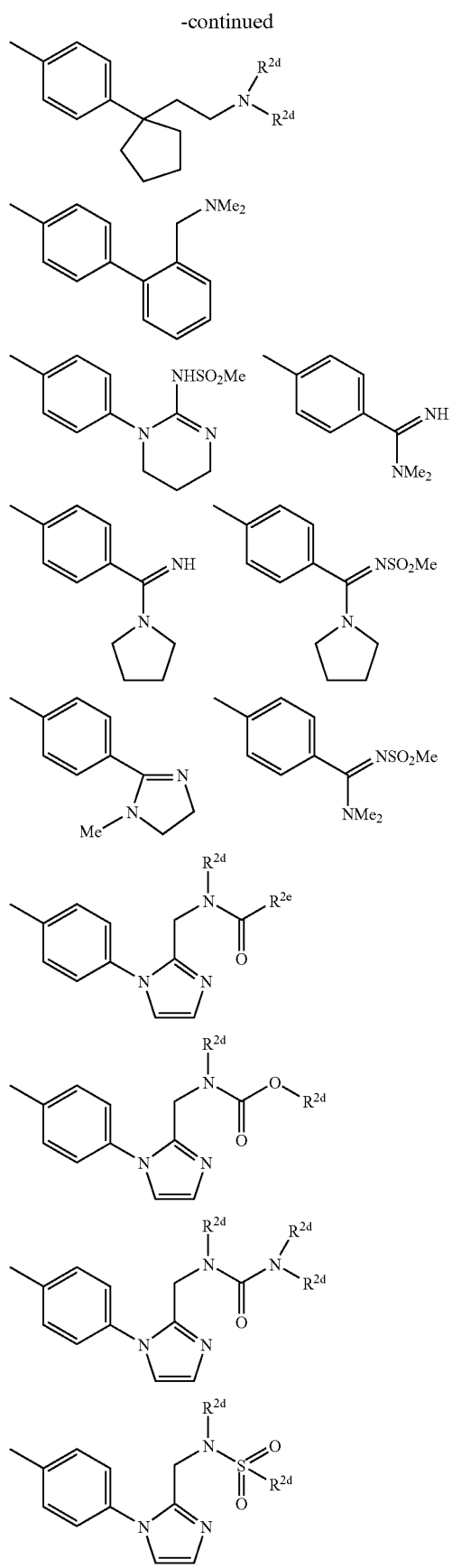
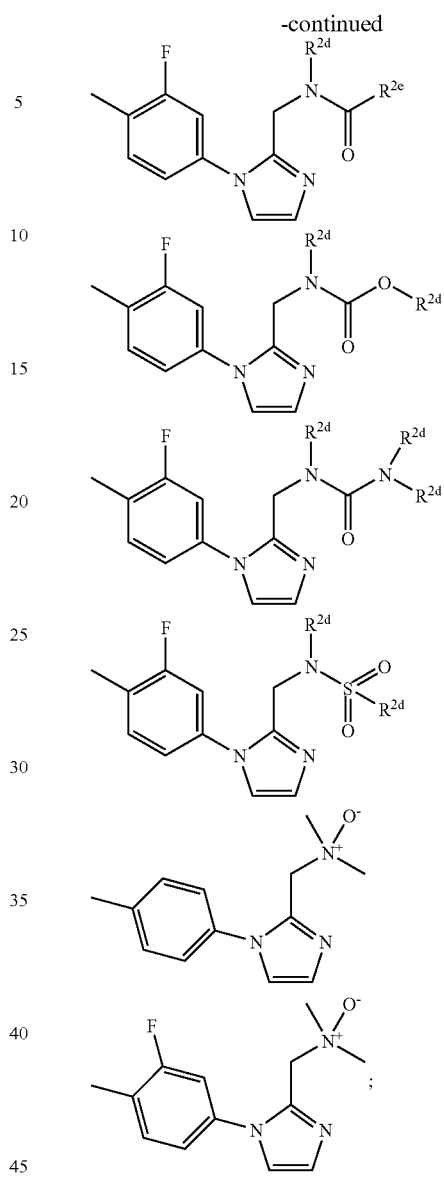

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$CCH, CH$_2$CH$_2$OH, CH$_2$C(O)NH$_2$, cyclopropyl, CH$_2$-cyclopropyl, cyclobutyl, cyclopentyl, and thiazolyl;

$R^{2e}$, at each occurrence, is selected from CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl;

$R^{4a}$ is substituted with 0-2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and $R^{4c}$ is selected from =O, OH, OCH$_3$, and CH$_3$.

In an eighth embodiment, the present invention provides a novel compound or a stereoisomer or pharmaceutically acceptable salt, solvate, or prodrug form thereof, wherein the compound is selected from the group: Examples 3-30, 32-33, 37-44, 61, 109-118, 135-146, 148-151, 154-165, 168-192, 195-199, 204-205, 207-213, 215, 217, 219-232, 235-237, 240-241, and, 244-255.

In a ninth embodiment, the present invention provides a novel compound, wherein the compound is of Formula IIIa, IIIb, or IIIc:

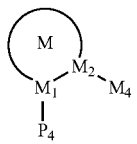

IIIa

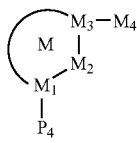

IIIb

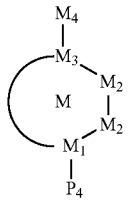

IIIc or a stereoisomer or pharmaceutically acceptable salt, solvate, or prodrug form thereof, wherein;

ring M, including $M_1$, $M_2$, and, if present, $M_3$, is phenyl or a 3-10 membered carbocyclic or 4-10 membered heterocyclic ring consisting of: carbon atoms and 1-4 heteroatoms selected from O, $S(O)_p$, N, and $NZ^2$;

ring M is substituted with 0-3 $R^{1a}$ and 0-2 carbonyl groups, and there are 0-3 ring double bonds;

one of $P_4$ and $M_4$ is -Z-A-B and the other -$G_1$-G;

G is a group of Formula IIa or IIb:

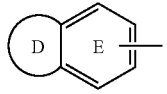

IIa

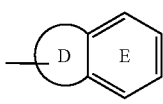

IIb in formula IIa, ring E is substituted with 1-2 $R^a$, provided that at least one $R^a$ is ortho to the point of attachment of ring E;

in formula IIb, ring D is substituted with 1-2 $R^a$, provided that at least one $R^a$ is ortho to the point of attachment of ring D;

ring D, including the two atoms of Ring E to which it is attached, is a 5-6 membered ring consisting of: carbon atoms and 0-2 heteroatoms selected from the group consisting of N, O, and $S(O)_p$;

ring D is substituted with 0-2 R and there are 0-3 ring double bonds;

E is selected from phenyl, pyridyl, pyrimidyl, pyrazinyl, and pyridazinyl, and is substituted with 0-2 R;

alternatively, ring D is absent, and ring E is selected from phenyl, pyridyl, pyrimidyl, and thienyl, and ring E is substituted with 0-2 R;

alternatively, ring D is absent, ring E is selected from phenyl, pyridyl, and thienyl, and ring E is substituted with 0-2 R and a 5-6 membered heterocycle consisting of: carbon atoms and 1-4 heteroatoms selected from the group consisting of N, O, and $S(O)_p$, wherein the 5-6 membered heterocycle is substituted with 0-2 carbonyl and 1-2 R and there are 0-3 ring double bonds;

R is selected from H, $C_{1-4}$ alkyl, F, Cl, OH, $OCH_3$, $OCH_2CH_3$, $OCH(CH_3)_2$, CN, C(=NH)NH$_2$, C(=NH)NHOH, C(=NH)NHOCH$_3$, NH$_2$, NH($C_{1-3}$ alkyl), N($C_{1-3}$ alkyl)$_2$, C(=NH)NH$_2$, CH$_2$NH$_2$, CH$_2$NH($C_{1-3}$ alkyl), CH$_2$N($C_{1-3}$ alkyl)$_2$, $(CR^8R^9)_rNR^7R^8$, C(O)NR$^7$R$^8$, CH$_2$C(O)NR$^7$R$^8$, $S(O)_p$NR$^7$R$^8$, CH$_2$S(O)$_p$NR$^7$R$^8$, SO$_2$R$^3$, and OCF$_3$;

alternatively, when 2 R groups are attached to adjacent atoms, they combine to form methylenedioxy or ethylenedioxy;

$R^a$ is $(CR^8R^9)_{0-1}R^b(CR^8R^{2b})_{0-4}R^b_{0-1}(CR^8R^9)_{0-1}R^c$;

$R^b$ is selected from O, C(O), C(O)NR$^3$, C(O)N((CH$_2$)$_{2-3}$R$^3$), S(O), S(O)$_2$, S(O)$_2$NR$^3$, NR$^3$, NR$^3$C(O), and NR$^3$S(O)$_2$;

$R^c$ is selected from H, OR$^3$, NR$^3$C(O)R$^3$, C(O)R$^3$, CO$_2$R$^3$, C(O)NR$^3$R$^{3a}$, S(O)$_2$NR$^3$R$^{3a}$, —CN, $C_{3-10}$ carbocycle substituted with 0-2 R$^4$, and 5-12 membered heterocycle substituted with 0-2 R$^4$ and consisting of: carbon atoms and 1-4 heteroatoms selected from the group consisting of N, O, and $S(O)_p$;

$R^c$ is selected from H, OR$^3$, NR$^3$C(O)R$^3$, C(O)R$^3$, CO$_2$R$^3$, C(O)NR$^3$R$^{3a}$, S(O)$_2$NR$^3$R$^{3a}$, $C_{5-10}$ carbocycle substituted with 0-2 R$^4$, and 5-10 membered heterocycle substituted with 0-2 R$^4$ and consisting of: carbon atoms and 1-4 heteroatoms selected from the group consisting of N, O, and $S(O)_p$;

provided that when the $(CR^8R^{2b})_{0-4}R^b_{0-1}(CR^8R^9)_{0-1}$ portion of $R^a$ is absent, then $R^c$ is selected from NR$^3$C(O)R$^3$, S(O)$_2$NR$^3$R$^{3a}$, $C_{5-10}$ carbocycle substituted with 0-2 R$^4$, and 5-10 membered heterocycle substituted with 0-2 R$^4$ and consisting of: carbon atoms and 1-4 heteroatoms selected from the group consisting of N, O, and $S(O)_p$;

further provided that when the $R^a$ is C(O)—NR*R* and NR*R* is a heterocyclic ring, then the heterocyclic ring is substituted with 1-2 R$^4$;

further provided that the $(CR^8R^{2b})_{0-4}R^b_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

A is selected from: $C_{5-10}$ carbocycle substituted with 0-2 R$^4$, and 5-10 membered heterocycle consisting of: carbon atoms and 1-4 heteroatoms selected from the group consisting of N, O, and $S(O)_p$ and substituted with 0-2 R$^4$;

B is selected from Y, X—Y, N(B$^1$)C(O)C(R$^3$R$^{3g}$)NB$^2$B$^3$, N(B$^1$)C(O)C(R$^3$R$^{3g}$)C(R$^3$R$^{3g}$)NB$^2$B$^3$,

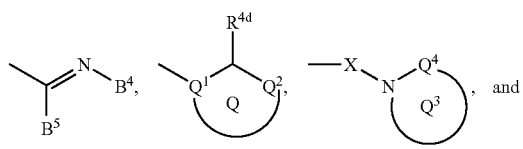

and

-continued

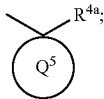

provided that Z and B are attached to different atoms on A, the $R^{4d}$ shown is other than OH, and that the A-X—N moiety forms other than a N—N—N group;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0-2 $R^{4b}$, and —$(CH_2)_{0-1}$-5-6 membered heterocycle consisting of: carbon atoms and 1-4 heteroatoms selected from the group consisting of N, O, and $S(O)_p$ and substituted with 0-2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0-1 $R^{4c}$, —$(CH_2)_{0-1}$-3-6 membered carbocycle substituted with 0-1 $R^5$, and a —$(CH_2)_{0-1}$-5-6 membered heterocycle consisting of: carbon atoms and 1-4 heteroatoms selected from the group consisting of N, O, and $S(O)_p$ and substituted with 0-1 $R^5$;

$B^4$ is selected from H, $SO_2R^{3b}$, $C(O)R^{3b}$, $SO_2NR^3R^{3b}$, $C(O)NR^3R^{3b}$, $OR^2$, and —CN;

$B^5$ is $NR^2R^{2f}$ or $CR^3R^2R^{2f}$;

ring Q is a 5-6 membered ring consisting of, in addition to the $Q^1$-$CR^{4d}$=$Q^2$ group shown, carbon atoms and 0-2 heteroatoms selected from N, O, and $S(O)_p$; and the ring is substituted with an additional 0-2 $R^{4d}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5-6 membered ring consisting of, in addition to the C—C—N shown, carbon atoms and from 0-1 additional heteroatoms selected from N, O, and $S(O)_p$, and this ring is substituted with 0-1 $R^5$;

$Q^4$ is selected from C=O and $SO_2$;

ring $Q^3$ is a 4-7 membered monocyclic or tricyclic ring consisting of, in addition to the N-$Q^4$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^4$;

alternatively, ring $Q^3$ is a 4-7 membered ring to which another ring is fused, wherein: the 4-7 membered ring consists of, in addition to the shown amide group, carbon atoms and 0-2 heteroatoms selected from $NR^{4c}$, O, S, S(O), and $S(O)_2$ and 0-1 double bonds are present within the ring; the fusion ring is phenyl or a 5-6 membered heteroaromatic consisting of carbon atoms and 1-2 heteroatoms selected from $NR^{4c}$, O, and S;

ring $Q^3$, which includes the 4-7 membered ring and the fusion ring, is substituted with 0-3 $R^4$;

ring $Q^5$ is a $C_{3-7}$ monocyclic carbocycle or 3-7 membered monocyclic heterocycle, wherein the carbocycle or heterocycle consists of: carbon atoms and 0-2 heteroatoms selected from N, O, and $S(O)_p$, the carbocycle or heterocycle further comprises 0-2 double bonds and 0-2 carbonyl groups, and the carbocycle or heterocycle is substituted with 0-2 $R^4$;

X is selected from —$(CR^2R^{2a})_{1-4}$—, —C(O)—, C(=$NR^{1c}$)—, —$CR^2(NR^{1b}R^2)$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, —$S(O)_2$—, —$NR^2S(O)_2$—, O, —$CR^2R^{2a}O$—, and —$OCR^2R^{2a}$—;

Y is selected from: $CY^1Y^2R^{4a}$, $NR^3R^{3a}$, and $C(O)NR^3R^{3a}$;

$Y^1$ and $Y^2$ are independently $C_{1-3}$ alkyl substituted with 0-2 $R^4$;

alternatively, Y is selected from one of the following carbocyclic and heterocycles that are substituted with 1 $R^{4a}$ and 0-2 $R^4$: cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

Z is selected from a bond, $CH_2$, $CH_2CH_2$, $CH_2O$, $OCH_2$, C(O), NH, $CH_2NH$, $NHCH_2$, $CH_2C(O)$, $C(O)CH_2$, C(O)NH, NHC(O), $NHC(O)CH_2C(O)NH$, $S(O)_2$, $CH_2S(O)_2$, $S(O)_2(CH_2)$, $SO_2NH$, and $NHSO_2$, wherein the right side of Z is attached to ring A, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0-2 $R^{4b}$, and 5-6 membered heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0-2 $R^{4b}$, $C_{5-6}$ carbocycle substituted with 0-2 $R^{4b}$, a $C_{5-6}$ carbocyclic-$CH_2$-group substituted with 0-2 $R^{4b}$, and 5-6 membered heterocycle consisting of: carbon atoms and 1-4 heteroatoms selected from the group consisting of N, O, and S(O)$_p$, and substituted with 0-2 R$^{4b}$;

R$^{2a}$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0-2 R$^{4b}$, C$_{5-6}$ carbocycle substituted with 0-2 R$^{4b}$, and 5-6 membered heterocycle consisting of: carbon atoms and 1-4 heteroatoms selected from the group consisting of N, O, and S(O)$_p$, and substituted with 0-2 R$^{4b}$;

alternatively, NR$^2$R$^{2a}$ forms a 5 or 6 membered saturated, partially saturated or unsaturated ring substituted with 0-2 R$^{4b}$ and consisting of: 0-1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0-2 R$^{4b}$, C$_{5-6}$ carbocycle substituted with 0-2 R$^{4b}$, and 5-6 membered heterocycle consisting of: carbon atoms and 1-4 heteroatoms selected from the group consisting of N, O, and S(O)$_p$, and substituted with 0-2 R$^{4b}$;

R$^{2c}$, at each occurrence, is selected from CF$_3$, OH, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0-2 R$^{4b}$, C$_{5-6}$ carbocycle substituted with 0-2 R$^{4b}$, and 5-6 membered heterocycle containing from 1-4 heteroatoms selected from the group consisting of N, O, and S(O)$_p$, and substituted with 0-2 R$^{4b}$;

R$^{2d}$, at each occurrence, is selected from H, R$^{4c}$, C$_{1-4}$ alkyl substituted with 0-2 R$^{4c}$, —(CR$^3$R$^{3a}$)$_r$—C$_{3-6}$ carbocycle substituted with 0-2 R$^{4c}$, and —(CR$^3$R$^{3a}$)$_r$-5-6 membered heterocycle substituted with 0-2 R$^{4c}$ and consisting of: carbon atoms and 1-4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

alternatively, NR$^{2d}$R$^{2d}$ forms a 5 or 6 membered saturated, partially saturated or unsaturated ring substituted with 0-2 R$^{4b}$ and consisting of: 0-1 additional heteroatoms selected from the group consisting of N, O, and S(O)$_p$;

R$^{2e}$, at each occurrence, is selected from H, R$^{4c}$, C$_{1-4}$ alkyl substituted with 0-2 R$^{4c}$, —(CR$^3$R$^{3a}$)$_r$—C$_{3-6}$ carbocycle substituted with 0-2 R$^{4c}$, and —(CR$^3$R$^{3a}$)$_r$-5-6 membered heterocycle substituted with 0-2 R$^{4c}$ and consisting of: carbon atoms and 1-4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CF$_3$, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0-1 R$^{4b}$, C$_{5-6}$ carbocycle substituted with 0-2 R$^{4b}$, and 5-6 membered heterocycle containing from 1-4 heteroatoms selected from the group consisting of N, O, and S(O)$_p$ and substituted with 0-2 R$^{4b}$;

alternatively, CR$^2$R$^{2f}$ forms a 5-6 membered ring consisting of: carbon atoms and 0-2 heteroatoms selected from N, O, and S(O)$_p$, and this ring is substituted with 0-2 R$^{4b}$;

alternatively, NR$^2$R$^{2f}$ forms a 5-6 membered ring consisting of: carbon atoms and 0-2 additional heteroatoms selected from N, O, and S(O)$_p$, and this ring is substituted with 0-2 R$^{4b}$;

alternatively, when B$^5$ is NR$^2$R$^{2f}$, B$^4$ and R$^{2f}$ combine to form a 5-6 membered ring consisting of: carbon atoms and 0-2 additional heteroatoms selected from N, O, and S(O)$_p$, and this ring is substituted with 0-2 R$^{4b}$ and the R$^2$ group of NR$^2$R$^{2f}$, in addition to the groups recited below, is selected from SO$_2$R$^{3b}$ and C(O)R$^{3b}$;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms and the nitrogen atom to which R$^3$ and R$^{3a}$ are attached;

R$^{3b}$, at each occurrence, is selected from H, CF$_3$, CH$_3$, CH$_2$CH$_3$, CH$_2$CH$_2$CH$_3$, CH(CH$_3$)$_2$, —(C$_{0-1}$ alkyl)-5-6 membered carbocycle substituted with 0-1 R$^{1a}$, and —(C$_{0-1}$ alkyl)-5-6 membered heterocycle substituted with 0-1 R$^{1a}$ and consisting of: carbon atoms and 1-4 heteroatoms selected from the group consisting of N, O, and S(O)$_p$;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^4$, at each occurrence, is selected from =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, SO$_2$NR$^2$R$^{2a}$, NR$^2$SO$_2$NR$^2$R$^{2a}$, S(O)$_p$R$^{5a}$, NR$_2$SO$_2$—C$_{1-4}$ alkyl, NR$^2$SO$_2$R$^5$, CF$_3$, CF$_2$CF$_3$, 5-6 membered carbocycle substituted with 0-1 R$^5$, and a 5-6 membered heterocycle consisting of: carbon atoms and 1-4 heteroatoms selected from the group consisting of N, O, and S(O)$_p$, and substituted with 0-1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$_3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$—CF$_3$;

R$^{4c}$, at each occurrence, is selected from =O, (CR$^3$R$^{3a}$)$_r$OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, C$_{2-3}$ alkenyl, C$_{2-3}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$R$^{5a}$, (CR$^3$R$^{3a}$)$_r$C(O)NR$^2$SO$_2$R$^{5a}$, (CR$^3$R$^{3a}$)$_r$S(O)$_p$R$^{5a}$, (CF$_2$)$_r$CF$_3$, (CR$^3$R$^{3a}$)$_r$C$_{3-10}$ carbocycle substituted with 0-2 R$^{4b}$, and (CR$^3$R$^{3a}$)$_r$5-10 membered heterocycle consisting of carbon atoms and from 1-4 heteroatoms selected from the group consisting of N, O, and S(O)$_p$ and substituted with 0-2 R$^{4b}$;

R$^{4d}$, at each occurrence, is selected from H, CH$_2$OR$^2$, OR$^2$, C$_{1-4}$ alkyl, CH$_2$—CN, —CN, CH$_2$NO$_2$, NO$_2$, CH$_2$NR$^2$R$^{2a}$, NR$^2$R$^{2a}$, CH$_2$—C(O)R$^{2c}$, C(O)R$^{2c}$, NR$^2$C(O)R$^{2b}$, (CH$_2$)$_r$C(O)NR$^2$R$^{2a}$, NR$^2$C(O)NR$^2$R$^{2a}$, (CH$_2$)$_r$SO$_2$NR$^2$R$^{2a}$, NR$^2$SO$_2$NR$^2$R$^{2a}$, NR$^2$SO$_2$R$^5$, (CH$_2$)$_r$S(O)$_p$R$^{5a}$, CH$_2$CF$_3$, CF$_3$, CH$_2$-5-6 membered carbocycle substituted with 0-1 R$^5$, 5-6 membered carbocycle substituted with 0-1 R$^5$, a CH$_2$-5-6 membered heterocycle consisting of: carbon atoms and 1-4 heteroatoms selected from the group consisting of N, O, and S(O)$_p$ and substituted with 0-1 R$^5$, and a 5-6 membered heterocycle consisting of: carbon atoms and 1-4 heteroatoms selected from the group consisting of N, O, and S(O)$_p$ and substituted with 0-1 R$^5$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$_3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0-2 R$^6$, naphthyl substituted with 0-2 R$^6$, and benzyl substituted with 0-2 R$^6$;

R$^{5a}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, CF$_3$, CF$_2$CF$_3$, phenyl substituted with 0-2 R$^6$, naphthyl substituted with 0-2 R$^6$, and benzyl substituted with 0-2 R$^6$, provided that R$^{5a}$ does not form a S—N or S(O)$_p$—C(O) bond; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl.

In a tenth embodiment, the present invention provides a novel compound or a stereoisomer or pharmaceutically acceptable salt, solvate, or prodrug form thereof, wherein the compound is selected from:

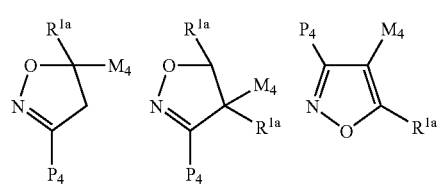

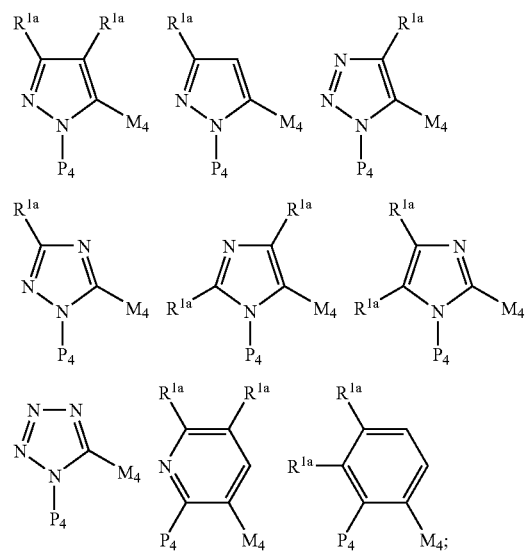

G is substituted with 1 R$^a$ and is selected from the following group, wherein R$^a$ is attached adjacent to the point of attachment of G:

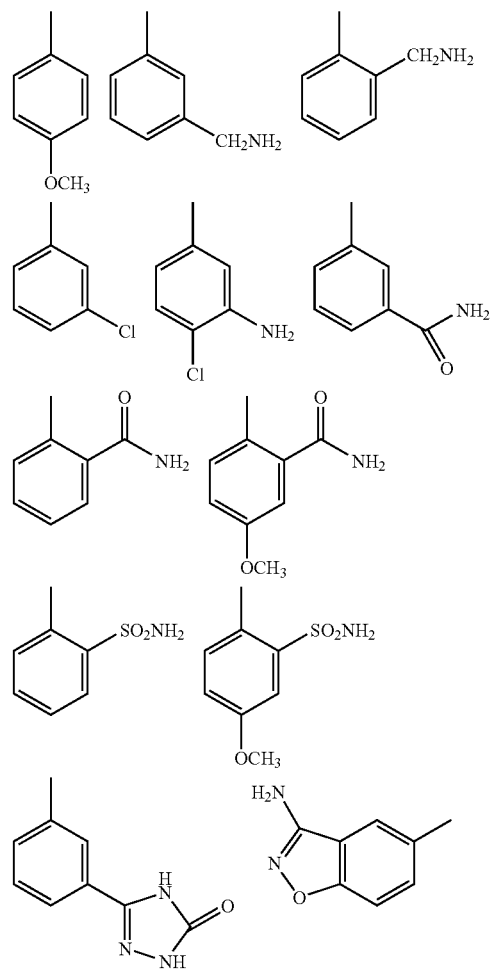

-continued

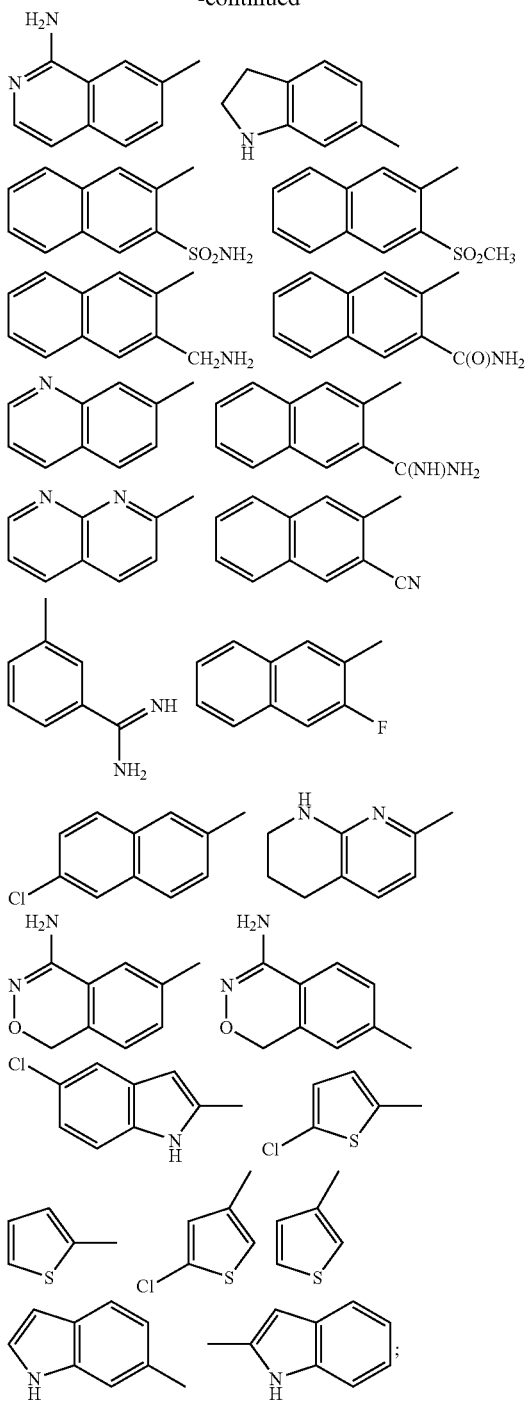

$R^a$ is $R(CR^8R^{2b})_{0-4}R^b{}_{0-1}(CR^8R^9)_{0-1}R^c$;
$R^b$ is selected from $C(O)NR^3$, $S(O)_2NR^3$, $NR^3C(O)$, and $NR^3S(O)_2$;
$R^c$ is selected from H, $OR^3$, $NR^3C(O)R^3$, $C(O)NR^3R^{3a}$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;
provided that when the $(CR^8R^{2b})_{0-4}R^b{}_{0-1}(CR^8R^9)_{0-1}$ portion of $R^a$ is absent, then $R^c$ is selected from $NR^3C(O)$ $R^3$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;
further provided that the $(CR^8R^{2b})_{0-4}R^b{}_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

$G_1$ is absent or is selected from $(CR^3R^{3a})_{1-3}$, $CR^3$=$CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, and $(CR^3R^{3a})_uS(O)_2 NR^{3b}(CR^3R^{3a})_w$, wherein u+w total 0, 1, or 2, wherein the right side of $G_1$ is attached to ring G, provided that $G_1$ does not form a N—S, $NCH_2N$, $NCH_2O$, or $NCH_2S$ bond with either group to which it is attached;

A is selected from one of the following carbocyclic and heterocyclic groups which are substituted with 0-2 $R^4$; cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, $CH_2CH_3$, $CH_2CH_2CH_3$, $CH(CH_3)_2$, —$(CH_2)_{0-1}$—$C_{5-6}$ carbocycle substituted with 0-2 $R^{4b}$, and —$(CH_2)_{0-1}$-5-6 membered heterocycle consisting of: carbon atoms and 1-4 heteroatoms selected from the group consisting of N, O, and $S(O)_p$ and substituted with 0-2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0-1 $R^{4c}$, —$(CH_2)_{0-1}$-3-6 membered carbocycle substituted with 0-1 $R^5$, and a —$(CH_2)_{0-1}$-5-6 membered heterocycle consisting of: carbon atoms and 1-4 heteroatoms selected from the group consisting of N, O, and $S(O)_p$ and substituted with 0-1 $R^5$;

$B^4$ is selected from H, $SO_2R^{3b}$ and $OR^2$;
$B^5$ is $NR^2R^{2f}$;

ring Q is a 5-6 membered ring consisting of, in addition to the N—$CR^{4d}$=N group shown, carbon atoms and 0-2 heteroatoms selected from N, O, and $S(O)_p$, and the ring is substituted with an additional 0-2 $R^{4a}$;

$Q^4$ is selected from C=O and $SO_2$;

ring $Q^3$ is a 5-7 membered ring consisting of, in addition to the N-$Q^4$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^{4a}$;

alternatively, ring $Q^3$ is a 5-7 membered ring to which another ring is fused, wherein: the 5-7 membered ring consists of, in addition to the shown amide group, carbon atoms and 0-2 heteroatoms selected from $NR^{4c}$, O, S, S(O), and $S(O)_2$, and 0-1 double bonds are present within the ring; the fusion ring is phenyl or a 5-6 membered heteroaromatic consisting of carbon atoms and 1-2 heteroatoms selected from $NR^{4c}$, O, and S;

ring $Q^3$, which includes the 5-7 membered ring and the fusion ring, is substituted with 0-3 $R^{4a}$;

ring $Q^5$, is a $C_{3-6}$ monocyclic carbocycle or 5-6 membered monocyclic heterocycle, wherein the carobocycle or heterocycle consists of carbon atoms and 0-2 heteroatoms selected from N, O, and $S(O)_p$, the carbocycle or heterocycle further comprises 0-1 double bonds and 0-1 carbonyl groups, and the carbocycle or heterocycle is substituted with 0-2 $R^4$;

X is selected from —$(CR^2R^{2a})_{1-2}$—, —C(=NR$^1$)—, —C(O)—, —S(O)$_2$—, —NR$^2$S(O)$_2$—, —NR$^2$S(O)$_2$—, —NR$^2$C(O)—, —C(O)NR$^2$—, —NR$^2$C(O)CR$^2$R$^{2a}$—, —NR$^2$C(O)NR$^2$—, NR$^2$, —NR$^2$CR$^2$R$^{2a}$—, —CR$^2$R$^{2a}$NR$^2$—, O, —OCR$^2$R$^{2a}$—, and —CR$^2$R$^{2a}$O—;

Y is selected from: $CY^1Y^2R^{4a}$, $NR^3R^{3a}$, and $C(O)NR^3R^{3a}$;

$Y^1$ and $Y^2$ are independently $C_{1-2}$ alkyl substituted with 0-2 $R^4$;

alternatively, Y is selected from one of the following carbocyclic and heterocycles that are substituted with 1 $R^{4a}$ and 0-1 $R^4$: cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

$R^{1a}$ is selected from H, $R^{1b}$, CH(CH$_3$)R$^{1b}$, C(CH$_3$)$_2$R$^{1b}$, CH$_2$R$^{1b}$, and CH$_2$CH$_2$R$^{1b}$, provided that $R^{1a}$ forms other than an N-halo, N—S, or N—CN bond;

alternatively, when two $R^{1a}$ groups are attached to adjacent atoms, together with the atoms to which they are attached they form a 5-6 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, CH$_3$, CH$_2$CH$_3$, F, Cl, Br, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, C(O)NR$^2$R$^{2a}$, SO$_2$NR$^2$R$^{2a}$, NR$^2$SO$_2$R$^2$, phenyl substituted with 0-2 $R^{4b}$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, CF$_3$, CH$_3$, CH$_2$CH$_3$, CH$_2$CH$_2$CH$_3$, CH(CH$_3$)$_2$, phenyl substituted with 0-2 $R^{4b}$, a benzyl substituted with 0-2 $R^{4b}$, and a 5-6 membered aromatic heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, CF$_3$, CH$_3$, CH$_2$CH$_3$, CH$_2$CH$_2$CH$_3$, CH(CH$_3$)$_2$, benzyl substituted with 0-2 $R^{4b}$, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

alternatively, NR$^2$R$^{2a}$ forms a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from CF$_3$, $C_{1-4}$ alkoxy, CH$_3$, CH$_2$CH$_3$, CH$_2$CH$_2$CH$_3$, CH(CH$_3$)$_2$, benzyl substituted with 0-2 $R^{4b}$, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from CF$_3$, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0-2 $R^{4b}$, phenyl substituted with 0-2 $R^{4b}$, and 5-6 membered aromatic heterocycle containing from 1-4 heteroatoms selected from the group consisting of N, O, and $S(O)_p$, and substituted with 0-2 $R^{4b}$;

$R^{2d}$, at each occurrence, is selected from H, $R^{4c}$, $C_{1-4}$ alkyl substituted with 0-2 $R^{4c}$, $C_{3-6}$ carbocycle substituted with 0-2 $R^{4c}$, —(CR$^3$R$^{3a}$)—$C_{3-6}$ carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and —(CR$^3$R$^{3a}$)-5-6 membered heterocycle substituted with 0-2 $R^{4c}$ and consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0-2 $R^{4c}$, $C_{3-6}$ carbocycle substituted with 0-2 $R^{4c}$, —(CR$^3$R$^{3a}$)—$C_{3-6}$ carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and —(CR$^3$R$^{3a}$)-5-6 membered heterocycle substituted with 0-2 $R^{4c}$ and consisting of: carbon atoms and 1-4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, CF$_3$, CH$_3$, CH$_2$CH$_3$, CH$_2$CH$_2$CH$_3$, CH(CH$_3$)$_2$, OCH$_3$, and benzyl;

alternatively, NR$^2$R$^{2f}$ forms a 5-6 membered ring consisting of: carbon atoms and 0-2 additional heteroatoms selected from N, O, and $S(O)_p$, and this ring is substituted with 0-2 $R^{4b}$;

alternatively, $B^4$ and $R^{2f}$ combine to form a 5-6 membered ring consisting of: carbon atoms and 0-1 additional heteroatoms selected from N, O, and $S(O)_p$, and this ring is substituted with 0-2 $R^{4b}$ and the $R^2$ group of NR$^2$R$^{2f}$, in addition to the groups recited below, can be SO$_2$R$^{3b}$;

$R^{3b}$, at each occurrence, is selected from H, CF$_3$, CH$_3$, CH$_2$CH$_3$, CH$_2$CH$_2$CH$_3$, and CH(CH$_3$)$_2$;

$R^4$, at each occurrence, is selected from H, =O, CH$_2$OR$^2$, (CH$_2$)$_2$OR$^2$, OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, SO$_2$NR$^2$R$^{2a}$, CF$_3$, and CF$_2$CF$_3$;

$R^{4a}$ is selected from —(CR$^3$R$^{3g}$)$_r$-5-6 membered carbocycle substituted with 0-3 $R^{4c}$, —(CR$^3$R$^{3g}$)$_r$-5-6 membered heterocycle substituted with 0-3 $R^{4c}$ and consisting of: carbon atoms and 1-4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r-NR^{2d}C(O)R^{2e}$, $(CR^3R^{3g})_r-C(O)R^{2e}$, $(CR^3R^{3g})_r-OC(O)R^{2e}$, $(CR^3R^{3g})_r-C(O)NR^{2d}R^{2d}$, $(CR^3R^{3g})_r-C(O)OR^{2d}$, $(CR^3R^{3g})_r-NR^{2d}C(O)NR^{2d}R^{2d}$, $(CR^3R^{3g})_r-NR^{2d}C(O)OR^{2d}$, $(CR^3R^{3g})_r-SO_2NR^{2d}R^{2d}$, $(CR^3R^{3g})_r-NR^{2d}SO_2R^{2d}$, and $(CR^3R^{3g})_r-S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2C(O)R^3$, $C(O)OR^{3c}$, $CH_2-C(O)OR^{3c}$, $NR^3C(O)R^{3a}$, $CH_2NR^3C(O)R^{3a}$, $C(O)NR^3R^{3a}$, $CH_2-C(O)NR^3R^{3a}$, $SO_2NR^3R^{3a}$, $CH_2SO_2NR^3R^{3a}$, $NR^3SO_2-C_{1-4}$ alkyl, $CH_2NR^3SO_2-C_{1-4}$ alkyl, $NR^3SO_2$-phenyl, $CH_2NR^3SO_2$-phenyl, $S(O)_pCF_3$, $CH_2S(O)_pCF_3$, $S(O)_p-C_{1-4}$ alkyl, $CH_2S(O)_p-C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{2-3}$ alkenyl, $C_{2-3}$ alkynyl, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0-2 $R^{4b}$, $(CR^3R^{3a})C_{3-10}$ carbocycle substituted with 0-2 $R^{4b}$, 5-10 membered heterocycle consisting of carbon atoms and from 1-4 heteroatoms selected from the group consisting of N, O, and $S(O)_p$ and substituted with 0-2 $R^{4b}$, and $(CR^3R^{3a})$-5-10 membered heterocycle consisting of carbon atoms and from 1-4 heteroatoms selected from the group consisting of N, O, and $S(O)_p$ and substituted with 0-2 $R^{4b}$;

$R^{4d}$, at each occurrence, is selected from H, $CH_2OR^2$, $OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $CH_2NR^2R^{2a}$, $NR^2R^{2a}$, $C(O)R^{2c}$, $NR^2C(O)R^{2b}$, $C(O)NR^2R^{2a}$, $NR^2C(O)NR^2R^{2a}$, $NR^2SO_2R^5$, $SO_2NR^2R^{2a}$, 6 membered carbocycle substituted with 0-1 $R^5$, and a 5-6 membered heterocycle consisting of: carbon atoms and 1-2 heteroatoms selected from the group consisting of N, O, and $S(O)_p$ and substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

In an eleventh embodiment, the present invention provides a novel compound or a stereoisomer or pharmaceutically acceptable salt, solvate, or prodrug form thereof, within the scope of the tenth embodiment, wherein:

G is substituted with 1 $R^a$ wherein $R^a$ is attached adjacent to the point of attachment of G:

$R^a$ is $R^b(CR^8R^{2b})_{0-3}R^b_{0-1}R^c$;

$R^b$ is $C(O)NR^3$;

$R^c$ is selected from H, $OR^3$, $C_{5-10}$ carbocycle substituted with 0-2 $R^4$, and 5-10 membered heterocycle substituted with 0-2 $R^4$ and consisting of: carbon atoms and 1-4 heteroatoms selected from the group consisting of N, O, and $S(O)_p$;

provided that when the $(CR^8R^{2b})_{0-4}R^b_{0-1}(CR^8R^9)_{0-1}$ portion of $R^a$ is absent, then $R^c$ is selected from $C_{5-10}$ carbocycle substituted with 0-2 $R^4$ and 5-11 membered heterocycle substituted with 0-2 $R^4$ and consisting of: carbon atoms and 1-4 heteroatoms selected from the group consisting of N, O, and $S(O)_p$;

further provided that the $(CR^8R^{2b})_{0-4}R^b_{0-1}(CR^8R^9)_{0-4}R^c$ portion of $R^a$ is other than $(CR^8R^{2b})_{0-3}$-unsubstituted-phenyl or $(CR^8R^9)_{0-3}$-unsubstituted-phenyl;

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, $NHC(O)$, $CH_2S(O)_2$, $S(O)_2(CH_2)$, $SO_2NH$, and $NHSO_2$, wherein the right side of $G_1$ is attached to ring G, provided that $G_1$ does not form a N—S, $NCH_2N$, $NCH_2O$, or $NCH_2S$ bond with either group to which it is attached;

A is selected from cyclohexyl, indolinyl, piperidinyl, piperazinyl, phenyl, pyridyl, and pyrimidyl, and is substituted with 0-2 $R^4$;

B is selected from Y, $N(B^1)C(O)C(R^3R^{3g})NB^2B^3$,

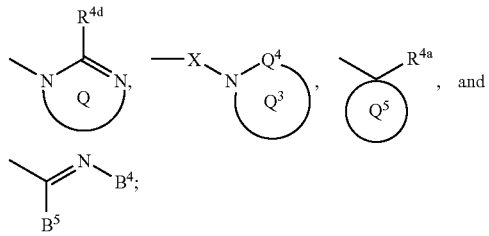

provided that Z and B are attached to different atoms on A, the $R^{4d}$ shown is other than OH, and that the A-X—N moiety forms other than a N—N—N group;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, $-(CH_2)_{0-1}$-3-6 membered carbocycle substituted with 0-1 $R^5$, and a $-(CH_2)_{0-1}$-5-6 membered heterocycle consisting of: carbon atoms and 1-4 heteroatoms selected from the group consisting of N, O, and $S(O)_p$ and substituted with 0-1 $R^5$;

$B^4$ is selected from H, $SO_2R^{3b}$, and $OR^2$;

$B^5$ is $NR^2R^{2f}$;

ring Q is a 5-6 membered ring consisting of, in addition to the N—$CR^{4d}$=N group shown, carbon atoms and 0-1 heteroatoms selected from N, O, and $S(O)_p$, and the ring is substituted with an additional 0-2 $R^{4d}$;

$Q^4$ is selected from C=O and $SO_2$;

ring $Q^3$ is a 6-7 membered ring consisting of, in addition to the N-$Q^4$ group shown, carbon atoms and 0-1 heteroatoms selected from $NR^{4c}$, O, S, S(O), and $S(O)_2$, wherein: 0-2 double bonds are present within the ring and the ring is substituted with 0-2 $R^4$;

alternatively, ring $Q^3$ is a 5-7 membered ring to which another ring is fused, wherein: the 5-7 membered ring consists of, in addition to the shown amide group, carbon atoms and 0-1 heteroatoms selected from $NR^{4c}$, O, S, S(O), and $S(O)_2$, and 0-1 double bonds are present within the ring; the fusion ring is phenyl;

ring $Q^3$, which includes the 5-7 membered ring and the fusion ring, is substituted with 0-2 $R^4$;

ring $Q^5$ is substituted with 0-1 $R^4$ and is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl;

X is selected from $CH_2$, C(O), $-S(O)_2-$, $-NHC(O)-$, $-C(O)NH-$, $-CH_2NH-$, O, and $-CH_2O-$;

Y is selected from $N(CH_3)_2$, $C(O)(CH_3)_2$, $C(CH_3)_2R^{4a}$ and $C(CH_2CH_3)_2R^{4a}$;

alternatively, Y is selected from phenyl, pyridyl, pyrrolidino, N-pyrrolidino-carbonyl, morpholino, N-morpholino-carbonyl, 1,2,3-triazolyl, imidazolyl, and benzimidazolyl, and is substituted with 1 $R^{4a}$ and 0-1 $R^4$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0-1 $R^{4b}$, phenyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

alternatively, $NR^2R^{2a}$ forms a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0-1 $R^{4b}$, phenyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0-1 $R^{4b}$, phenyl substituted with 0-1 $R^{4b}$, and 5-6 membered aromatic heterocycle containing from 1-4 heteroatoms selected from the group consisting of N, O, and $S(O)_p$, and substituted with 0-1 $R^{4b}$;

$R^{2d}$, at each occurrence, is selected from H, $R^{4c}$, $C_{1-4}$ alkyl substituted with 0-2 $R^{4c}$, $C_{3-6}$ carbocycle substituted with 0-2 $R^{4c}$, $-(CH_2)-C_{3-6}$ carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and $-(CH_2)$-5-6 membered heterocycle substituted with 0-2 $R^{4c}$ and consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0-2 $R^{4c}$, $C_{3-6}$ carbocycle substituted with 0-2 $R^{4c}$, $-(CH_2)-C_{3-6}$ carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and $-(CH_2)$-5-6 membered heterocycle and consisting of: carbon atoms and 1-4 heteroatoms selected from the group consisting of N, O, and $S(O)_p$, provided that $R^{2e}$ forms other than a C(O)-halo or $C(O)-S(O)_p$ moiety;

$R^{2f}$ at each occurrence, is selected from H, $CH_3$, $CH_2CH_3$, $OCH_3$, and benzyl;

alternatively, $NR^2R^{2f}$ forms a 5-6 membered ring consisting of: carbon atoms and 0-1 additional heteroatoms selected from N, O, and $S(O)_p$, and this ring is substituted with 0-1 $R^{4b}$;

alternatively, $B^4$ and $R^{2f}$ combine to form a 5 membered ring consisting of: carbon atoms and 0-1 additional heteroatoms selected from N, O, and $S(O)_p$, and this ring is substituted with 0-2 $R^{4b}$ and the $R^2$ group of $NR^2R^{2f}$, in addition to the groups recited below, can be $SO_2R^{3b}$;

$R^{3b}$, at each occurrence, is selected from H and $CH_3$;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from $-(CR^3R^{3g})_r$-5-6 membered carbocycle substituted with 0-3 $R^{4c}$, $-(CR^3R^{3g})_r$-5-6 membered heterocycle substituted with 0-3 $R^{4c}$ and consisting of: carbon atoms and 1-4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r-C(O)NR^{2d}R^{2d}$, $(CR^3R^{3g})_r-NR^{2d}C(O)R^{2e}$, $(CR^3R^{3g})_r-C(O)R^{2e}$, $(CR^3R^{3g})_r-NR^{2d}C(O)NR^{2d}R^{2d}$, $(CR^3R^{3g})_r-NR^{2d}C(O)OR^{2d}$, $(CR^3R^{3g})_r-NR^{2d}SO_2R^{2d}$, and $(CR^3R^{3g})_r-S(O)_pR^{2d}$, provided that $S(O)_pR^{2d}$ forms other than $S(O)_2H$ or S(O)H;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2$-phenyl, $S(O)_p-C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-3}$ alkenyl, $C_{2-3}$ alkynyl, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0-2 R$^{4b}$, (CH$_2$)C$_{3-6}$ carbocycle substituted with 0-2 R$^{4b}$, 5-6 membered heterocycle consisting of carbon atoms and from 1-4 heteroatoms selected from the group consisting of N, O, and S(O)$_p$ and substituted with 0-2 R$^{4b}$, and (CH$_2$)-5-6 membered heterocycle consisting of carbon atoms and from 1-4 heteroatoms selected from the group consisting of N, O, and S(O)$_p$ and substituted with 0-2 R$^{4b}$;

R$^{4d}$, at each occurrence, is selected from H, CH$_2$OR$^2$, OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CH$_2$NR$^2$R$^{2a}$, NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0-1 R$^5$, and a 5-6 membered heterocycle consisting of: carbon atoms and 1 heteroatom selected from the group consisting of N, O, and S(O)$_p$ and substituted with 0-1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0-2 R$^6$, naphthyl substituted with 0-2 R$^6$, and benzyl substituted with 0-2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

In a twelfth embodiment, the present invention provides a novel compound or a stereoisomer or pharmaceutically acceptable salt, solvate, or prodrug form thereof, within the scope of the eleventh embodiment, wherein:

G$_1$ is absent or is selected from CH$_2$NH, NHCH$_2$, CH$_2$C(O), C(O)CH$_2$, C(O)NH, NHC(O), NHC(O)NH, CH$_2$S(O)$_2$, S(O)$_2$(CH$_2$), SO$_2$NH, and NHSO$_2$, wherein the right side of G$_1$ is attached to ring G, provided that G$_1$ does not form a N—S, NCH$_2$N, NCH$_2$O, or NCH$_2$S bond with either group to which it is attached;

A is selected from the group: cyclohexyl, indolinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from Y, N(B$^1$)C(O)C(R$^3$R$^{3g}$)NB$^2$B$^3$,

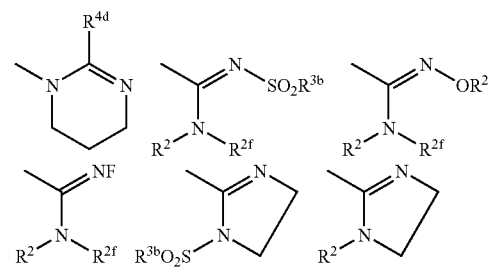

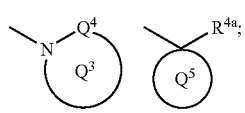

provided that Z and B are attached to different atoms on A and that the R$^{4d}$ shown is other than OH;

B$^1$ is selected from H, CH$_3$, CH$_2$CH$_3$, and CH$_2$CH$_2$CH$_3$;

B$^2$ is selected from H, CH$_3$, and CH$_2$CH$_3$;

B$^3$ is selected from CH$_3$, CH$_2$CH$_3$, CH$_2$CH$_2$CH$_3$, CH(CH$_3$)$_2$, CH$_2$CH$_2$CH$_2$CH$_3$, C(CH$_3$)$_3$, CH(CH$_3$)CH$_2$CH(CH$_3$)$_2$, CH$_2$CH$_2$OH, CH(CH$_3$)CH$_2$OH, CH(phenyl)CH$_2$CH$_3$, cyclopropyl, cyclobutyl, cyclopentyl, cyclohexyl, and CH$_2$-cyclopropyl;

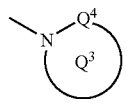

is attached to a different atom on A than M and is selected from the group:

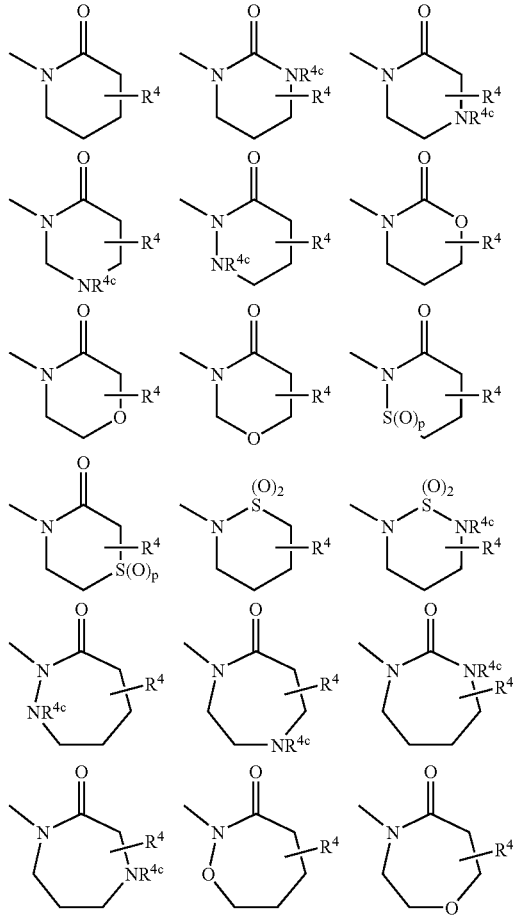

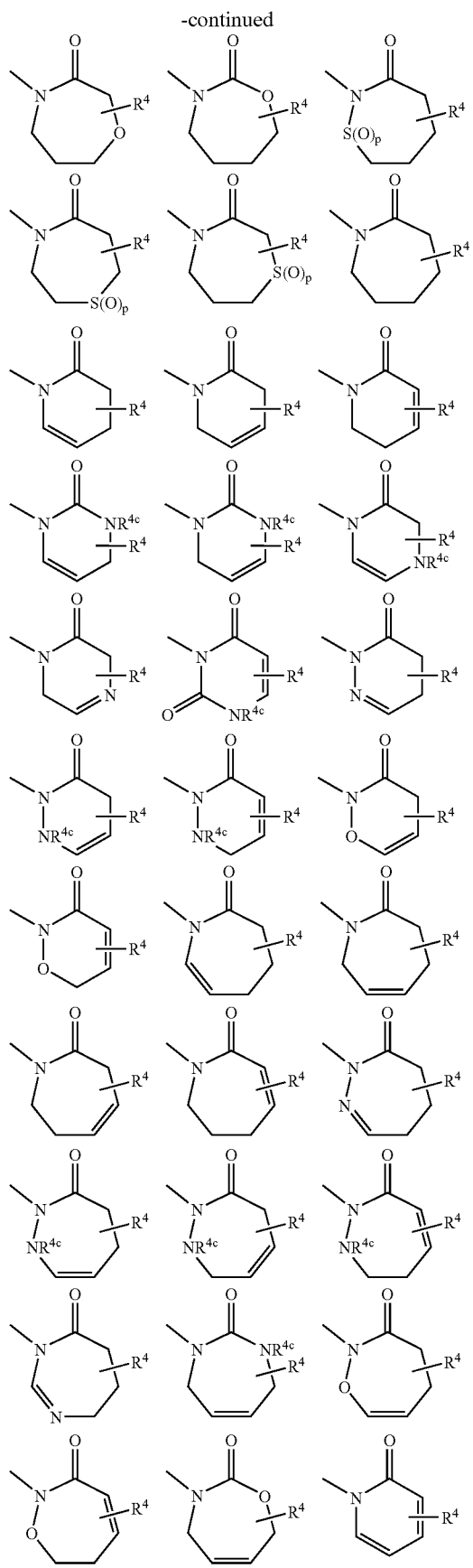

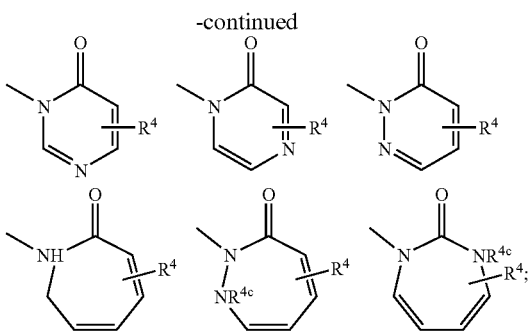

ring $Q^5$ is selected from cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position), 4-piperdinonyl (attached to A and $R^{4a}$ at the 3-position), tetrahydrofuranyl, and tetrahydropyranyl (attached to A and $R^{4a}$ at the 4-position);

Y is selected from $N(CH_3)_2$, $C(O)(CH_3)_2$, $C(CH_3)_2R^{4a}$ and $C(CH_2CH_3)_2R^{4a}$;

alternatively, Y is selected from phenyl, pyridyl, 1,2,3-triazolyl, imidazolyl, and benzimidazolyl, and is substituted with 1 $R^{4a}$;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0-2 $R^{4c}$, $C_{3-6}$ cycloalkyl substituted with 0-2 $R^{4c}$, phenyl substituted with 0-2 $R^{4c}$, and 5-6 membered aromatic heterocycle substituted with 0-2 $R^{4c}$ and consisting of: carbon atoms and 1-4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0-2 R$^{4c}$, C$_{3-6}$ cycloalkyl substituted with 0-2 R$^{4c}$, phenyl substituted with 0-2 R$^{4c}$, and 5-6 membered aromatic heterocycle substituted with 0-2 R$^{4c}$ and consisting of: carbon atoms and 1-4 heteroatoms selected from the group consisting of N, O, and S(O)$_p$, provided that R$^{2e}$ forms other than a C(O)-halo or C(O)—S(O)$_p$ moiety;

R$^{2f}$, at each occurrence, is selected from H, CH$_3$, CH$_2$CH$_3$, and OCH$_3$;

alternatively, NR$^2$R$^{2f}$ forms a ring selected from morpholine, piperazine, piperidine, and pyrrolidine;

R$^4$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, and C(CH$_3$)$_3$;

R$^{4a}$ is selected from —(CH$_2$)$_r$-5-6 membered carbocycle substituted with 0-3 R$^{4c}$, —(CH$_2$)$_r$-5-6 membered heterocycle substituted with 0-3 R$^{4c}$ and consisting of: carbon atoms and 1-4 heteroatoms selected from the group consisting of N, O, and S(O)$_p$, (CH$_2$)$_r$NR$^{2d}$R$^{2d}$, (CH$_2$)$_r$N(→O)R$^{2d}$R$^{2d}$, (CH$_2$)$_r$OR$^{2d}$, (CH$_2$)$_r$—C(O)NR$^{2d}$R$^{2d}$, (CH$_2$)$_r$—NR$^{2d}$C(O)R$^{2e}$, (CH$_2$)$_r$—C(O)R$^{2e}$, (CH$_2$)$_r$—NR$^{2d}$C(O)NR$^{2d}$R$^{2d}$, (CH$_2$)$_r$—NR$^{2d}$C(O)OR$^{2d}$, (CH$_2$)$_r$—NR$^{2d}$SO$_2$R$^{2d}$, and (CH$_2$)$_r$—S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$-phenyl, S(O)$_2$CH$_3$, S(O)$_2$-phenyl, and CF$_3$;

R$^{4c}$, at each occurrence, is selected from =O, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, C$_{2-3}$ alkenyl, C$_{2-3}$ alkynyl, CH$_2$OH, CH$_2$OCH$_3$, CH$_2$OCH$_2$CH$_3$, CH$_2$OCH$_2$CH$_2$CH$_3$, CH$_2$OCH(CH$_3$)$_2$, F, Br, Cl, CF$_3$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, cyclopropyl substituted with 0-1 R$^{4b}$, cyclobutyl substituted with 0-1 R$^{4b}$, cyclopentyl substituted with 0-1 R$^{4b}$, phenyl substituted with 0-1 R$^{4b}$, —CH$_2$-cyclopropyl substituted with 0-1 R$^{4b}$, —CH$_2$-cyclobutyl substituted with 0-1 R$^{4b}$, —CH$_2$-cyclopentyl substituted with 0-1 R$^{4b}$, benzyl substituted with 0-2 R$^{4b}$, 5-6 membered aromatic heterocycle consisting of carbon atoms and from 1-4 heteroatoms selected from the group consisting of N, O, and S(O)$_p$ and substituted with 0-2 R$^{4b}$, and (CH$_2$)-5-6 membered aromatic heterocycle consisting of carbon atoms and from 1-4 heteroatoms selected from the group consisting of N, O, and S(O)$_p$ and substituted with 0-2 R$^{4b}$;

R$^{4d}$, at each occurrence, is selected from H, OCH$_3$, CH$_3$, CH$_2$CH$_3$, CH$_2$CH$_2$CH$_3$, CH(CH$_3$)$_2$, NR$^2$R$^{2a}$, NR$^2$C(O)R$^{2b}$, NR$^2$SO$_2$R$^5$, phenyl, 2-oxo-pyrrolidinyl, and 2-oxo-piperidinyl;

R$^5$, at each occurrence, is selected from H, =O, CH$_3$, CH$_2$CH$_3$, OR$^3$, CH$_2$OR$^3$, F, Cl, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_2$—CH$_3$, S(O)$_2$-phenyl, CF$_3$, phenyl substituted with 0-2 R$^6$, naphthyl substituted with 0-2 R$^6$, and benzyl substituted with 0-2 R$^6$; and R$^6$, at each occurrence, is selected from H, OH, OR$^2$, F, Cl, CH$_3$, CH$_2$CH$_3$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

In a thirteenth embodiment, the present invention provides a novel compound or a stereoisomer or pharmaceutically acceptable salt, solvate, or prodrug form thereof, within the scope of the twelfth embodiment, wherein:

A is selected from the group: indolinyl, phenyl, 2-pyridyl, 2-pyrimidyl, and 2-F-phenyl, wherein B is substituted at the 4-position of A, except when A is indolinyl, then B is substituted at the 6-position of A;

B is selected from:

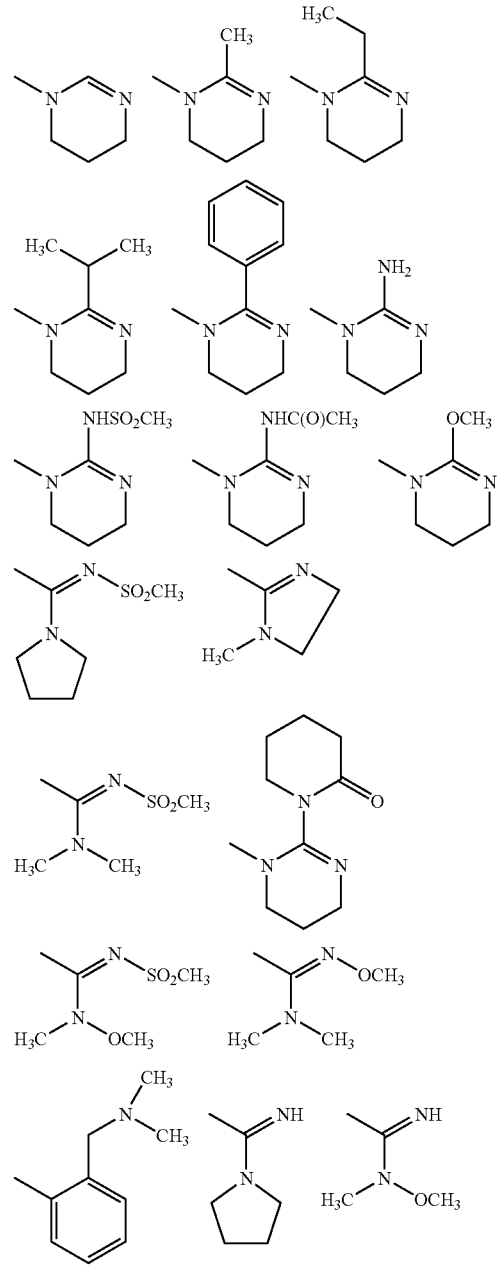

-continued

[chemical structures]

$R^{2d}$, at each occurrence, is selected from H, $C_{1-4}$ alkyl substituted with 0-1 $R^{4c}$, $C_{3-6}$ cycloalkyl substituted with 0-2 $R^{4c}$, phenyl substituted with 0-2 $R^{4c}$, and a 5-6 membered aromatic heterocycle consisting of: carbon atoms and 1-4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0-1 $R^{4c}$, $C_{3-6}$ cycloalkyl substituted with 0-2 $R^{4c}$, phenyl, substituted with 0-2 $R^{4c}$, and 5-6 membered aromatic heterocycle consisting of: carbon atoms and 1-4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5-6 membered carbocycle substituted with 0-2 $R^{4c}$, —$(CH_2)$-5-6 membered carbocycle substituted with 0-2 $R^{4c}$, 5-6 membered heterocycle substituted with 0-2 $R^{4c}$ and consisting of: carbon atoms and 1-4 heteroatoms selected from the group consisting of N, O, and $S(O)_p$, and —$(CH_2)$-5-6 membered heterocycle substituted with 0-2 $R^{4c}$ and consisting of: carbon atoms and 1-4 heteroatoms selected from the group consisting of N, O, and $S(O)_p$ provided that $S(O)_pR^{2d}$ forms other than $S(O)_2H$ or $S(O)H$; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

In a fourteenth embodiment, the present invention provides a novel compound or a stereoisomer or pharmaceutically acceptable salt, solvate, or prodrug form thereof, within the scope of the thirteenth embodiment, wherein the compound is selected from:

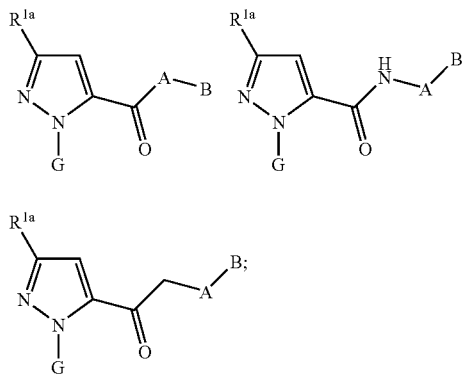

$P_4$ is -G;
A-B is selected from:
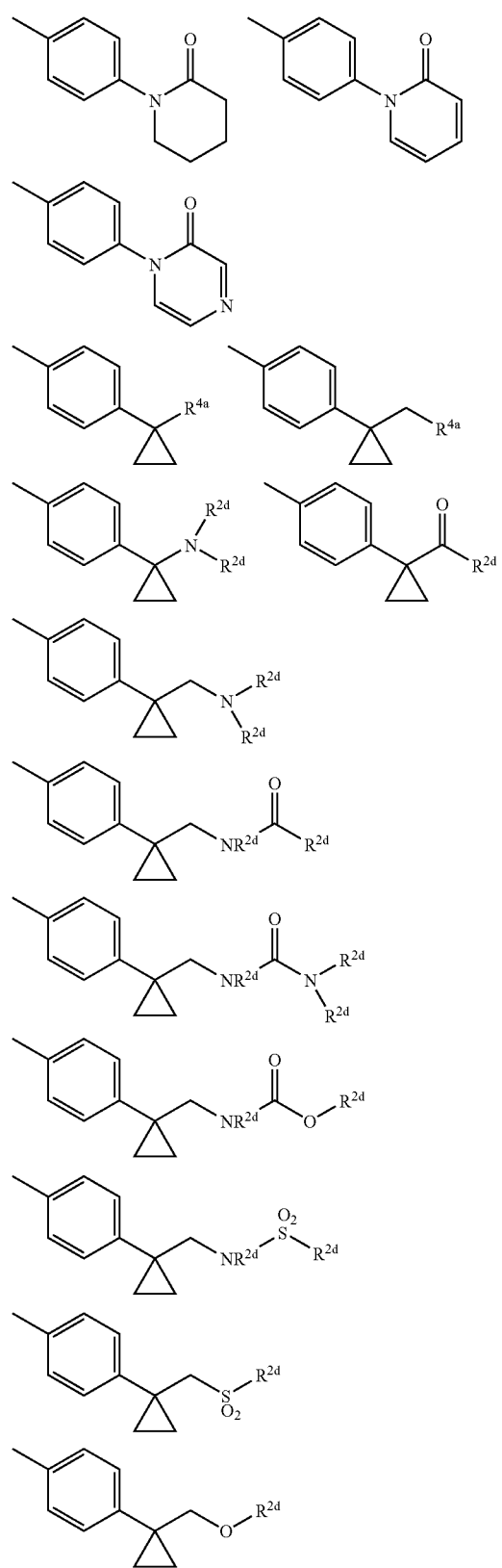
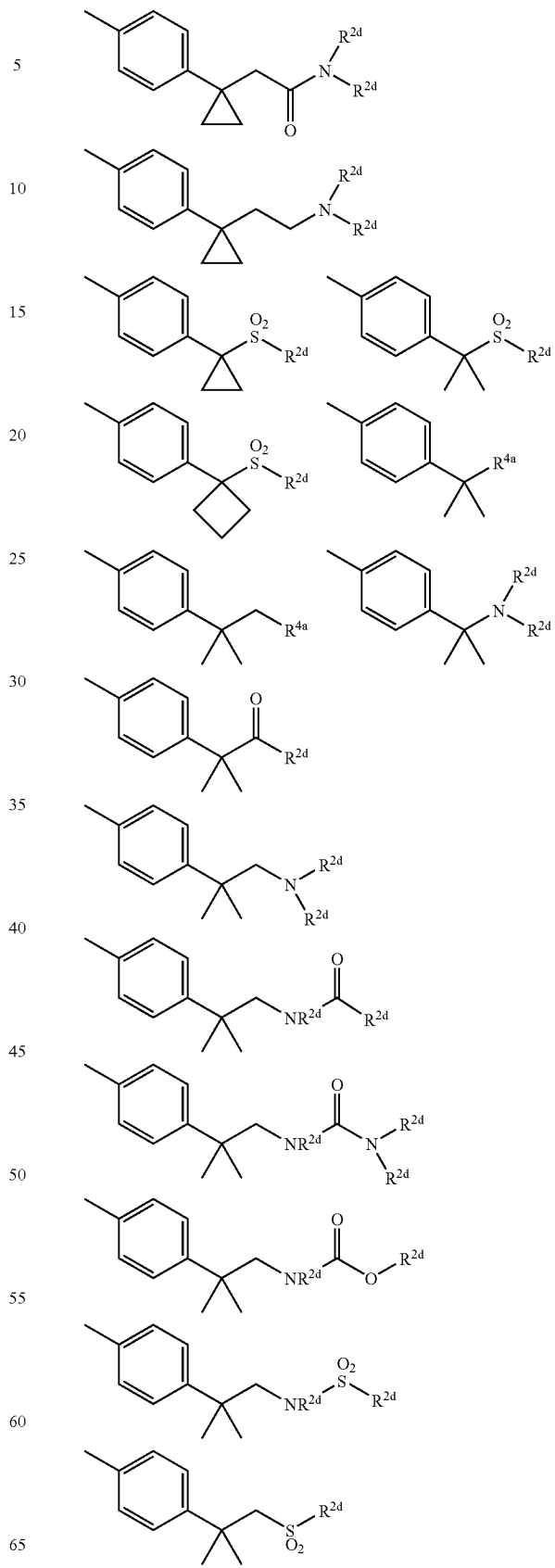

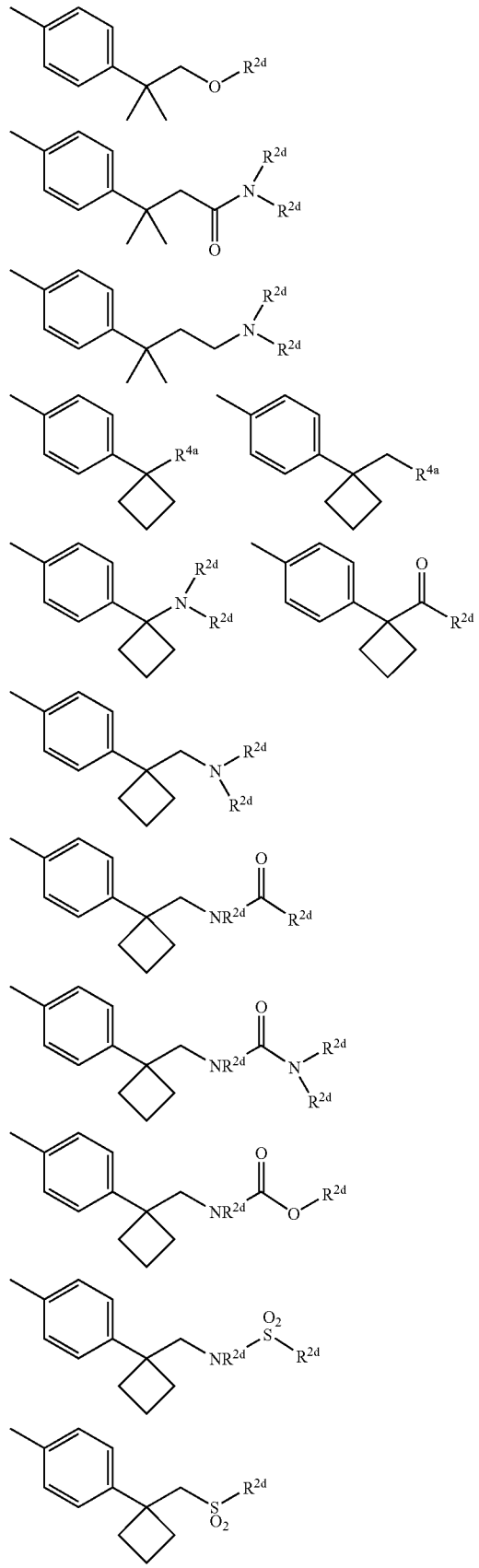
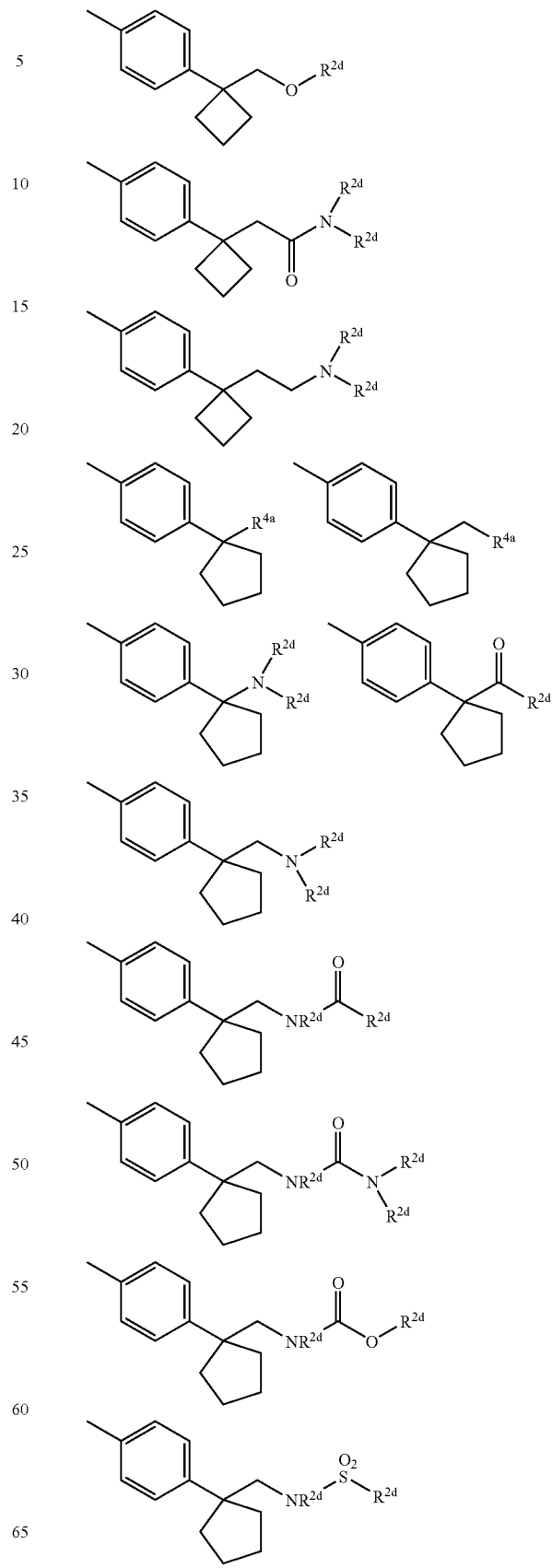

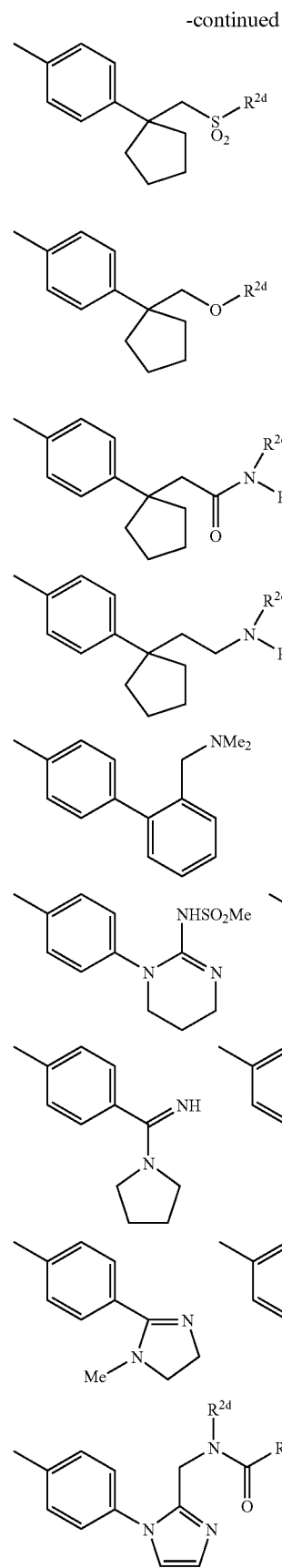
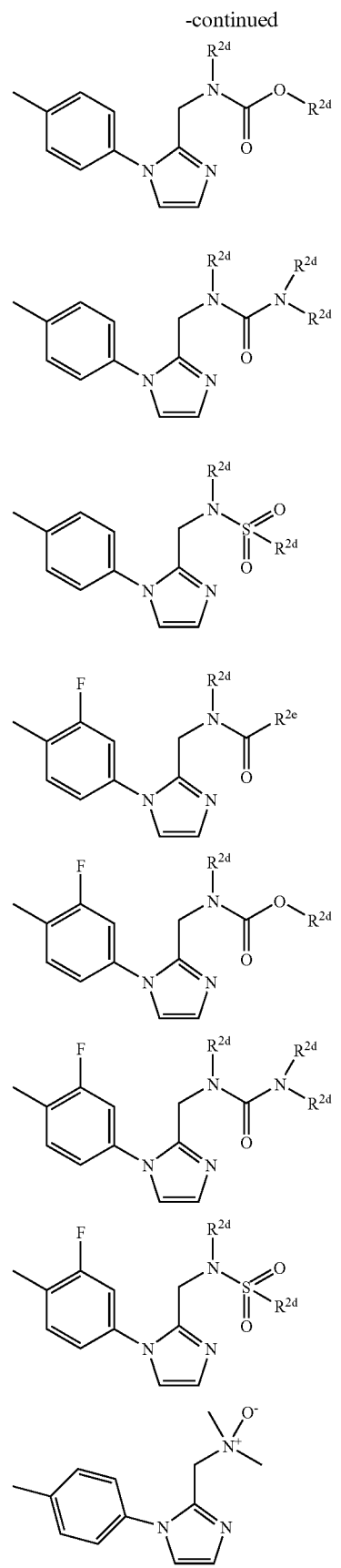

-continued

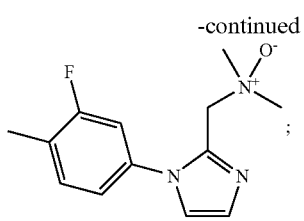

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$CCH, CH$_2$CH$_2$OH, CH$_2$C(O)NH$_2$, cyclopropyl, CH$_2$-cyclopropyl, cyclobutyl, cyclopentyl, and thiazolyl;

$R^{2e}$, at each occurrence, is selected from CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl;

$R^{4a}$ is substituted with 0-2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and $R^{4c}$ is selected from =O, OH, OCH$_3$, and CH$_3$.

In a fifteenth embodiment, the present invention provides a novel compound, wherein the compound is selected from the group: Examples 62-102 and 105-106 or a stereoisomer or pharmaceutically acceptable salt, solvate, or prodrug form thereof.

In another embodiment, the present invention provides a novel pharmaceutical composition, comprising: a pharmaceutically acceptable carrier and a therapeutically effective amount of a compound of the present invention or a pharmaceutically acceptable salt, solvate, or prodrug form thereof.

In another embodiment, the present invention provides a novel method for treating a thromboembolic disorder, comprising: administering to a patient in need thereof a therapeutically effective amount of a compound of the present invention or a pharmaceutically acceptable salt, solvate, or prodrug form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0-2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of: carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of: carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge. When the term "heterocycle" is used, it is intended to include heteroaryl.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two;

generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs,* edited by H. Bundgaard, (Elsevier, 1985), and *Methods in Enzymology,* Vol. 42, at pp. 309-396, edited by K. Widder, et. al. (Academic Press, 1985);

b) *A Textbook of Drug Design and Development,* edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews,* Vol. 8, p. 1-38 (1992);

d) H. Bundgaard, et al., *Journal of Pharmaceutical Sciences,* Vol. 77, p. 285 (1988); and e) N. Kakeya, et. al., *Chem Phar Bull.,* Vol. 32, p. 692 (1984).

Preparation of prodrugs is well known in the art and described in, for example, *Medicinal Chemistry: Principles and Practice,* ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., $=O$) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27-55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

Synthesis

All references cited herein are hereby incorporated in their entirety by reference.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. Those skilled in the art of organic synthesis understand that the functionality present on the molecule should be consistent with the transformations proposed. This will sometimes require a judgment to modify the order of the synthetic steps or to select one particular process scheme over another in order to obtain a desired compound of the invention.

Another major consideration in the planning of any synthetic route in this field is the judicious choice of the protecting group used for protection of reactive functional groups present in the compounds described in this invention. An authoritative account describing the many alternatives to the trained practitioner is Greene and Wuts (*Protective Groups In Organic Synthesis*, Wiley and Sons, 1999).

The synthesis of compounds of the present invention that involves the usage of intermediate A-B is accomplished via standard methods known to those skilled in the art.

Construction of compounds with general structure G-$G_1$-P-M-Z-A-B can be performed in two directions: 1) From G to G-$G_1$-P-M (or a derivative of P-M) then to G-$G_1$-P-M-Z-A-B or 2) From A-B to P-M-Z-A-B (or a derivative of P-M) then to G-$G_1$-P-M-Z-A-B. The general route that involves this type of methodology is outlined in Scheme 1. During the synthesis of these compounds, protecting groups to prevent cross-reaction during the coupling conditions optionally protect the functional groups of the substituents. Examples of suitable blocking groups and their uses are described in "The Peptides: Analysis, Synthesis, Biology", Academic Press, Vol. 3 (Groii, et. al. Eds., 1981). Functional group transformations and coupling reactions that can be used to prepare compounds of the present invention are described in "Advanced Organic Chemistry: Reaction, Mechanism, and Structure" (March, et. al. fourth Ed.) and "Comprehensive Organic Transformations" (Larock, second Ed.).

Scheme 1

1)

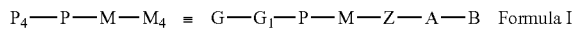

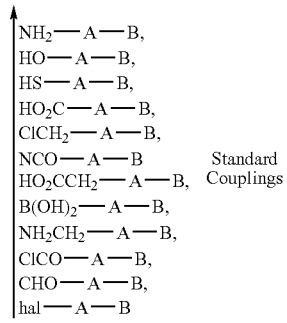

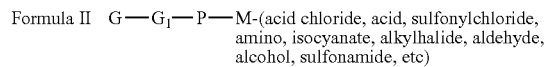

2)

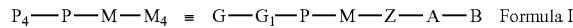

Compounds of the present invention where B is Y—$R^{4a}$ (provided that A and $R^{4a}$ are attached to the same carbon atom in Y and Y is $C_3$-$C_7$ cycloalkyl) can be prepared as shown in Scheme 2. Commercially available 4-nitrophenylacetonitrile (or properly protected 4-aminophenylacetonitrile) can be used as the starting material. Alkylation with NaH, t-BuOK, $NaNH_2$, n-BuLi, s-BuLi, NaOEt, aq NaOH, etc. as the base, and X—$(CH_2)_n$—Y (X and Y can be Cl, Br, I, OMs, OTs, or $^+S(CH_3)_2$ and n=2-6) as the alkylating reagent can afford the cycloalkyl intermediate 1. Hydrolysis of the nitrile group, followed by reduction of the ester group can provide the alcohol 2. Oxidation of 2, then reductive amination with $NHR^{2d}R^{2d}$ can provide 3. Reduction of the nitro group or deprotection of the amino group can produce the A-B precursor 4, which can be coupled with 5 using standard coupling conditions as described in Scheme 1 to provide 6. When one of the $R^{2d}$ groups is H, 6 can react with acid chlorides, carbamoyl chlorides, sulfonyl chlorides, and isocyanates to provide compounds of the invention with structures 7, 8, 9, and 10. Alternatively, alcohol 2 can react with alkyl halides and amines to form compounds of the invention with structures 11 and 12. Alcohol 2 can also be transformed into a halide or its equivalents (X=Cl, Br, I, OMs, or OTs), followed by alkylation with a variety of alkylating reagents to afford compounds of the invention with structures 13, 14, and 15.

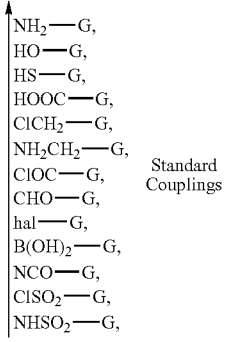

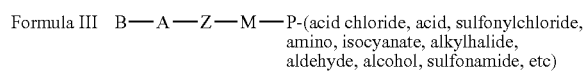

Scheme 2

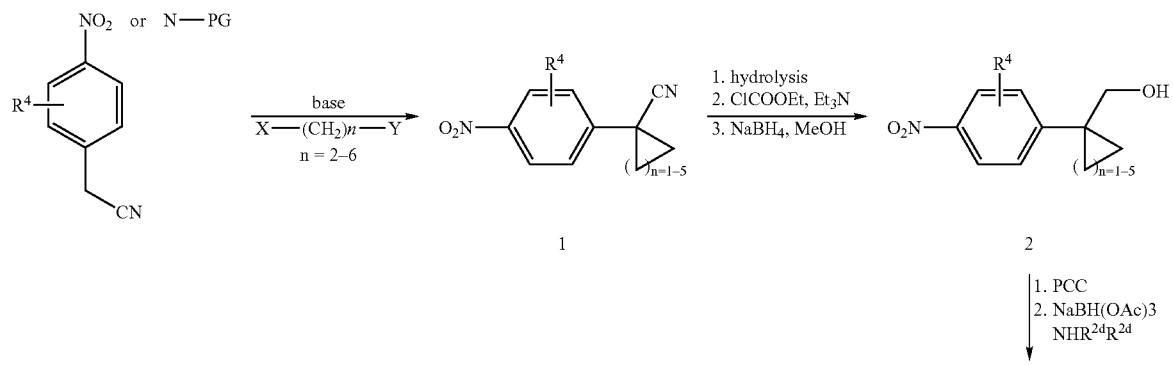

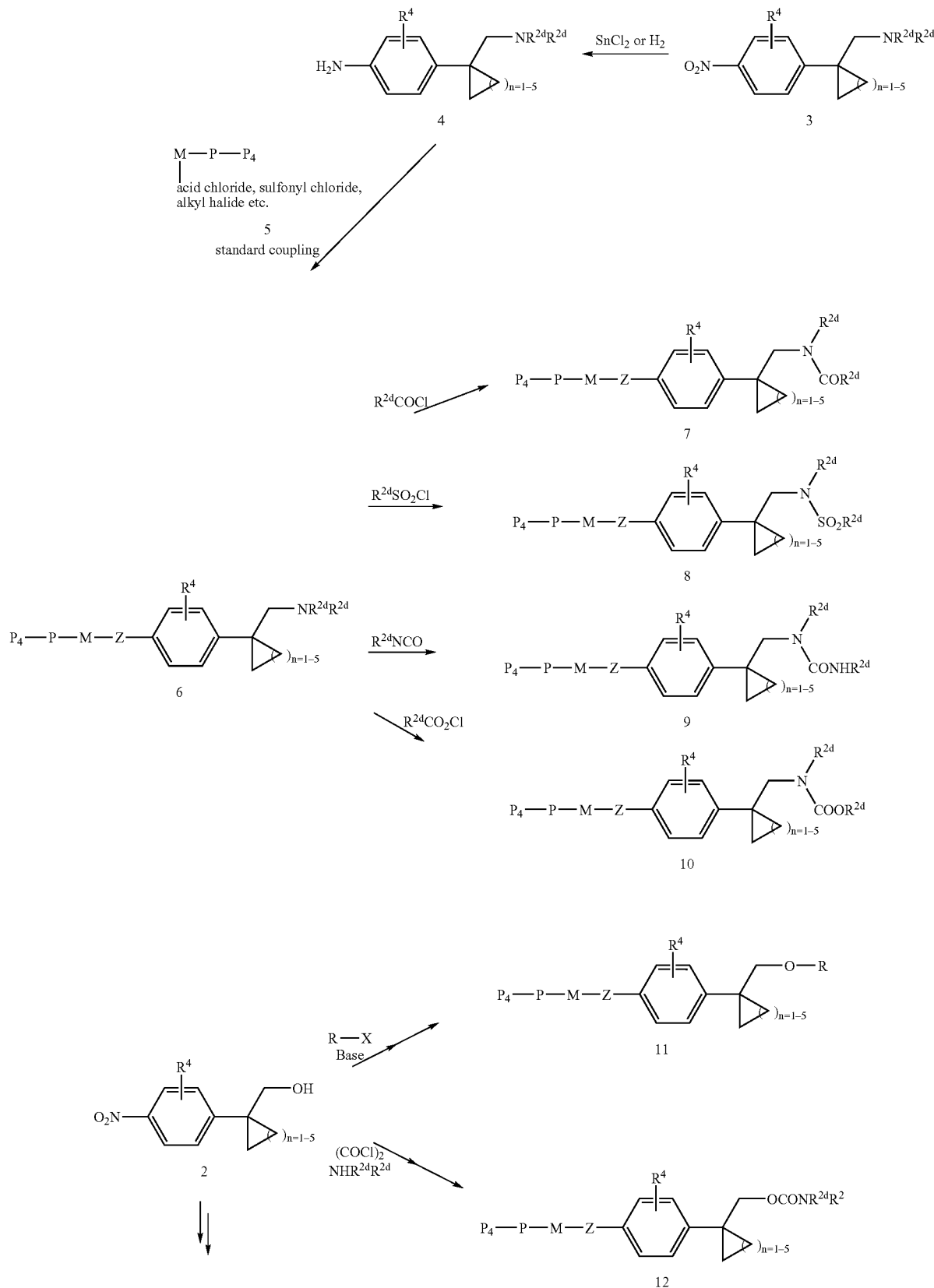

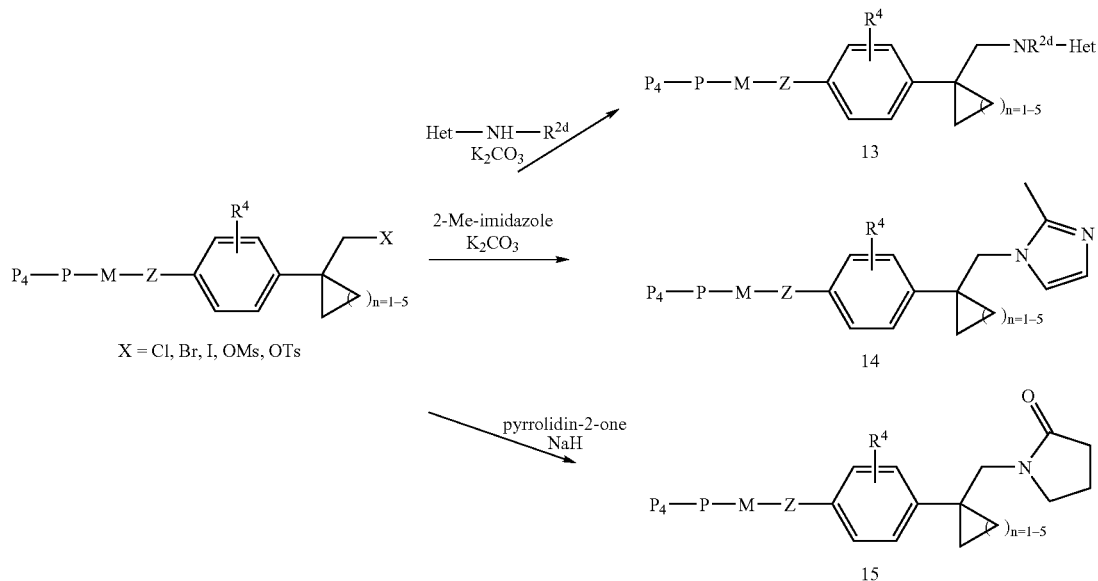

Other compounds of the present invention where Y is a cycloalkyl derivative can be prepared using commercially available 1-phenylcycloalkylcarboxylic acids (or 1-phenyl-cycloalkylcarbonitriles) as the starting materials as illustrated in Scheme 3. Nitration, followed by reduction of the NO$_2$ group and protection of the acid group can provide the A-B precursor 16, which can be coupled with 5 using standard coupling conditions to provide 17.

Alternatively, iodination can provide the desired para-substituted compound 18, which can in turn be transformed to the amine 16 via Buchwald palladium-catalyzed amination (*Tetrahedron Lett.* 1997, 38, 6367-6370) and to the acid 19 via paladium-catalyzed carboxylation (CO, Pd(OAc)$_2$, dppf). Additional A-B intermediates can be synthesized by chemical manipulation of the amino and carboxylic acid functionality in 16 and 19, respectively. Compound 19 can be homologated via the Arndt-Eistert methodology to afford other A-B intermediates in 20. Alternatively, the acid functionality in 19 can be reduced to the alcohol that in turn can be converted to a variety of A-B intermediates 20 by procedures known to those skilled in the art. Further elaboration of these intermediates using the methods described above and by those known in the art should provide compounds of the present invention.

Scheme 3

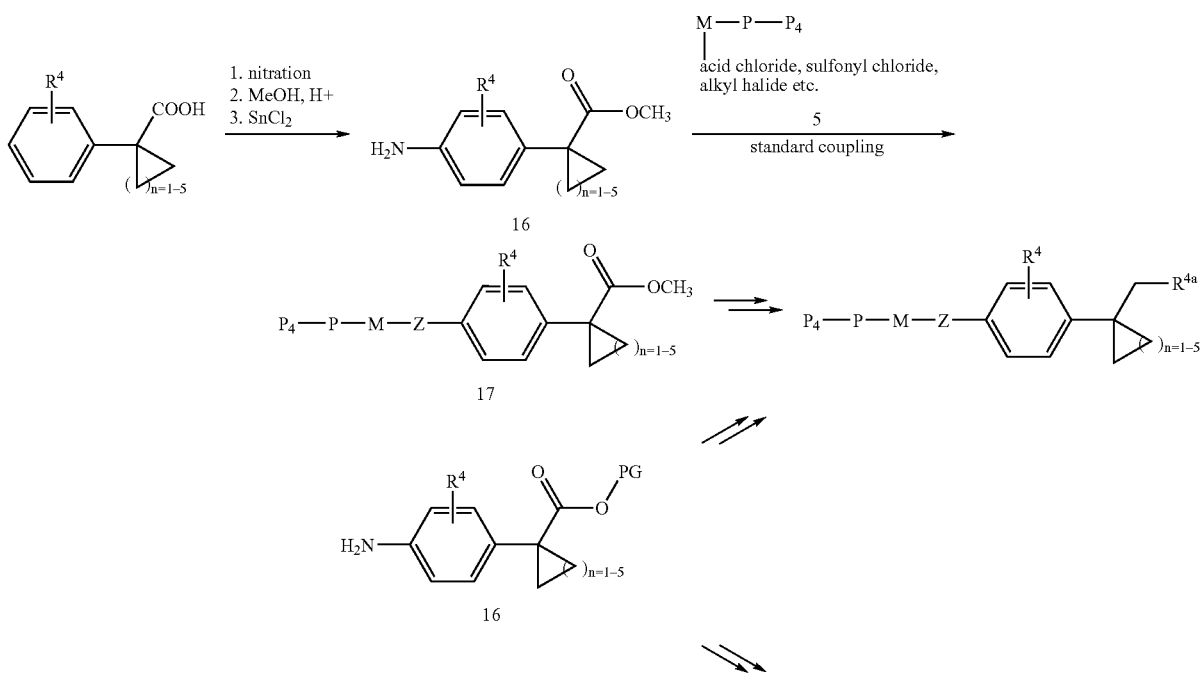

-continued

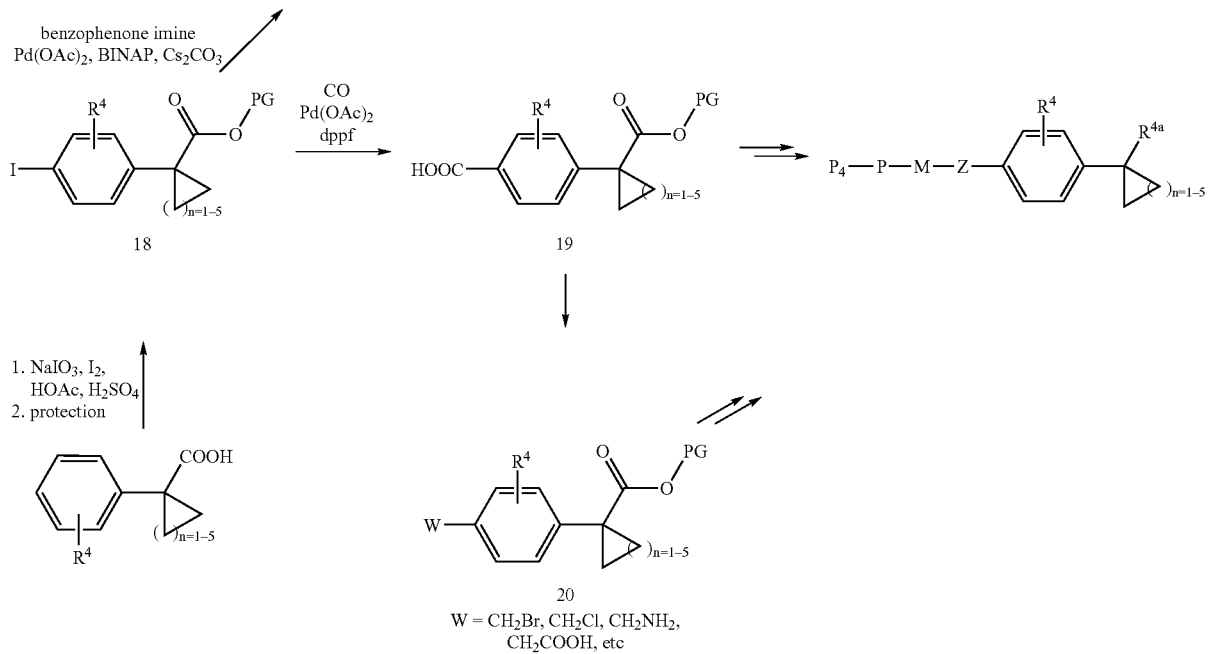

Other compounds of the present invention where Y is a cycloalkyl derivative can be prepared using organometalic reagents 21 (Zn, Mg, etc.) as starting materials as shown in Scheme 4. Reaction of 21 with properly substituted cycloalkyl halides 22 (X=Cl, Br, I, OMs, OTs, etc.) using Pd(dba)$_2$/1,2-bis(diphenylphosphino)ethane (dppe) or NiCl$_2$ (PPh$_3$)$_2$ as the catalyst system can provide intermediate 23. Alternatively, Grignard reaction of 21 with cycloalkyl ketones can provide intermediate 24. Further elaboration of 23 and 24 using the methods described above and by those known in the art should provide compounds of the present invention.

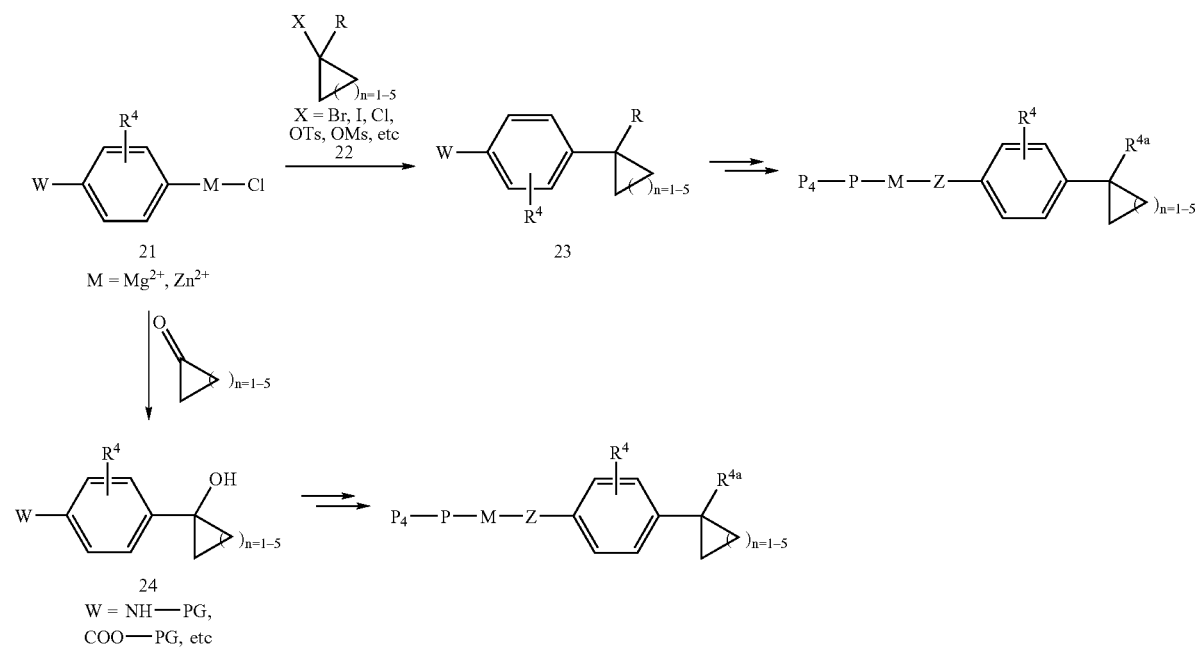

Compounds of the present invention where Y is a pyrrolidine or piperidine derivative can be prepared as shown in Scheme 5. Phenylcyanoacetate can be alkylated with X—(CH$_2$)$_n$—Cl (X and Y=Br, I, OMs, OTs, etc. and n=2-3) to provide chloronitrile 25, which can be reduced to the corresponding primary amine, followed by cyclization in refluxing EtOH to form 3-pyrrolidine or 3-piperdine derivatives 26. Alkylation or reductive amination can provide N-substituted intermediate 27. Further elaboration using the methods described above and by those known in the art should provide compounds of the present invention.

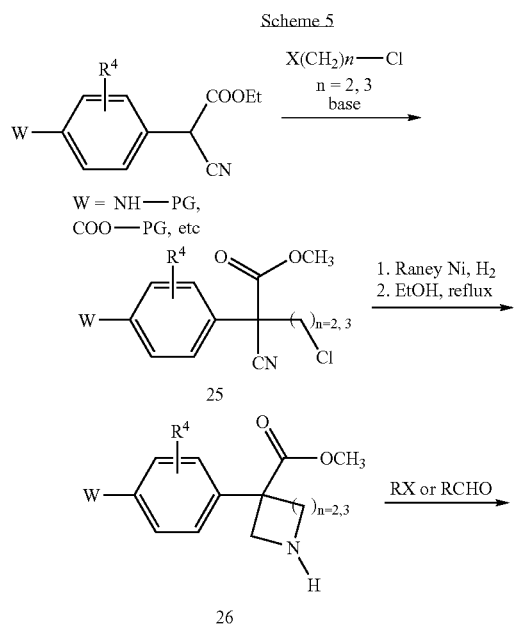

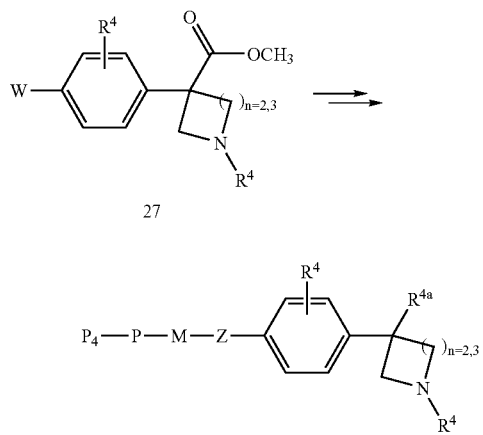

Compounds of the present invention where Y is a pyrrolidine derivative can also be prepared as illustrated in Scheme 6. The Grignard reaction of 1-substituted 4-piperidone 28 with an appropriate arylmagnesium halide followed by dehydration should give tetrahydropyridine derivative 29. Epoxidation followed by rearrangement with heating in boron trifluoride etherate (*Chem. Pharm. Bull.* 1980, 28(5), 1387-1393) can provide pyrrolidine aldehyde 30. Alternatively, radical cyclization of alkyl azide 31 (*Tetrahedron Lett.* 1997, 38, 3915-3918) can provide pyrrolidine intermediate 32. Further elaboration of these intermediates using the methods described above and by those known in the art should provide compounds of the present invention.

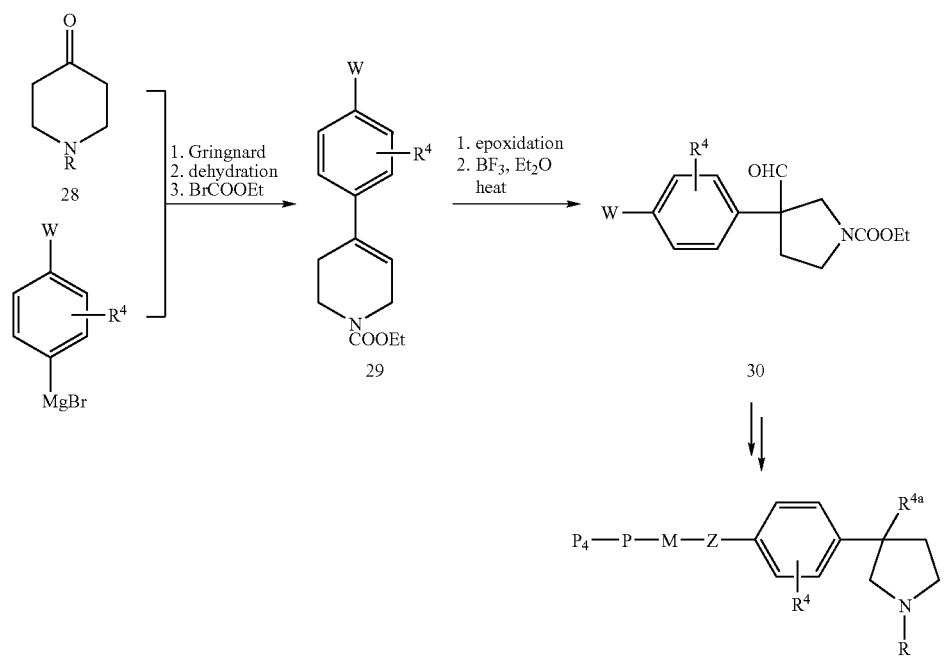

-continued

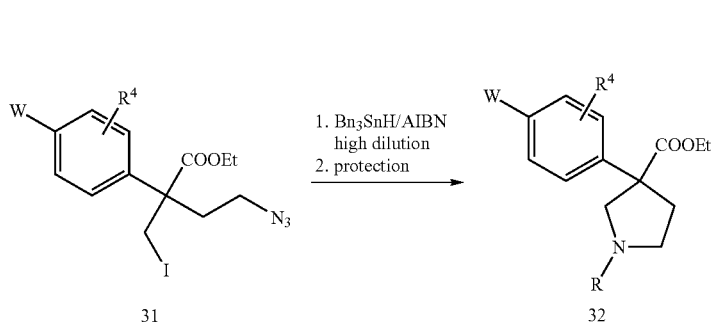

W = NH—PG, COO—PG, etc

Compounds of the present invention where Y is a 4-piperidine derivative can be prepared using 2-aryl acetonitriles 33 as starting materials as shown in Scheme 7. Dialkylation of 33 with bromoacetaldehyde dimethyl acetal, followed by hydrolysis of the acetals and reductive amination should give the 4-aryl-4-cyanopiperidine 34. Further elaboration of these intermediates using the methods described above and by those known in the art should provide compounds of the present invention.

Compounds of the present invention where Y is a 4-tetrahydrfuran derivative can be prepared using diol 35 as the starting material as illustrated in Scheme 8. Cyclization of 35 with HBr should give 4-aryl-4-substituted tetrahydrofuran 36. Further elaboration using the methods described above and by those known in the art should provide compounds of the present invention.

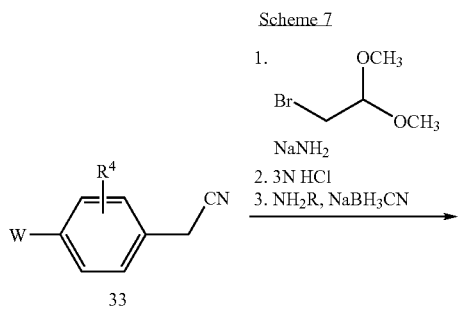

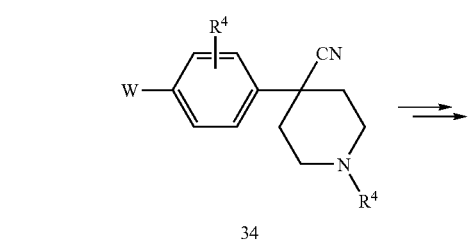

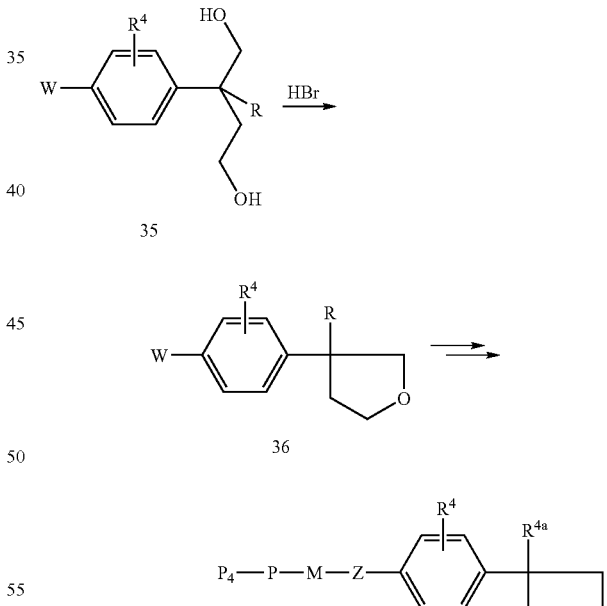

Compounds of the present invention where Y is a 4-tetrahydropyran derivative can be prepared using 2-aryl acetonitriles 33 as starting materials as shown in Scheme 9. Alkylation of 33 with di-2-chloroethyl ether should give the 4-aryl-4-cyanotetrahydropyran 37. Further elaboration using the methods described above and by those known in the art should provide compounds of the present invention.

Scheme 9

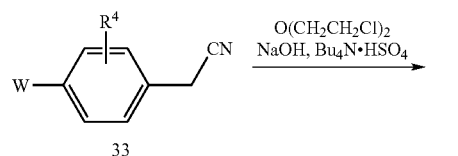

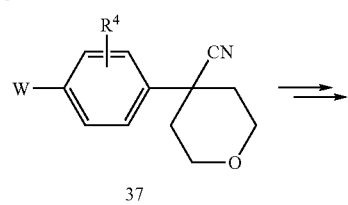

W = NH—PG, COO—PG, etc

Compounds of the present invention where Y is a lactam derivative can be prepared using intermediate 38 as the starting material as shown in Scheme 10. Reduction of the nitro or nitrile group can provide the primary amine 39, which can be coupled intramolecularly with the acid or ester to form the lactam 40. Further elaboration using the methods described above and by those known in the art should provide compounds of the present invention.

Scheme 10

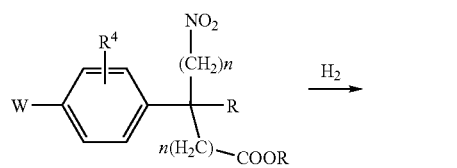

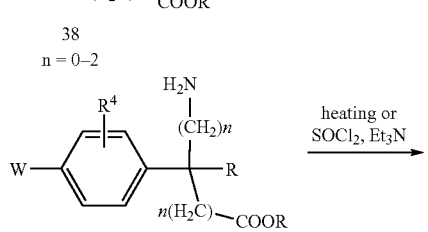

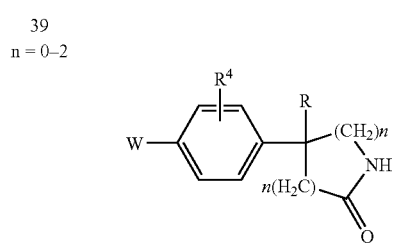

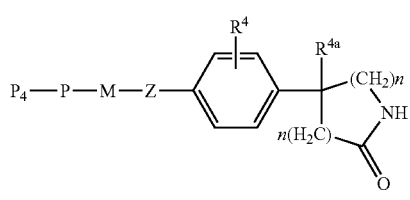

n = 0–2

W = NH—PG, COO—PG, etc

Aminopyridyl, aminopyrimidyl, cyclohexyl, and piperidinyl A-B analogs (see structures in Scheme 11) can be prepared using routes similar to those of Schemes 2-10 and by those known in the art. These intermediates can then be further manipulated to compounds of the present invention via procedures previously described.

Scheme 11

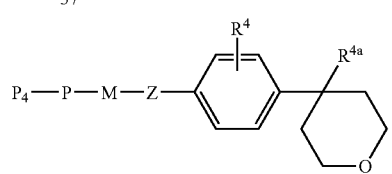

A-B                A-B

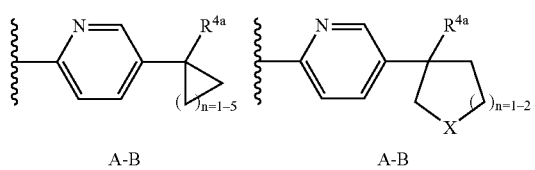

A-B                A-B

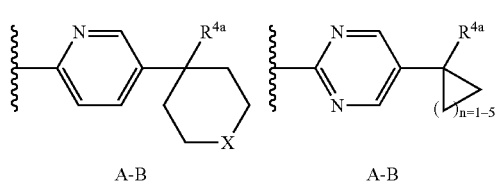

A-B

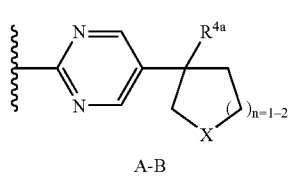

A-B                A-B

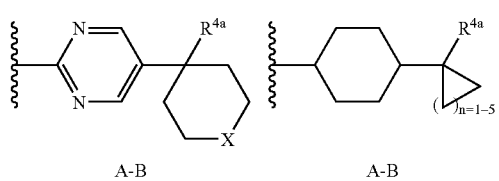

A-B

-continued

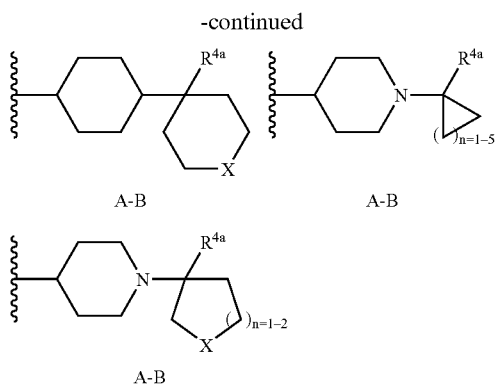

Compounds of the present invention (Scheme 1) where $R^{4a}$ is $CH_2CH_2NR^{2d}R^{2d}$ or $CH_2CONR^{2d}R^{2d}$ can be prepared as outlined in Scheme 12 and via standard methods known to those skilled in the art. The ester or nitrile intermediates 41 illustrated in Scheme 12 can be subjected to alkylation conditions, followed by other manipulations as described in Schemes 2-10 to form 42. Homologation of intermediates 42 with $TMSCHN_2$ as the reagent can afford 43. Further elaboration of 43 to form 44 and compounds of the present invention can be achieved using the methods described above and by those known in the art.

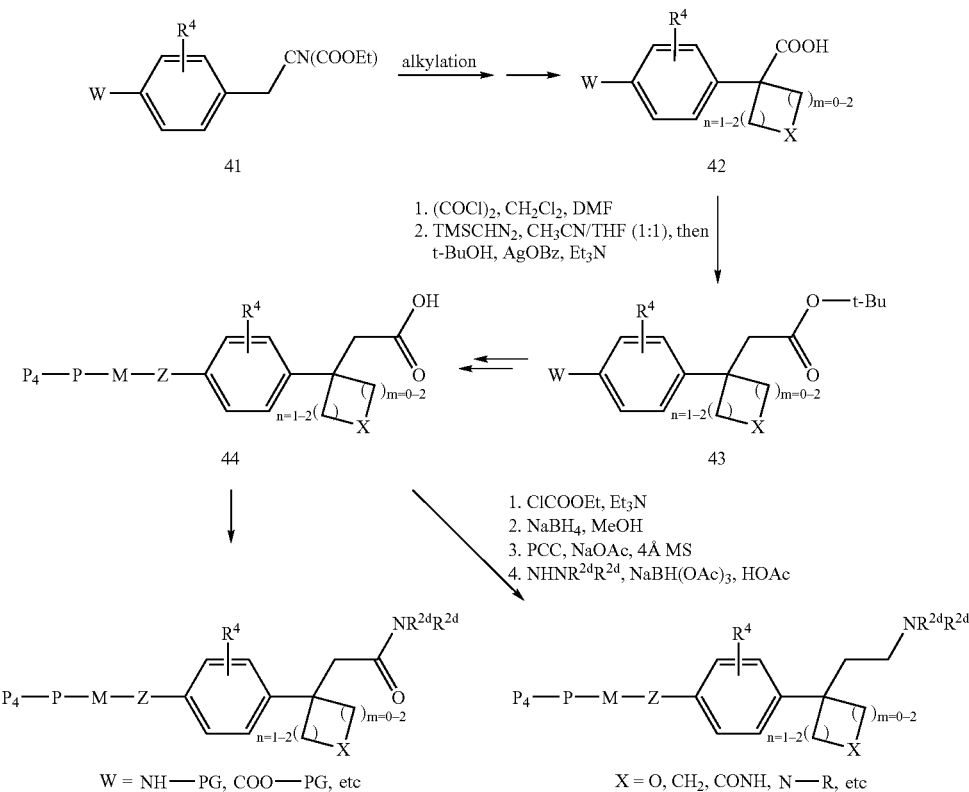

Scheme 12

-continued

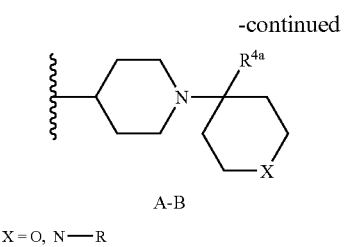

Compounds of the present invention where $R^{4a}$ is $NR^{2d}R^{2d}$ can be prepared as outlined in Scheme 13 and via standard methods known to those skilled in the art. The acid intermediates 42 illustrated in Scheme 13 can undergo Curtius rearrangement with DPPA in $CH_2Cl_2$ followed by heating in t-BuOH to afford Boc-protected cyclopropylamine intermediates 45. Alkylation of 45 with $R^{2d}$—I and NaH in THF followed by manipulations described previously should give amines 46. Reductive amination of 46 with aqueous formaldehyde and $NaBH_3CN$ in $CH_3CN$ can afford the methyl alkyl amine analogues. On the other hand, alkylation with dibromides using $K_2CO_3$ as the base can afford tertiary or cyclic amines, respectively. Further elaboration of 46 to form compounds of the present invention can be achieved using the methods described above and by those known in the art.

that other routes to the $Y^1Y^2$-disubstituted intermediates are available. The remainder of the chemistry shown in Scheme 2 will then follow. In Scheme 3, instead of use the starting 1-phenylcycloalkylcarboxylic acids or 1-phenylcycloalkyl-

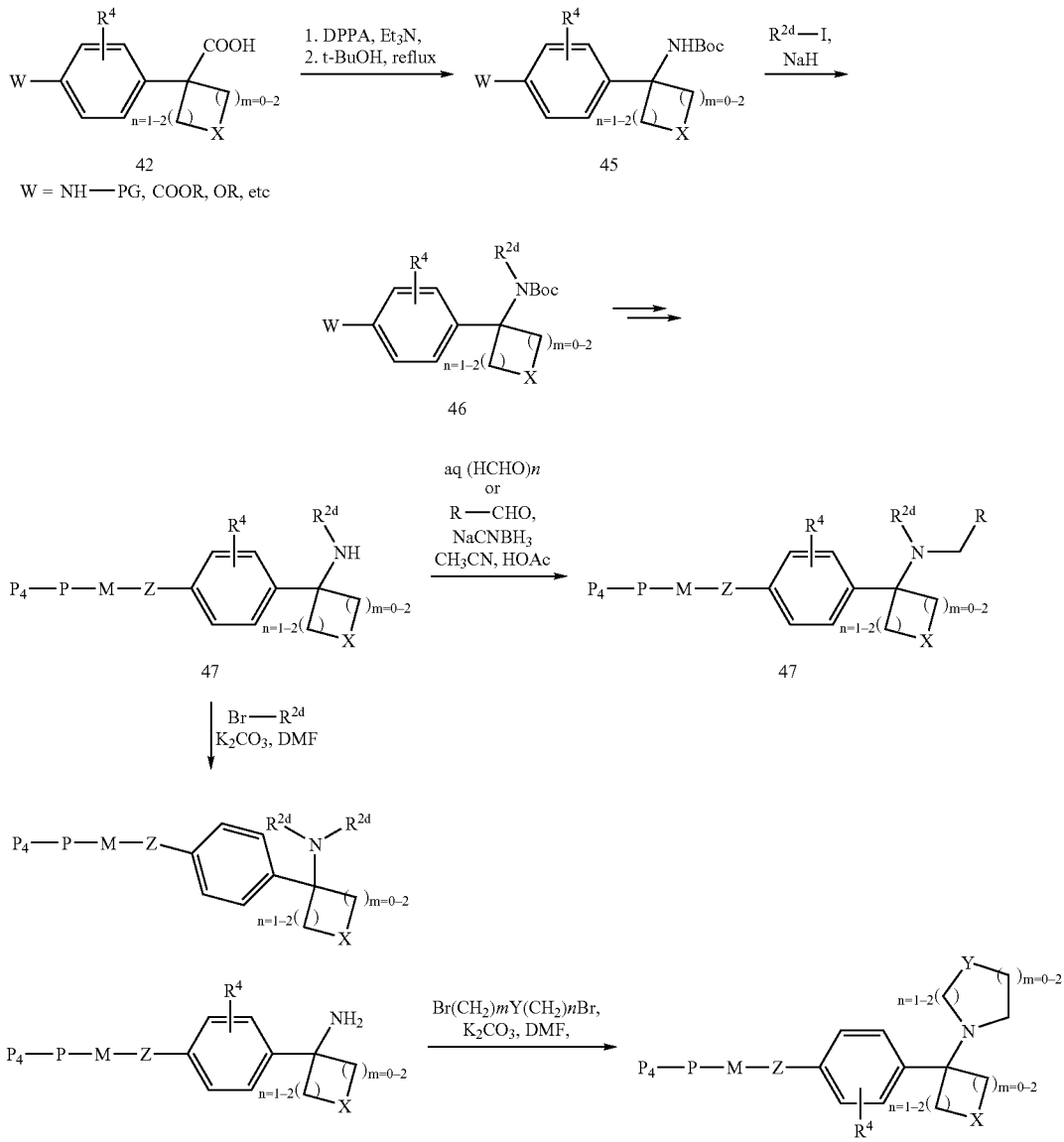

Schemes 2-13 describe how to make the A-B moieties of the present invention and how to couple them to prepare compounds of the present invention. Schemes 2-13 describe A-B wherein B is Y—$R^{4a}$ and Y is a cycloalkyl or heterocyclyl. Compounds of the present invention wherein Y is $CY^1Y^2$ can be made analogously to the cycloalkyl/heterocyclyl compounds of Schemes 2-13. For example, in Scheme 2, instead of intermediate 1 being a cycloalkyl intermediate, it can be $Y^1Y^2$ disubstituted intermediate. This intermediate could be made by a number of methods including di-substituting the starting 4-nitrophenyl-acetonitrile by reaction with a base and a $Y^1$-leaving group and a $Y^2$-leaving group. One of ordinary skill in the art would recognize carbonitriles, one could use the corresponding $Y^1Y^2$-disubstituted intermediates. As in Scheme 2, these intermediates could be prepared by di-substituting a phenylcarboxylic acid or phenylcarbonitrile. One of ordinary skill in the art would recognize that other routes to these types of $Y^1Y^2$ disubstituted intermediate are also available. The remainder of the chemistry shown in Scheme 3 will then follow.

Compounds of the present invention wherein Y is $N(B^1)$ $C(O)C(R^3R^{3g})_{1-4}NB^2B^3$ can be made as described in Schemes 14-16. Scheme 14 describes the syntheses of an A-B intermediate via Buchwald Ullmann coupling reaction (J. Am. Chem. Soc. 2001, 123, 7727) using CuI and 1,2-cyclohexyldiamine or 1,10-phenanthroline as the catalyst.

Scheme 14

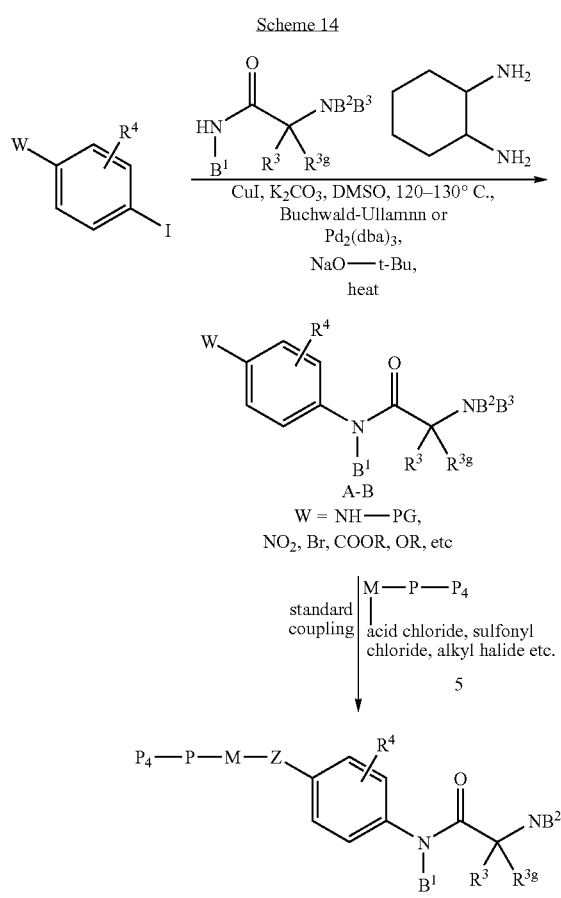

Alternatively, the A-B intermediates containing amides $NH(B^1)C(O)C(R^3R^{3g})_{1-4}NB^2B^3$ can also be prepared from readily available anilines as shown in Scheme 15.

Scheme 15

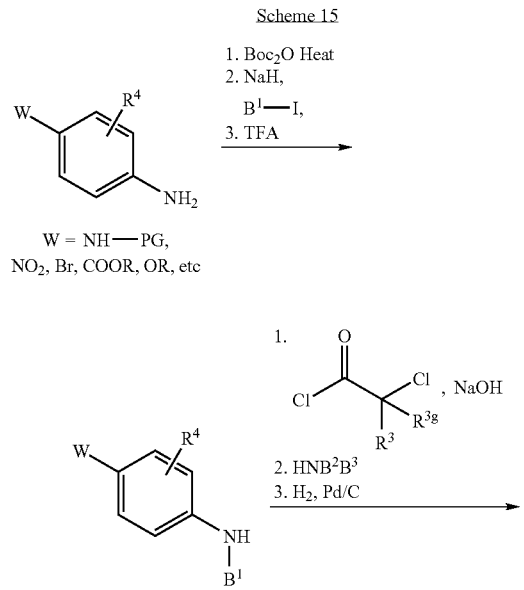

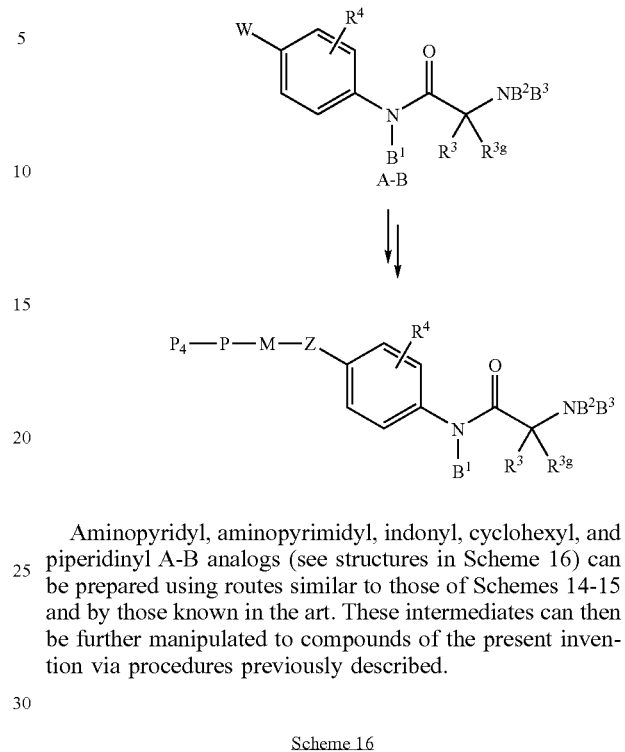

Aminopyridyl, aminopyrimidyl, indonyl, cyclohexyl, and piperidinyl A-B analogs (see structures in Scheme 16) can be prepared using routes similar to those of Schemes 14-15 and by those known in the art. These intermediates can then be further manipulated to compounds of the present invention via procedures previously described.

Scheme 16

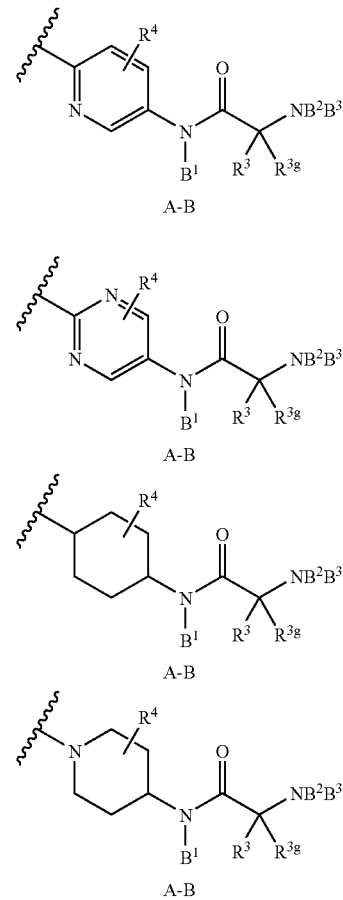

Compounds of the present invention wherein B is a cyclic phenyl amidino derivative can be prepared following the general procedure outlined in Scheme 17. Boc-protection of the aniline followed by alkylation with chloroiodo-alkane can provide the Boc-protected intermediate. Azide displacement followed by reduction and deprotection can afford the diamine compound. Reaction with ethylformate, etc. can generate the corresponding A-B intermediate. Compounds wherein $R^{4a}$ is H, alkyl, or ether can then be obtained using the methods described previously and by those known in the art.

Scheme 17

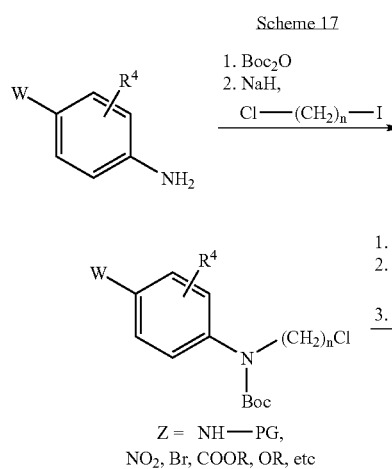

-continued

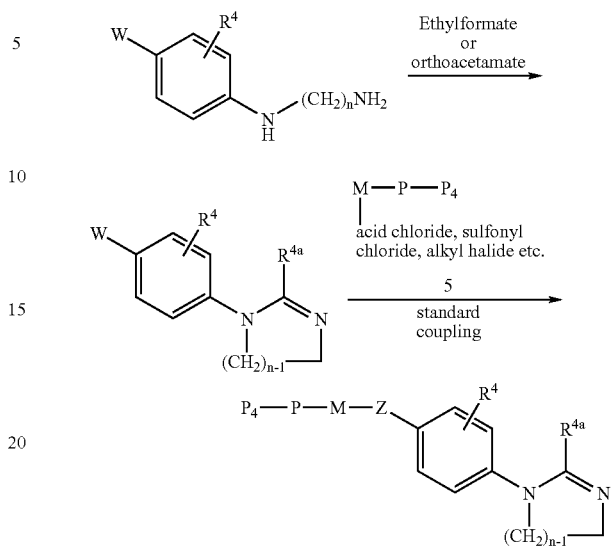

The diamino intermediate from Scheme 17 can also be transformed to an alcohol intermediate followed by treatment with $POCl_3$, $POBr_3$, $Tf_2O$, or an alkylating agent. Further manipulations of these versatile intermediates to the compounds of the present invention can be achieved using the methods described in Scheme 18 and by those known in the art.

Scheme 18

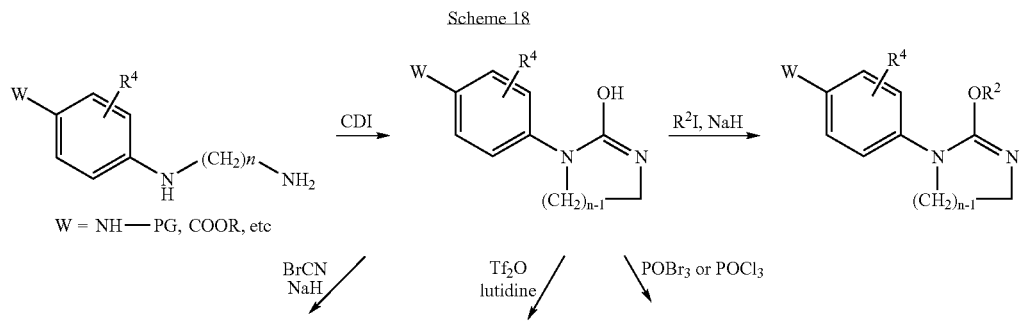

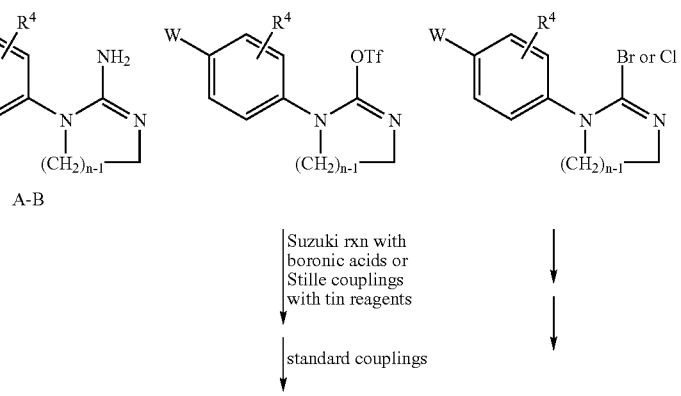

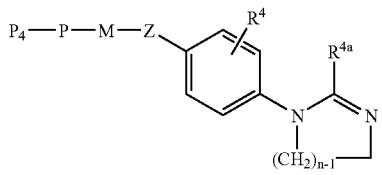

R<sup>4a</sup> = aryls or heteroaryls

The guanidino derivative from Scheme 18 can be converted to a number of compounds of the present invention by techniques known to those of skill in the art of organic synthesis, as outlined in Scheme 19.

-continued

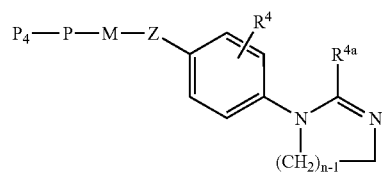

Using the methodologies outlined above, other compounds of the present invention can be obtained as shown in Scheme 20 by functional manipulations and cyclization techniques known to those of skill in the art of organic synthesis.

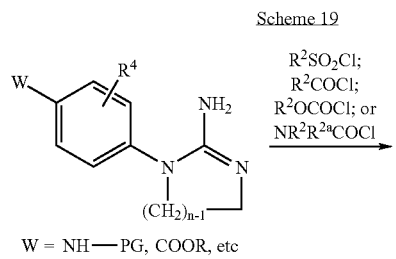

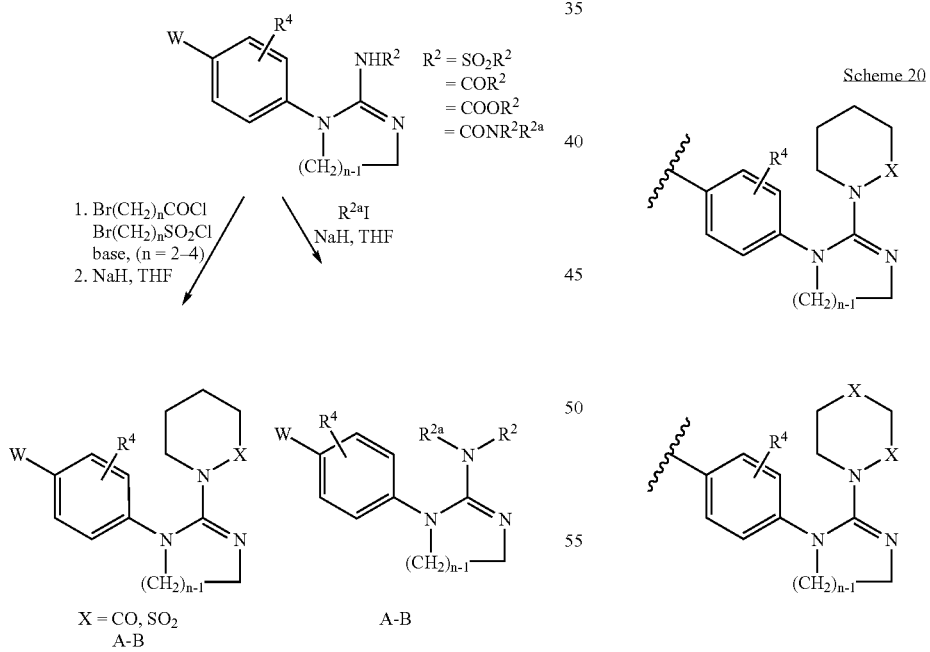

Phenylamidino-sulfonyl and -carbonyl compounds of the present invention can be obtained from the readily available amidino compounds shown in Scheme 21 below.

Scheme 21

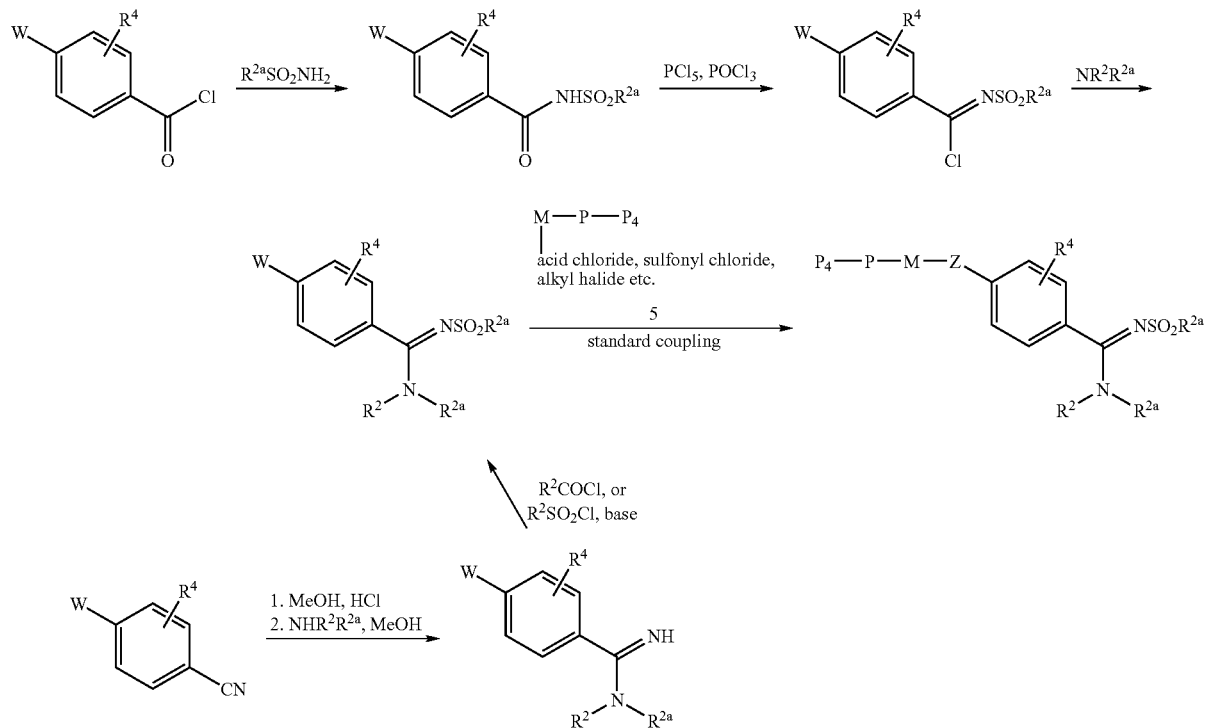

The chemistry leading to the compounds of the present invention described above can be implemented at various stages of the synthetic process. Those knowledgeable in the art may decide to prepare various sulfonyl, carbonylamidino, or suitably protected cyclic amidino intermediates and couple these via known techniques to various templates described herein to afford compounds of the present invention.

The compounds of this invention and the intermediates described above wherein the B group contains an oxidizable group can be oxidized, e.g., N to N-oxide.

The functionalized G moiety of the present invention can be commercially available or can be prepared using methods known to those of ordinary skill in the art. All of the following patents and publications are incorporated herein by reference. For compounds wherein G is a ring substituted with a basic moiety, one of ordinary skill in the art can look to U.S. Pat. Nos. 5,939,418, 5,925,635, 6,057,342, 6,187,797, 6,020,357, 6,060,491, 6,191,159, WO98/57951, WO99/32454 WO00/059902, WO01/32628, WO00/39131, WO02/00651, WO02/102380, WO02/094197, USPA 2003/0078255, and USPA 2003/0018023 for starting materials. For compounds wherein G is a ring substituted with a non-basic group, one of ordinary skill in the art can look to U.S. Pat. No. 5,998,424, WO00/39131, WO00/059902, WO01/32628, WO02/00651, WO02/102380, WO02/094197, USPA 2003/0078255, and USPA 2003/0018023 for starting materials. For compounds wherein G is a bicyclic moiety, one of ordinary skill in the art can look to WO98/57951 WO00/039108, WO00/39131, WO02/00651, WO02/102380, WO02/094197, USPA 2003/0078255, and USPA 2003/0018023 for starting materials. For compounds wherein A is an indoline or similar bicycle, one of ordinary skill in the art can look to WO01/005785 for starting materials and intermediates to which the present B group can be coupled or from which the present A-B groups can be formed.

Compounds of the type where G is phenyl substituted with 0-2 R and 1-2 $R^a$ and M is fused pyrazolo compound may be synthesized as shown in Scheme 22.

Scheme 22

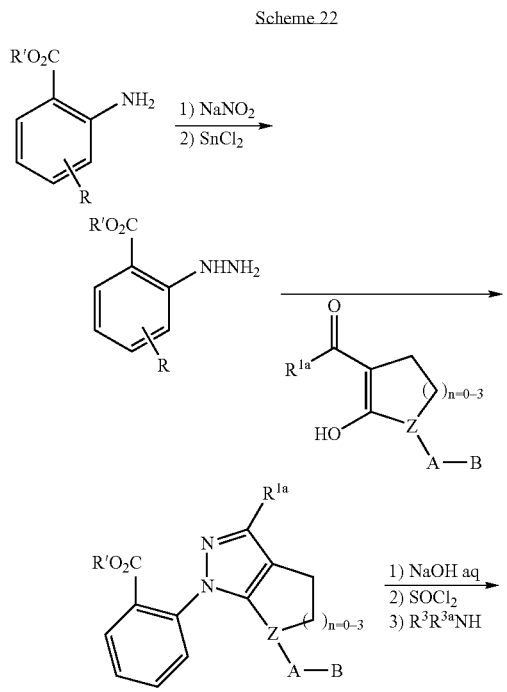

-continued

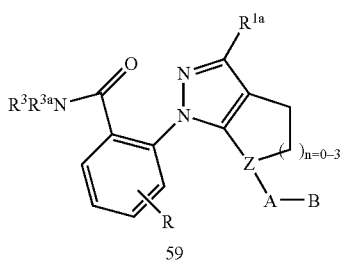

59

Additional compounds may be accessed where the pyrazole moiety is replaced by other heterocycles are described in WO 00/39131 and WO 03/26652.

Scheme 23 describes the synthesis of phenyl substituted pyrazoles. Additional examples may be found in WO 98/57951 and WO 99/32454.

Scheme 23

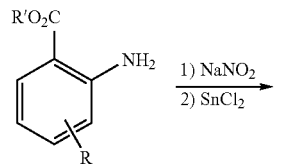

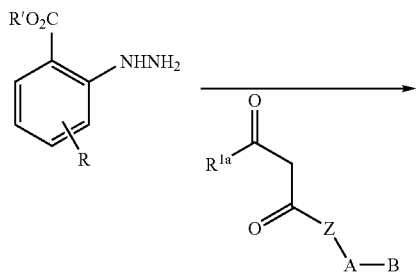

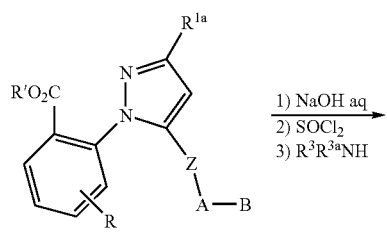

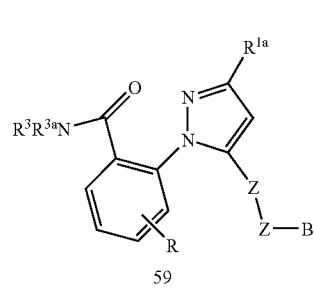

59

Compounds of the type where G is phenyl substituted with 0-2 R and 1-2 $R^a$ and M is phenyl may be synthesized as shown in Scheme 24 for carboxamides and Scheme 25 for sulfonamides.

Scheme 24

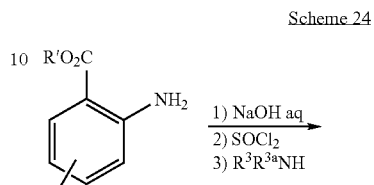

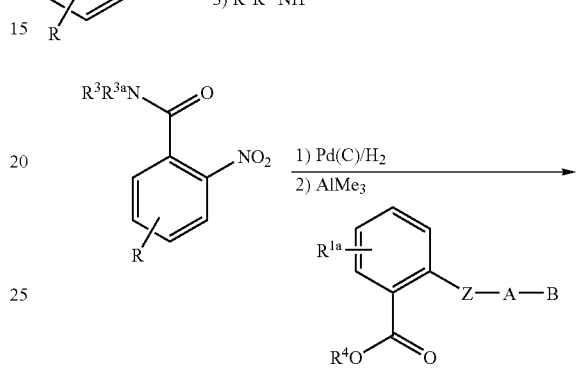

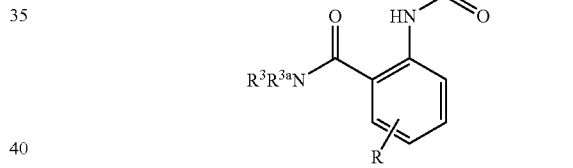

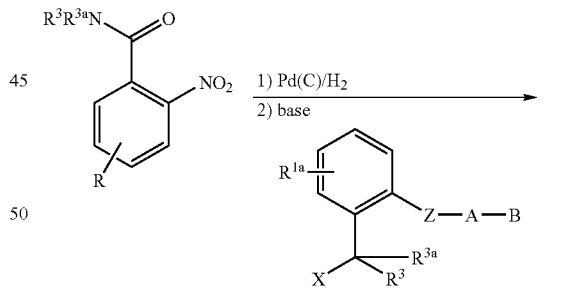

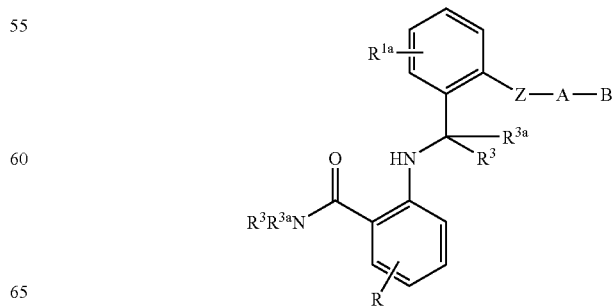

Scheme 25

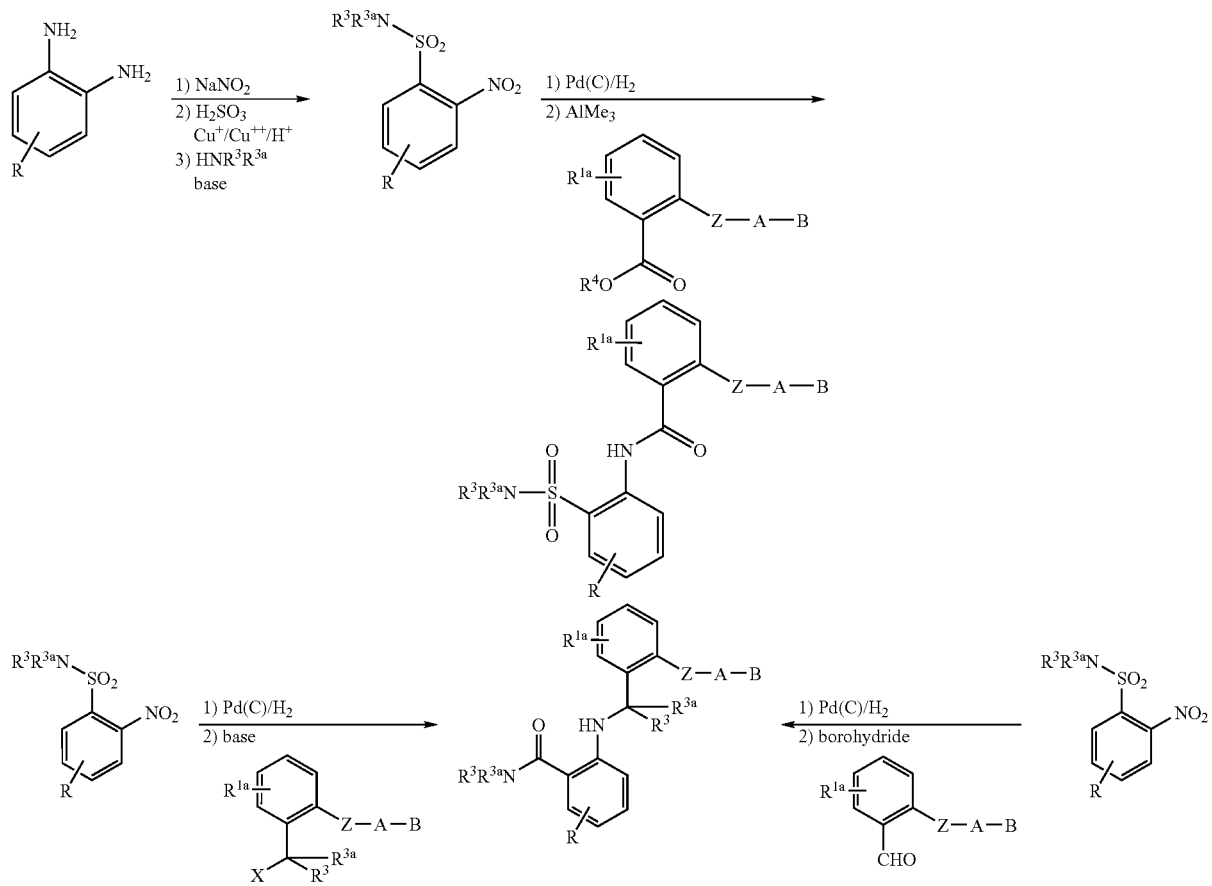

One stereoisomer of a compound of Formula I may display superior activity compared with the other. Thus, compounds of the present invention may be chiral and accordingly in various enantiomeric forms. They therefore may exist in racemic or in optically active form. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis. An enantiomerically pure compound can be obtained with enantiomerically pure starting materials. Alternately, single stereoisomers can be obtained by chiral synthesis known to the person with skills in the art.

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nm. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2-0.5 nM human factor Xa (Enzyme Research Laboratories, South Bend, Ind.) to react with the substrate (0.20 mM-1 mM) in the presence of inhibitor. Reactions were allowed to go for 30 min and the velocities (rate of absorbance change vs. time) were measured in the time frame of 25-30 min. The following relationship was used to calculate $K_i$ values:

$$(v_o - v_s)/v_s = I/(K_i(1+S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289-18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin, for example LOVENOX™), synthetic pentasaccharide, direct acting thrombin inhibitors including hirudin and argatrobanas, factor VIIa, IXa, XIa inhibitors, well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid-dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of The present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of The present invention and about 50 to 150 milligrams of the anti-platelet agent, preferably about 0.1 to 1 milligrams of the compound of The present invention and about 1 to 3 milligrams of antiplatelet agents, per kilogram of patient body weight.

Where the compounds of The present invention are administered in combination with thrombolytic agent, typically a daily dosage may be about 0.1 to 1 milligrams of the compound of The present invention, per kilogram of patient body weight and, in the case of the thrombolytic agents, the usual dosage of the thrombolyic agent when administered alone may be reduced by about 70-80% when administered with a compound of The present invention.

Where two or more of the foregoing second therapeutic agents are administered with the compound of The present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of The present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

2-[6-(2'-methanesulfonyl-biphenyl-4-yl)-7-oxo-3-trifluoromethyl-4,5,6,7-tetrahydro-pyrazolo[3,4-c]pyridin-1-yl]-5-methoxy-benzamide

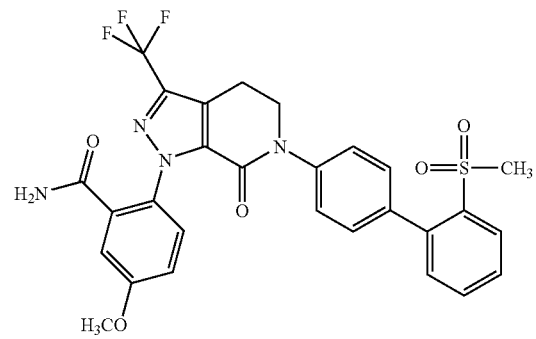

Part A: To a 0° C. solution of 5-methoxyanthranilic acid (5.0 g, 29.9 mmol) in concentrated hydrochloric acid (10 mL) was added dropwise an ice cold solution of sodium nitrite (2.06 g, 29.9 mmol) in water (5 mL) and stirring was continued at 0° C. for 30 minutes. Stannous chloride dihydrate (16.8 g, 74.8 mmol) was dissolved in concentrated hydrochloric acid (16 mL), cooled to 0° C., and added slowly to the solution of the diazonium salt. The precipitate was agitated, kept at 0° C. for 30 minutes, and then filtered. The solids were washed successively with ice cold brine and petroleum ether and dried under a stream of air and then under vacuum. The crude hydrazine salt and 3-hydroxy-1-(4-iodo-phenyl)-4-(2,2,2-trifluoro-acetyl)-5,6-dihydro-1H-pyridin-2-one (12.3 g, 29.9 mmol) were combined in glacial acetic acid (50 mL) and heated to 80° C. Upon completion of the reaction the solvent was evaporated to a viscous oil which was subjected to silica gel column chromatography to yield 2-[6-(4-iodo-phenyl)-7-oxo-3-trifluoromethyl-4,5,6,7-tetrahydro-pyrazolo[3,4-c]pyridin-1-yl]-5-methoxy-benzoic acid methyl ester (4.12 g, 24%). MS (AP+) 571.9 (100%).

Part B: 2-[6-(4-Iodo-phenyl)-7-oxo-3-trifluoromethyl-4,5,6,7-tetrahydro-pyrazolo[3,4-c]pyridin-1-yl]-5-methoxy-benzoic acid methyl ester (2.00 g, 3.50 mmol), 2-(methylthio)phenylboronic acid (647 mg, 3.85 mmol), bis(triphenylphosphine)palladium(II) chloride (122 mg, 0.175 mmol), tetrabutylammonium bromide (56 mg, 0.175 mmol), and sodium carbonate (1.11 g, 10.5 mmol) were combined, the flask purged with argon and degassed benzene (50 mL) and water (5 mL) were added. The flask was heated to reflux for 14 h, cooled to ambient temperature, and poured into ethyl acetate/water. The phases were separated and the aqueous phase extracted once with ethyl acetate. The organic phases were combined, dried over sodium sulfate, filtered, and evaporated. The crude 5-methoxy-2-[6-(2'-methylsulfanyl-biphenyl-4-yl)-7-oxo-3-trifluoromethyl-4,5,6,7-tetrahydro-pyrazolo[3,4-c]pyridin-1-yl]-benzoic acid methyl ester was dissolved in dichloromethane (50 mL) and meta-chloroperbenzoic acid (2.41 g, 70%, 9.8 mmol) was added as a solid. Upon completion the reaction was poured into water (50 mL), and sodium sulfite was added until the aqueous layer tested negative to starch/potassium iodide paper. The phases were separated, and the organic was washed once with sodium bicarbonate, dried over sodium sulfate, filtered, and evaporated. The solid was subjected to silica gel column chromatography to yield 2-[6-(2'-methanesulfonyl-biphenyl-4-yl)-7-oxo-3-trifluoromethyl-4,5,6,7-tetrahydro-pyrazolo[3,4-c]pyridin-1-yl]-5-methoxy-benzoic acid methyl ester (1.70 g, 81%) as a colorless solid. This material (1.69 g, 2.81 mmol) was stirred in dioxane (15 mL) and 10% sodium hydroxide (15 mL). The reaction was acidified with concentrated hydrochloric acid to pH 3 and extracted with ethyl acetate (3×10 mL). The combined extracts were washed with water (5×10 mL), dried over sodium sulfate, filtered, and evaporated. 2-[6-(2'-Methanesulfonyl-biphenyl-4-yl)-7-oxo-3-trifluoromethyl-4,5,6,7-tetrahydro-pyrazolo[3,4-c]pyridin-1-yl]-5-methoxy-benzoic acid was isolated as a colorless solid in nearly quantitative yield. This material (59.2 mg, 0.101 mmol) was dissolved in dry chloroform (3 mL) to which was added thionyl chloride (37 μL, 0.505 mmol), and the reaction heated to reflux. The solvent was evaporated, and the residue dried under vacuum to give 2-[6-(2'-methanesulfonyl-biphenyl-4-yl)-7-oxo-3-trifluoromethyl-4,5,6,7-tetrahydro-pyrazolo[3,4-c]pyridin 1-yl]-5-methoxy-benzoyl chloride.

Part C: 2-[6-(2'-Methanesulfonyl-biphenyl-4-yl)-7-oxo-3-trifluoromethyl-4,5,6,7-tetrahydro-pyrazolo[3,4-c]pyridin-1-yl]-5-methoxy-benzoyl chloride (0.10 mmol) was dissolved in dry dichloromethane (1 mL) under a nitrogen atmosphere, and a stream of ammonia gas was introduced for 30 sec. The solvent was evaporated, and the residue was purified by reverse phase HPLC to give the title compound as a colorless solid. MS (ES+) 607.1 (M+Na)⁺(100%); $^1$H NMR (DMSO-$d_6$) δ 8.08 (d, 1H, J=6.6 Hz), 7.79-7.34 (m, 10H), 7.16 (d, 1H, J=2.9 Hz), 7.09 (dd, 1H, J=8.5, 2.6), 4.11 (t, 2H, J=6.4 Hz), 3.84 (s, 3H), 3.11 (t, 2H, J=6.4), 2.81 (s, 3H).

Example 2

2-[6-(2'-Methanesulfonyl-biphenyl-4-yl)-7-oxo-3-trifluoromethyl-4,5,6,7-tetrahydro-pyrazolo[3,4-c]pyridin-1-yl]-benzamide

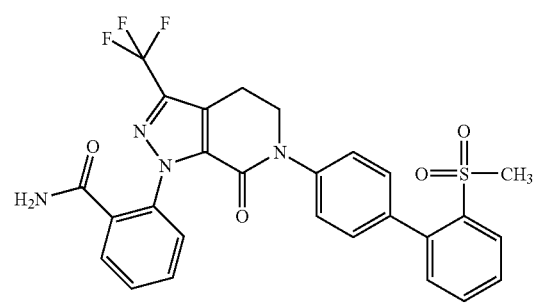

The title compound was synthesized from 2-aminobenzoic acid methyl ester in an analogous manner to Example 1. MS (ES+) 555.1 (M+H)⁺(100%).

Examples 3-32

The compounds shown in Table 1 (examples 3-32) were prepared in an analogous manner to Example 1 employing the general procedure (Example 1, part C) and substituting the appropriate amine.

TABLE 1

| Ex. | Structure | MF | MS:(M + H)⁺ |
|---|---|---|---|
| 3 | 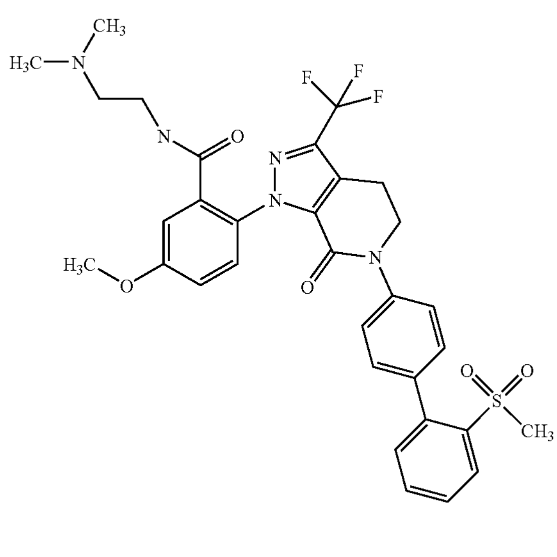 | $C_{32}H_{32}F_3N_5O_5S$ | 656.2 |

TABLE 1-continued

| Ex. | Structure | MF | MS:(M + H)+ |
|---|---|---|---|
| 4 | 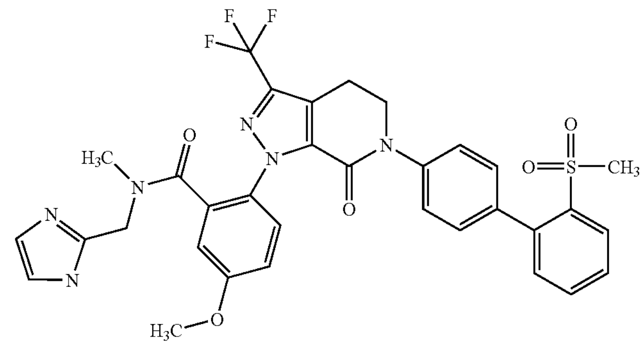 | $C_{33}H_{29}F_3N_6O_5S$ | 679.2 |
| 5 | 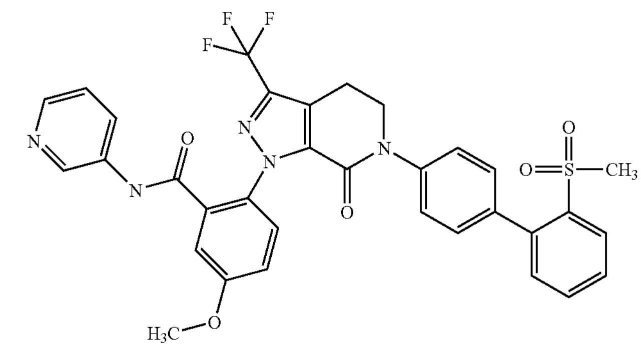 | $C_{33}H_{26}F_3N_5O_5S$ | 662.2 |
| 6 | 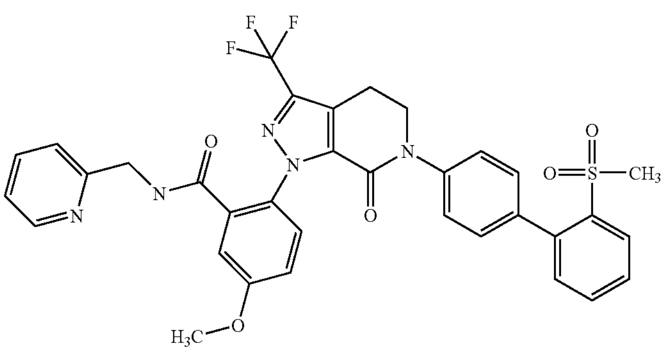 | $C_{34}H_{28}F_3N_5O_5S$ | 676.2 |
| 7 | 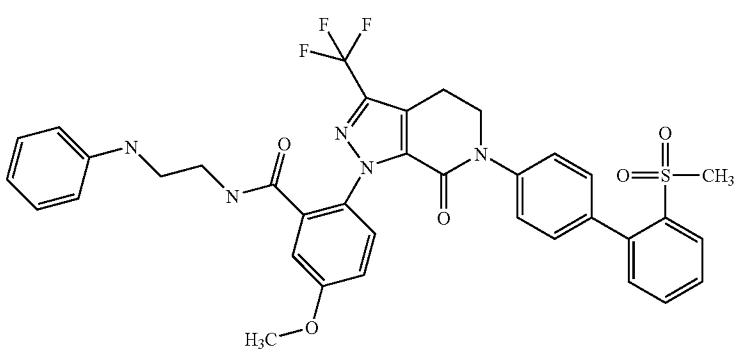 | $C_{36}H_{32}F_3N_5O_5S$ | 704.2 |

TABLE 1-continued

| Ex. | Structure | MF | MS:(M + H)+ |
|---|---|---|---|
| 8 | 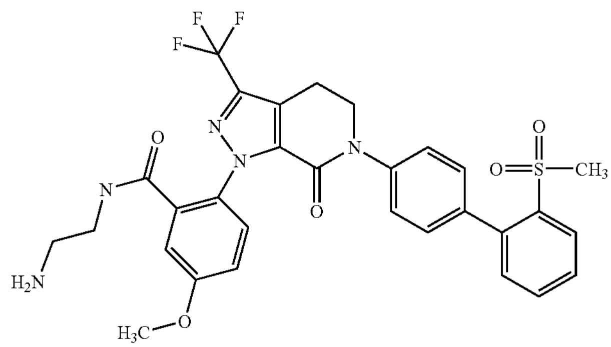 | $C_{30}H_{28}F_3N_5O_5S$ | 628.2 |
| 9 | 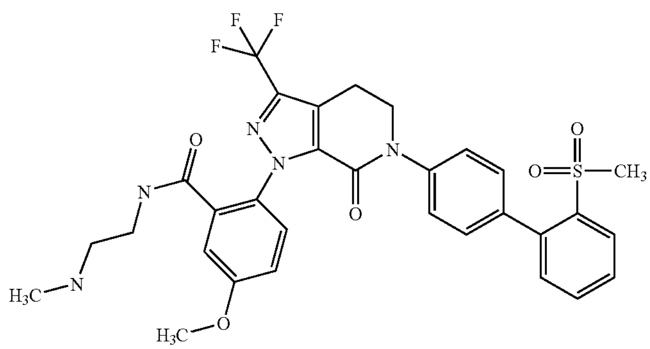 | $C_{31}H_{30}F_3N_5O_5S$ | 642.2 |
| 10 | 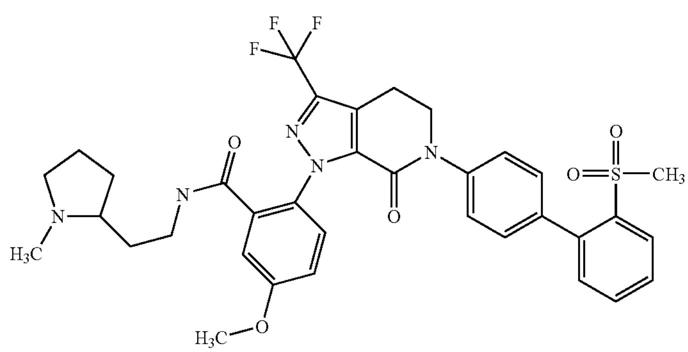 | $C_{35}H_{36}F_3N_5O_5S$ | 696.2 |
| 11 | 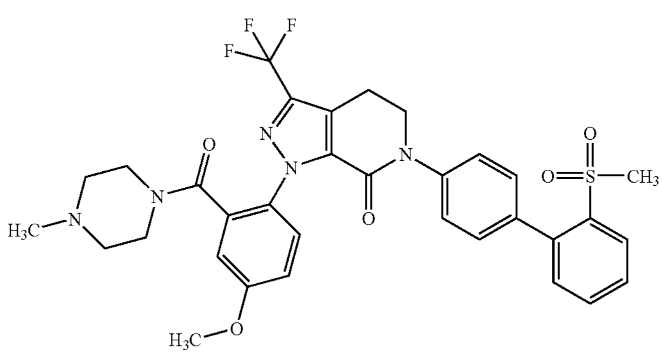 | $C_{33}H_{32}F_3N_5O_5S$ | 668.2 |

TABLE 1-continued

| Ex. | Structure | MF | MS:(M + H)+ |
|---|---|---|---|
| 12 | 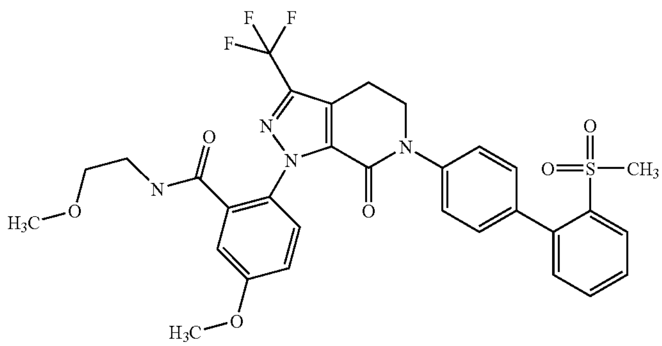 | $C_{31}H_{29}F_3N_4O_6S$ | 643.2 |
| 13 | 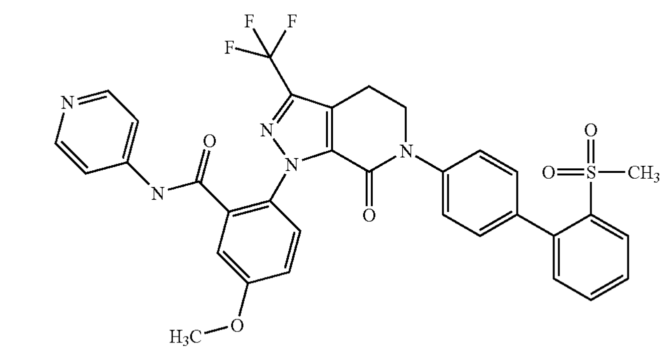 | $C_{33}H_{26}F_3N_5O_5S$ | 662.2 |
| 14 | 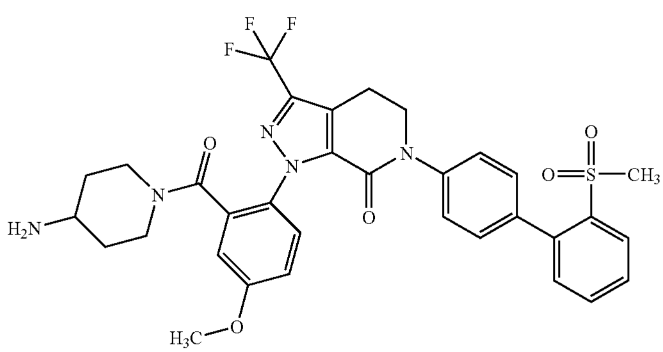 | $C_{33}H_{32}F_3N_5O_5S$ | 668.2 |
| 15 | 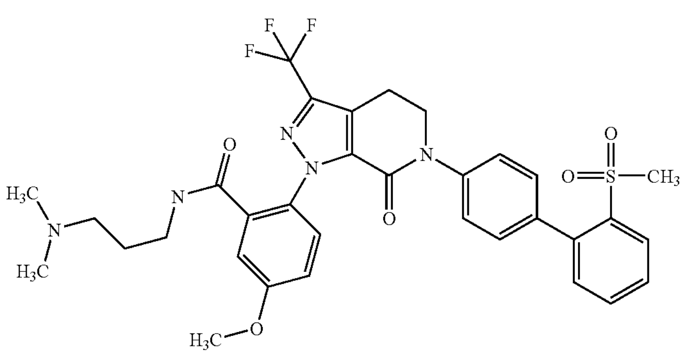 | $C_{33}H_{34}F_3N_5O_5S$ | 670.2 |

TABLE 1-continued

| Ex. | Structure | MF | MS:(M + H)+ |
|---|---|---|---|
| 16 | 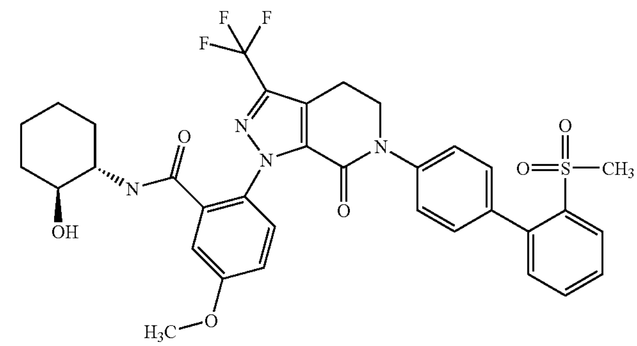 | $C_{34}H_{33}F_3N_4O_6S$ | 683.2 |
| 17 | 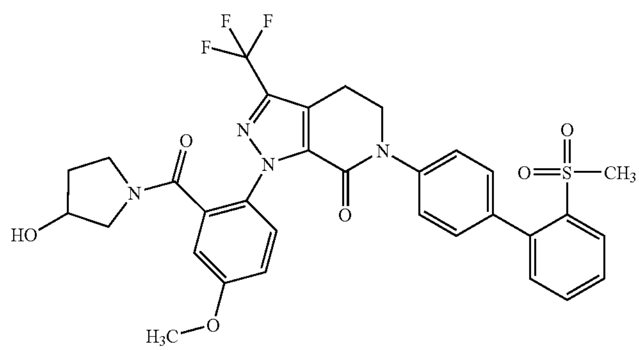 | $C_{32}H_{29}F_3N_4O_6S$ | 655.2 |
| 18 | 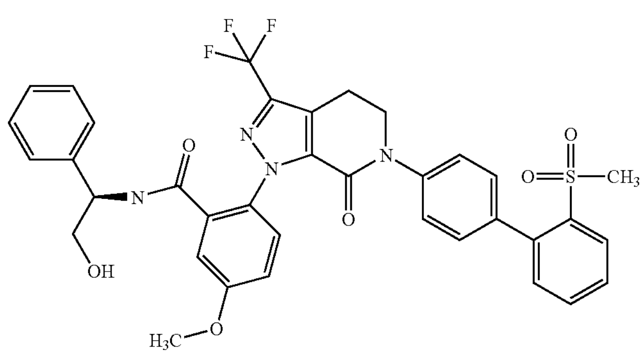 | $C_{36}H_{31}F_3N_4O_6S$ | 705.2 |
| 19 | 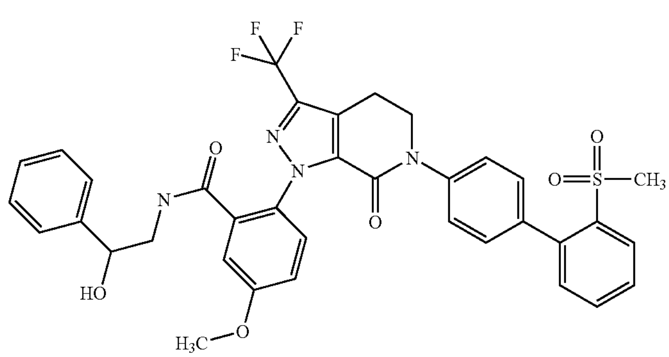 | $C_{36}H_{31}F_3N_4O_6S$ | 705.2 |

TABLE 1-continued
| Ex. | Structure | MF | MS:(M + H)+ |
|---|---|---|---|
| 20 | 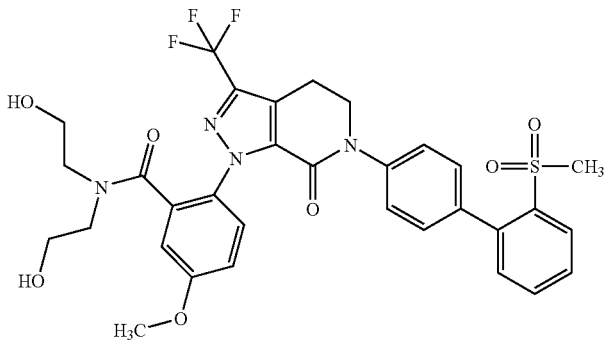 | $C_{32}H_{31}F_3N_4O_7S$ | 673.2 |
| 21 | 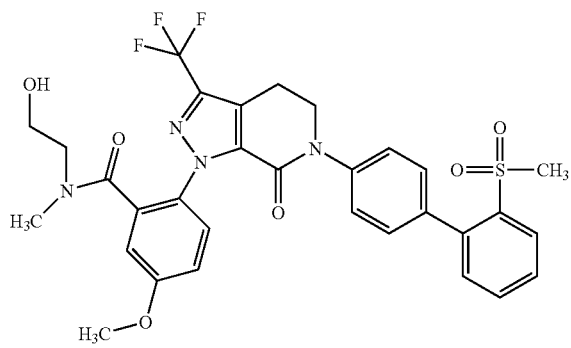 | $C_{31}H_{29}F_3N_4O_6S$ | 643.2 |
| 22 | 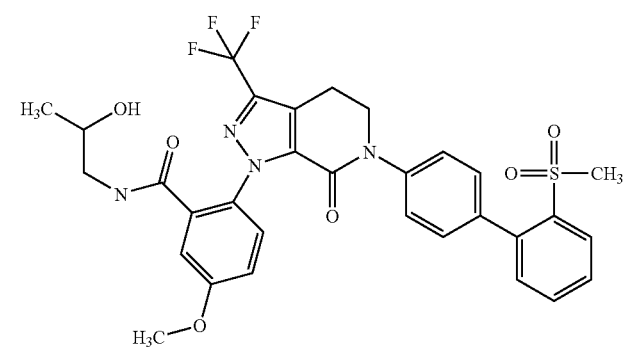 | $C_{31}H_{29}F_3N_4O_6S$ | 643.2 |
| 23 | 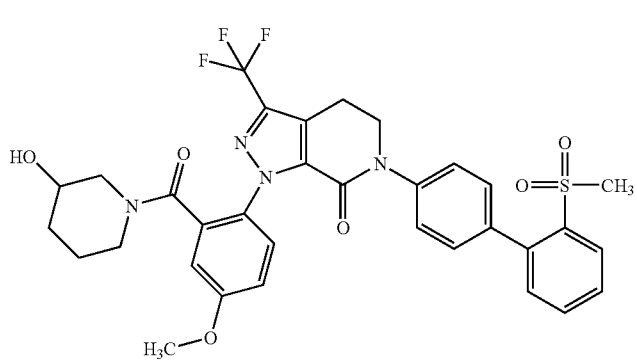 | $C_{33}H_{31}F_3N_4O_6S$ | 669.2 |

TABLE 1-continued

| Ex. | Structure | MF | MS:(M + H)+ |
|---|---|---|---|
| 24 | 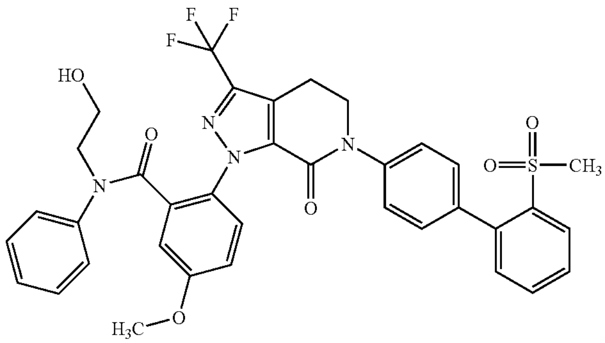 | $C_{36}H_{31}F_3N_4O_6S$ | 705.2 |
| 25 | 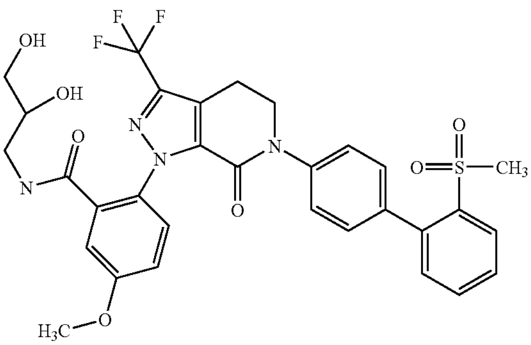 | $C_{31}H_{29}F_3N_4O_7S$ | 659.2 |
| 26 | 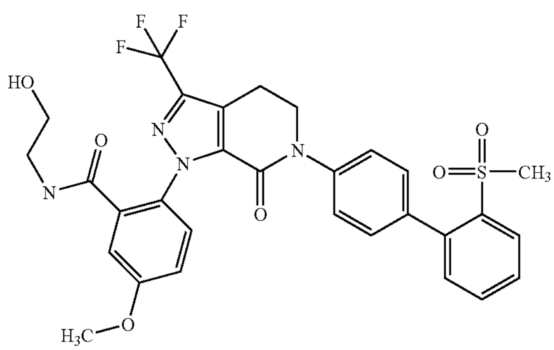 | $C_{30}H_{27}F_3N_4O_6S$ | 629.2 |
| 27 | 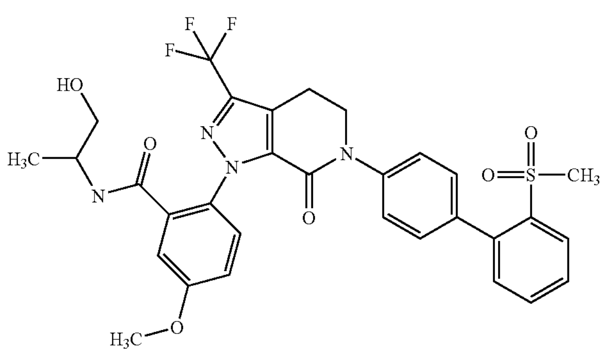 | $C_{31}H_{29}F_3N_4O_6S$ | 643.2 |

TABLE 1-continued

| Ex. | Structure | MF | MS:(M + H)+ |
|---|---|---|---|
| 28 | 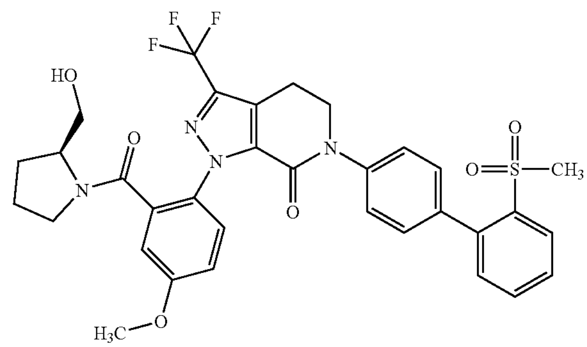 | $C_{33}H_{31}F_3N_4O_6S$ | 669.2 |
| 29 | 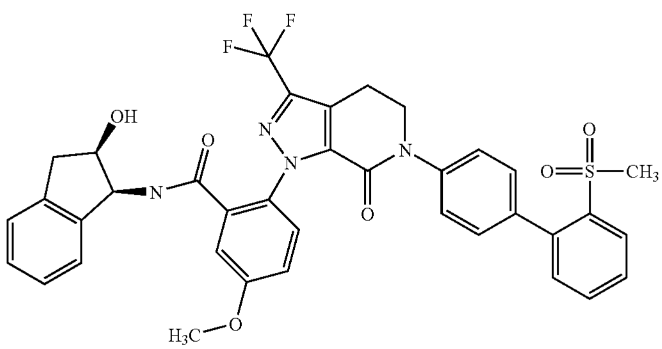 | $C_{37}H_{31}F_3N_4O_6S$ | 717.2 |
| 30 | 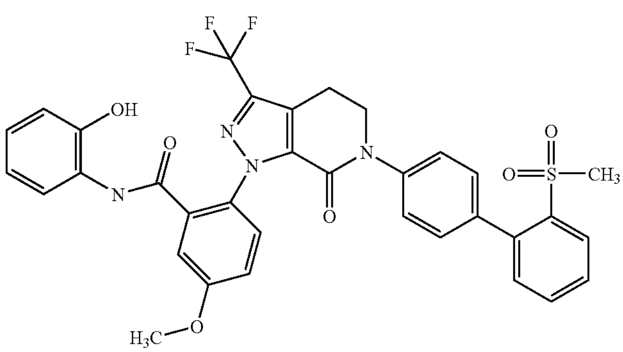 | $C_{34}H_{27}F_3N_4O_6S$ | 677.2 |
| 31 | 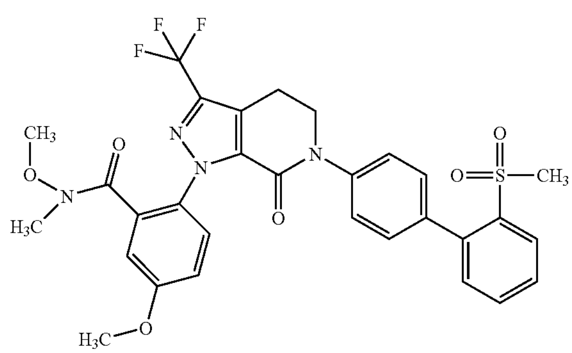 | $C_{30}H_{27}F_3N_4O_6S$ | 629.2 |

| Ex. | Structure | MF | MS:(M + H)+ |
|---|---|---|---|
| 32 | 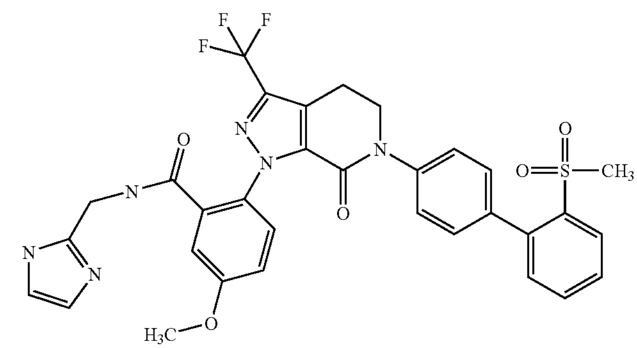 | C₃₂H₂₇F₃N₆O₅S | 665.2 |

Example 33

5-Methoxy-N-[2-(1-methyl-pyrrolidin-2-yl)-ethyl]-2-{7-oxo-6-[4-(2-oxo-2H-pyridin-1-yl)phenyl]-3-trifluoromethyl-4,5,6,7-tetrahydro-pyrazolo[3,4-c]pyridin-1-yl}-benzamide, trifluoroacetic acid salt

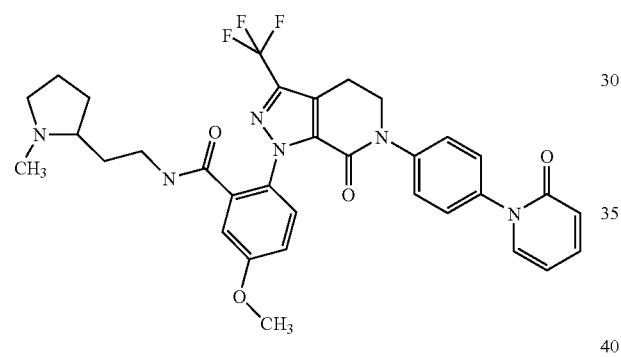

The title compound was prepared from 2-[6-(4-iodo-phenyl)-7-oxo-3-trifluoromethyl-4,5,6,7-tetrahydro-pyrazolo[3,4-c]pyridin-1-yl]-5-methoxy-benzoic acid methyl ester as obtained in Example 1. The ester (159 mg, 0.278 mmol) was dissolved in ethylene glycol (2 mL) containing 2-(1-methyl-pyrrolidin-2-yl)-ethylamine (400 μL, 2.78 mmol) and heated to 85° C. for 12 h. The reaction was poured into water and extracted with ethyl acetate (3×10 mL). The combined extracts were washed with water (5×10 mL), dried over sodium sulfate, filtered, and evaporated. The residue was purified by preparative thin layer chromatography to give 2-[6-(4-iodo-phenyl)-7-oxo-3-trifluoromethyl-4,5,6,7-tetrahydro-pyrazolo[3,4-c]pyridin-1-yl]-5-methoxy-N-[2-(1-methyl-pyrrolidin-2-yl)-ethyl]-benzamide (60 mg, 32%) as a faint yellow solid. MS (ES+) 668.4 (M+H)+ (100%). This material (60 mg, 0.089 mmol) was combined with 2-pyridone (17 mg, 0.18 mmol), anhydrous potassium carbonate (49 mg, 0.36 mmol), copper(I) iodide (3.4 mg, 0.018 mmol), 1,10-phenanthroline (3.2 mg, 0.018 mmol), and dry-degassed dimethylsulfoxide (1.0 mL) and heated to 140° C. for 6 h. The mixture was cooled to ambient temperature and diluted with 6N ammonium hydroxide and ethyl acetate. The phases were separated, and the aqueous phase extracted once with ethyl acetate. The combined organic extracts were washed successively with water (2×) and 3N ammonium hydroxide, dried over sodium sulfate, filtered, and evaporated. The residue was purified by preparative HPLC to give the title compound as a colorless solid. MS (ES+) 635.5 (M+H)+(100%).

Example 34

2-[6-(4-Iodo-phenyl)-7-oxo-3-trifluoromethyl-4,5,6,7-tetrahydro-pyrazolo[3,4-c]pyridin-1-yl]-5-methoxy-N-pyridin-3-yl-benzamide The title compound was prepared from 2-[6-(4-iodo-phenyl)-7-oxo-3-trifluoromethyl-4,5,6,7-tetrahydro-pyrazolo[3,4-c]pyridin-1-yl]-5-methoxy-benzoic acid methyl ester as obtained in Example 1. The ester (270 mg, 0.47 mmol) was stirred in tetrahydrofuran (1 mL) and 10% sodium hydroxide (1 mL) for 5 h. The reaction was acidified with 1N hydrochloric acid to pH 3 and extracted with ethyl acetate (3×5 mL). The combined extracts were washed with water (2×5 mL), dried over sodium sulfate, filtered, and evaporated to give 2-[6-(4-iodo-phenyl)-7-oxo-3-trifluoromethyl-4,5,6,7-tetrahydro-pyrazolo[3,4-c]pyridin-1-yl]-5-methoxy-benzoic acid (263 mg, 100%) as a colorless solid. The acid (263 mg, 0.47 mmol) was dissolved in dimethylformamide (3 mL) to which were added triethylamine (233 mL, 1.68 mmol) and 3-aminopyridine (54 mg, 0.58 mmol). After 10 minutes benzotriazol-1-yloxytris(dimethylamino) phosphonium hexafluorophosphate (BOP reagent) was added and stirring continued for 24 hr. The reaction was poured into ethyl acetate/water, and the phases were separated. The aqueous was extracted twice with ethyl acetate. The combined organics were washed with water (4×) and once with brine, dried over sodium sulfate, filtered, and evaporated to give 278 mg (91%) of a light orange colored solid. The material was purified by preparative HPLC to give the title compound as a colorless solid. MS (ES+) 634.0 (M+H)+(100%).

Example 35

5-Methoxy-2-(7-oxo-6-phenyl-3-trifluoromethyl-4,5,6,7-tetrahydro-pyrazolo[3,4-c]pyridin-1-yl)-N-pyridin-3-yl-benzamide

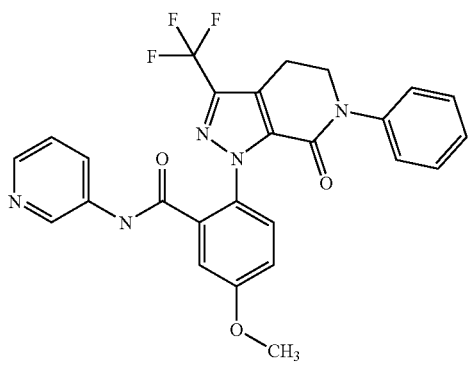

2-[6-(4-Iodo-phenyl)-7-oxo-3-trifluoromethyl-4,5,6,7-tetrahydro-pyrazolo[3,4-c]pyridin-1-yl]-5-methoxy-N-pyridin-3-yl-benzamide (15 mg, 0.023 mmol) was combined with 5% palladium on carbon and stirred in ethanol under 1 atmosphere of hydrogen for 12 h. The reaction mixture was filtered through diatomaceous earth and the solvent evaporated to give the title compound (11 mg, 95%) as a colorless solid. MS (ES+) 508.0 (M+H)+(100%).

Example 36

N-(1H-Imidazol-2-ylmethyl)-2-[6-(4-iodo-phenyl)-7-oxo-3-trifluoromethyl-4,5,6,7-tetrahydro-pyrazolo[3,4-c]pyridin-1-yl]-5-methoxy-benzamide, bis-trifluoroacetic acid salt

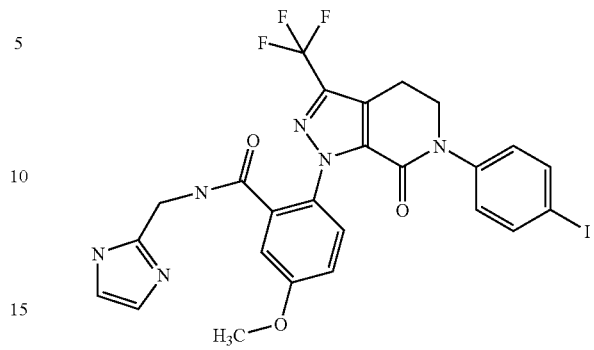

2-[6-(4-Iodo-phenyl)-7-oxo-3-trifluoromethyl-4,5,6,7-tetrahydro-pyrazolo[3,4-c]pyridin-1-yl]-5-methoxy-benzoic acid (186 mg, 0.334 mmol) was dissolved in dry chloroform (10 mL) to which was added thionyl chloride (243 µL, 3.34 mmol), and the reaction heated to reflux. The solvent was evaporated, and the residue dried under vacuum to give 2-[6-(4-iodo-phenyl)-7-oxo-3-trifluoromethyl-4,5,6,7-tetrahydro-pyrazolo[3,4-c]pyridin-1-yl]-5-methoxy-benzoyl chloride as a pale yellow foam. This material was dissolved in dry methylene chloride (10 mL) to which were added pyridine (0.14 mL, 1.67 mmol), N,N-dimethylaminopyridine (4 mg, 0.033 mmol), and lastly C-(1H-imidazol-2-yl)-methylamine bis-hydrochloride (114 mg, 0.668 mmol). Upon completion of the reaction the solvent was evaporated, and the residue was purified by preparative HPLC to give the title compound (69 mg, 24%) as a colorless solid. MS (ES+) 636.9 (M+H)+(100%).

Examples 37-45

The compounds shown in Table 2 (examples 37-45) were prepared in an analogous manner to Example 1 employing the general procedure (Example 1, part C) and substituting the appropriate amine.

TABLE 2

| Ex. | Structure | MF | (M + H)+ |
|---|---|---|---|
| 37 | 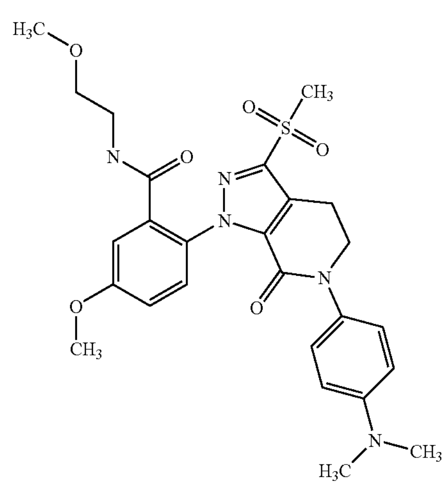 | $C_{26}H_{31}N_5O_6S$ | 542.2 |

TABLE 2-continued

| Ex. | Structure | MF | (M + H)+ |
|---|---|---|---|
| 38 | 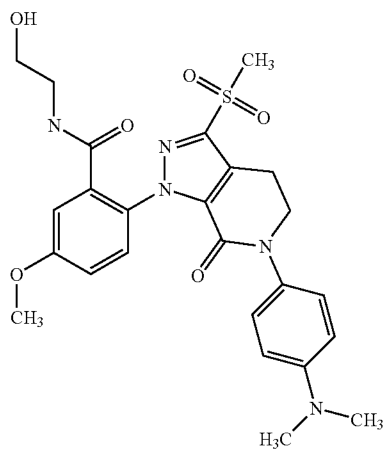 | C25H29N5O6S | 528.2 |
| 39 | 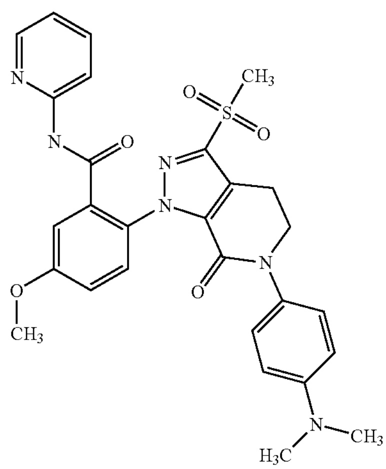 | C28H28N6O5S | 561.2 |
| 40 | 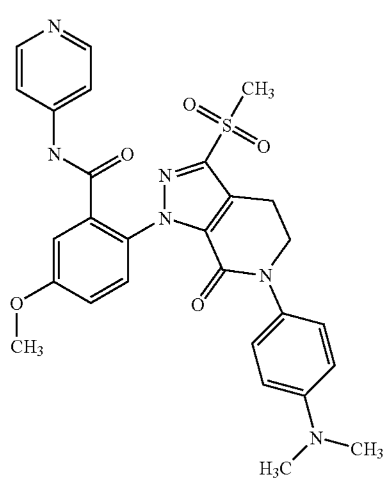 | C28H28N6O5S | 561.2 |

TABLE 2-continued

| Ex. | Structure | MF | (M + H)+ |
|---|---|---|---|
| 41 | 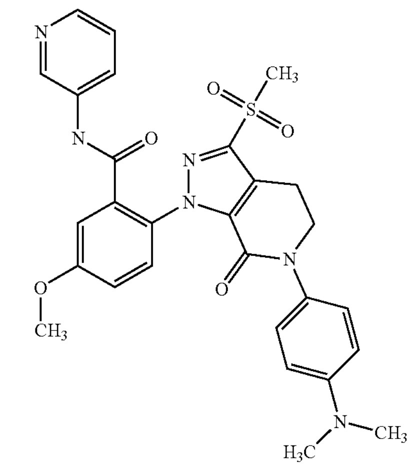 | C28H28N6O5S | 561.2 |
| 42 | 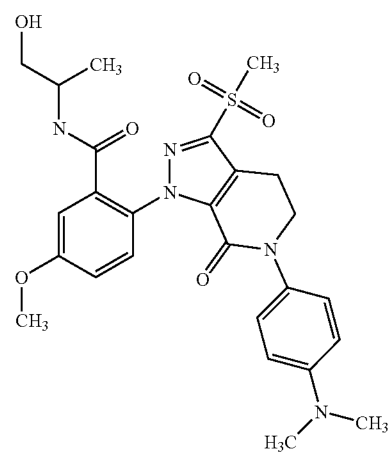 | C26H31N5O6S | 542.2 |
| 43 | 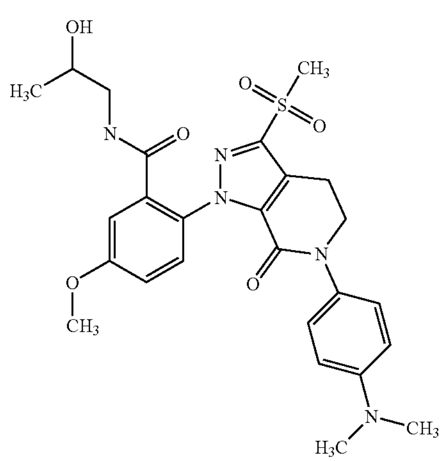 | C26H31N5O6S | 542.2 |

TABLE 2-continued

| Ex. | Structure | MF | (M + H)+ |
|---|---|---|---|
| 44 | 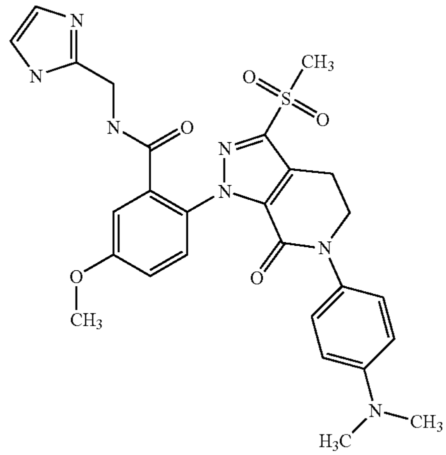 | $C_{27}H_{29}N_7O_5S$ | 564.2 |
| 45 | 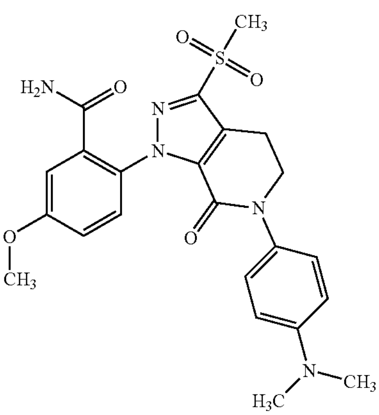 | $C_{23}H_{25}N_5O_5S$ | 484.2 |

Example 46

2-[6-(4-Chloro-phenyl)-3-methyl-7-oxo-4,5,6,7-tetrahydro-pyrazolo[3,4-c]pyridin-1-yl]-5-methoxy-benzenesulfonamide

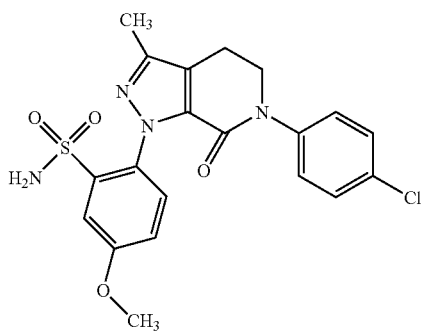

(2-[6-(4-Chloro-phenyl)-3-methyl-7-oxo-4,5,6,7-tetrahydro-pyrazolo[3,4-c]pyridin-1-yl]-5-methoxy-benzenesulfonic acid is synthesized from anisidine-2-sulfonic acid in an analogous manner as described in Example 1.

Examples 47-61

The compounds shown in Table 3 (examples 47-61) were prepared in analogous manner to Example 46 employing the general procedure (example 1) and methods described in WO 03/26652 and substituting the appropriate amine.

TABLE 3

| Ex. | Structure | MF | (M + H)+ |
|---|---|---|---|
| 47 | 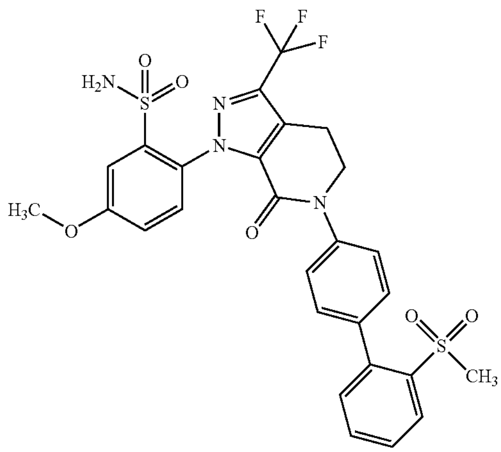 | C27H23F3N4O6 | 621.1 |
| 48 | 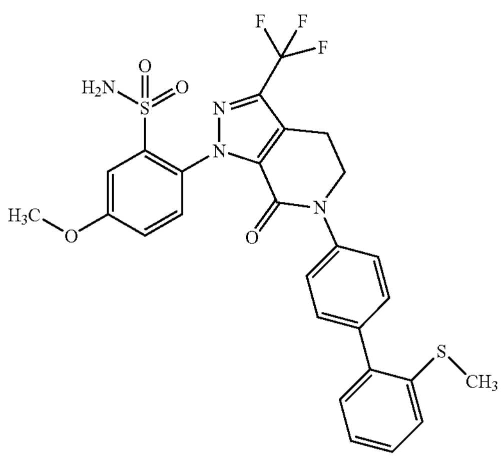 | C27H23F3N4O4S2 | 589.1 |
| 49 | 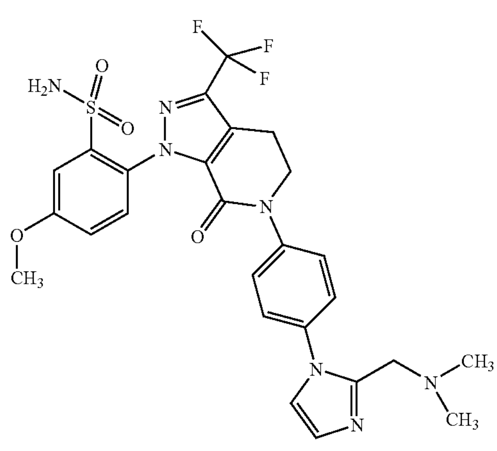 | C26H26F3N7O4S | 590.2 |

TABLE 3-continued

| Ex. | Structure | MF | (M + H)+ |
|---|---|---|---|
| 50 | 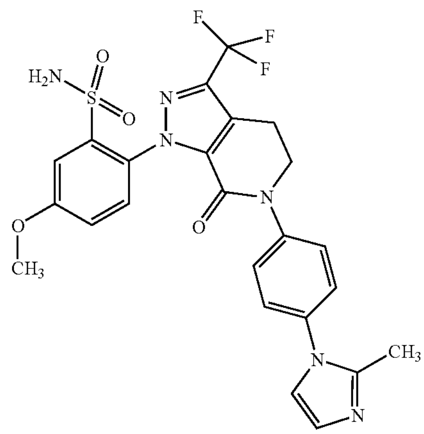 | C24H21F3N6O4S | 547.1 |
| 51 | 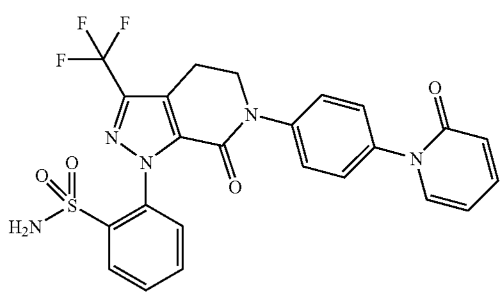 | C24H18F3N5O4S | 530.1 |
| 52 | 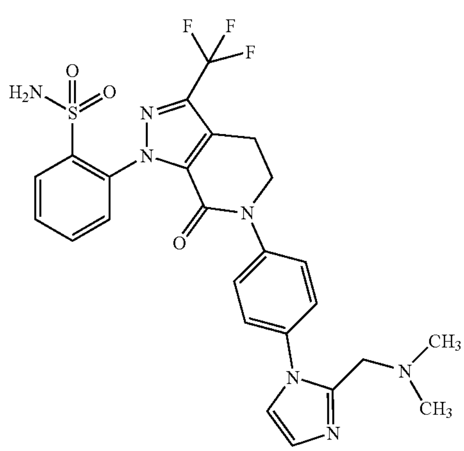 | C25H24F3N7O3S | 560.2 |

TABLE 3-continued

| Ex. | Structure | MF | (M + H)+ |
|---|---|---|---|
| 53 | 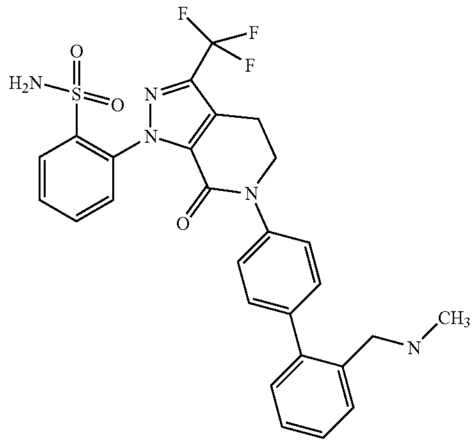 | C27H24F3N5O3S | 556.2 |
| 54 | 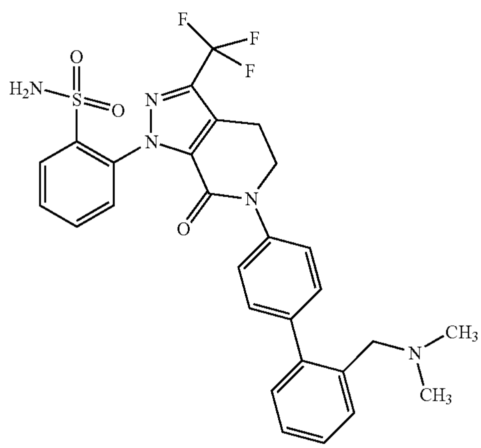 | C28H26F3N5O3S | 570.2 |
| 55 | 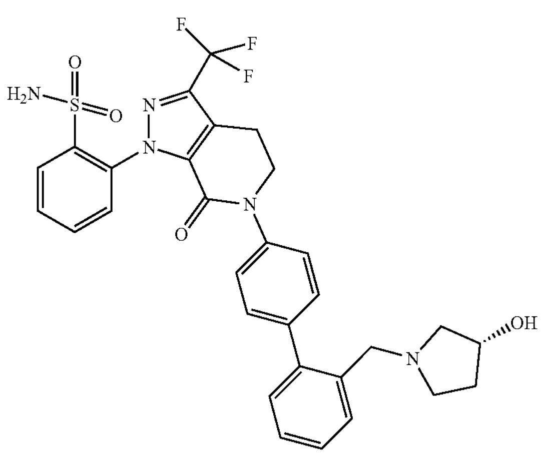 | C30H28F3N5O4S | 612.2 |

TABLE 3-continued

| Ex. | Structure | MF | (M + H)+ |
|---|---|---|---|
| 56 | 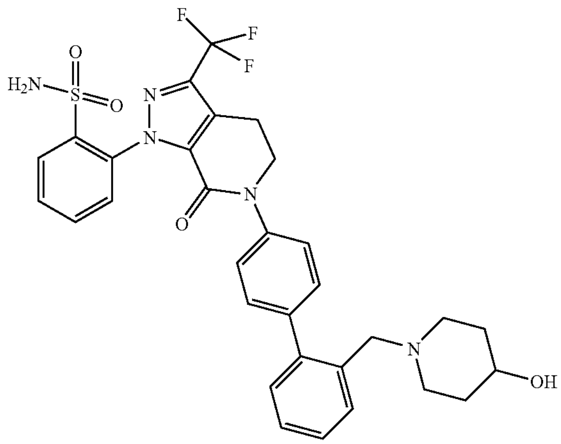 | C31H30F3N5O4S | 626.2 |
| 57 | 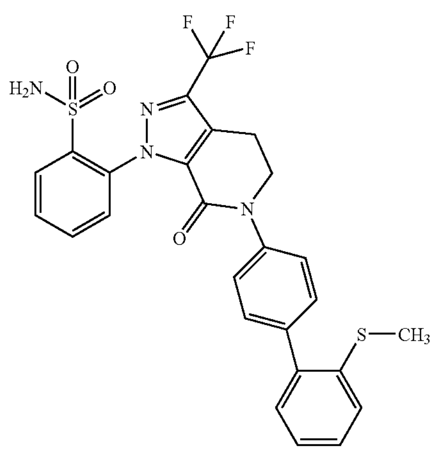 | C26H21F3N4O3S2 | 559.1 |
| 58 | 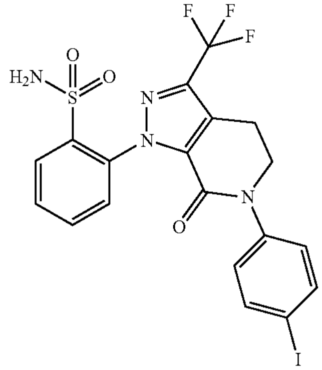 | C19H14F3IN4O3S | 563.0 |

TABLE 3-continued
| Ex. | Structure | MF | (M + H)+ |
|---|---|---|---|
| 59 | 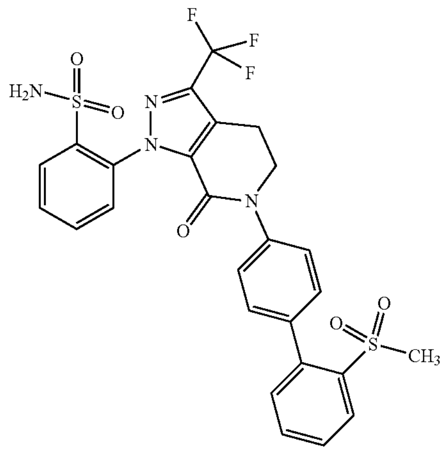 | $C_{26}H_{21}F_3N_4O_5S_2$ | 591.1 |
| 60 | 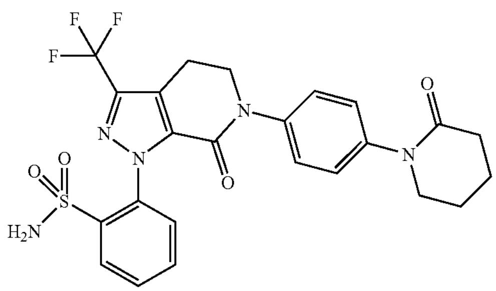 | $C_{24}H_{22}F_3N_5O_4S$ | 534.1 |
| 61 | 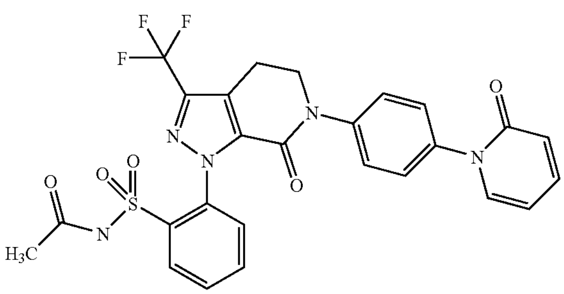 | $C_{26}H_{20}F_3N_5O_5S$ | 572.1 |
Examples 62-106
The compounds shown in Table 4 (examples 62-106) were prepared according to the general procedure described below.
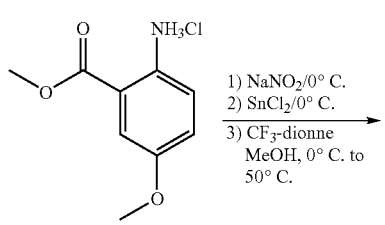
1) NaNO₂/0° C.
2) SnCl₂/0° C.
3) CF₃-dionne
   MeOH, 0° C. to 50° C.
-continued
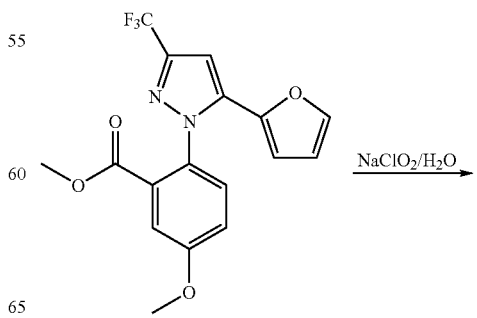
NaClO₂/H₂O

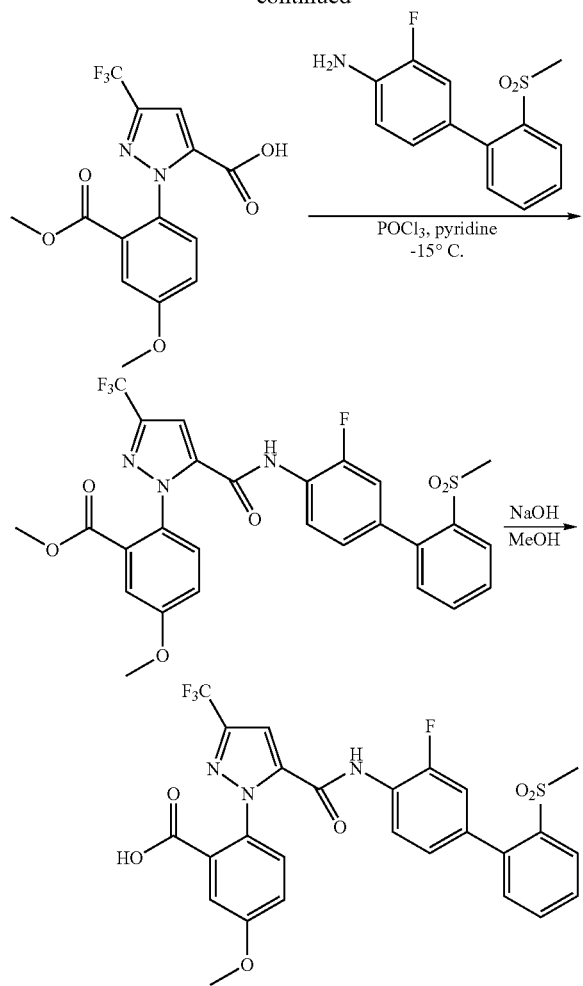

Part A: Preparation of 2-(5-furan-2-yl-3-trifluoromethyl-pyrazol-1-yl)-5-methoxy-benzoic acid methyl ester. To a solution of 2-amino-5-methoxy-benzoic acid methyl ester hydrochloride (201 mg, 0.922 mmol) in 1N hydrochloric acid (6 mL) cooled to 0° C. was added dropwise an ice cold solution of sodium nitrite (68 mg, 0.992 mmol) in water (1 mL). The solution was stirred at 0° C. for 45 minutes after which an ice cold solution of stannous chloride dihydrate (520 mg, 2.30 mmol) in 1N hydrochloric acid (2 mL) was added dropwise and stirred rapidly for an additional 15 min. at 0° C. A solution of 4,4,4-trifluoro-1-furan-2-yl-butane-1,3-dione in methanol (2 mL) was added, the cooling bath removed, and the reaction allowed to warm to ambient temperature. The solution was heated to 50° C. for 15 h and upon completion of the reaction the solvent volume was reduced under reduced pressure. Ethyl acetate was added, and the phases were separated. The aqueous layer was extracted once with ethyl acetate, and the combined organics were washed once with water, brine, dried over sodium sulfate, filtered, and evaporated to give 270 mg (80%) of 2-(5-furan-2-yl-3-trifluoromethyl-pyrazol-1-yl)-5-methoxy-benzoic acid methyl ester.

Part B: Preparation of 2-(4-methoxy-2-methoxycarbonyl-phenyl)-5-trifluoromethyl-2H-pyrazole-3-carboxylic acid. A solution 2-(5-furan-2-yl-3-trifluoromethyl-pyrazol-1-yl)-5-methoxy-benzoic acid methyl ester (1.00 g, 2.73 mmol) in acetonitrile (9 mL) was added to a solution of sodium dihydrogenphosphate (1.63 g, 13.6 mmol) in water (2 mL) cooled to 0° C. To this mixture was added, using an addition funnel, a solution of sodium chlorite (3.1 g, 80%, 27.3 mmol) in water (9 mL) in three equal portions with ten minutes between each addition. The reaction was allowed to warm to ambient temperature and stirred for 14 h. Upon completion of the reaction, a solution of 1N sodium hydroxide (10 mL) was added, and the mixture was extracted with chloroform (2×25 mL). The combined chloroform extracts were extracted with saturated sodium bicarbonate. The combined basic layers were made acidic (pH 2.0) with concentrated hydrochloric acid and extracted twice with ethyl acetate, dried over magnesium sulfate, and evaporated to give 348 mg (37%) of 2-(4-methoxy-2-methoxycarbonyl-phenyl)-5-trifluoromethyl-2H-pyrazole-3-carboxylic acid.

Part C: Preparation of 2-[5-(3-Fluoro-2'-methanesulfonyl-biphenyl-4-ylcarbamoyl)-3-trifluoromethyl-pyrazol-1-yl]-5-methoxy-benzoic acid methyl ester. 3-Fluoro-2'-methanesulfonyl-biphenyl-4-ylamine (231 mg, 0.87 mmol) and 2-(4-methoxy-2-methoxycarbonyl-phenyl)-5-trifluoromethyl-2H-pyrazole-3-carboxylic acid (300 mg, 0.87 mmol) were combined in a flask and placed under a nitrogen atmosphere. Pyridine (4.0 mL) was added, and the flask was cooled to −15° C. After stirring for five minutes, phosphorous oxychloride (97 μL, 1.04 mmol) was added dropwise followed by additional stirring for one hour while maintaining a reaction temperature of −10 to −15° C. The reaction was diluted with dichloromethane, washed with 0.1 M hydrochloric acid (3×), dried over magnesium sulfate, filtered, evaporated under reduced pressure, and dried under high vacuum for 12 h. 2-[5-(3-Fluoro-2'-methanesulfonyl-biphenyl-4-ylcarbamoyl)-3-trifluoromethyl-pyrazol-1-yl]-5-methoxy-benzoic acid methyl ester (514 mg, 84%) was isolated in sufficient purity to be used in the next step.

Part D: Preparation of 2-[5-(3-Fluoro-2'-methanesulfonyl-biphenyl-4-ylcarbamoyl)-3-trifluoromethyl-pyrazol-1-yl]-5-methoxy-benzoic acid. 2-[5-(3-Fluoro-2'-methanesulfonyl-biphenyl-4-ylcarbamoyl)-3-trifluoromethyl-pyrazol-1-yl]-5-methoxybenzoic acid methyl ester (1.70 g, 2.80 mmol) was dissolved in methanol (22 mL), 1N sodium hydroxide (5.8 mL) was added, and the solution refluxed for 6 hours. The reaction was cooled to ambient temperature and diluted with water (30 mL). 3N hydrochloric acid was added to adjust the pH to 2, and the resulting precipitate collected by filtration. The solid was dried under vacuum in a desiccator to give 1.45 g (86%) of (3-fluoro-2'-methanesulfonyl-biphenyl-4-ylcarbamoyl)-3-trifluoromethyl-pyrazol-1-yl]-5-methoxy-benzoic acid. $^1$H NMR (CD$_3$OD) δ 8.12 (dd, J=1.5, 8.1 Hz, 1H), 7.86 (t, J=8.4 Hz, 1H), 7.70 (dt, J=1.5, 7.7 Hz, 1H), 7.61 (dt, J=1.5, 7.7 Hz, 1H), 7.37 (m, 3H), 7.25 (dd, J=2.2, 11.7 Hz, 1H) 7.16 (m, 3H) 3.87 (s, 3H), 2.67 (s, 3H).

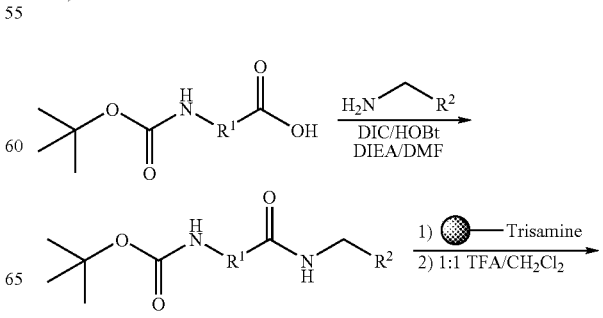

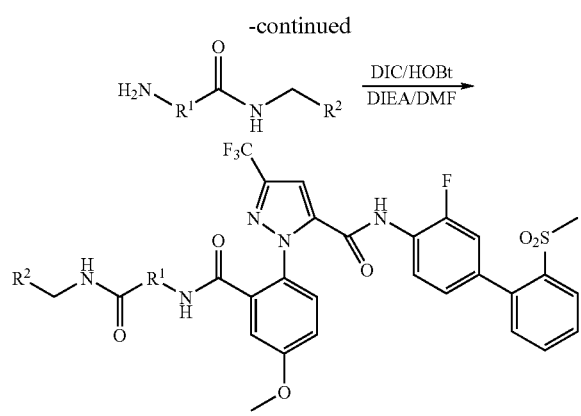

Part E: Preparation of tert-Butoxycarbonylamino-N-alkylcarboxamides: tert-Butoxycarbonylamino-carboxylic acid (0.50 mmol) was dissolved in N,N-dimethylformamide (6.0 mL); 1-hydroxybenzotriazole (132 mg, 0.98 mmol) was added and the solution was stirred at ambient temperature for 30 minutes. 1,3-Diisopropylcarbodiimide (153 mg, 0.98 mmol) and amine (0.50 mmol) were added and stirring continued for 12 h at ambient temperature. PS-Trisamine (592 mg, 2.0 mmol) was added and stirring continued for three hours, after which the reaction was filtered and the solvent evaporated. To the residue was added trifluoroacetic acid/dichloromethane (1:1)(1.5 mL), stirring was continued for 30 minutes, and the solvent was evaporated under reduced pressure, yielding a nearly quantitative yield (crude) of a yellow-orange amorphous solid.

To a portion of the carboxylic acid 3 (0.134 mmol) was added dimethylformamide (1.0 mL) followed by 1-hydroxybenzotriazole (21 mg, 0.134 mmol) and 1,3-diisopropylcarbodiimide (17 mg, 0.134 mmol), which was then stirred for 30 minutes at ambient temperature. 2-[5-3-Fluoro-2'-methanesulfonyl-biphenyl-4-ylcarbamoyl)-3-trifluoromethyl-pyrazol-1-yl]-5-methoxybenzoic acid (20 mg, 0.067 mmol) and N,N-diisopropylethylamine (35 µL, 0.201 mmol) were added and stirring was continued at ambient temperature for 12 h. The solvent was evaporated under reduced pressure and the residue purified by reverse phase HPLC, collecting products using a mass-directed trigger.

TABLE 4

| Ex. | Structure | MF | MS:(M + H)$^+$ |
|---|---|---|---|
| 62 | 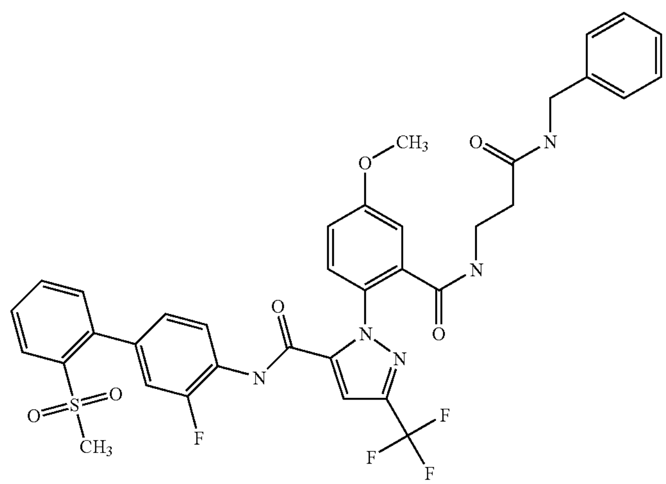 | $C_{36}H_{31}F_4N_5O_6S$ | 738.2 |
| 63 | 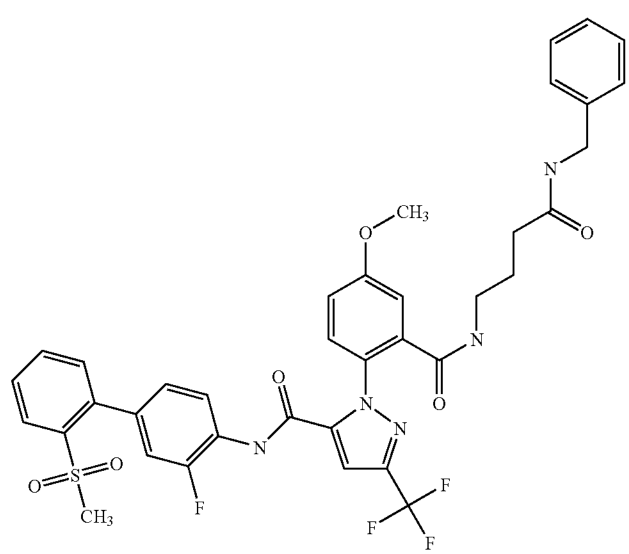 | $C_{37}H_{33}F_4N_5O_6S$ | 752.2 |

TABLE 4-continued
| Ex. | Structure | MF | MS:(M + H)+ |
|---|---|---|---|
| 64 | 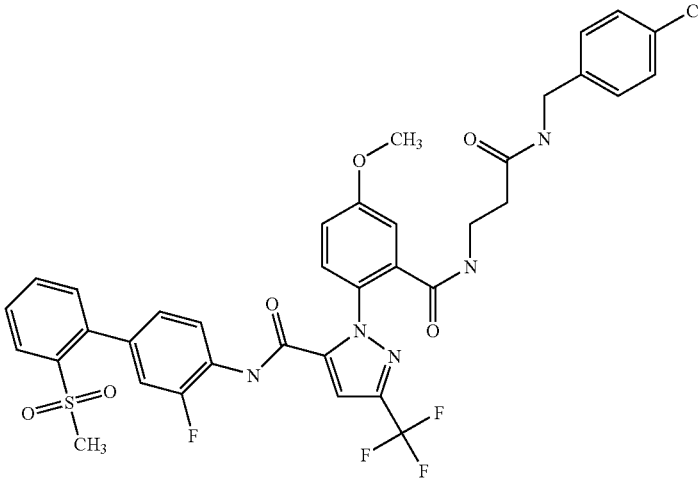 | C36H30ClF4N5O6S | 772.2 |
| 65 | 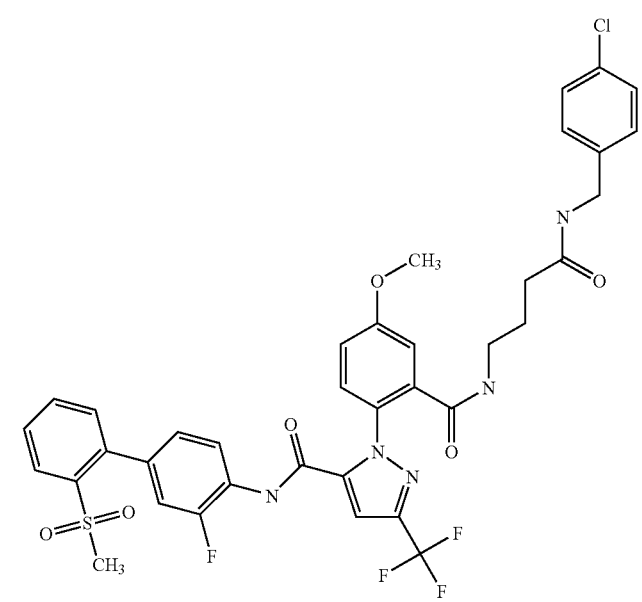 | C37H32ClF4N5O6S | 786.2 |
| 66 | 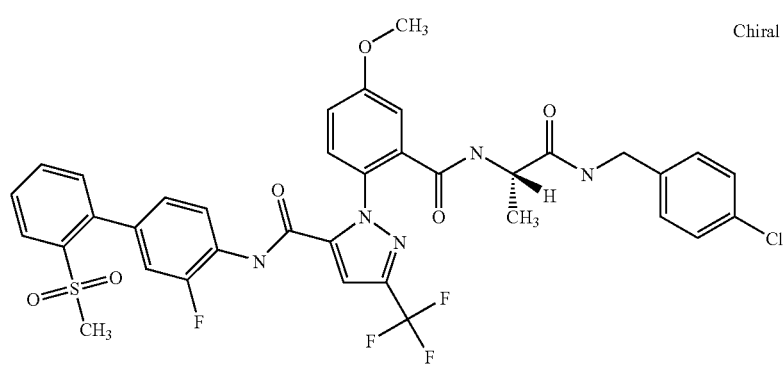  Chiral | C36H30ClF4N5O6S | 772.2 |

TABLE 4-continued

| Ex. | Structure | MF | MS:(M + H)⁺ |
|---|---|---|---|
| 67 | 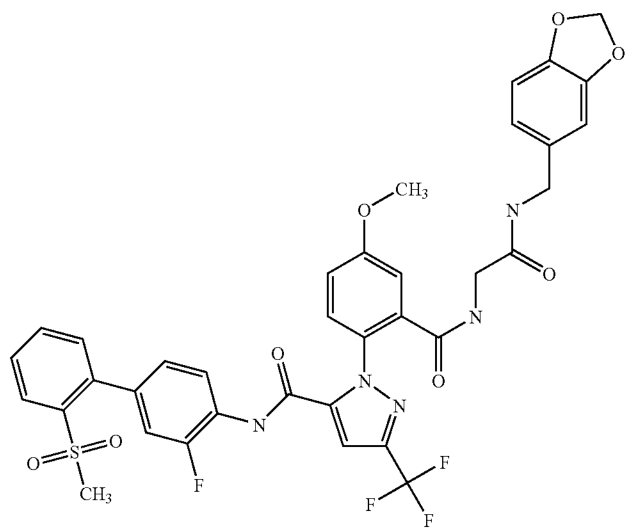 | $C_{36}H_{29}F_4N_5O_8S$ | 768.2 |
| 68 | 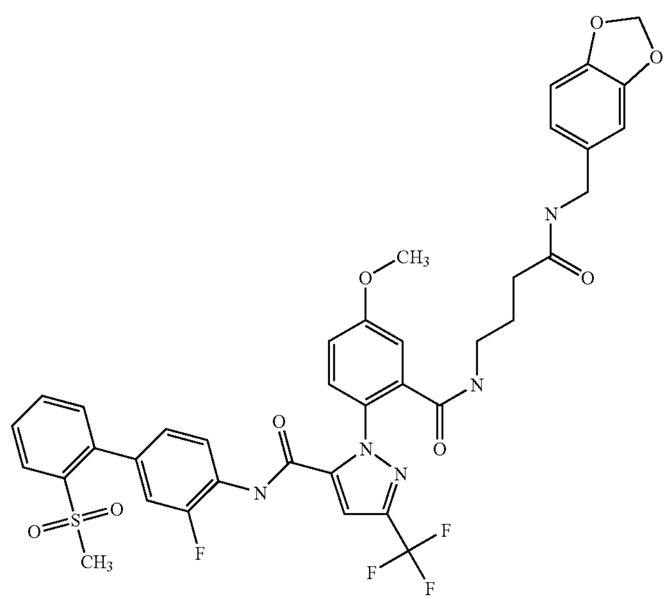 | $C_{38}H_{33}F_4N_5O_8S$ | 796.2 |
| 69 | Chiral | $C_{37}H_{31}F_4N_5O_8S$ | 782.2 |

TABLE 4-continued

| Ex. | Structure | | MF | MS:(M + H)+ |
|---|---|---|---|---|
| 70 | 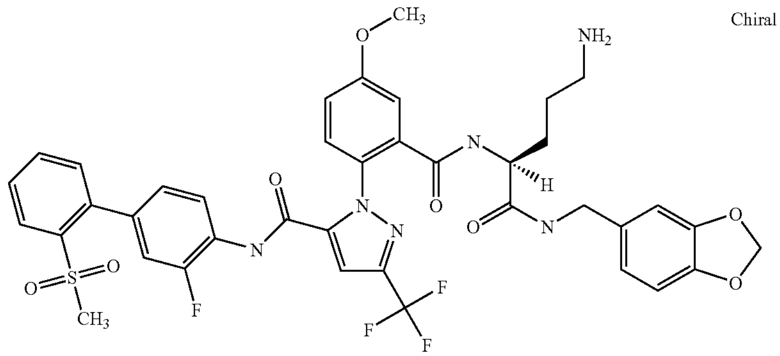 | Chiral | C₃₉H₃₆F₄N₆O₈S | 825.2 |
| 71 | 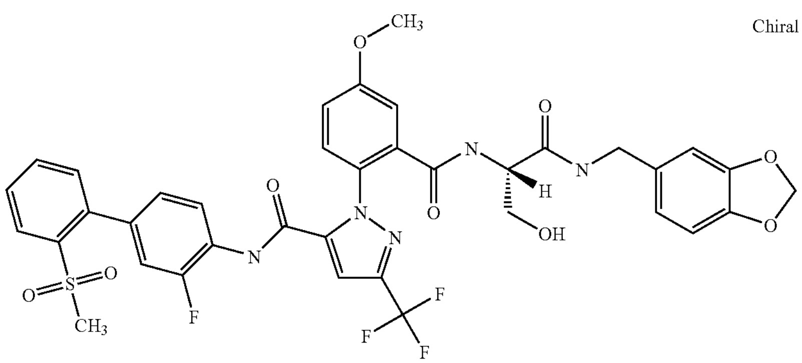 | Chiral | C₃₇H₃₁F₄N₅O₉S | 798.2 |
| 72 | 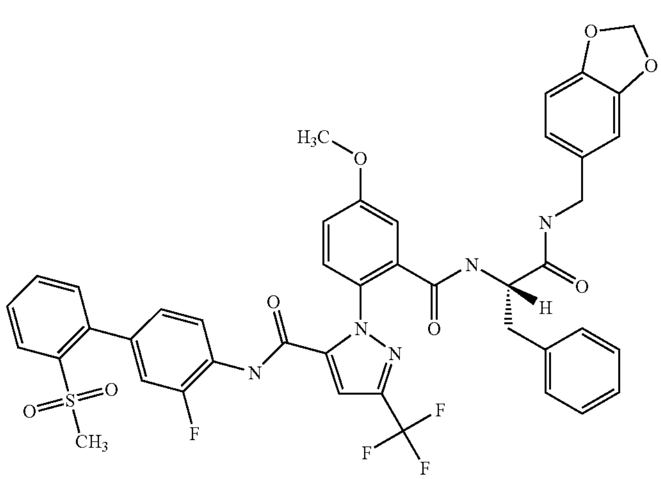 | Chiral | C₄₃H₃₅F₄N₅O₈S | 858.2 |

TABLE 4-continued

| Ex. | Structure | MF | MS:(M + H)+ |
|---|---|---|---|
| 73 | 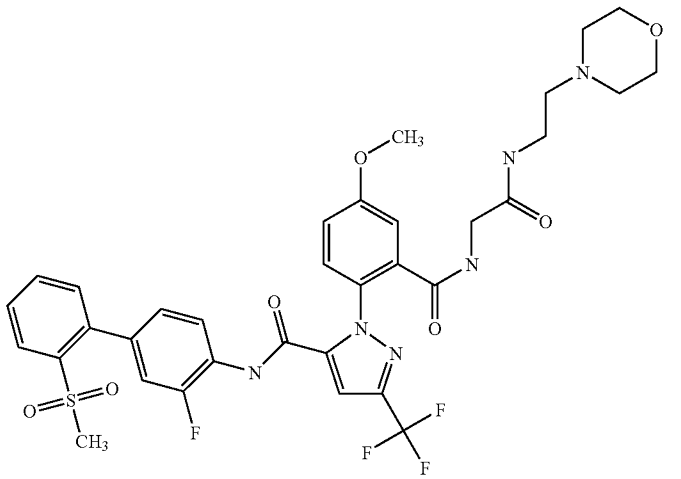 | $C_{34}H_{34}F_4N_6O_7S$ | 747.2 |
| 74 | 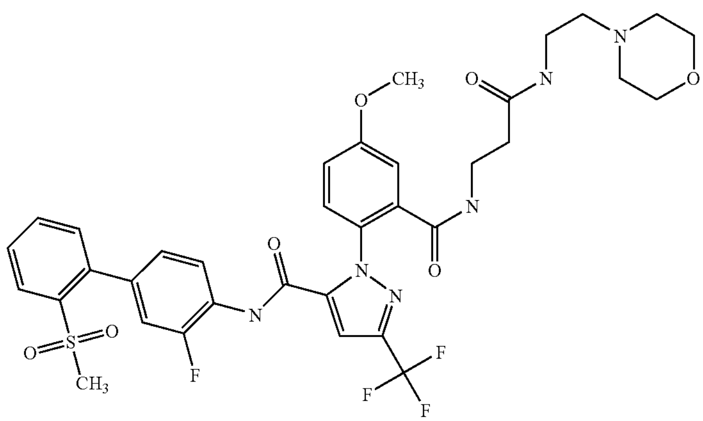 | $C_{35}H_{36}F_4N_6O_7S$ | 761.2 |
| 75 | 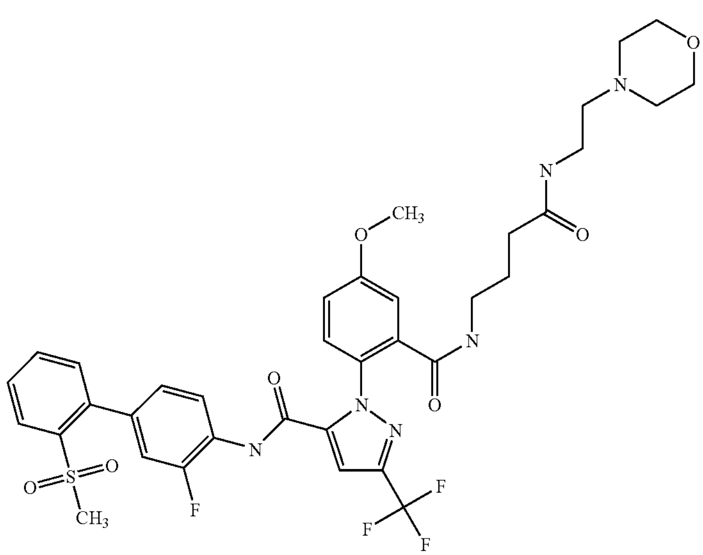 | $C_{36}H_{38}F_4N_6O_7S$ | 775.3 |

TABLE 4-continued
| Ex. | Structure | MF | MS:(M + H)+ |
|---|---|---|---|
| 76 | 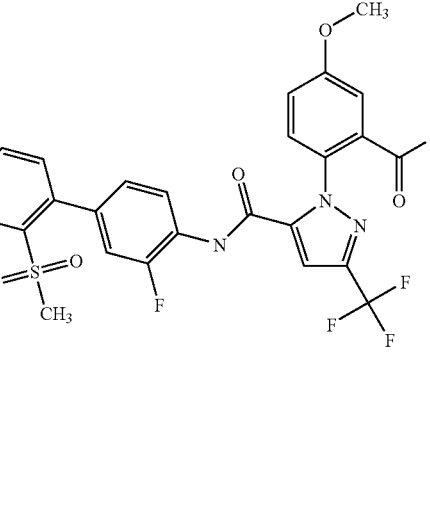 | C35H29F4N5O6S | 724.2 |
| 77 | 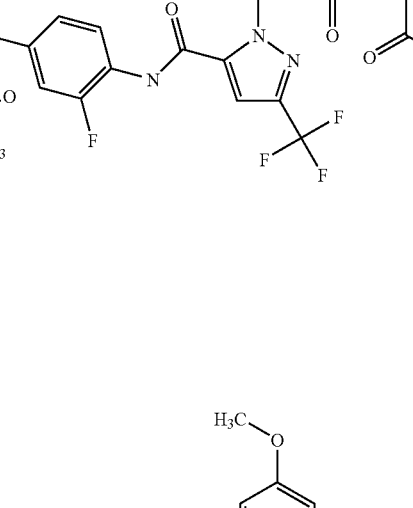 Chiral | C38H36F4N6O6S | 781.2 |
| 78 | 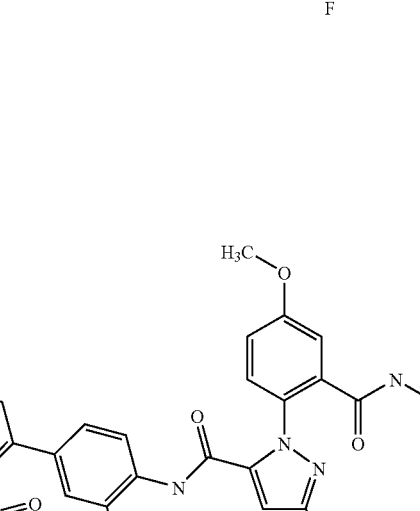 Chiral | C42H35F4N5O6S | 814.2 |

TABLE 4-continued

| Ex. | Structure | MF | MS:(M + H)+ |
|---|---|---|---|
| 79 | 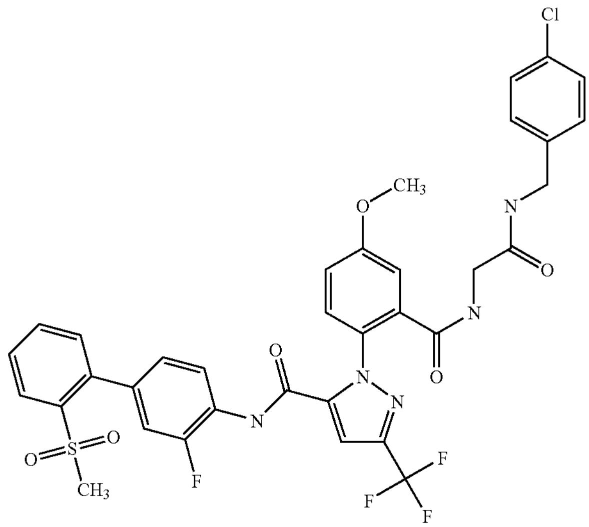 | C35H28ClF4N5O6S | 758.1 |
| 80 | Chiral | C37H30ClF4N5O8S | 816.2 |
| 81 | Chiral | C38H35ClF4N6O6S | 815.2 |

TABLE 4-continued
| Ex. | Structure | MF | MS:(M + H)+ |
|---|---|---|---|
| 82 | 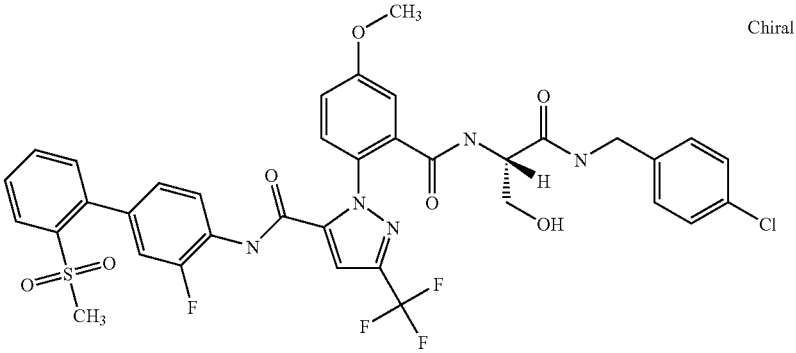 Chiral | C36H30ClF4N5O7S | 788.2 |
| 83 | 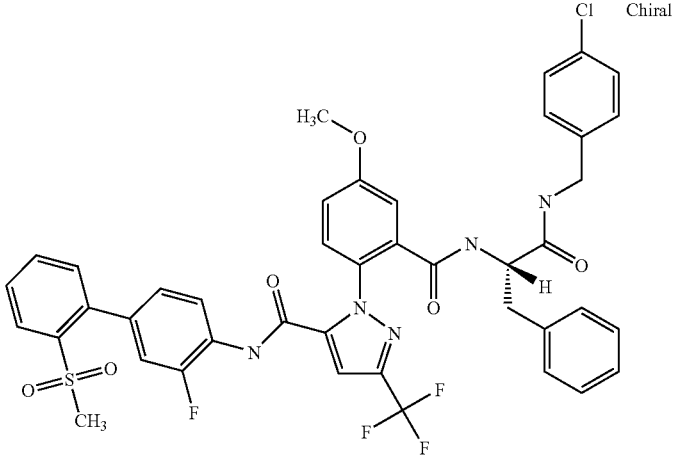 Chiral | C42H34ClF4N5O6S | 848.2 |
| 84 | 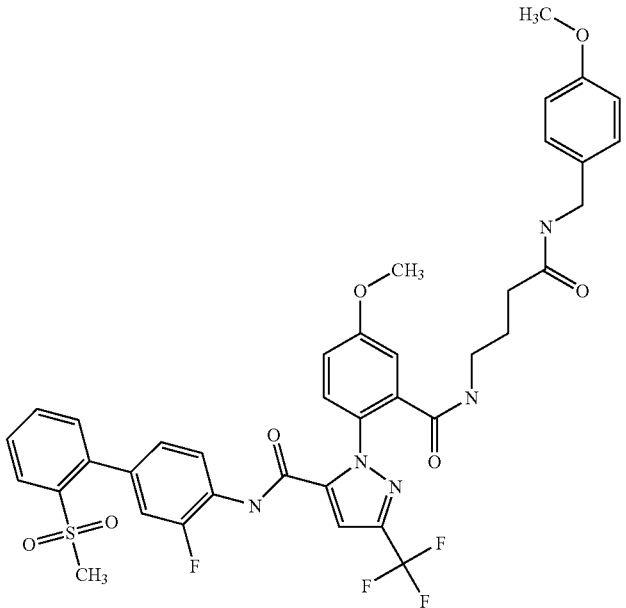 | C38H35F4N5O7S | 782.2 |

TABLE 4-continued

| Ex. | Structure | MF | MS:(M + H)+ |
|---|---|---|---|
| 85 | 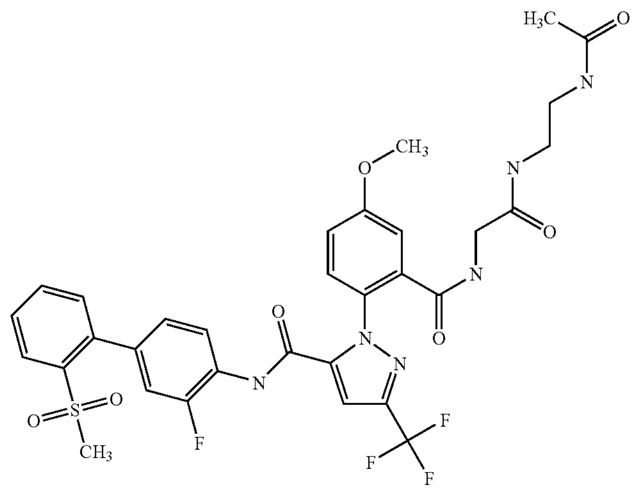 | $C_{32}H_{30}F_4N_6O_7S$ | 719.2 |
| 86 | 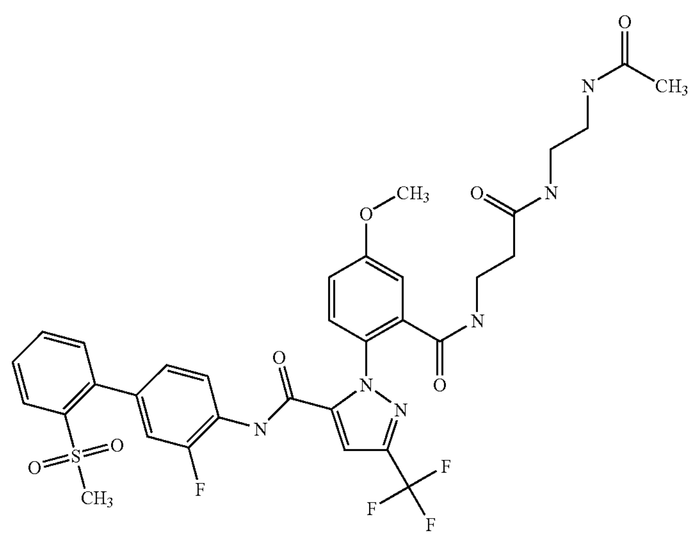 | $C_{33}H_{32}F_4N_6O_7S$ | 733.2 |
| 87 | 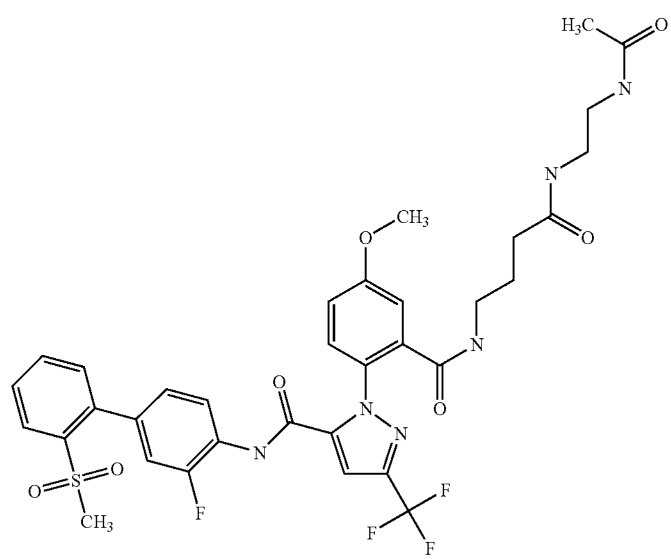 | $C_{34}H_{34}F_4N_6O_7S$ | 747.2 |

TABLE 4-continued

| Ex. | Structure | MF | MS:(M + H)+ |
|---|---|---|---|
| 88 | 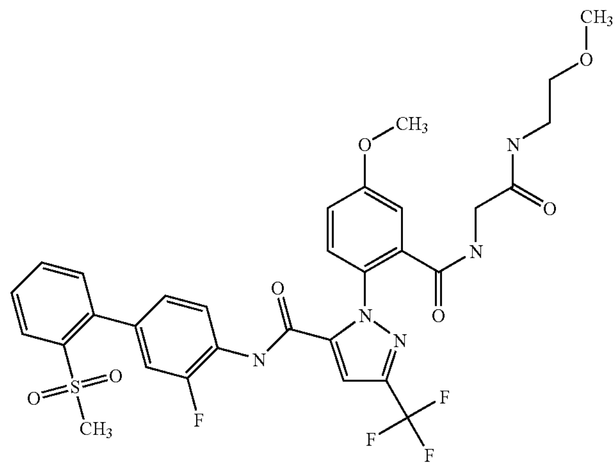 | $C_{31}H_{29}F_4N_5O_7S$ | 692.2 |
| 89 | 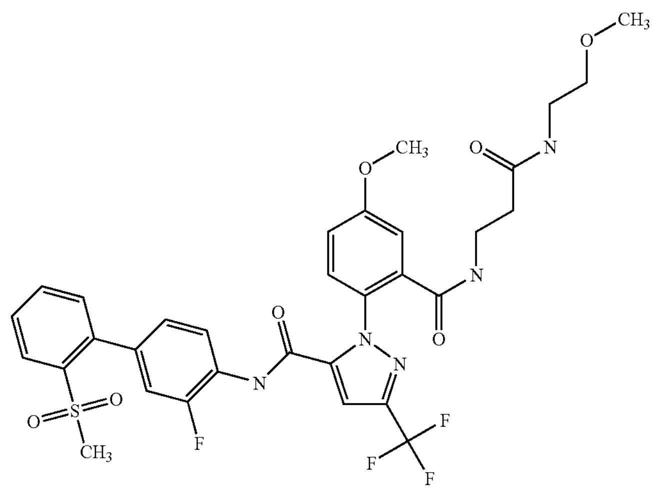 | $C_{32}H_{31}F_4N_5O_7S$ | 706.2 |
| 90 | 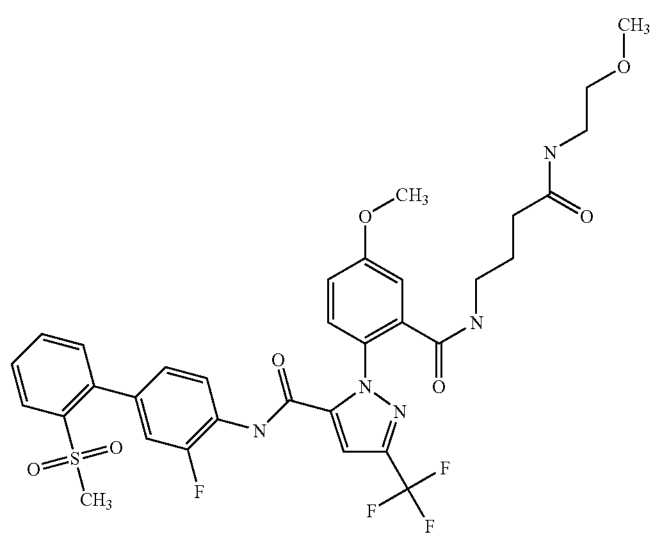 | $C_{33}H_{33}F_4N_5O_7S$ | 720.2 |

TABLE 4-continued

| Ex. | Structure | MF | MS:(M + H)+ |
|---|---|---|---|
| 91 | 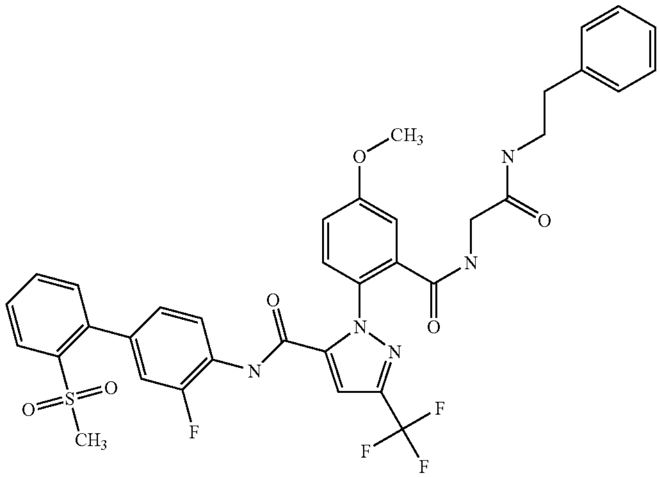 | C36H31F4N5O6S | 738.2 |
| 92 | 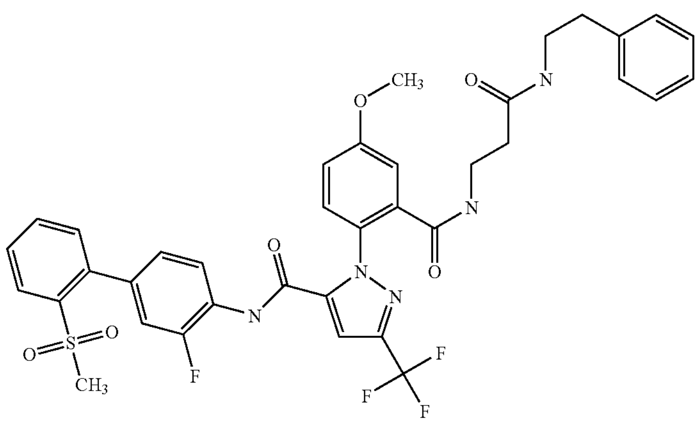 | C37H33F4N5O6S | 752.2 |
| 93 | 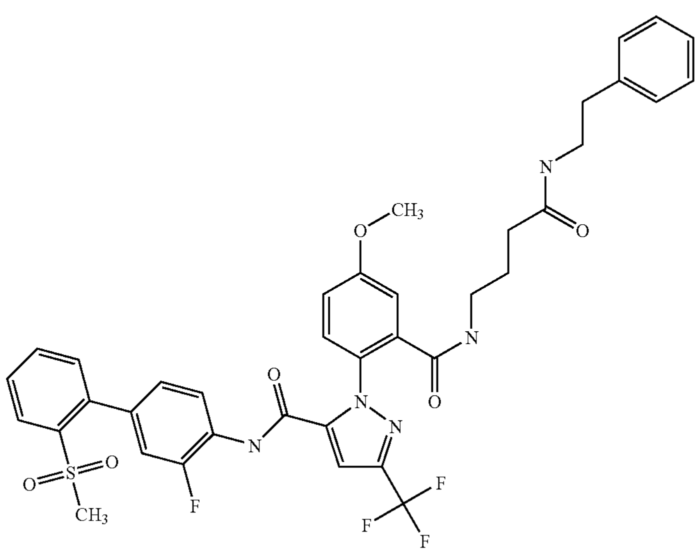 | C38H35F4N5O6S | 766.2 |

TABLE 4-continued
| Ex. | Structure | MF | MS:(M + H)+ |
|---|---|---|---|
| 94 | 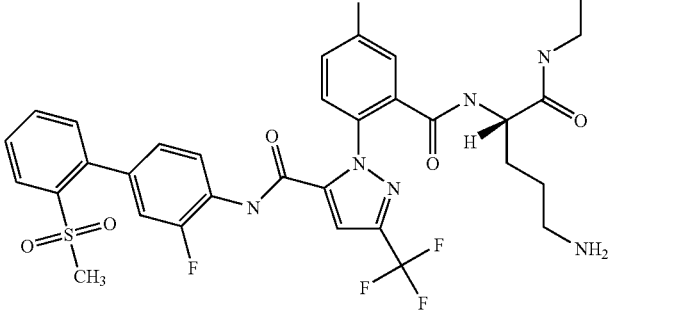 Chiral | C39H38F4N6O6S | 795.3 |
| 95 | 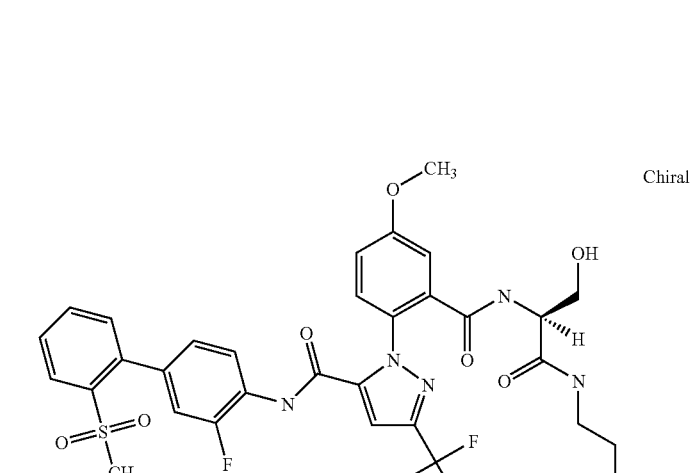 Chiral | C37H33F4N5O7S | 768.2 |
| 96 | 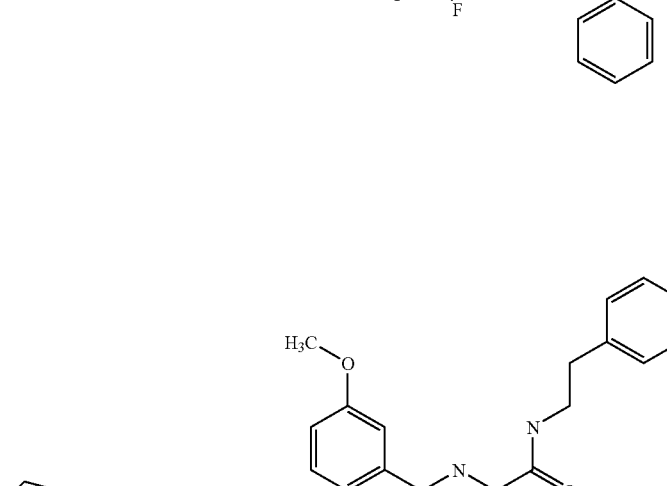 Chiral | C43H37F4N5O6S | 828.2 |

TABLE 4-continued

| Ex. | Structure | MF | MS:(M + H)+ |
|---|---|---|---|
| 97 | 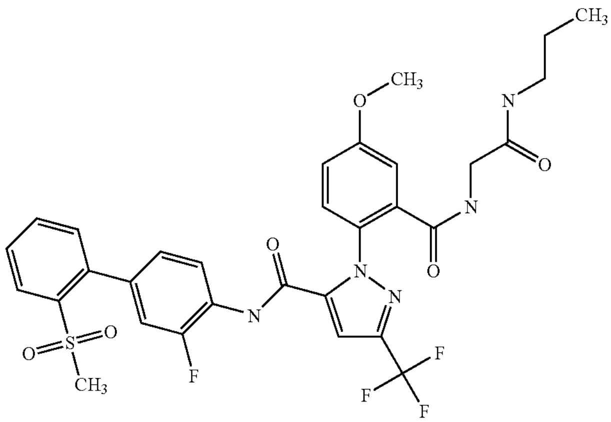 | C31H29F4N5O6S | 676.2 |
| 98 | 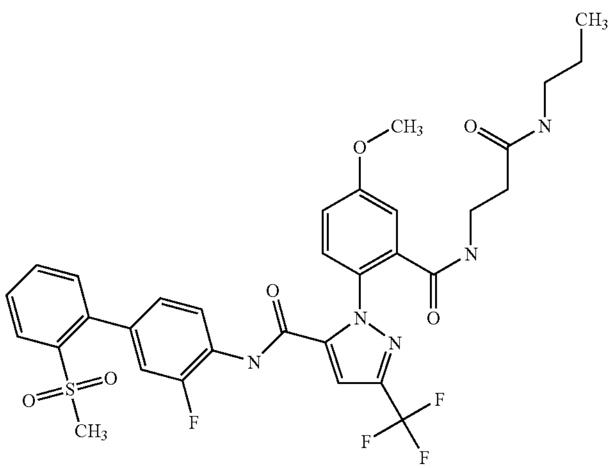 | C32H31F4N5O6S | 690.2 |
| 99 | Chiral | C32H31F4N5O6S | 690.2 |

TABLE 4-continued

| Ex. | Structure | MF | MS:(M + H)+ |
|---|---|---|---|
| 100 | 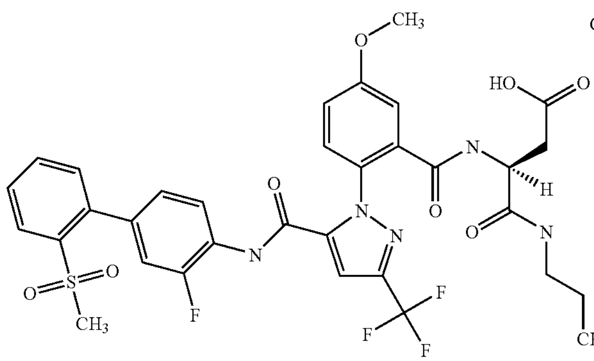 | $C_{33}H_{31}F_4N_5O_8S$ | 734.2 |
| 101 | 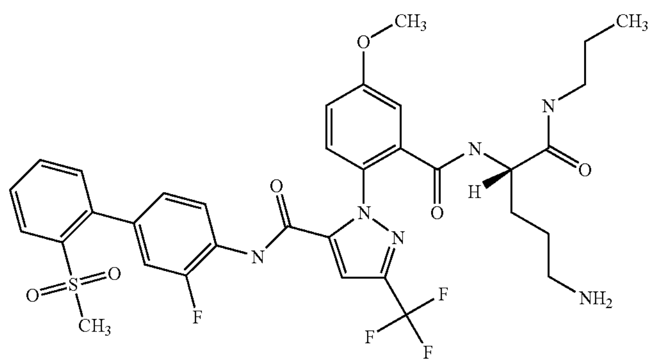 | $C_{34}H_{36}F_4N_6O_6S$ | 733.2 |
| 102 | 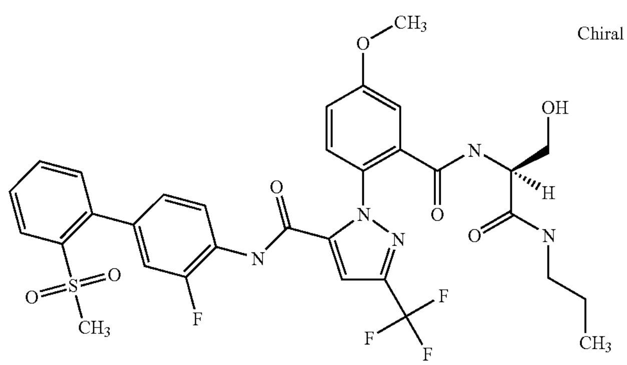 | $C_{32}H_{31}F_4N_5O_7S$ | 706.2 |
| 103 | 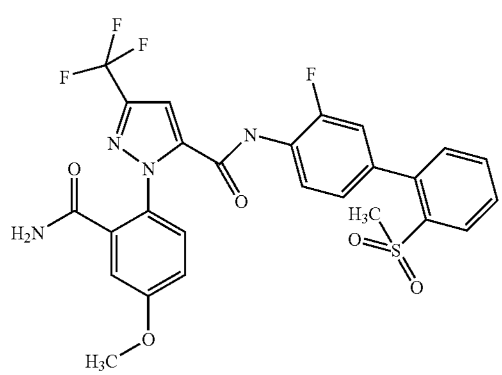 | $C_{26}H_{20}F_4N_4O_5S$ | 577.1 |

TABLE 4-continued

| Ex. | Structure | MF | MS:(M + H)+ |
|---|---|---|---|
| 104 | 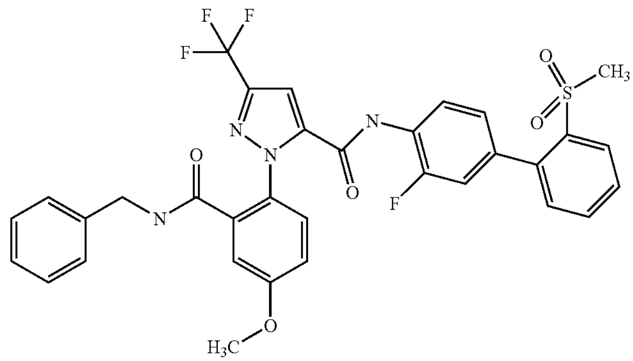 | C₃₃H₂₆F₄N₄O₅S | 667.2 |
| 105 | 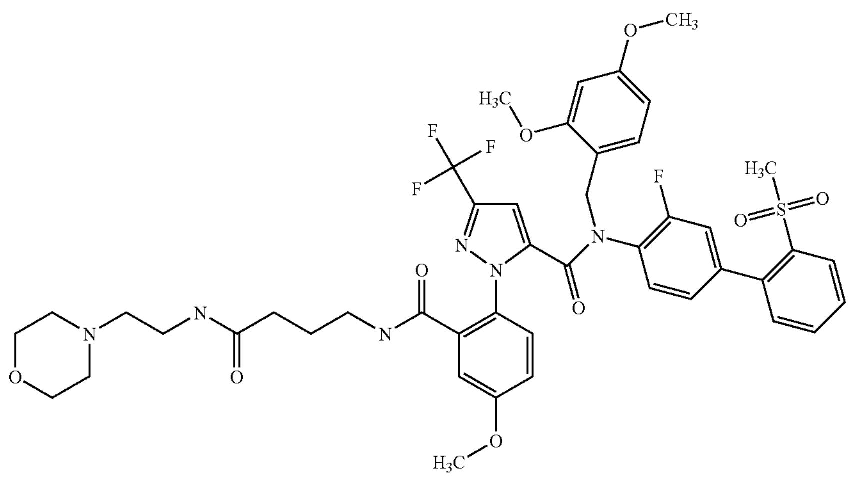 | C₄₅H₄₈F₄N₆O₉S | 925.3 |
| 106 | 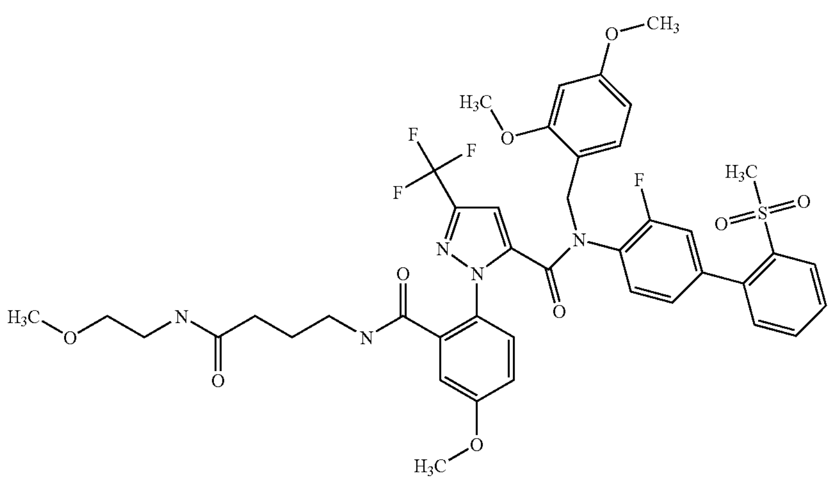 | C₄₂H₄₃F₄N₅O₉S | 870.3 |

Example 107

2-(2-Carbamoyl-4-methoxy-phenyl)-5-trifluoromethyl-2H-pyrazole-3-carboxylic acid (4-dimethylamino-phenyl)-amide

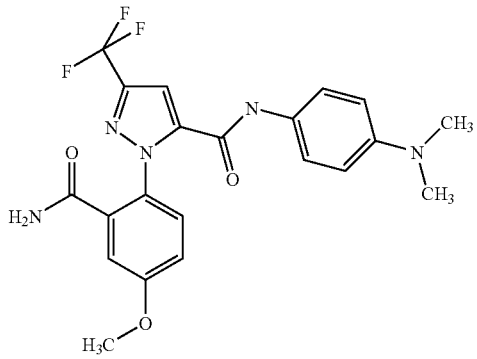

The title compound was prepared in a analogous manner to the general procedure for examples 62-106. $C_{21}H_{20}F_3N_5O_3$. MS:(M+H)$^+$ 448.2.

Examples 108-255

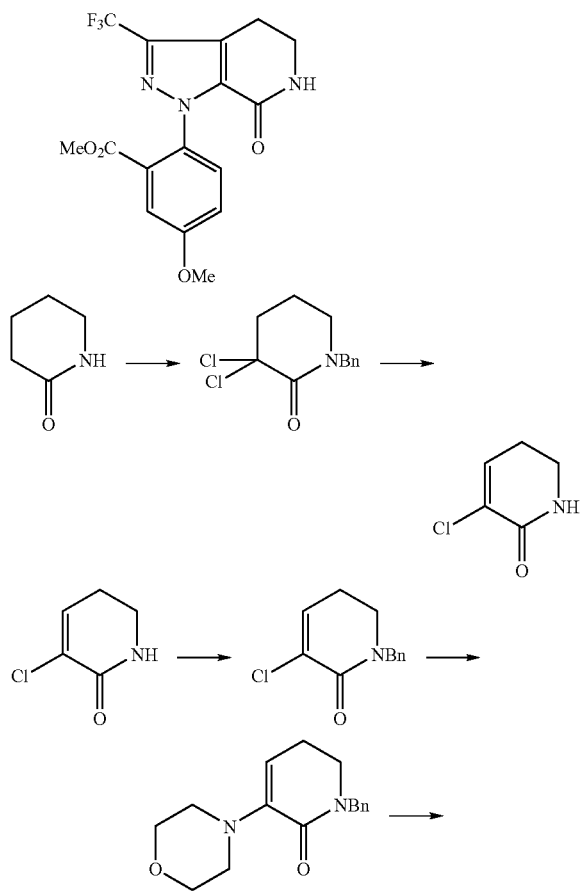

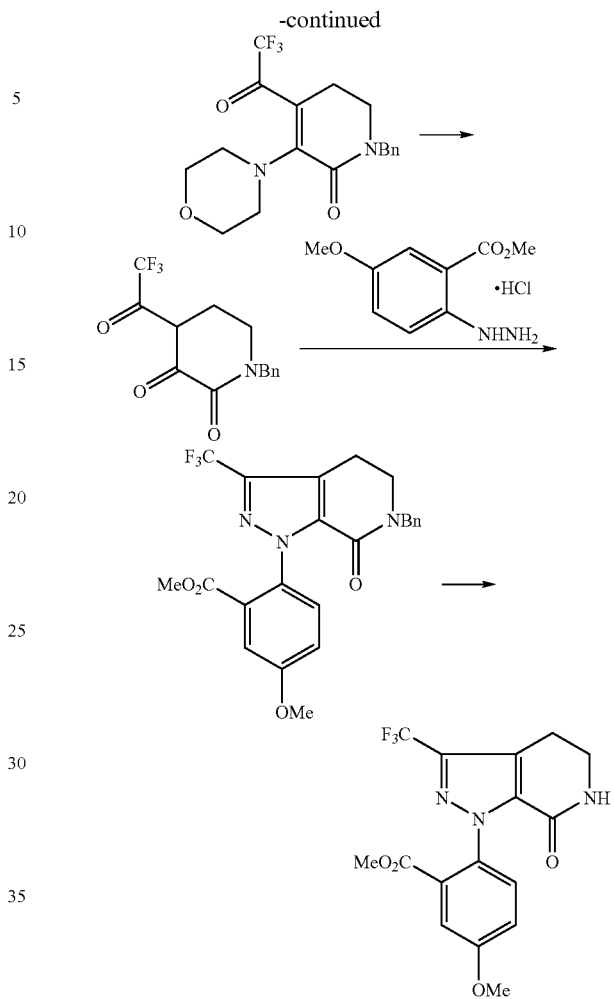

Part A: Preparation of 3-chloro-5,6-dihydro-1H-pyridin-2-one. A solution of piperidin-2-one (900 g, 9.08 mol) in chloroform (2 L) was added to a stirred mixture of phosphorous pentachloride (5.66 kg, 27.2 mol) in chloroform (10 L). Additional chloroform (6 L) was added, and the mixture heated under reflux for 21 h. The cooled mixture was added to ice while keeping the temperature around 10° C. The pH was adjusted to 9-10 by adding 50% aqueous sodium hydroxide while keeping the temperature below 40° C. The phases were separated and the aqueous phase extracted with dichloromethane (5 L). The combined organic phases were washed with brine (5 L), dried, and concentrated under vacuum to give 1-benzyl-3,3-dichloro-piperidin-2-one (1200 g, 79%), which was used for the following step without further purification.

Part B: Preparation of 3-chloro-5,6-dihydro-1H-pyridin-2-one. Lithium chloride (290 g, 6.84 mol) and lithium carbonate (505 g, 6.84 mol) were added to a stirred mixture of 1-benzyl-3,3-dichloro-piperidin-2-one (1150 g, 6.84 mol) in dimethylformamide (4.8 L) and the mixture heated at 130° C. for 4.5 h. The reaction mixture was cooled to 70° C. and then concentrated in vacuo to remove approximately 3 L of dimethylformamide. The mixture was cooled to 45-50° C. and ethyl acetate (4.5 L) was added. The mixture was cooled to 0-5° C. overnight. The resulting mixture was filtered through diatomaceous earth, washing the filter bed with ethyl acetate (4.5 L). The filtrate was concentrated under vacuum, and the residue was purified by chromatography (9:1 dichloromethane/methanol) followed by trituration with hexanes/toluene (3:1) to give 3-chloro-5,6-dihydro-1H-pyridin-2-one (620 g, 70%).

Part C: Preparation of 1-benzyl-3-chloro-5,6-dihydro-1H-pyridin-2-one. A mixture of 3-chloro-5,6-dihydro-1H-pyridin-2-one (40 g, 304 mmol) and benzyl bromide (104 g, 608 mmol) in tetrahydrofuran (800 mL) was added to a suspension of potassium hydride (18.3 g, 456 mmol) in tetrahydrofuran (800 mL) at 0° C. After the addition was complete, the reaction mixture was stirred at room temperature for 20 h, then quenched cautiously with water and extracted with ethyl acetate. The combined organic phases were washed with water and brine, dried, and concentrated under vacuum. The residue was purified by column chromatography (9:1 to 1:1 hexanes/ethyl acetate) to give 1-benzyl-3-chloro-5,6-dihydro-1H-pyridin-2-one (41 g, 61%).

Part D: Preparation of 1-benzyl-3-morpholin-4-yl-5,6-dihydro-1H-pyridin-2-one. A mixture of 1-benzyl-3-chloro-5,6-dihydro-1H-pyridin-2-one (41 g, 185 mmol) and morpholine (500 mL) was heated under reflux for 24 h and then concentrated under vacuum. The residue was purified by column chromatography (7:3 to 1:1 hexanes/ethyl acetate) to give 1-benzyl-3-morpholin-4-yl-5,6-dihydro-1H-pyridin-2-one (35.4 g, 70%).

Part E. Preparation of 1-benzyl-3-morpholin-4-yl-4-(2,2,2-trifluoro-acetyl)-5,6-dihydro-1H-pyridin-2-one. Trifluoroacetic anhydride (32.8 g, 156 mmol) was added to a solution of 1-benzyl-3-morpholin-4-yl-5,6-dihydro-1H-pyridin-2-one (35.4 g, 130 mmol) and N,N-dimethyaminopyridine (19.1 g, 156 mmol) in dichloromethane (875 mL) at OC, while maintaining the internal temperature below 5° C. After the addition was complete, the reaction mixture was stirred at room temperature for 2 h and then quenched with water and extracted with dichloromethane. The combined organic phases were washed with water and then brine, dried, and concentrated under vacuum to give 1-benzyl-3-morpholin-4-yl-4-(2,2,2-trifluoro-acetyl)-5,6-dihydro-1H-pyridin-2-one (44.3 g, 92%), which was used in the following step without further purification.

Part F: Preparation of 1-benzyl-4-(2,2,2-trifluoro-acetyl)-piperidine-2,3-dione. A mixture of 1-benzyl-3-morpholin-4-yl-4-(2,2,2-trifluoro-acetyl)-5,6-dihydro-1H-pyridin-2-one (44.3 g, 120 mmol), diethyl ether (1300 mL), and 6 M hydrochloric acid (1300 mL) was stirred at room temperature for 16 h and then extracted with tert-butyl methyl ether. The combined extracts were washed with water and then with brine, dried, and concentrated under vacuum to give 1-benzyl-4-(2,2,2-trifluoro-acetyl)-piperidine-2,3-dione (31.8 g, 89%), which was used in the following step without further purification.

Part G: Preparation of 2-(6-benzyl-7-oxo-3-trifluoromethyl-4,5,6,7-tetrahydro-pyrazolo[3,4-c]pyridin-1-yl)-5-methoxy-benzoic acid methyl ester. A mixture of 1-benzyl-4-(2,2,2-trifluoro-acetyl)-piperidine-2,3-dione (13.2 g, 44.1 mmol) and 2-hydrazino-5-methoxy-benzoic acid methyl ester hydrochloride (14.4 g, 61.7 mmol) in acetic acid (400 mL) was heated under reflux for 22 h and then concentrated under vacuum. The residue was purified by column chromatography (2:1 hexanes/ethyl acetate) to give 2-(6-benzyl-7-oxo-3-trifluoromethyl-4,5,6,7-tetrahydro-pyrazolo[3,4-c]pyridin-1-yl)-5-methoxy-benzoic acid methyl ester (15 g, 74%).

Part H: Preparation of 5-Methoxy-2-(7-oxo-3-trifluoromethyl-4,5,6,7-tetrahydro-pyrazolo[3,4-c]pyridin-1-yl)-benzoic acid methyl ester. A mixture of 2-(6-benzyl-7-oxo-3-trifluoromethyl-4,5,6,7-tetrahydro-pyrazolo[3,4-c]pyridin-1-yl)-5-methoxy-benzoic acid methyl ester (22 g, 47.9 mmol), 20% Pd(OH)$_2$/C (9.8 g), methanol (120 mL), and 4M hydrochloric acid in dioxane (50 mL) was hydrogenated at 50 psi hydrogen at 50° C. for 90 h. The mixture was cautiously filtered through diatomaceous earth, and the filtrate was concentrated under vacuum. The residue was purified by column chromatography (7:3 hexanes/ethyl acetate) to give 5-methoxy-2-(7-oxo-3-trifluoromethyl-4,5,6,7-tetrahydro-pyrazolo[3,4-c]pyridin-1-yl)-benzoic acid methyl ester (11 g, 62%).

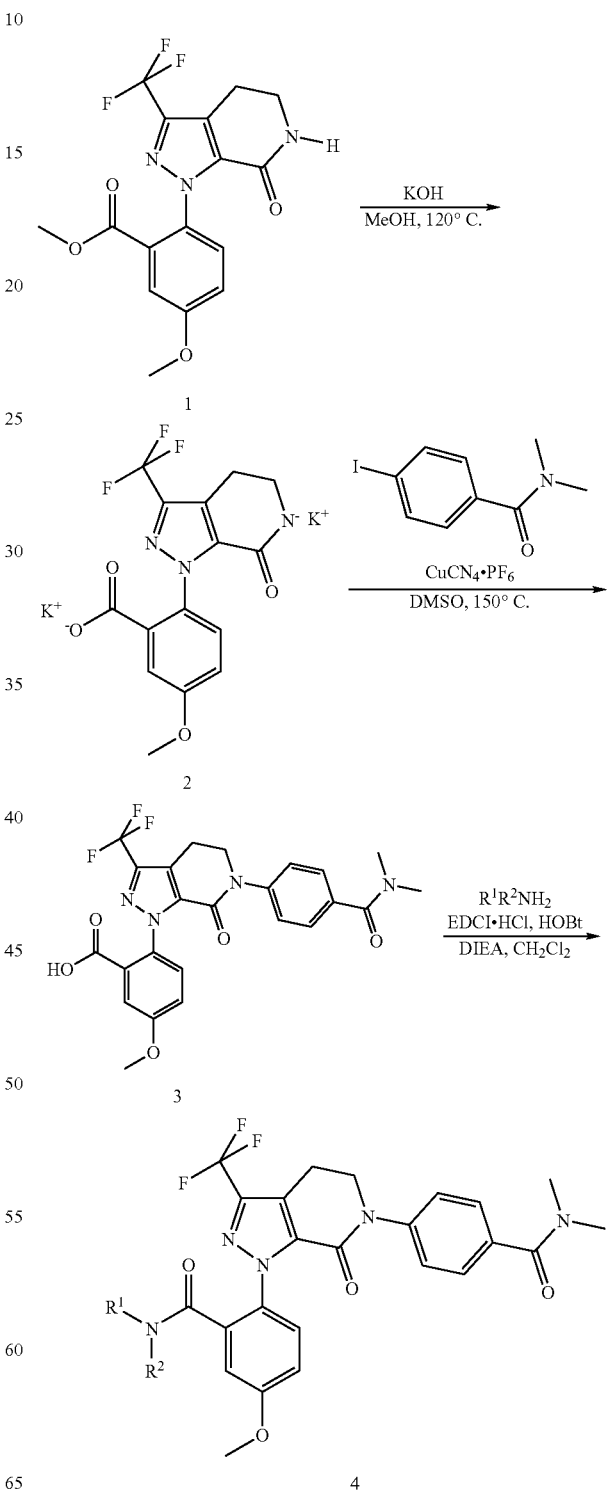

Part I: Preparation of 5-methoxy-2-(7-oxo-3-trifluoromethyl-4,5,6,7-tetrahydro-pyrazolo[3,4-c]pyridin-1-yl)-benzoic acid bis-potassium salt. Potassium hydroxide pellets (118 mg, 2.1 mmol) were dissolved in methanol (5 mL) with stirring. 5-Methoxy-2-(7-oxo-3-trifluoromethyl-4,5,6,7-tetrahydro-pyrazolo[3,4-c]pyridin-1-yl)-benzoic acid methyl ester (370 mg, 1.0 mmol) was added in one portion with stirring. The solid did not completely dissolve before microwave heating at 120° C. for 15 minutes. The solution was evaporated under a nitrogen stream to give a colorless residue. LC/MS M−H=354.4.

Part J: Preparation of 2-[6-(4-dimethylcarbamoyl-phenyl)-7-oxo-3-trifluoromethyl-4,5,6,7-tetrahydro-pyrazolo[3,4-c]pyridin-1-yl]-5-methoxy-benzoic acid. 4-Iodo-N,N-dimethylbenzamide (410 mg, 1.5 mmol) and tetrakisacetonitrilecopper(I) hexafluorophosphate (37.2 mg, 0.1 mmol) were dissolved in degassed dimethylsulfoxide (5 mL) and added to 5-methoxy-2-(7-oxo-3-trifluoromethyl-4,5,6,7-tetrahydro-pyrazolo[3,4-c]pyridin-1-yl)-benzoic acid bis-potassium salt. This mixture was vigorously stirred to dissolve the solids. The solution was purged with nitrogen before heating in a microwave at 150° C. for 60 minutes. After cooling to ambient temperature the resulting brown solution was quickly added to aqueous 1N hydrochloric acid (100 ml) to produce a yellow suspension which was stirred for 30 minutes. The yellow solid was collected by filtration and washed with water (30 mL), dissolved in ethyl acetate (50 mL) and extracted into aqueous sodium bicarbonate (20 mL water and 3 mL saturated sodium bicarbonate). The ethyl acetate was extracted a second time with aqueous sodium bicarbonate and the aqueous extracts combined and washed with ethyl acetate (50 mL). The aqueous extract was acidified with aqueous 1N hydrochloric acid (15 mL) and extracted twice with ethyl acetate (30 mL). The combined ethyl acetate extracts were washed with water (20 mL), dried over sodium sulfate, filtered, and evaporated to give 410 mg (80%) of 2-[6-(4-dimethylcarbamoyl-phenyl)-7-oxo-3-trifluoromethyl-4,5,6,7-tetrahydro-pyrazolo[3,4-c]pyridin-1-yl]-5-methoxybenzoic acid as an amber glass in 85% purity. LC/MS (M+H)$^+$: 503.3. $^1$H NMR (CD$_3$OD) δ 7.53 (d, J=2.9 1H), 7.40 (m, 5H), 7.2 (dd, J=2.9, 8.8 Hz, 1H), 4.10 (t, J=6.6 Hz, 2H), 3.85 (s, 3H), 3.15 (t, J=6.6 Hz, 2H), 3.05 (s, 3H), 2.95 (s, 3H).

Preparation of 2-[6-(4-dimethylcarbamoyl-phenyl)-7-oxo-3-trifluoromethyl-4,5,6,7-tetrahydro-pyrazolo[3,4-c]pyridin-1-yl]-5-methoxybenzamides: 2-[6-(4-dimethylcarbamoyl-phenyl)-7-oxo-3-trifluoromethyl-4,5,6,7-tetrahydro-pyrazolo[3,4-c]pyridin-1-yl]-5-methoxybenzoic acid (10 mg, 0.020 mmol), 1-[3-(dimethylamino)propyl]-3-ethylcarbodiimide hydrochloride (5.8 mg, 0.030 mmol), 1-hydroxybenzotriazole (4.6 mg, 0.030 mmol), and N,N-diisopropylethyl amine (18 mL, 0.100 mmol) were combined in dichloromethane (0.350 mL). After 15 minutes, this solution was added to a mixture of the amine and n-methylpyrrolidinone (0.050 mL) and shaken at ambient temperature for 12 h. The solvent was evaporated under reduced pressure and the residue was purified by reverse phase HPLC, collecting products using a MS trigger.

TABLE 5

| Ex. | Structure | MF | (M + H)$^+$ |
|---|---|---|---|
| 108 | 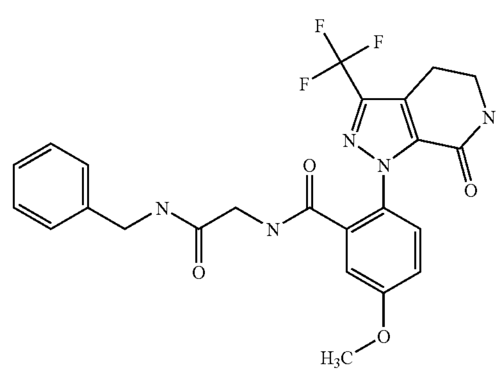 | C$_{24}$H$_{22}$F$_3$N$_5$O$_4$ | 502.2 |
| 109 | 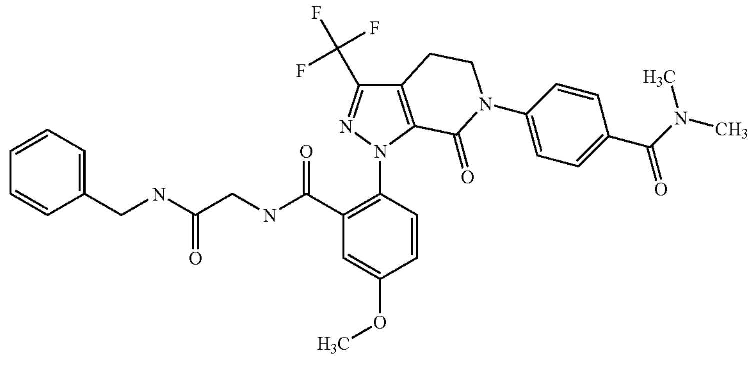 | C$_{33}$H$_{31}$F$_3$N$_6$O$_5$ | 649.2 |

TABLE 5-continued

| Ex. | Structure | MF | (M + H)+ |
|---|---|---|---|
| 110 | 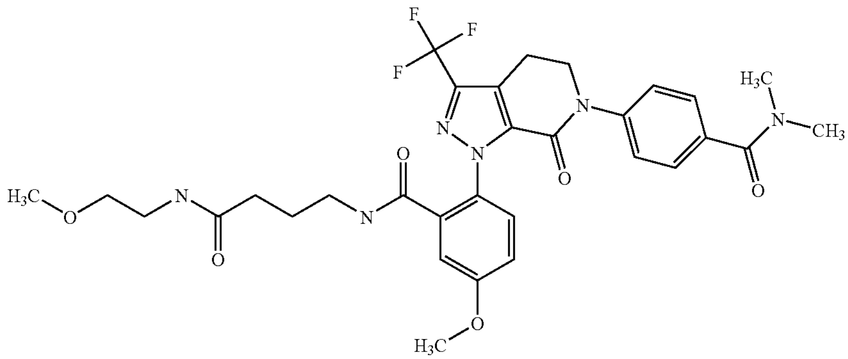 | C31H35F3N6O6 | 645.3 |
| 111 | 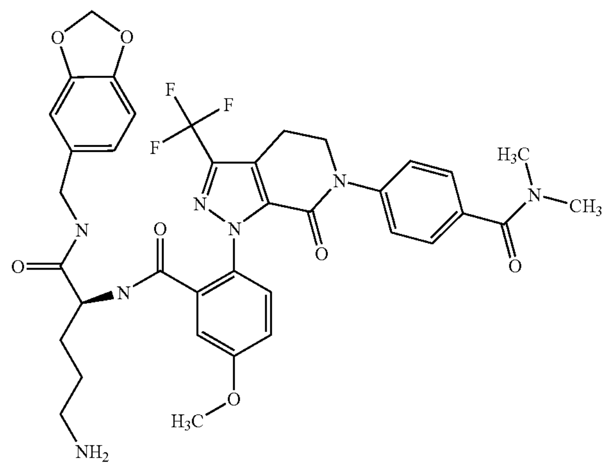 | C37H38F3N7O7 | 750.3 |
| 112 | Chiral | C32H38F3N7O5 | 658.3 |
| 113 | 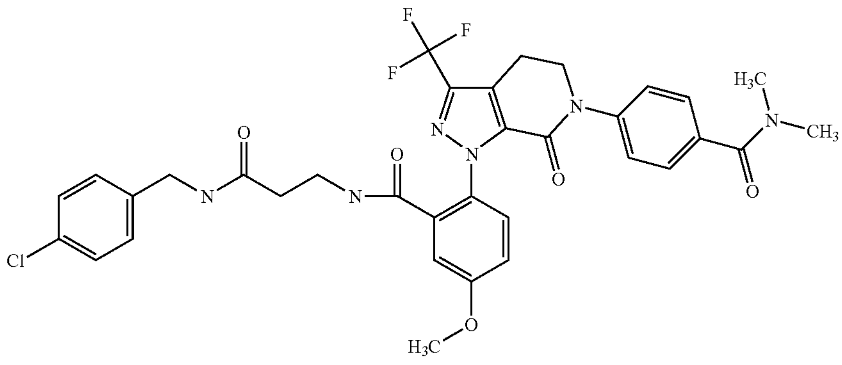 | C34H32ClF3N6O5 | 697.2 |

TABLE 5-continued
| Ex. | Structure | MF | (M + H)+ |
|---|---|---|---|
| 114 | 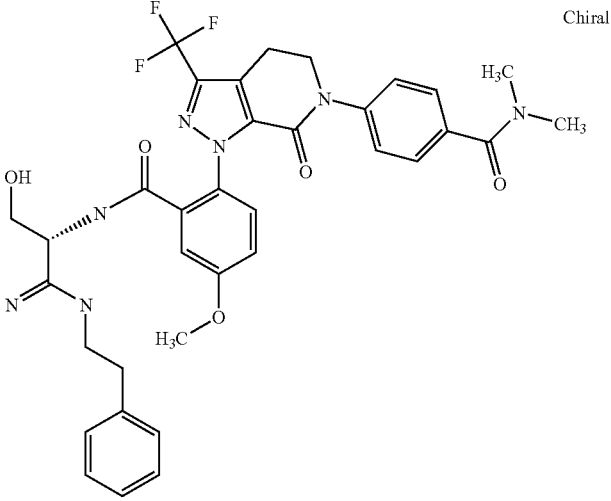 Chiral | $C_{35}H_{35}F_3N_6O_6$ | 693.3 |
| 115 | 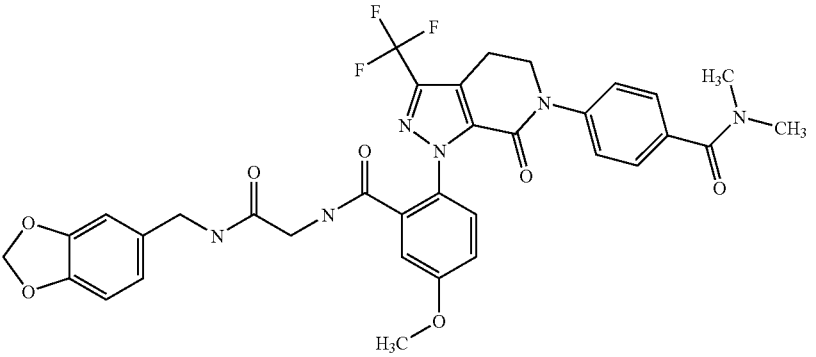 | $C_{34}H_{31}F_3N_6O_7$ | 693.2 |
| 116 | 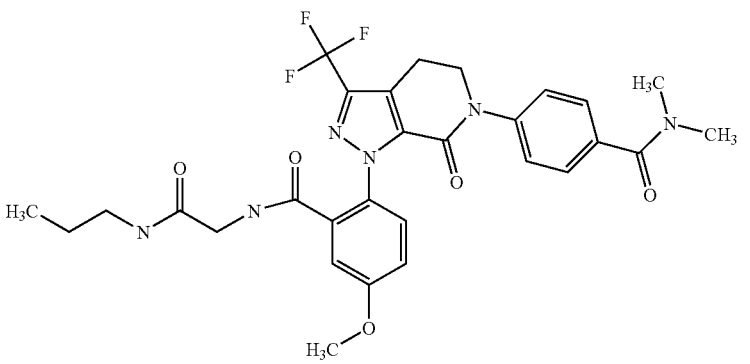 | $C_{29}H_{31}F_3N_6O_5$ | 601.2 |

TABLE 5-continued

| Ex. | Structure | | MF | (M + H)+ |
|---|---|---|---|---|
| 117 | 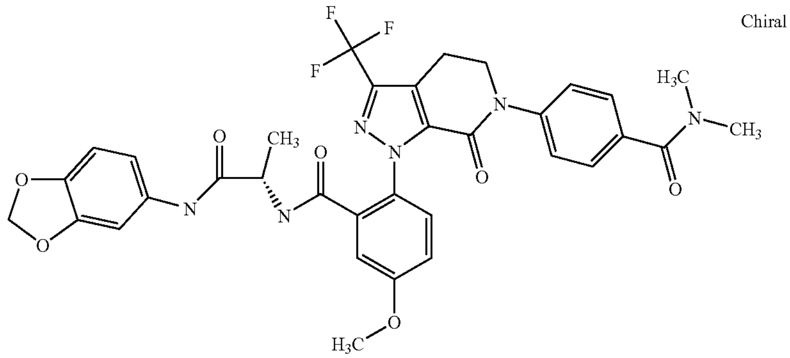 | Chiral | C34H31F3N6O7 | 693.2 |
| 118 | 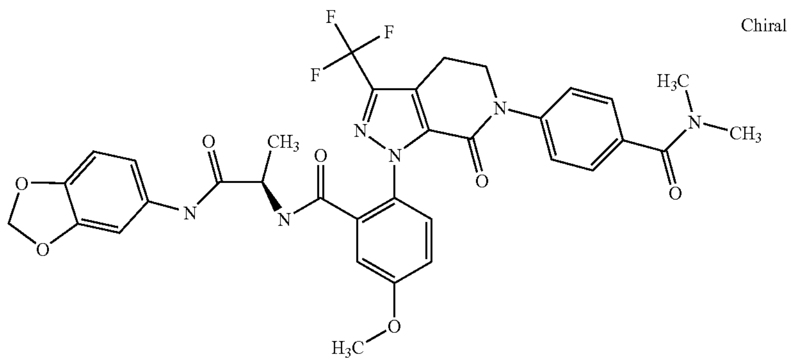 | Chiral | C34H31F3N6O7 | 693.2 |
| 119 | 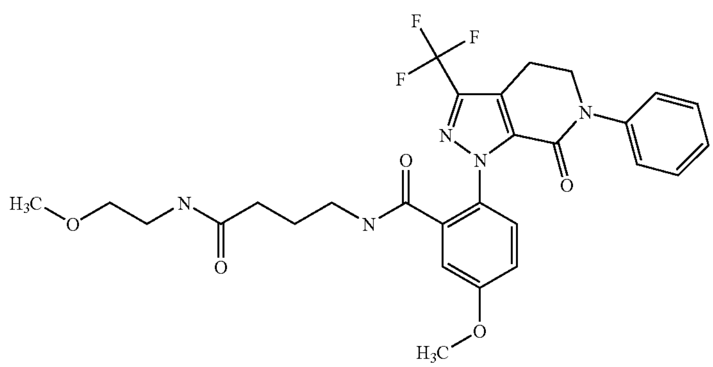 | | C28H30F3N5O5 | 574.2 |
| 120 | 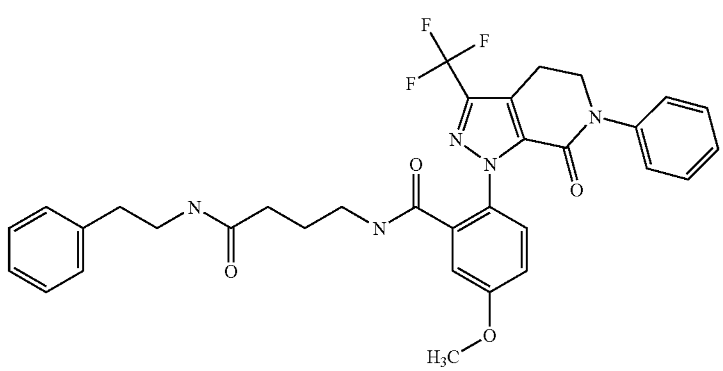 | | C33H32F3N5O4 | 620.2 |

TABLE 5-continued

| Ex. | Structure | MF | (M + H)+ |
|---|---|---|---|
| 121 | 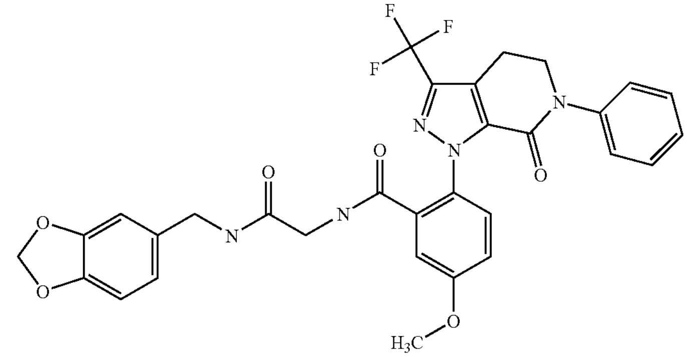 | C31H26F3N5O6 | 622.2 |
| 122 | 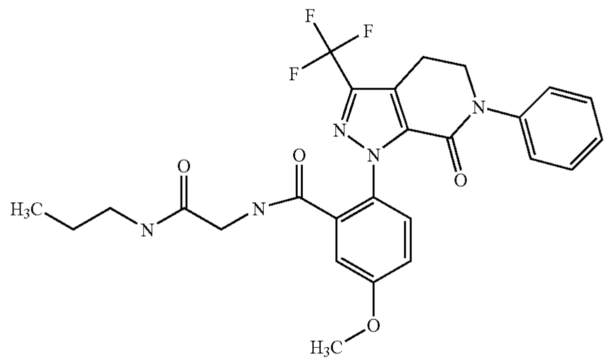 | C26H26F3N5O4 | 530.2 |
| 123 | Chiral | C32H30F3N5O5 | 622.2 |
| 124 | 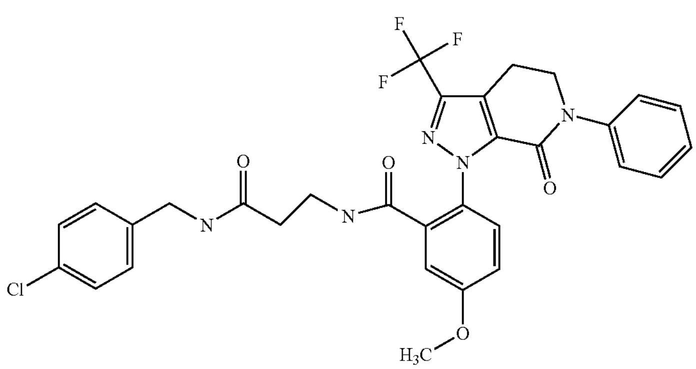 | C31H27ClF3N5O4 | 626.2 |

TABLE 5-continued

| Ex. | Structure | | MF | (M + H)+ |
|---|---|---|---|---|
| 125 | 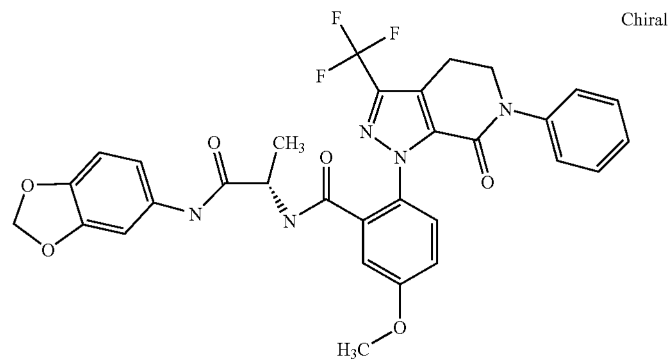 | Chiral | C₃₁H₂₆F₃N₅O₆ | 622.2 |
| 126 | 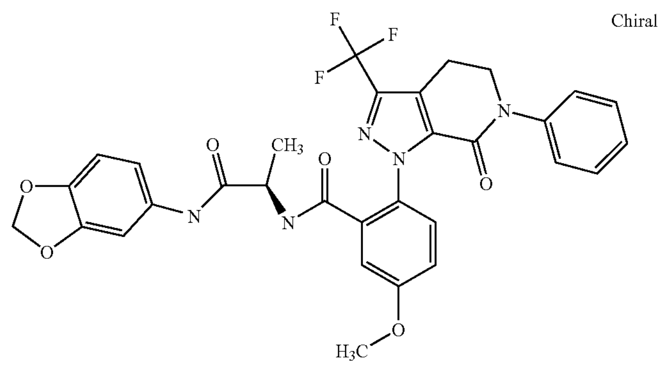 | Chiral | C₃₁H₂₆F₃N₅O₆ | 622.2 |
| 127 | 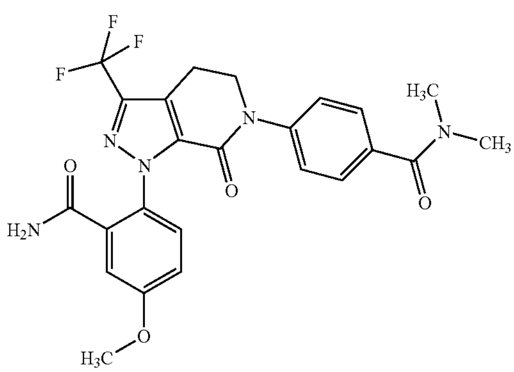 | | C₂₄H₂₂F₃N₅O₄ | 502.2 |
| 128 | 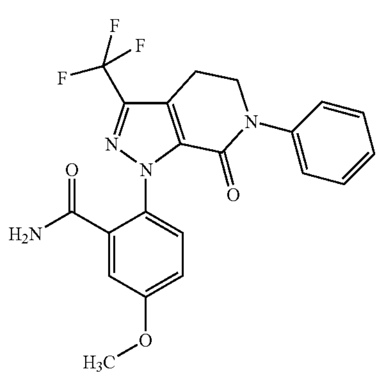 | | C₂₁H₁₇F₃N₄O₃ | 431.1 |

TABLE 5-continued

| Ex. | Structure | MF | (M + H)+ |
|---|---|---|---|
| 129 | 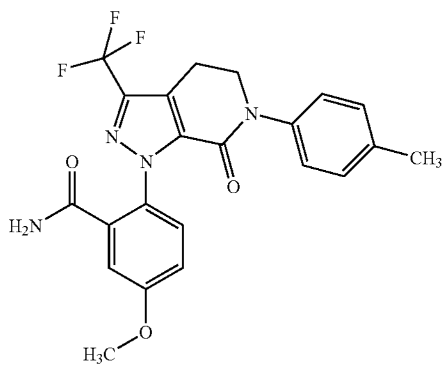 | C22H19F3N4O3 | 445.1 |
| 130 | 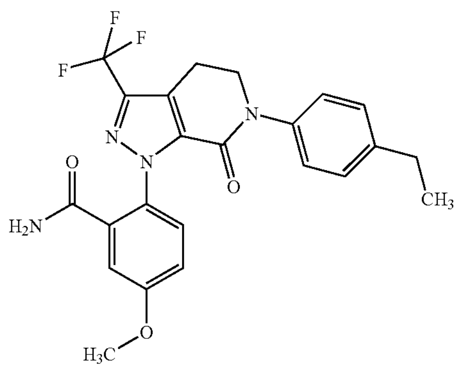 | C23H21F3N4O3 | 459.2 |
| 131 | 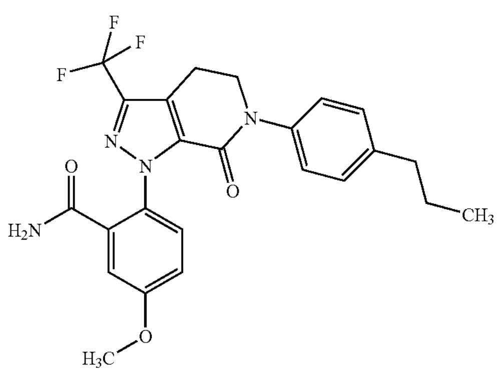 | C24H23F3N4O3 | 473.2 |
| 132 | 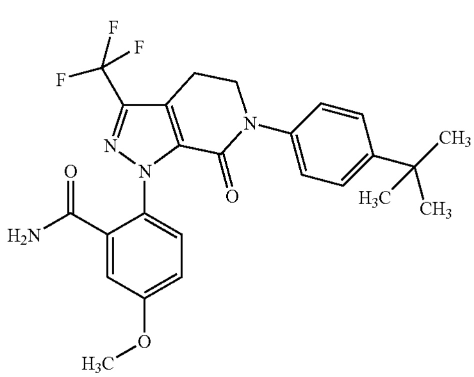 | C25H25F3N4O3 | 487.2 |

TABLE 5-continued

| Ex. | Structure | MF | (M + H)+ |
|---|---|---|---|
| 133 | 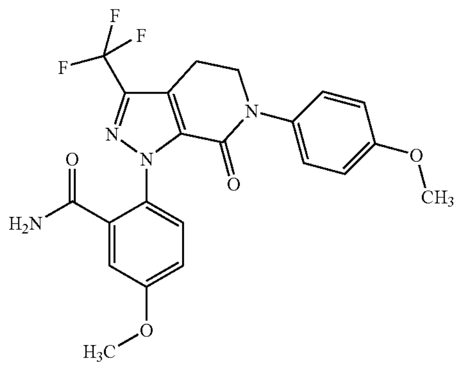 | C22H19F3N4O4 | 461.1 |
| 134 | 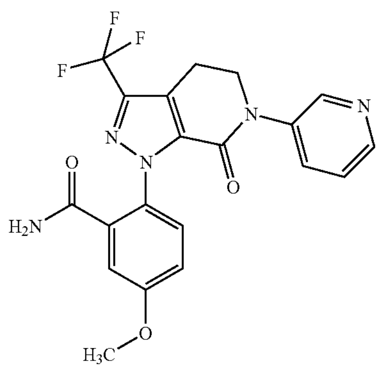 | C20H16F3N5O3 | 432.1 |
| 135 | 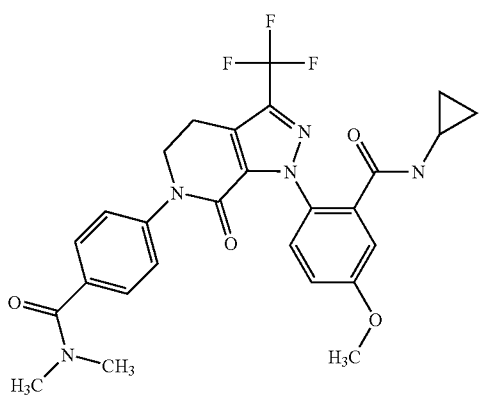 | C27H26F3N5O4 | 542.2 |
| 136 | 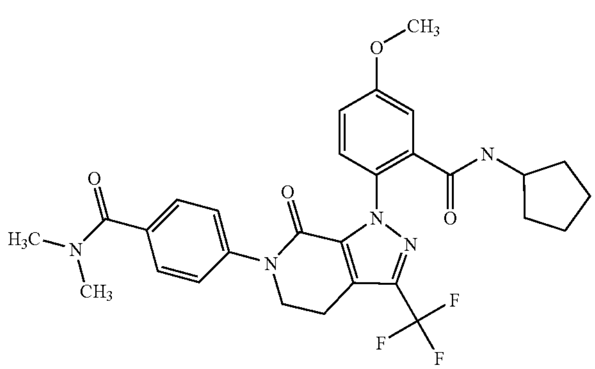 | C29H30F3N5O4 | 570.2 |

TABLE 5-continued

| Ex. | Structure | MF | (M + H)+ |
|---|---|---|---|
| 137 | 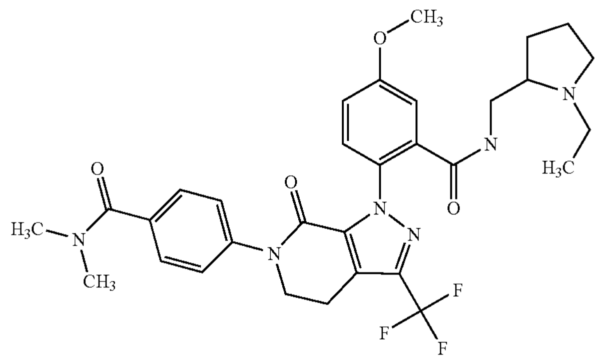 | C31H35F3N6O4 | 613.3 |
| 138 | 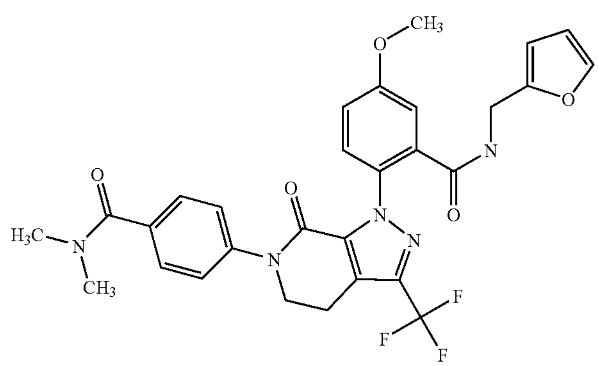 | C29H26F3N5O5 | 582.2 |
| 139 | 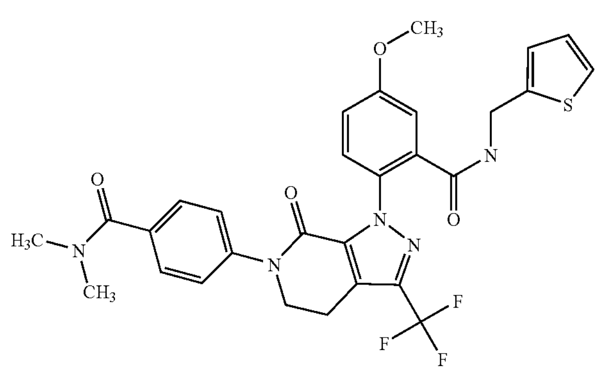 | C29H26F3N5O4S | 598.2 |

TABLE 5-continued
| Ex. | Structure | MF | (M + H)+ |
|---|---|---|---|
| 140 | 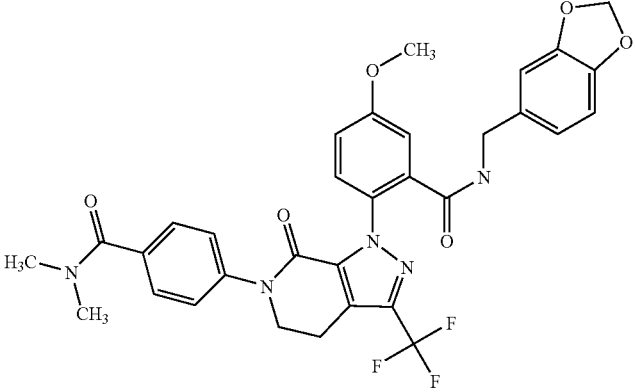 | C32H28F3N5O6 | 636.2 |
| 141 | 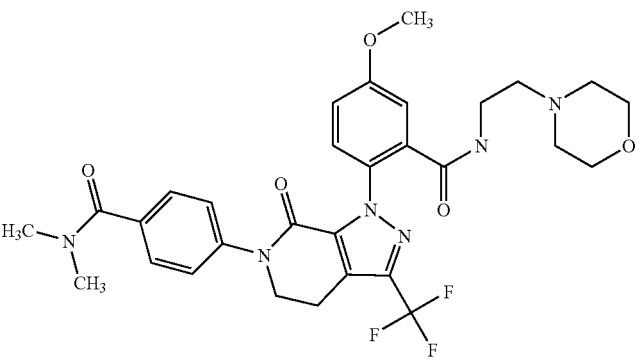 | C30H33F3N6O5 | 615.3 |
| 142 | 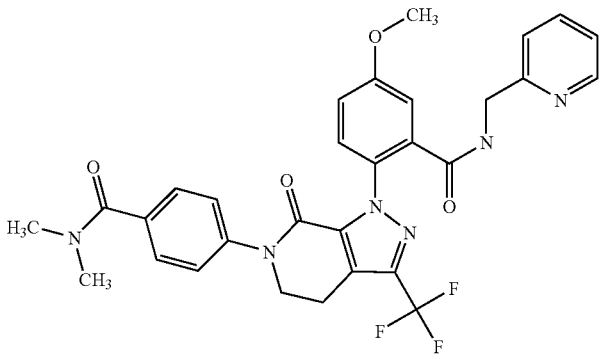 | C30H27F3N6O4 | 593.2 |
| 143 | 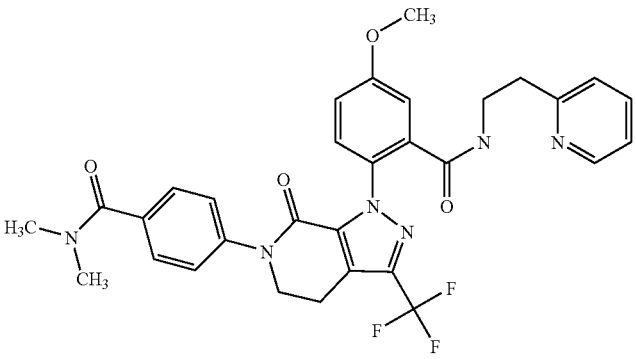 | C31H29F3N6O4 | 607.2 |

TABLE 5-continued

| Ex. | Structure | MF | (M + H)+ |
|---|---|---|---|
| 144 | 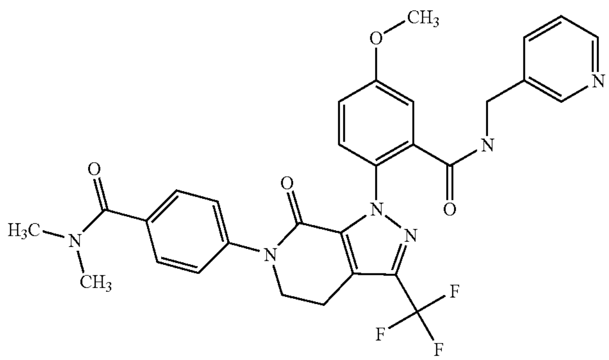 | C₃₀H₂₇F₃N₆O₄ | 593.2 |
| 145 | 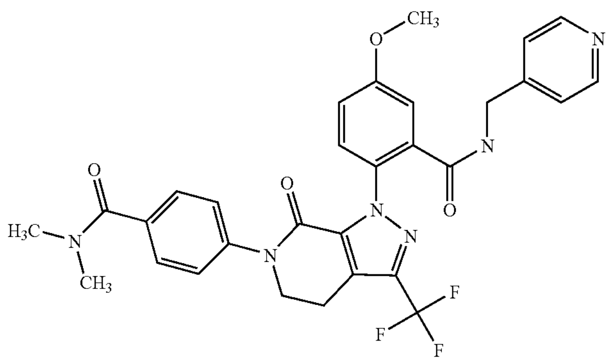 | C₃₀H₂₇F₃N₆O₄ | 593.2 |
| 146 | 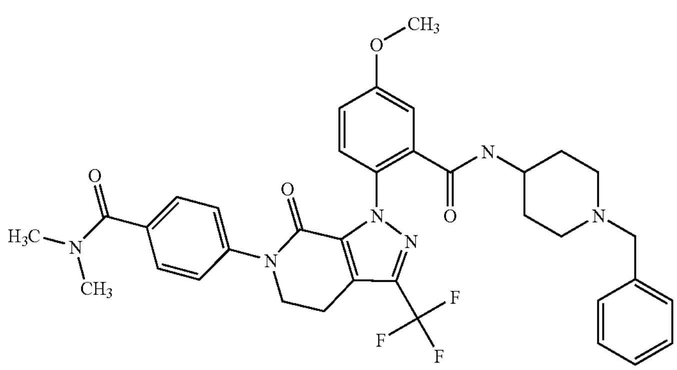 | C₃₆H₃₇F₃N₆O₄ | 675.3 |
| 147 | 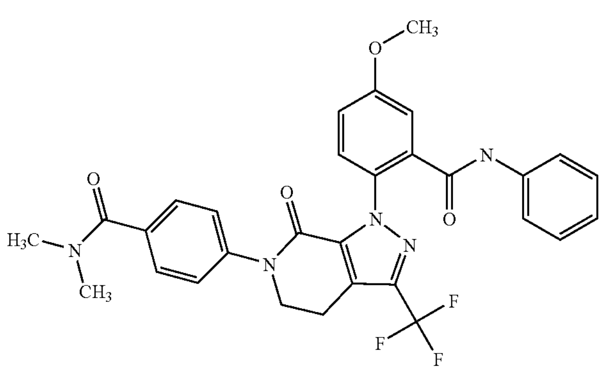 | C₃₀H₂₆F₃N₅O₄ | 578.2 |

TABLE 5-continued

| Ex. | Structure | MF | (M + H)+ |
|---|---|---|---|
| 148 | 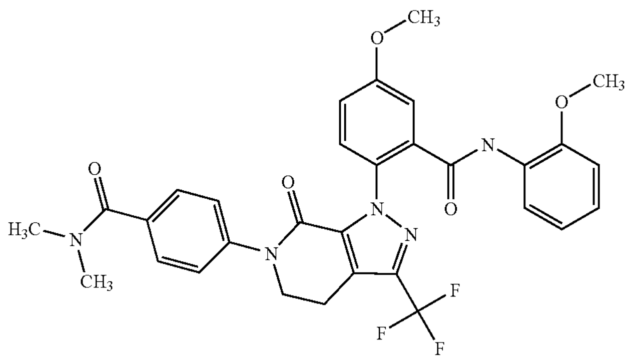 | C31H28F3N5O5 | 608.2 |
| 149 | 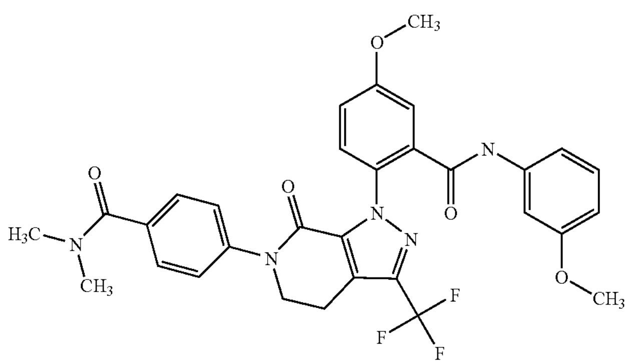 | C31H28F3N5O5 | 608.2 |
| 150 | 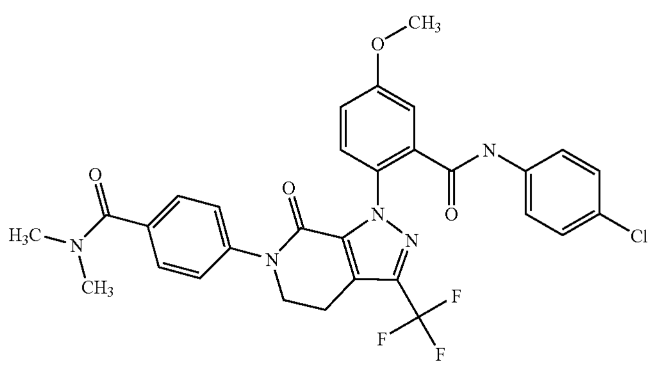 | C30H25ClF3N5O4 | 612.2 |
| 151 | 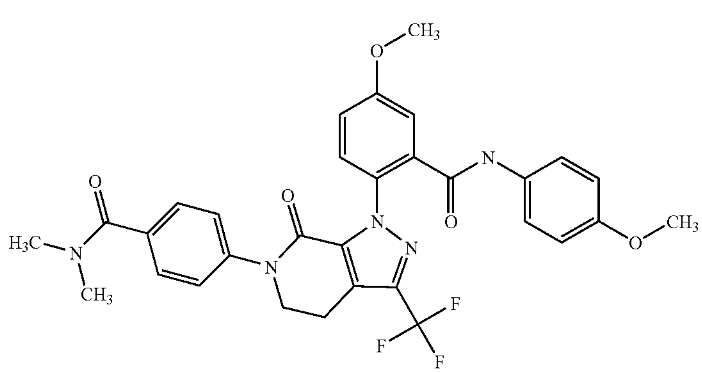 | C31H28F3N5O5 | 608.2 |

TABLE 5-continued

| Ex. | Structure | MF | (M + H)+ |
|---|---|---|---|
| 152 | 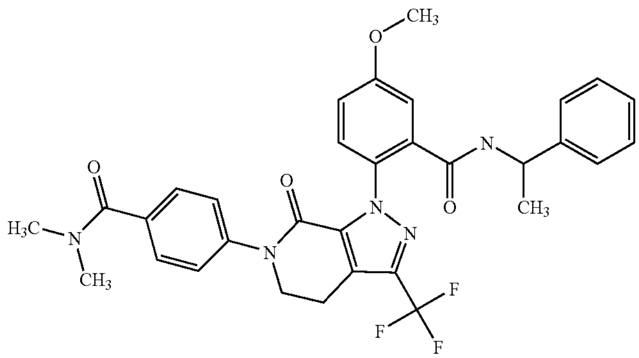 | C₃₂H₃₀F₃N₅O₄ | 606.2 |
| 153 | 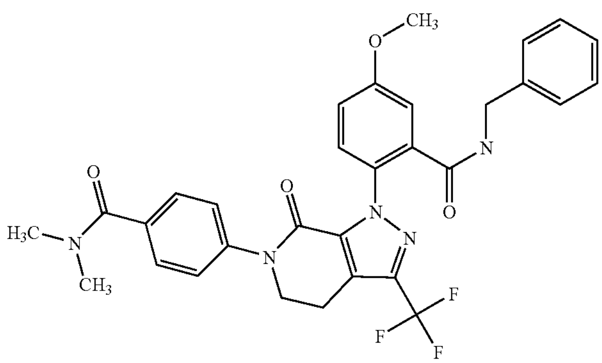 | C₃₁H₂₈F₃N₅O₄ | 592.2 |
| 154 | 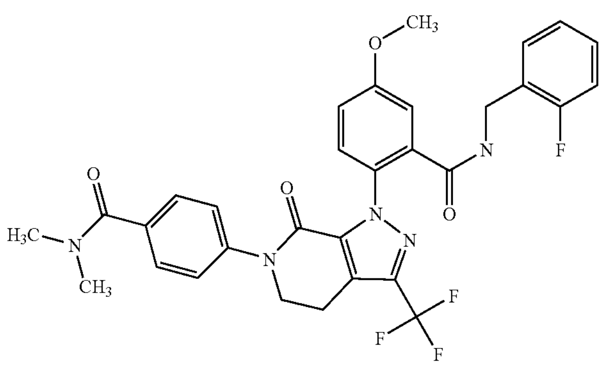 | C₃₁H₂₇F₄N₅O₄ | 610.2 |
| 155 | 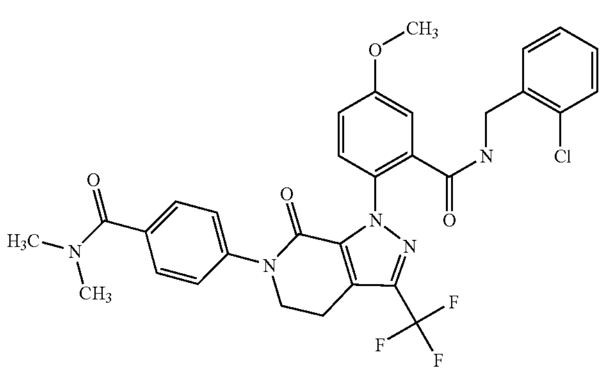 | C₃₁H₂₇ClF₃N₅O₄ | 626.2 |

TABLE 5-continued

| Ex. | Structure | MF | (M + H)+ |
|---|---|---|---|
| 156 | 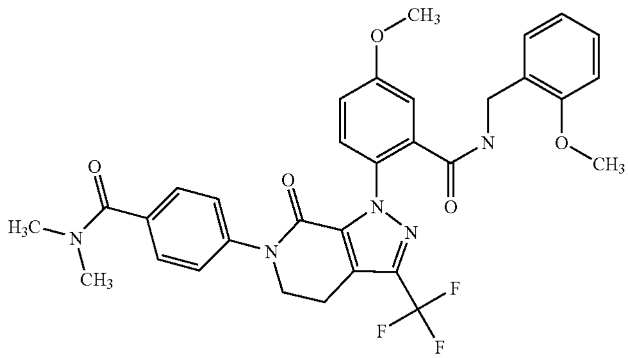 | C32H30F3N5O5 | 622.2 |
| 157 | 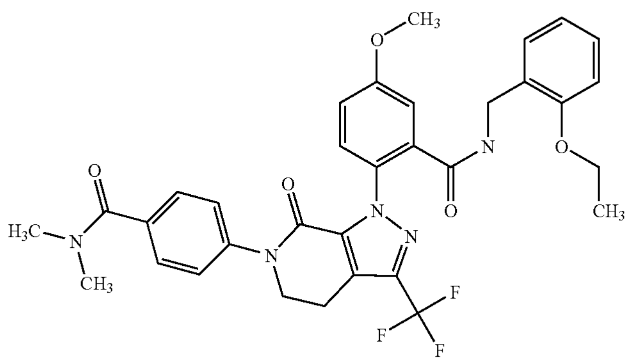 | C33H32F3N5O5 | 636.2 |
| 168 | 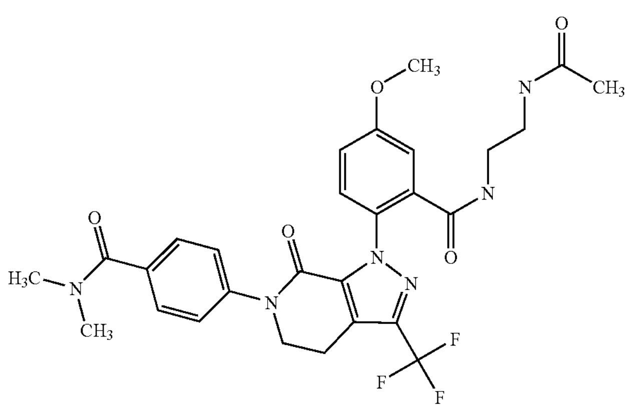 | C28H29F3N6O5 | 587.2 |
| 169 | 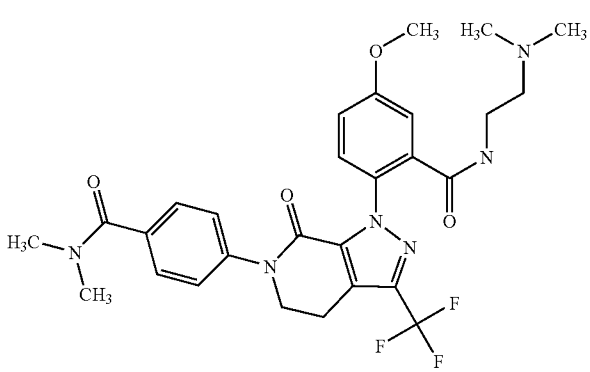 | C28H31F3N6O4 | 573.2 |

TABLE 5-continued

| Ex. | Structure | MF | (M + H)+ |
|---|---|---|---|
| 170 | 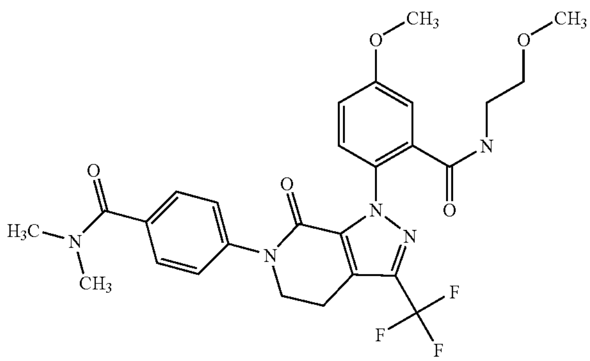 | C27H28F3N5O5 | 560.2 |
| 171 | 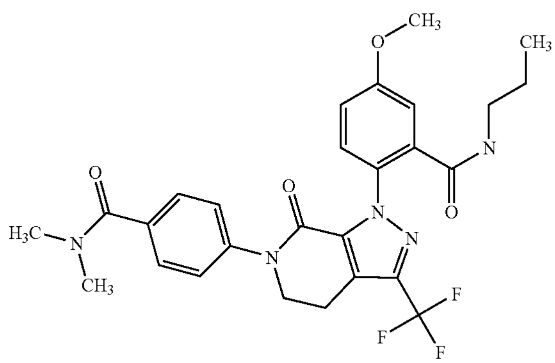 | C27H28F3N5O4 | 544.2 |
| 172 | 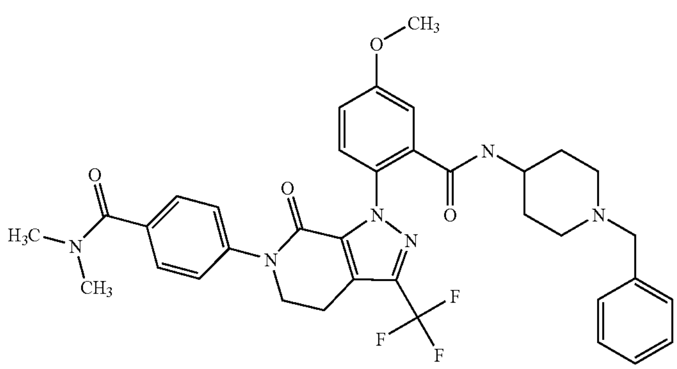 | C29H32F3N5O5 | 588.2 |
| 173 | 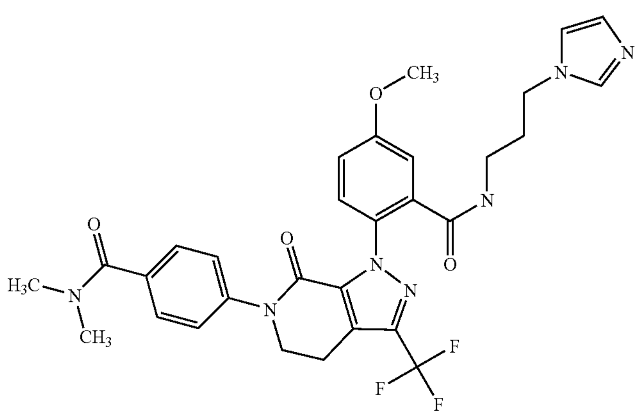 | C30H30F3N7O4 | 610.2 |

TABLE 5-continued

| Ex. | Structure | MF | (M + H)+ |
|---|---|---|---|
| 174 | 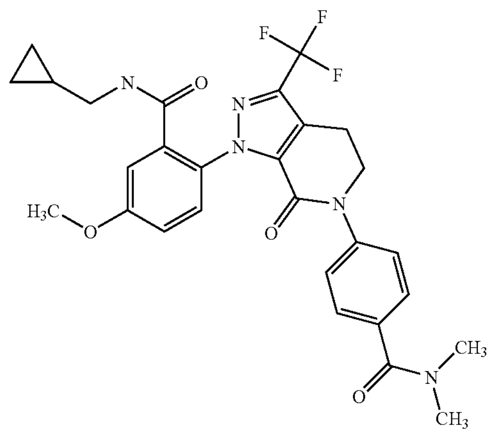 | $C_{28}H_{28}F_3N_5O_4$ | 556.2 |
| 175 | 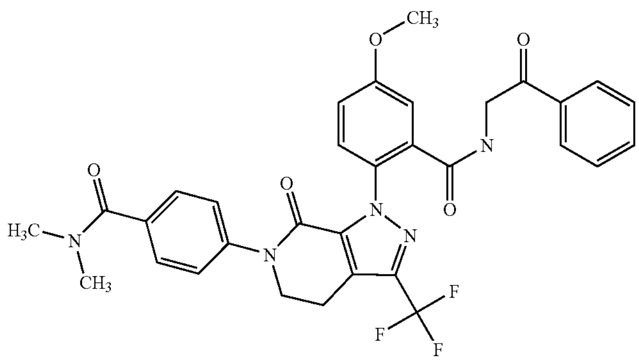 | $C_{32}H_{28}F_3N_5O_5$ | 620.2 |
| 176 | 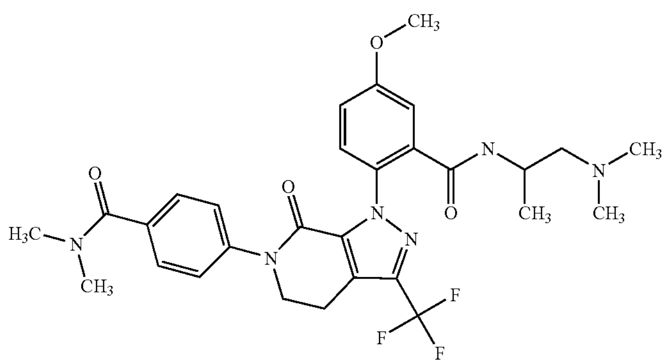 | $C_{29}H_{33}F_3N_6O_4$ | 587.3 |
| 177 | 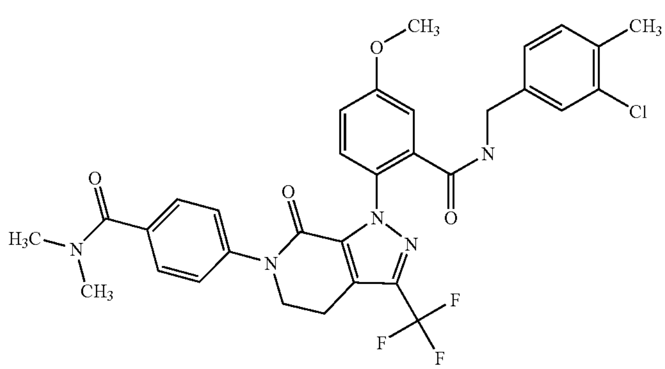 | $C_{32}H_{29}ClF_3N_5O_4$ | 640.2 |

TABLE 5-continued

| Ex. | Structure | MF | (M + H)+ |
|---|---|---|---|
| 178 | 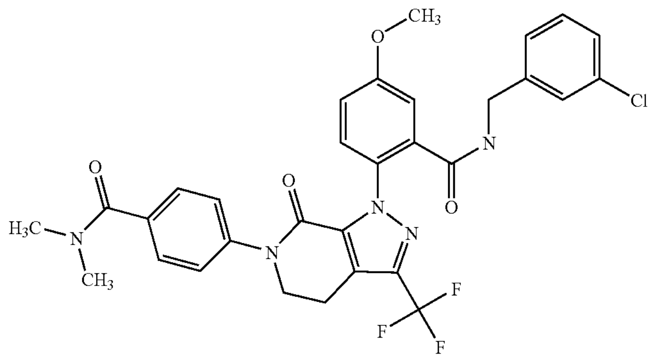 | $C_{31}H_{27}ClF_3N_5O_4$ | 626.2 |
| 179 | 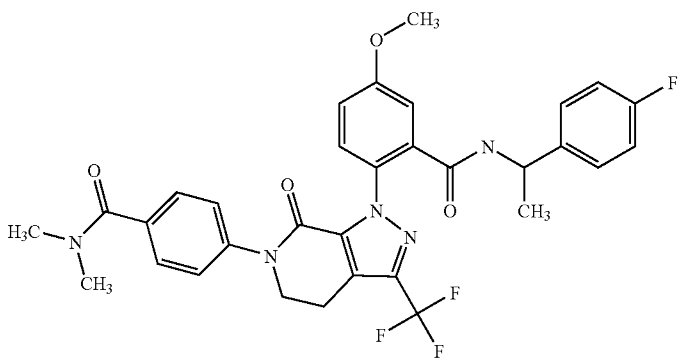 | $C_{32}H_{29}F_4N_5O_4$ | 624.2 |
| 180 | 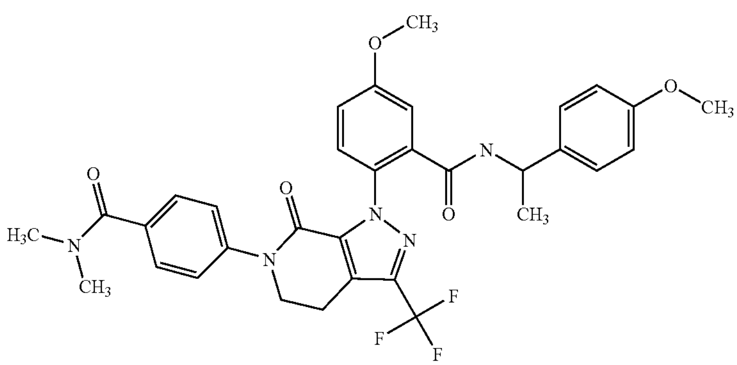 | $C_{33}H_{32}F_3N_5O_5$ | 636.2 |
| 181 | 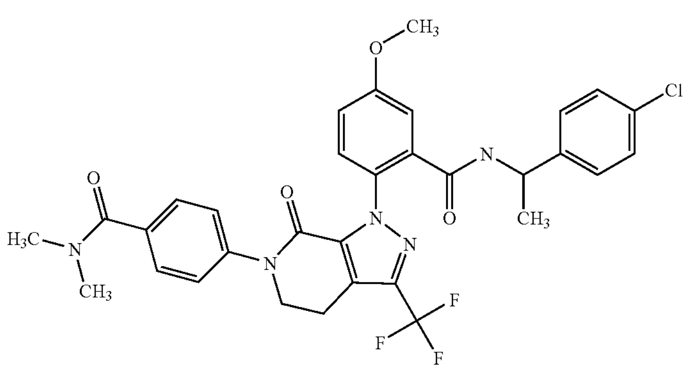 | $C_{32}H_{29}ClF_3N_5O_4$ | 640.2 |

TABLE 5-continued

| Ex. | Structure | MF | (M + H)+ |
|---|---|---|---|
| 182 | 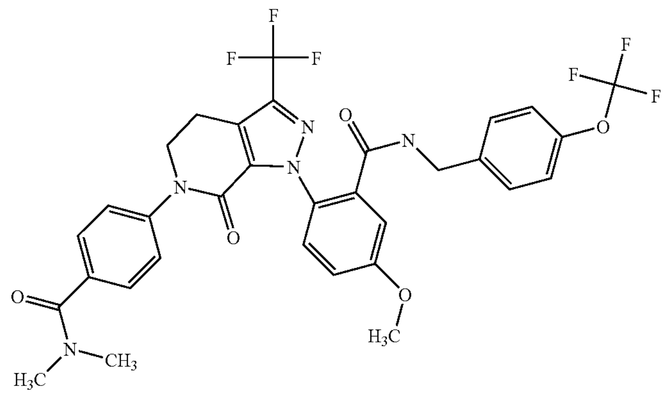 | C32H27F6N5O5 | 676.2 |
| 183 | 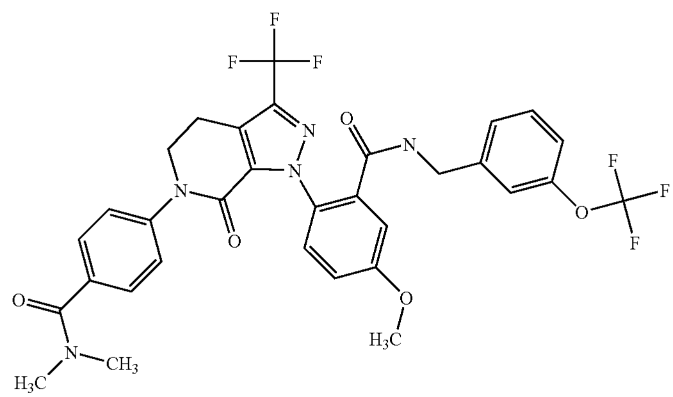 | C32H27F6N5O5 | 676.2 |
| 184 | (Chiral) | C33H32F3N5O4 | 620.2 |
| 185 | 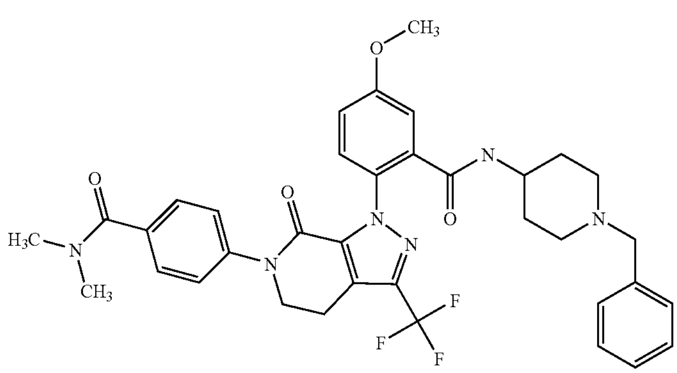 | C32H27F6N5O5 | 676.2 |

TABLE 5-continued

| Ex. | Structure | MF | (M + H)+ |
|---|---|---|---|
| 186 | 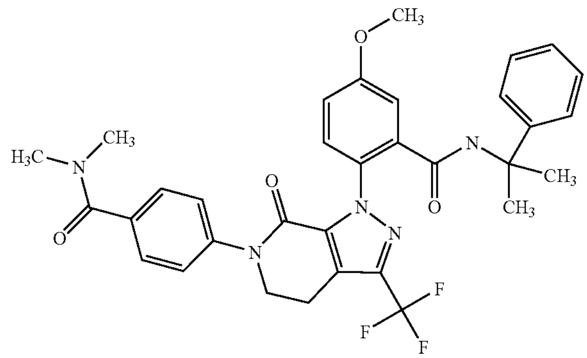 | C33H32F3N5O4 | 620.2 |
| 187 | 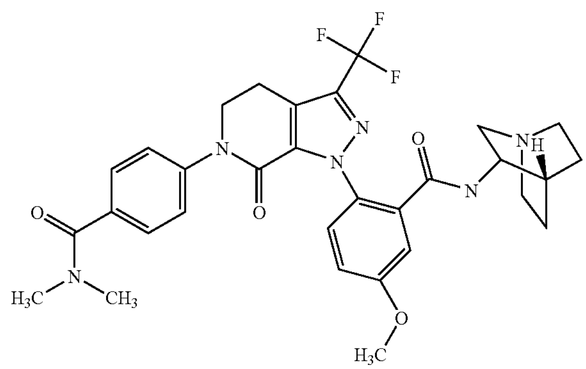 | C31H33F3N6O4 | 611.3 |
| 188 | 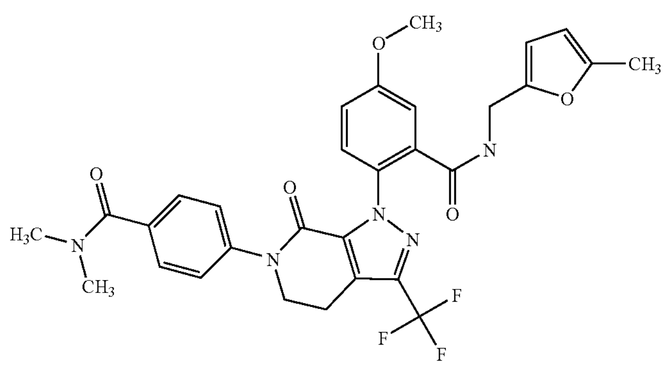 | C30H28F3N5O5 | 596.2 |
| 189 | 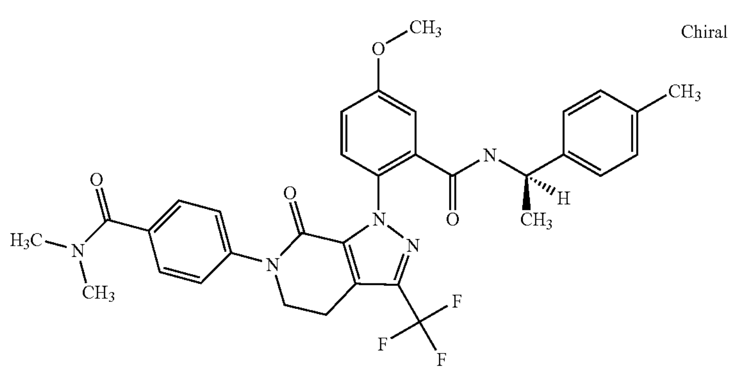 | C33H32F3N5O4 | 620.2 |

TABLE 5-continued

| Ex. | Structure | MF | (M + H)+ |
|---|---|---|---|
| 190 | 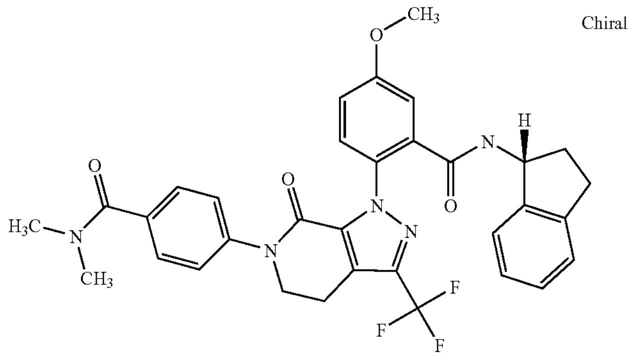 | C33H30F3N5O4 | 618.2 |
| 191 | 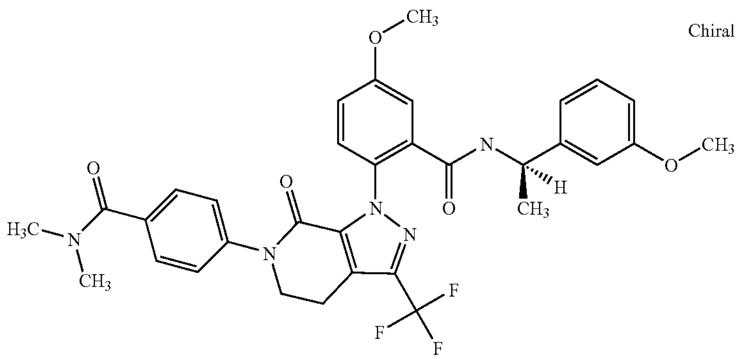 | C33H32F3N5O5 | 636.2 |
| 192 | 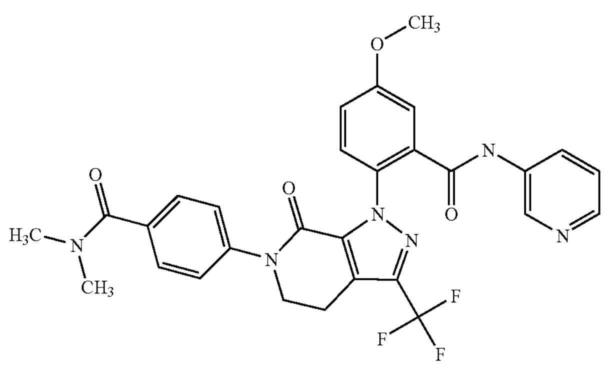 | C29H25F3N6O4 | 579.2 |
| 193 | 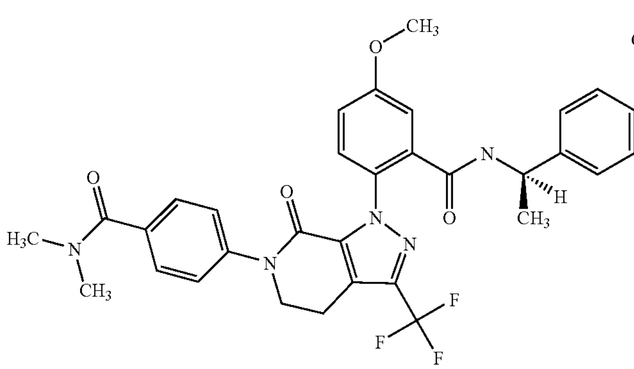 | C32H30F3N5O4 | 606.2 |

TABLE 5-continued
| Ex. | Structure | MF | (M + H)+ |
|---|---|---|---|
| 194 | 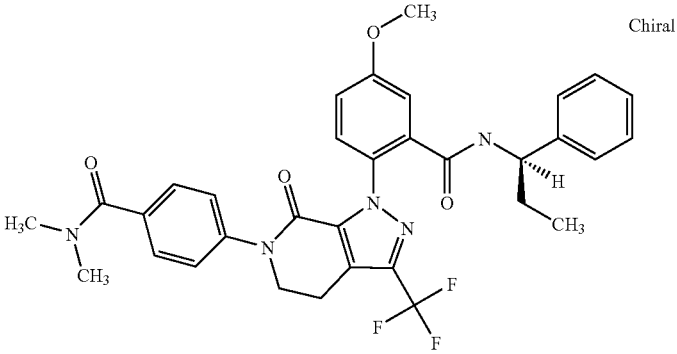 | C33H32F3N5O4 | 620.2 |
| 195 | 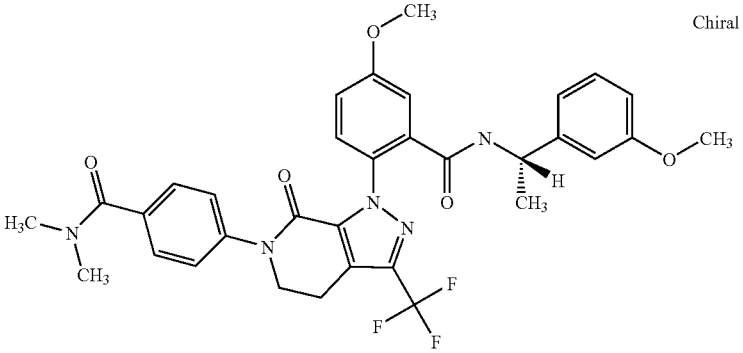 | C33H32F3N5O5 | 636.2 |
| 196 | 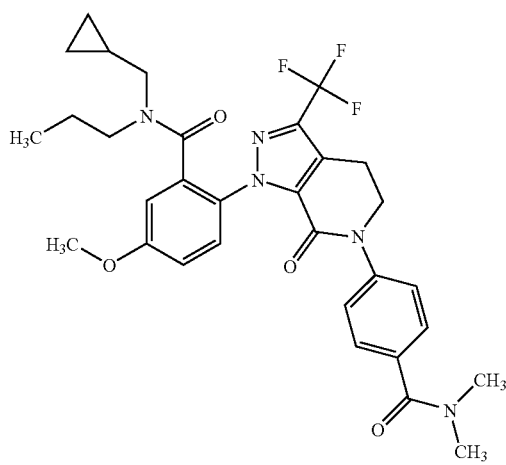 | C31H34F3N5O4 | 598.3 |
| 197 | 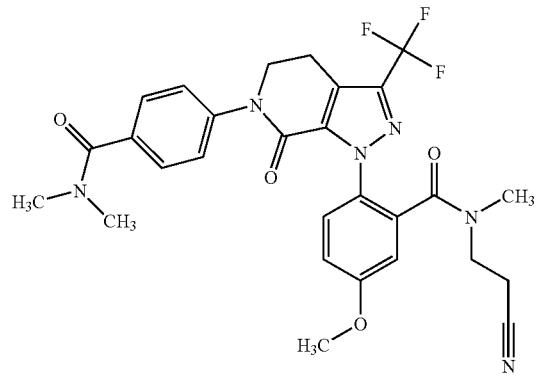 | C28H27F3N6O4 | 569.2 |

TABLE 5-continued

| Ex. | Structure | MF | (M + H)+ |
|---|---|---|---|
| 198 | 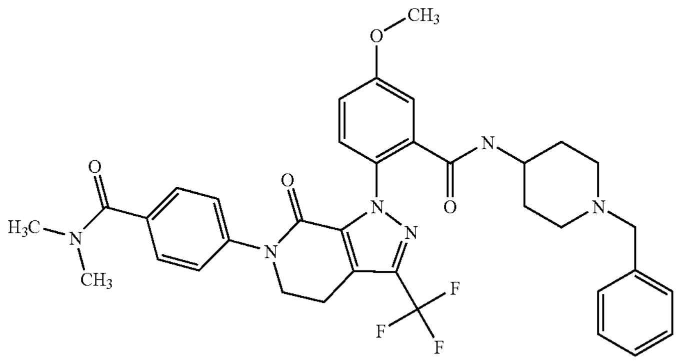 | C32H36F3N5O4 | 612.3 |
| 199 | 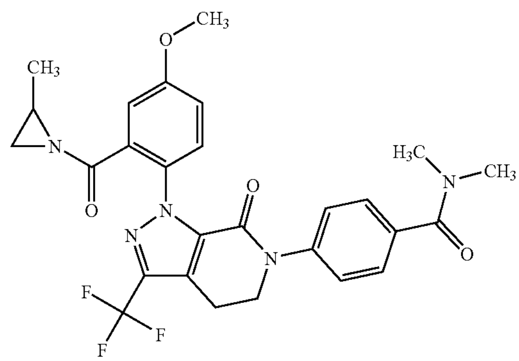 | C27H26F3N5O4 | 542.2 |
| 200 | 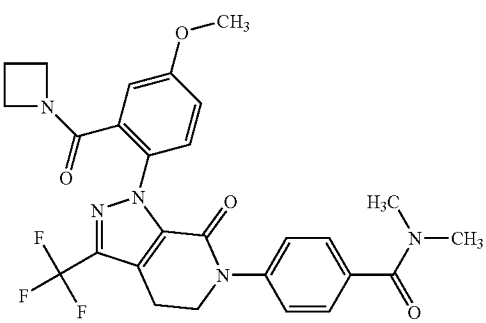 | C27H26F3N5O4 | 542.2 |
| 201 | 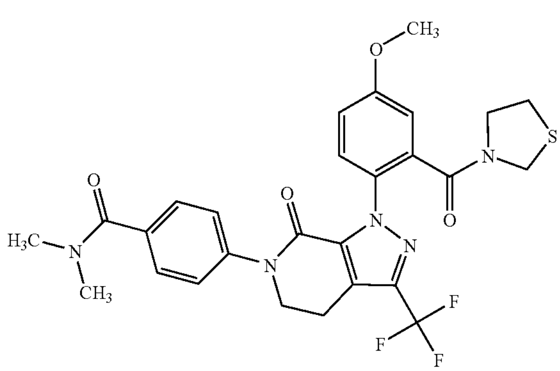 | C27H26F3N5O4S | 574.2 |

TABLE 5-continued

| Ex. | Structure | MF | (M + H)⁺ |
|---|---|---|---|
| 202 | 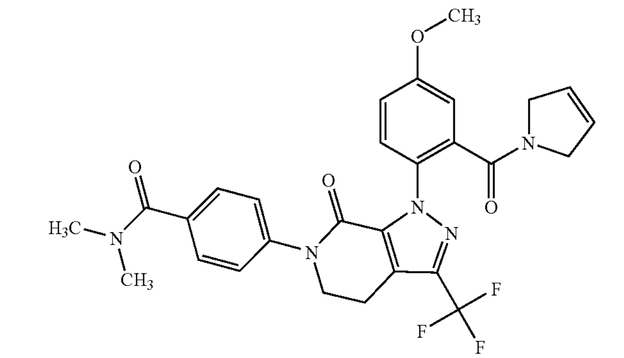 | $C_{28}H_{26}F_3N_5O_4$ | 554.2 |
| 203 | 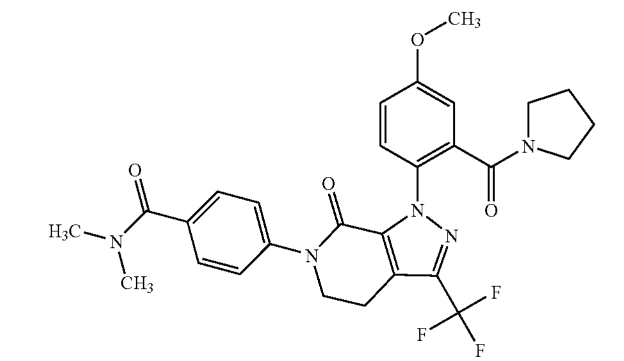 | $C_{28}H_{28}F_3N_5O_4$ | 556.2 |
| 204 | Chiral | $C_{29}H_{29}F_3N_6O_5$ | 599.2 |
| 205 | 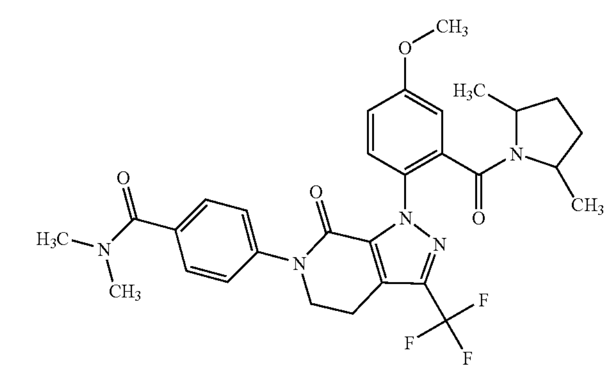 | $C_{30}H_{32}F_3N_5O_4$ | 584.2 |

TABLE 5-continued

| Ex. | Structure | MF | (M + H)+ |
|---|---|---|---|
| 206 | 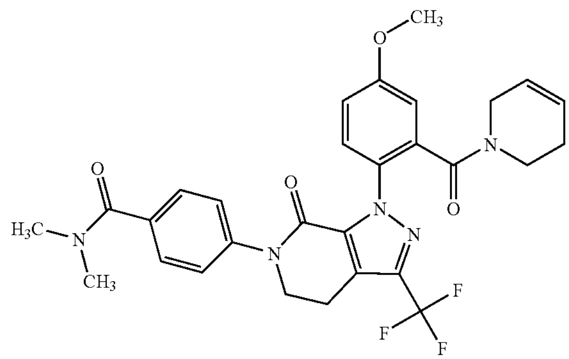 | C29H28F3N5O4 | 568.2 |
| 207 | 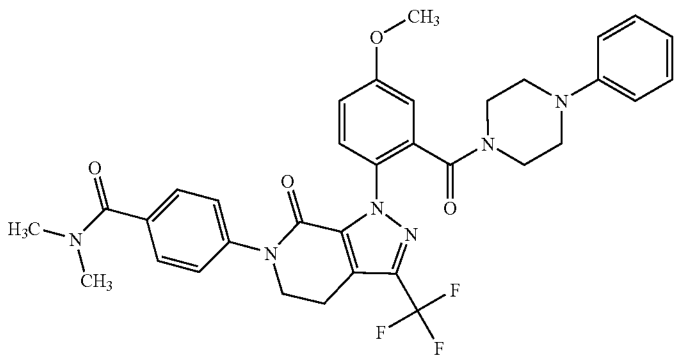 | C34H33F3N6O4 | 647.3 |
| 208 | 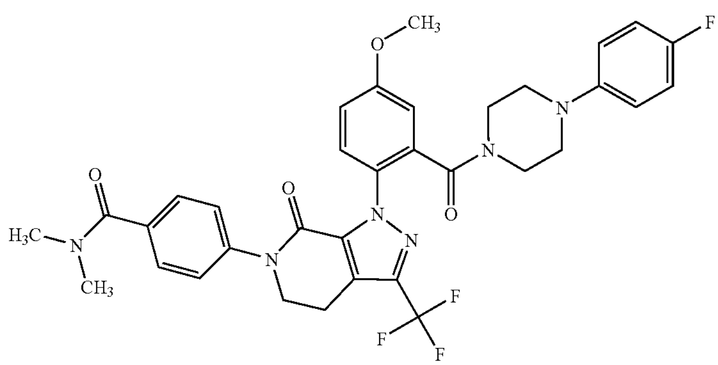 | C34H32F4N6O4 | 665.2 |
| 209 | 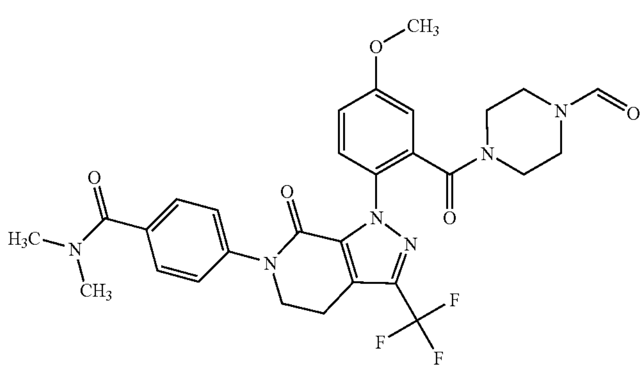 | C29H29F3N6O4 | 599.2 |

TABLE 5-continued

| Ex. | Structure | MF | (M + H)+ |
|---|---|---|---|
| 210 | 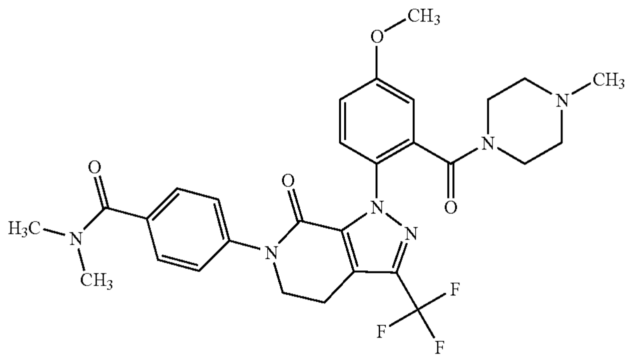 | $C_{29}H_{31}F_3N_6O_4$ | 585.2 |
| 211 | 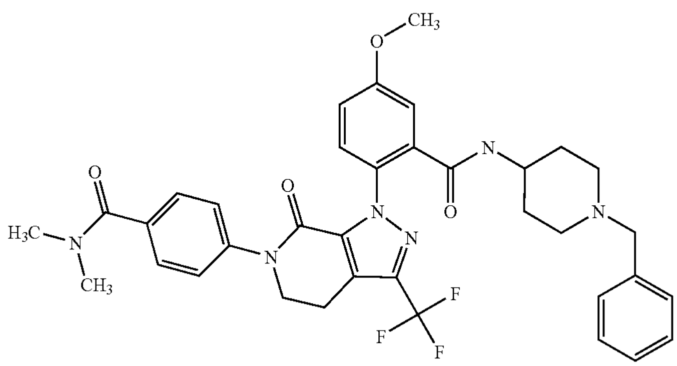 | $C_{35}H_{35}F_3N_6O_4$ | 661.3 |
| 212 | 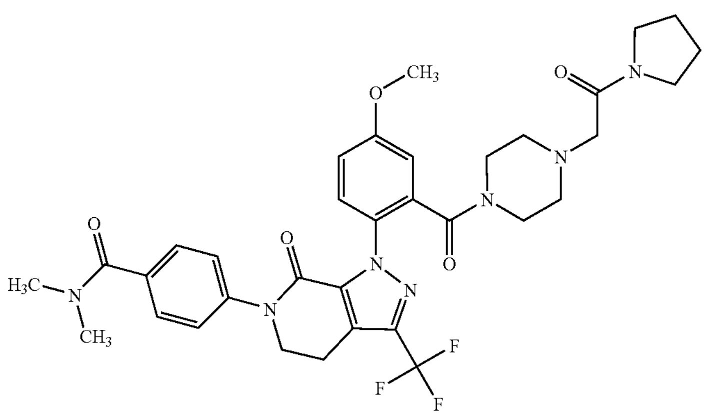 | $C_{34}H_{38}F_3N_7O_5$ | 682.3 |
| 213 | 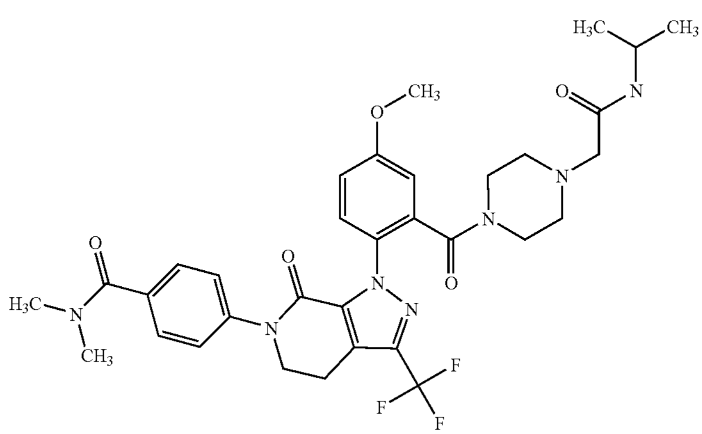 | $C_{33}H_{38}F_3N_7O_5$ | 670.3 |

TABLE 5-continued

| Ex. | Structure | MF | (M + H)+ |
|---|---|---|---|
| 214 | 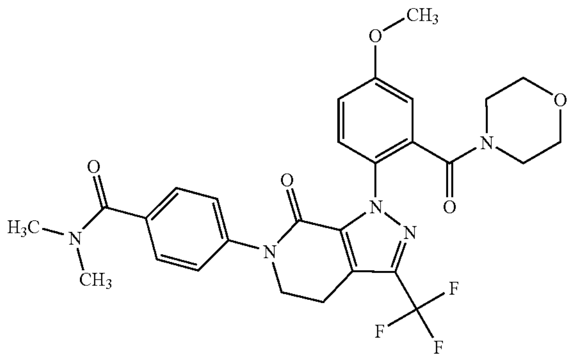 | C28H28F3N5O5 | 572.2 |
| 215 | 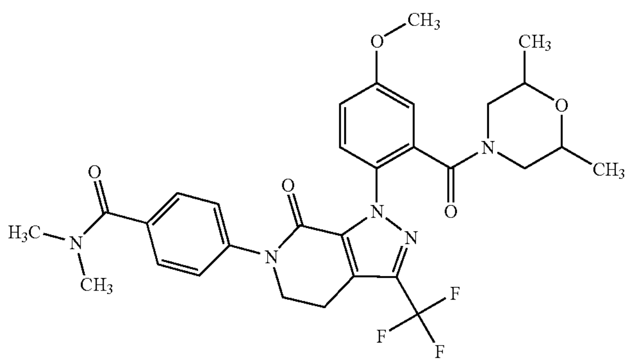 | C30H32F3N5O5 | 600.2 |
| 216 | 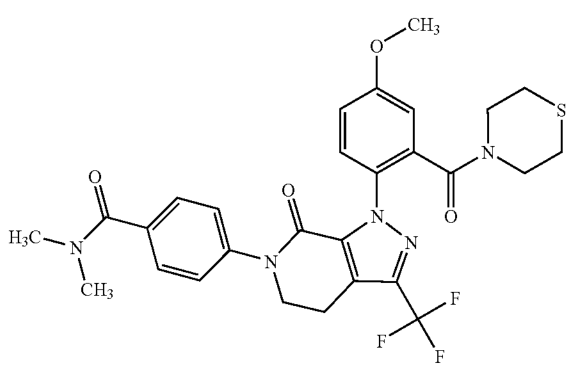 | C28H28F3N5O4S | 588.2 |
| 217 | 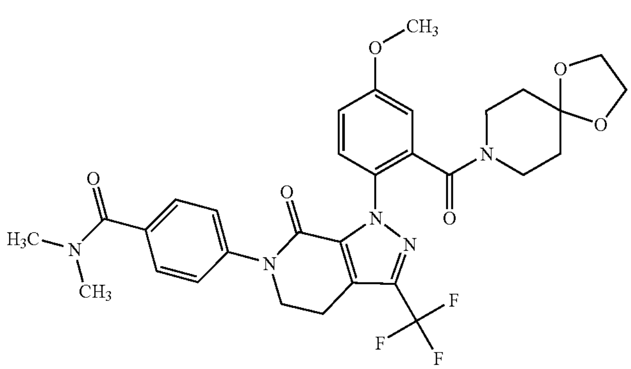 | C31H32F3N5O6 | 628.2 |

TABLE 5-continued

| Ex. | Structure | MF | (M + H)+ |
|---|---|---|---|
| 218 | 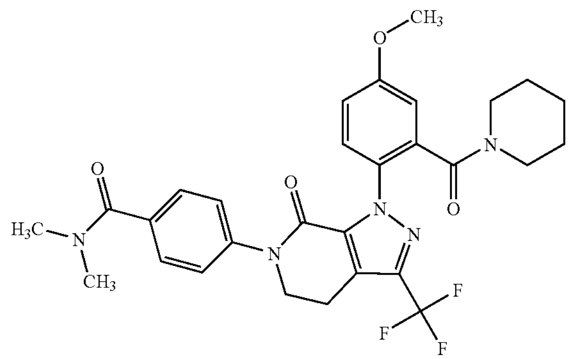 | C29H30F3N5O4 | 570.2 |
| 219 | 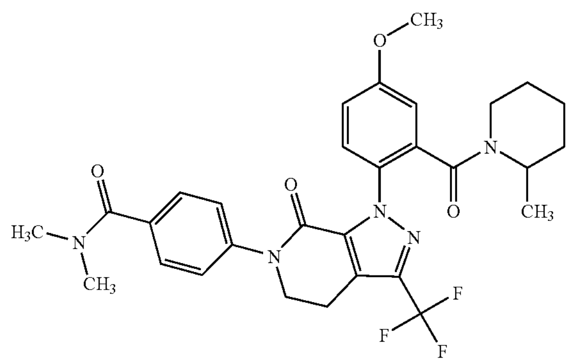 | C30H32F3N5O4 | 584.2 |
| 220 | 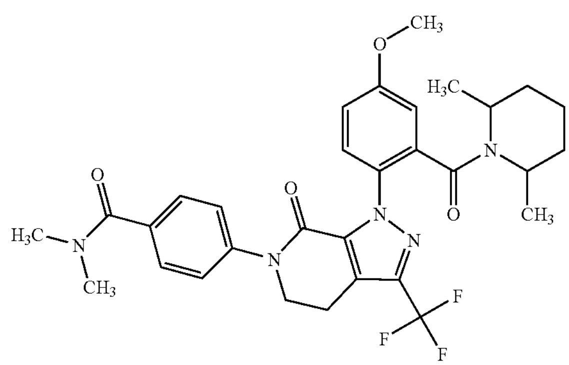 | C31H34F3N5O4 | 598.3 |
| 221 | 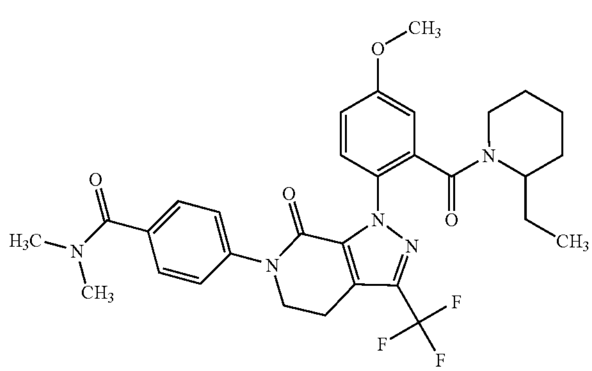 | C31H34F3N5O4 | 598.3 |

TABLE 5-continued

| Ex. | Structure | MF | (M + H)+ |
|---|---|---|---|
| 222 | 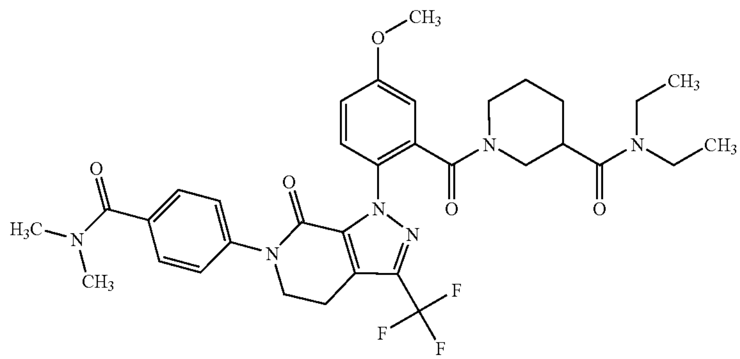 | C34H39F3N6O5 | 669.3 |
| 223 | 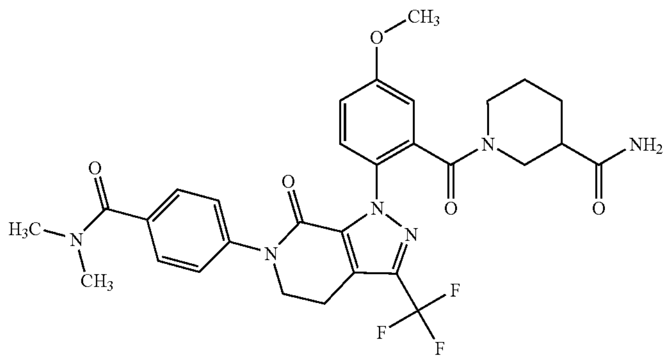 | C30H31F3N6O5 | 613.2 |
| 224 | 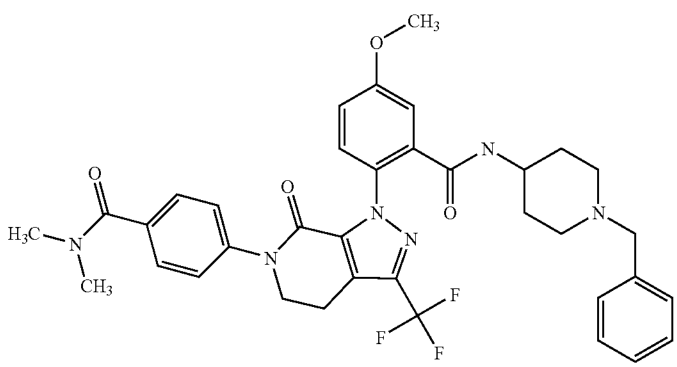 | C30H32F3N5O4 | 584.2 |
| 225 | 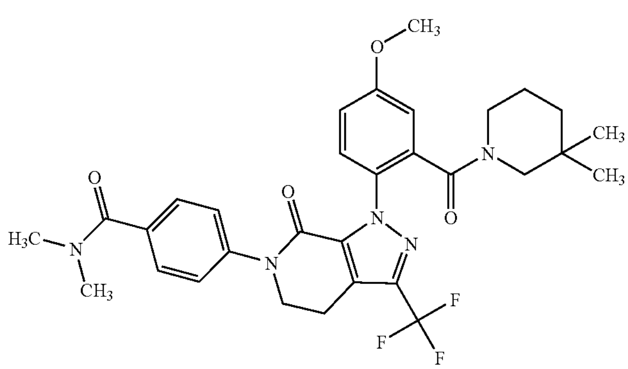 | C31H34F3N5O4 | 598.3 |

TABLE 5-continued

| Ex. | Structure | MF | (M + H)+ |
|---|---|---|---|
| 226 | 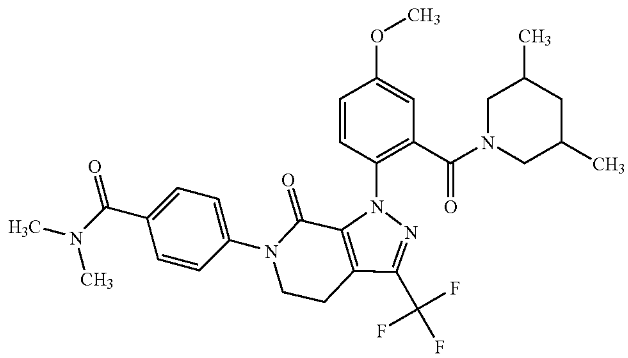 | C31H34F3N5O4 | 598.3 |
| 227 | 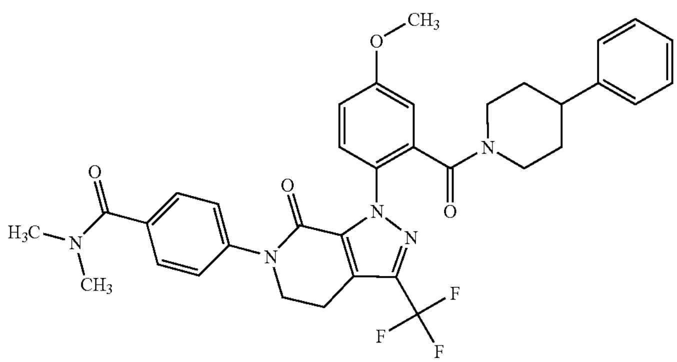 | C35H34F3N5O4 | 646.3 |
| 228 | 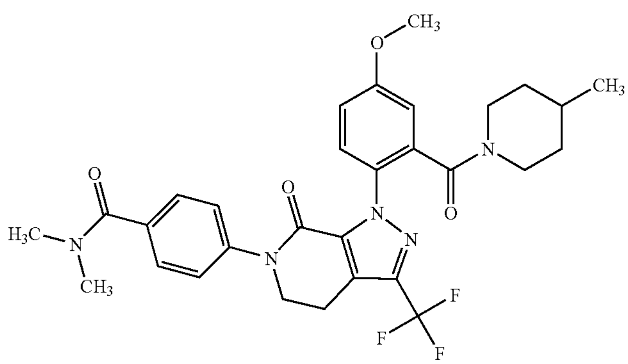 | C30H32F3N5O4 | 584.2 |
| 229 | 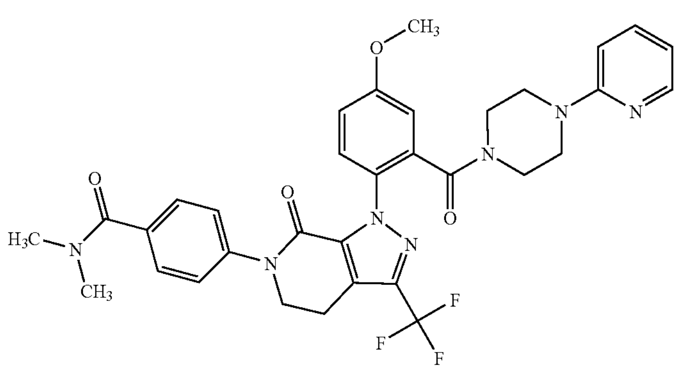 | C33H32F3N7O4 | 648.3 |

TABLE 5-continued

| Ex. | Structure | MF | (M + H)+ |
|---|---|---|---|
| 230 | 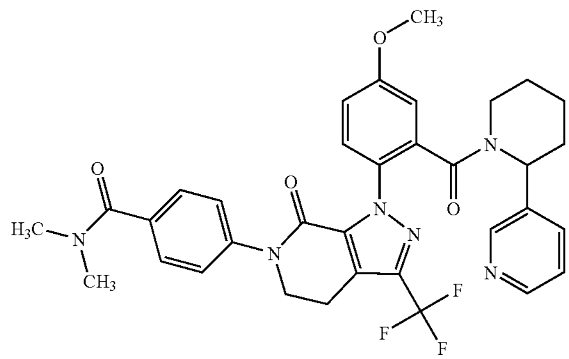 | C34H33F3N6O4 | 647.3 |
| 231 | 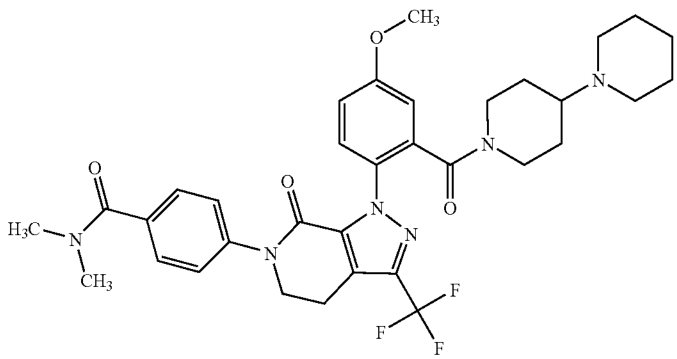 | C34H39F3N6O4 | 653.3 |
| 232 | 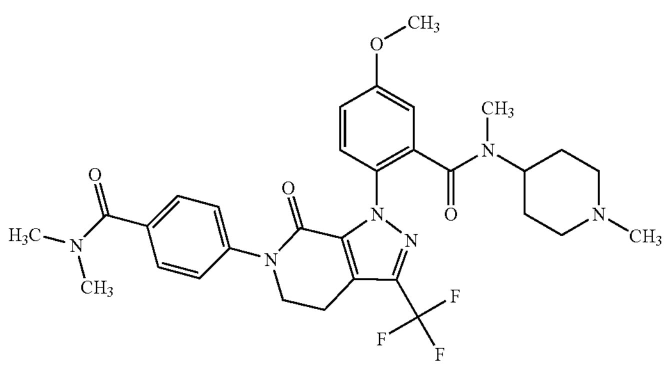 | C31H35F3N6O4 | 613.3 |
| 233 | 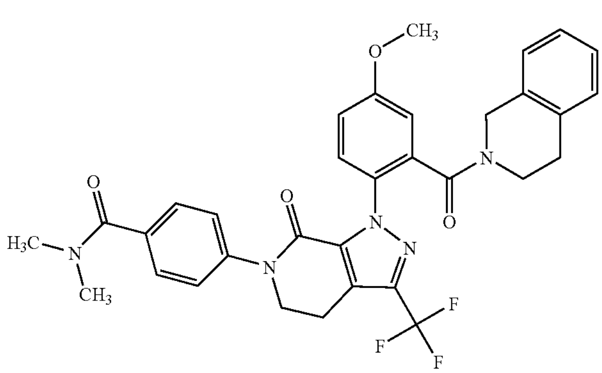 | C33H30F3N5O4 | 618.2 |

TABLE 5-continued

| Ex. | Structure | MF | (M + H)+ |
|---|---|---|---|
| 234 | 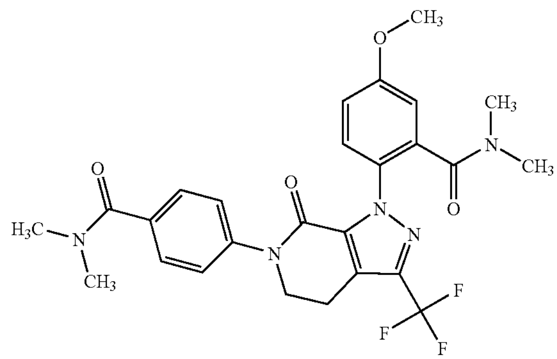 | $C_{26}H_{26}F_3N_5O_4$ | 530.2 |
| 235 | 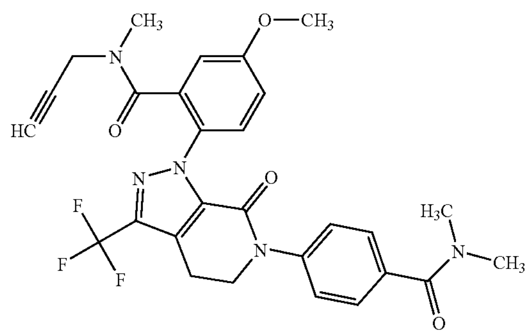 | $C_{28}H_{26}F_3N_5O_4$ | 554.2 |
| 236 | 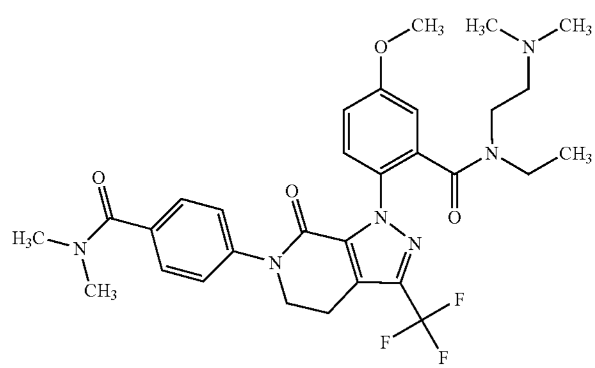 | $C_{30}H_{35}F_3N_6O_4$ | 601.3 |
| 237 | 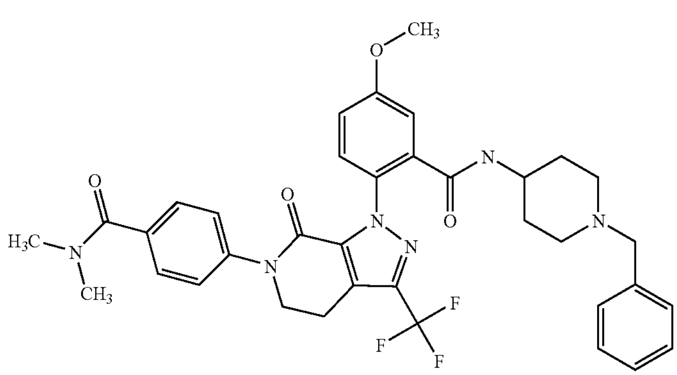 | $C_{31}H_{37}F_3N_6O_4$ | 615.3 |

TABLE 5-continued

| Ex. | Structure | MF | (M + H)+ |
|---|---|---|---|
| 238 | 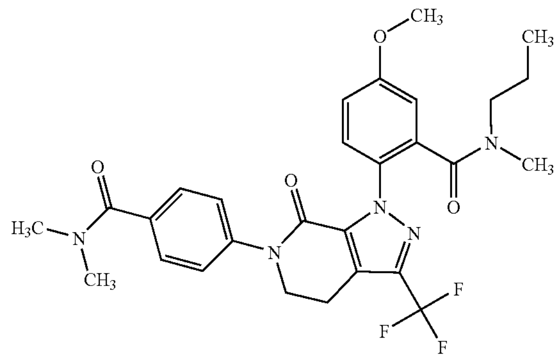 | C28H30F3N5O4 | 558.2 |
| 239 | 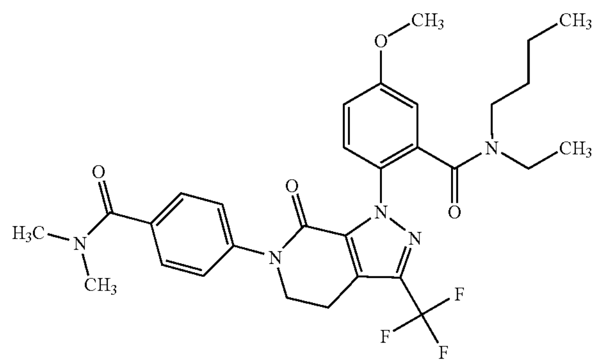 | C30H34F3N5O4 | 586.3 |
| 240 | 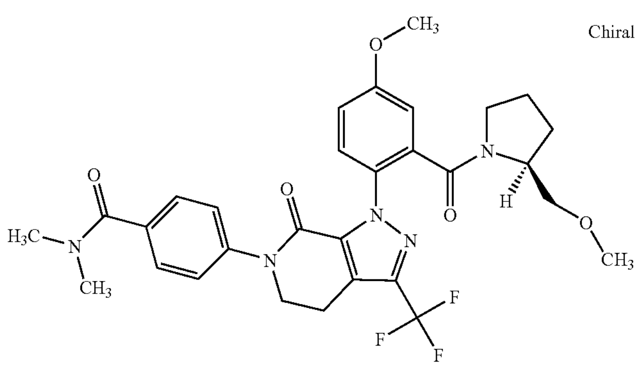 | C30H32F3N5O5 | 600.2 |
| 241 | 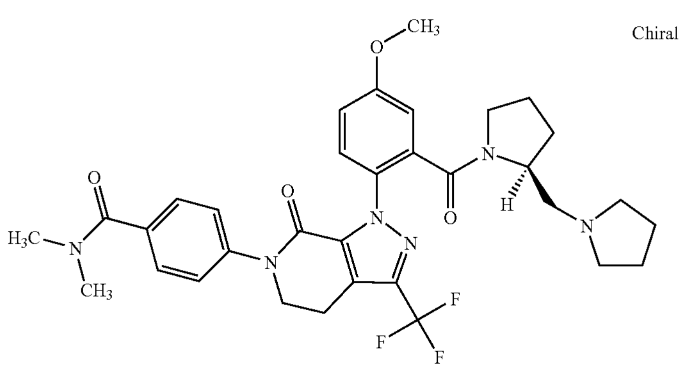 | C33H37F3N6O4 | 639.3 |

TABLE 5-continued

| Ex. | Structure | MF | (M + H)+ |
|---|---|---|---|
| 242 | 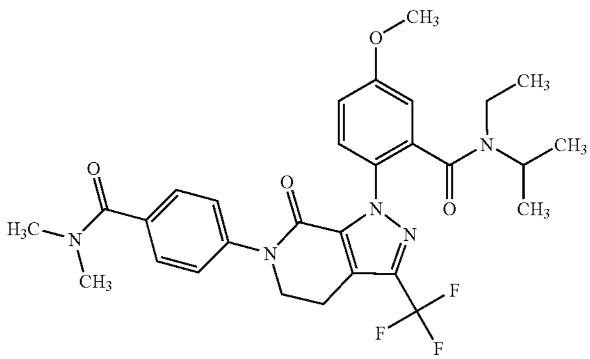 | C29H32F3N5O4 | 572.2 |
| 243 | 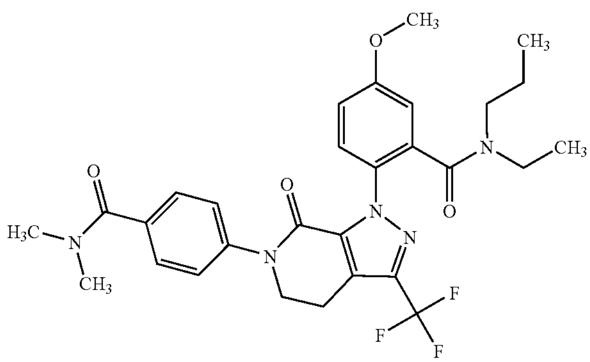 | C29H32F3N5O4 | 572.2 |
| 244 | (Chiral) | C35H35F3N6O4 | 661.3 |
| 245 | 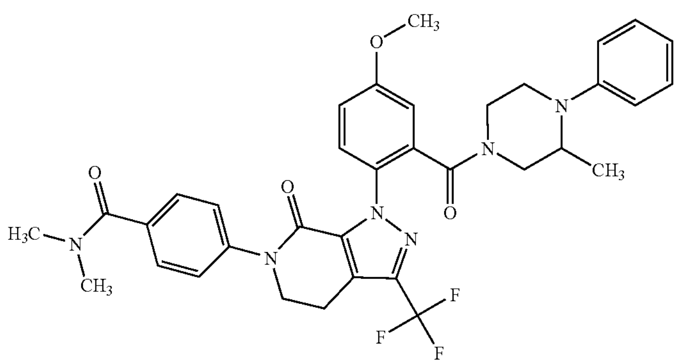 | C35H35F3N6O4 | 661.3 |

TABLE 5-continued

| Ex. | Structure | MF | (M + H)+ |
|---|---|---|---|
| 246 | 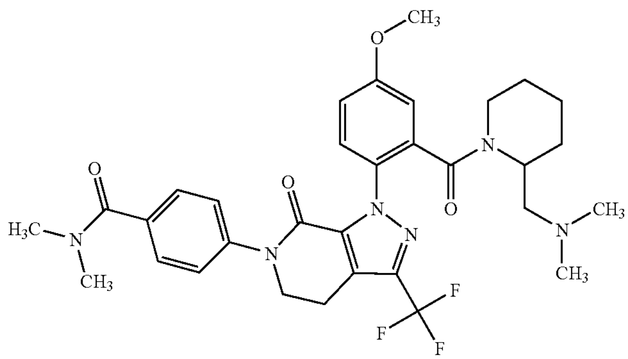 | C₃₂H₃₇F₃N₆O₄ | 627.3 |
| 247 | 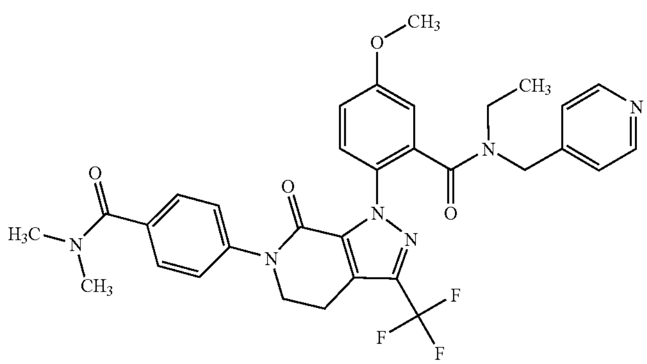 | C₃₂H₃₁F₃N₆O₄ | 621.2 |
| 248 | 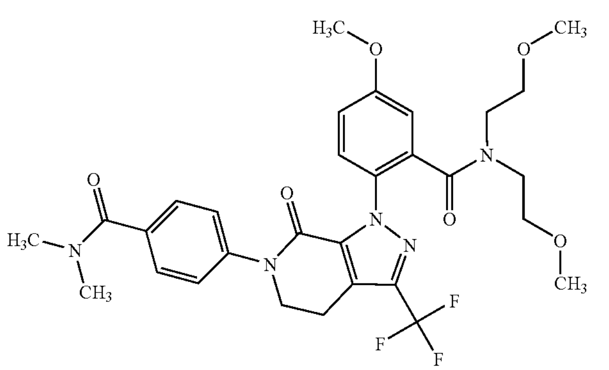 | C₃₀H₃₄F₃N₅O₆ | 618.3 |
| 249 | 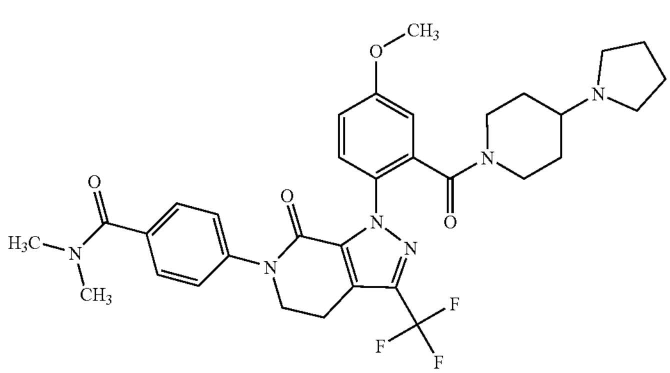 | C₃₃H₃₇F₃N₆O₄ | 639.3 |

TABLE 5-continued

| Ex. | Structure | MF | (M + H)+ |
|---|---|---|---|
| 250 | 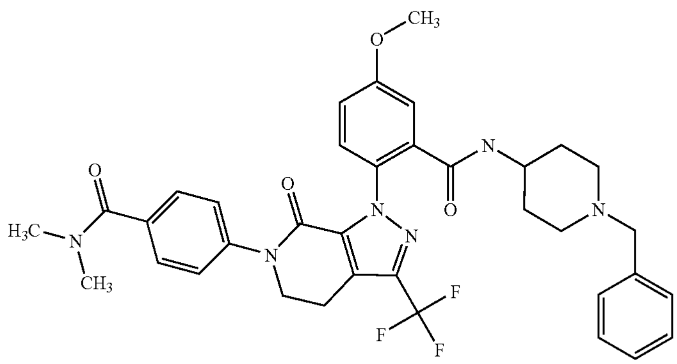 | C30H31F3N6O5 | 613.2 |
| 251 | 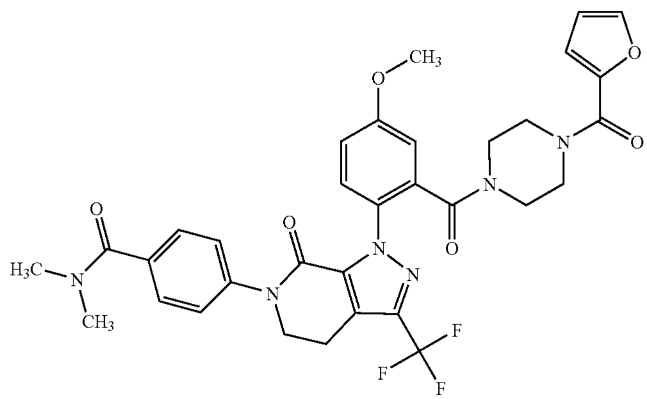 | C33H31F3N6O6 | 665.2 |
| 252 | 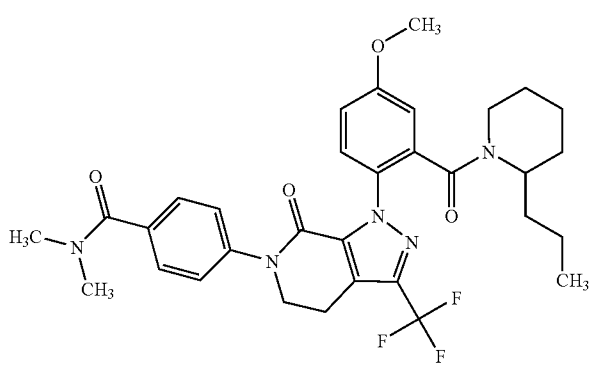 | C32H36F3N5O4 | 612.3 |
| 253 | 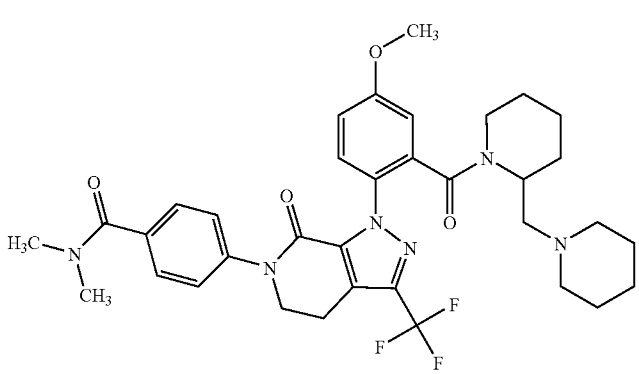 | C35H41F3N6O4 | 667.3 |

TABLE 5-continued

| Ex. | Structure | | MF | (M + H)+ |
|---|---|---|---|---|
| 254 | 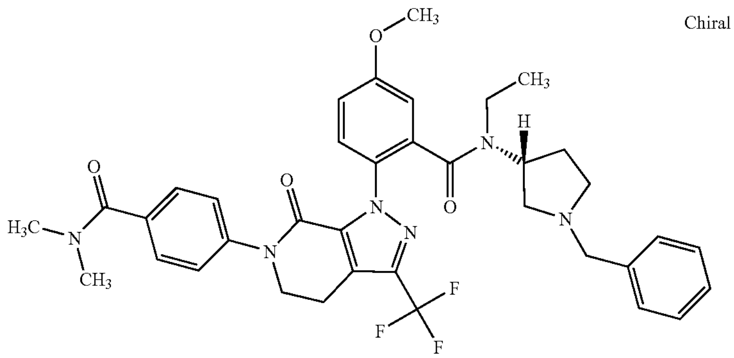 | Chiral | $C_{37}H_{39}F_3N_6O_4$ | 689.3 |
| 255 | 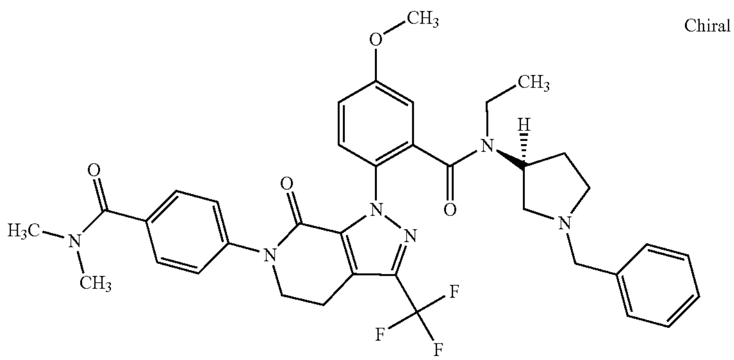 | Chiral | $C_{37}H_{39}F_3N_6O_4$ | 689.3 |

Numerous modifications and variations of the present invention are possible in light of the above teachings. It is therefore to be understood that within the scope of the appended claims, the invention may be practiced otherwise that as specifically described herein.

What is claimed is:

1. A compound selected from the group:

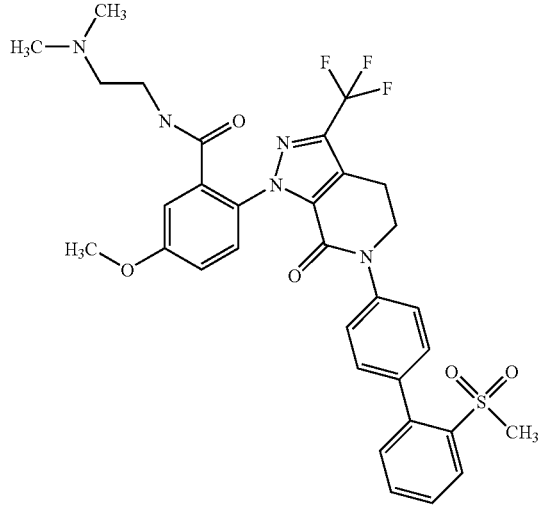

-continued

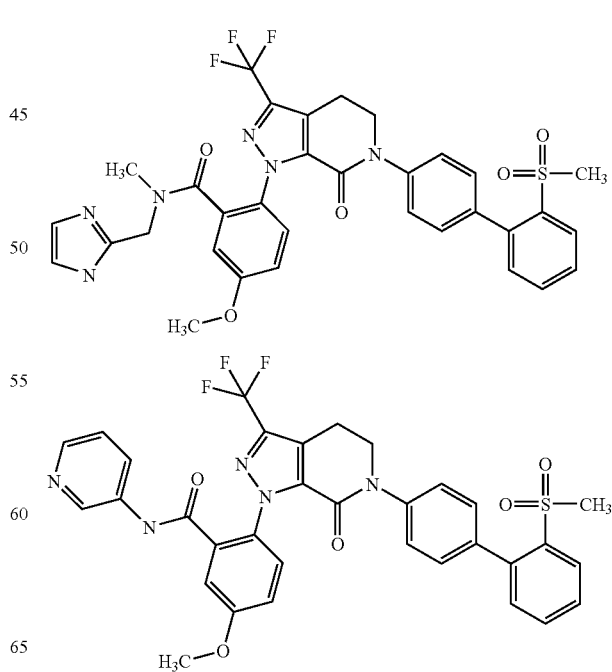

265 266
-continued -continued
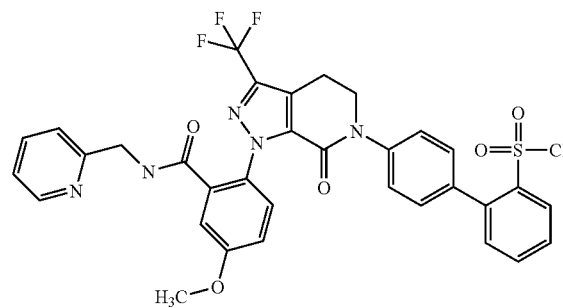 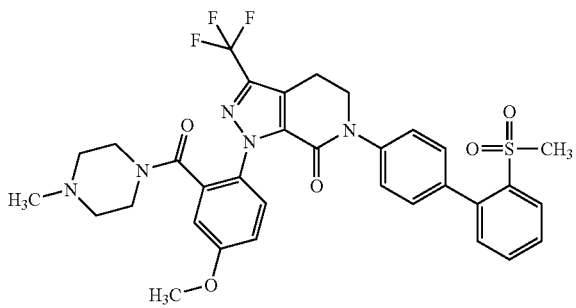
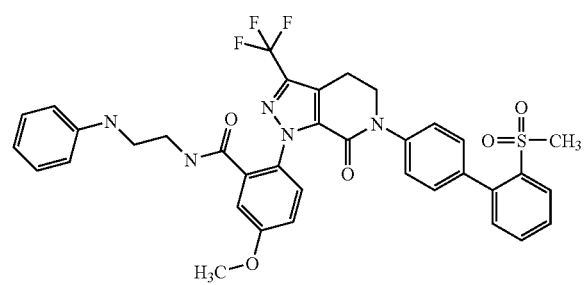 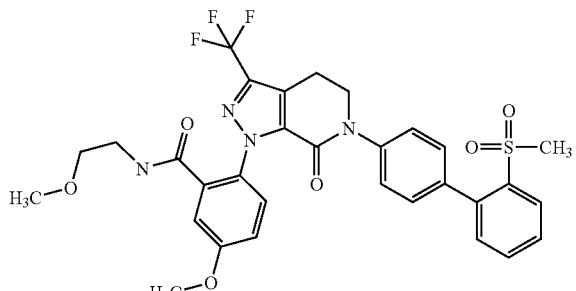
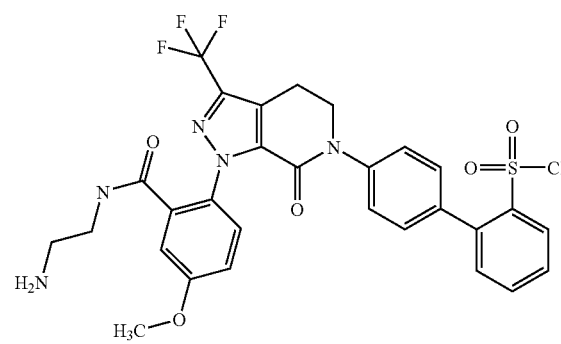 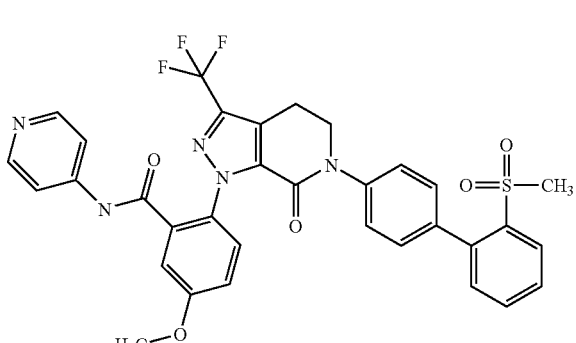
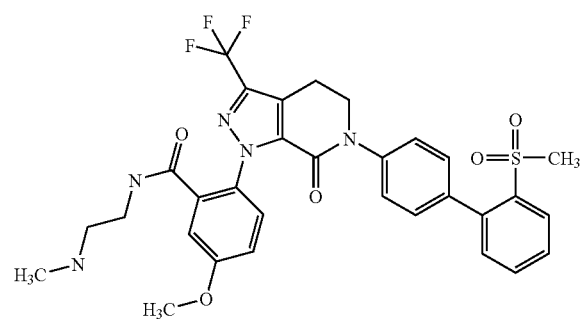 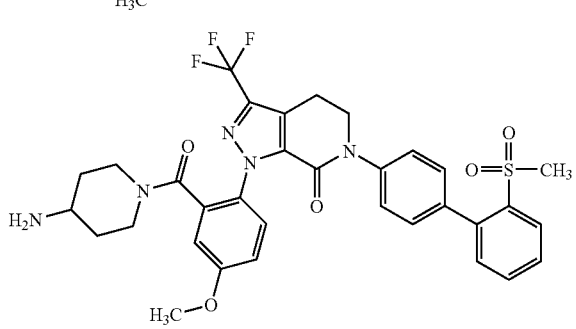
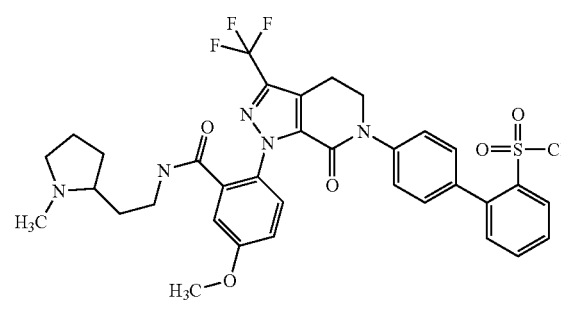 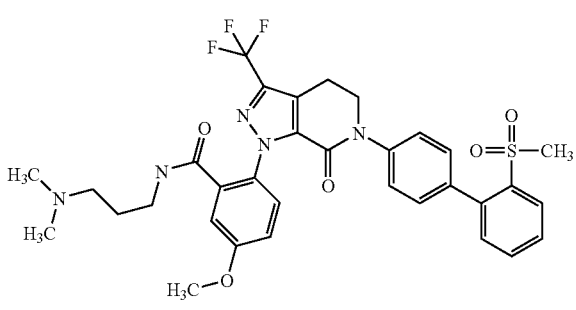

267
-continued
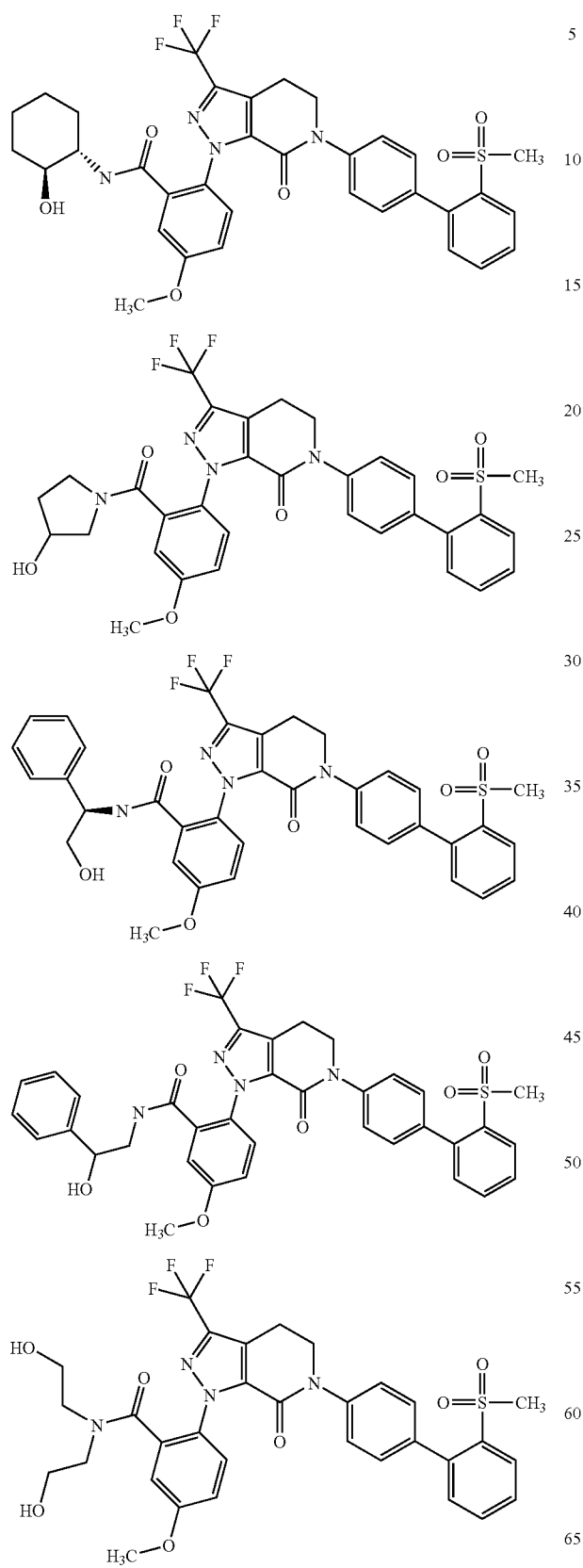
268
-continued
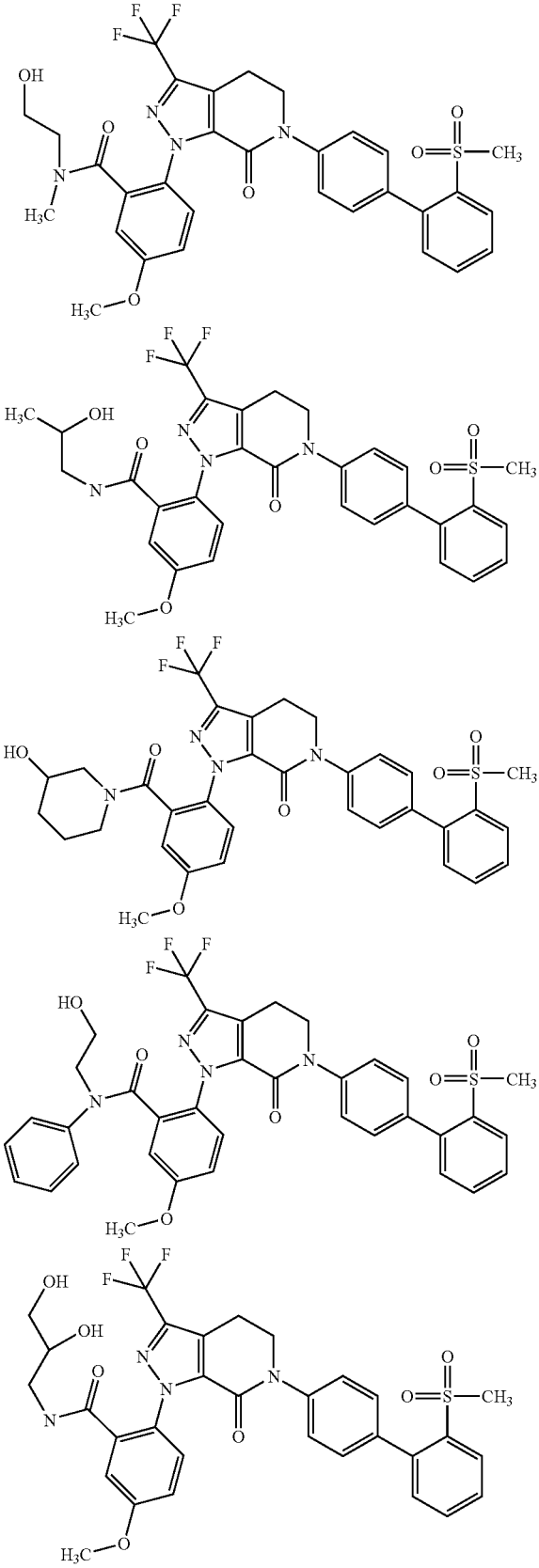

269
-continued
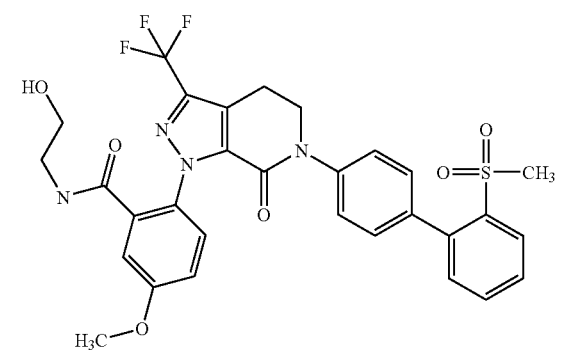
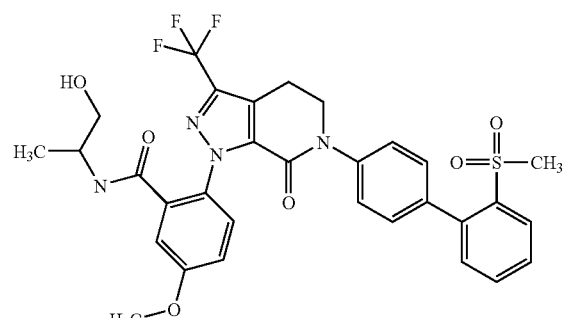
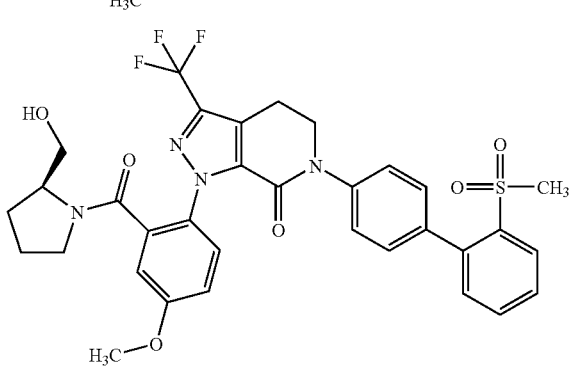
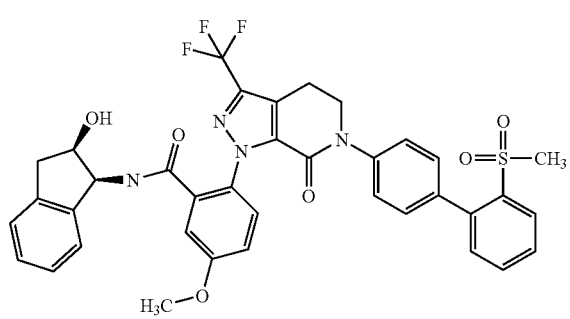
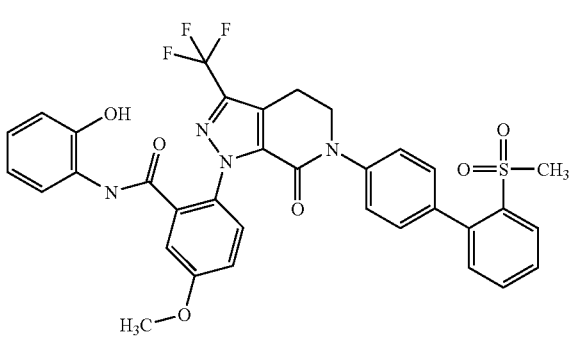
270
-continued
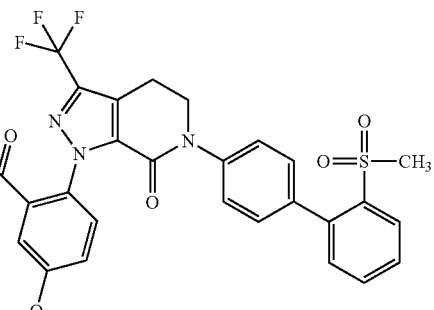
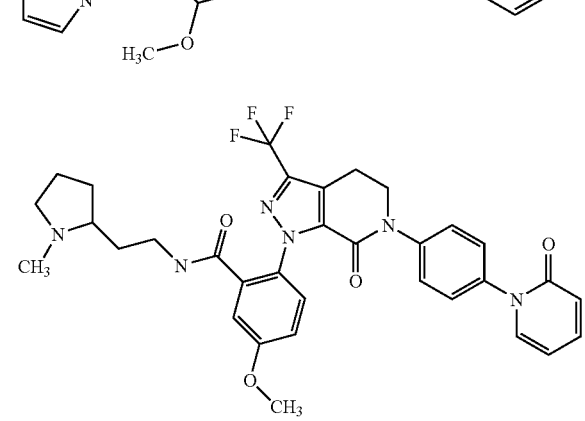
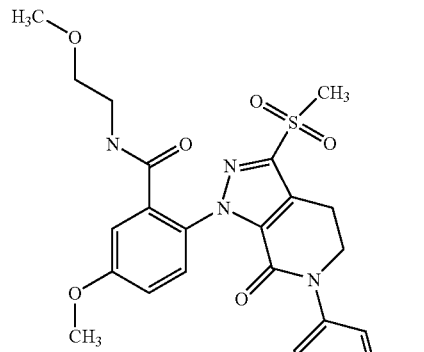
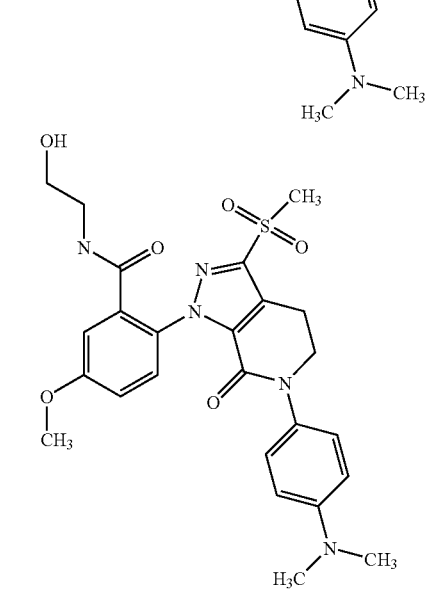

-continued
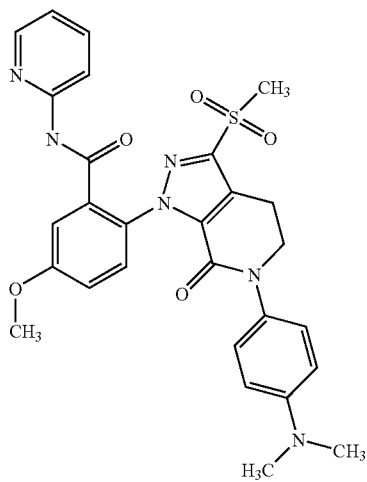
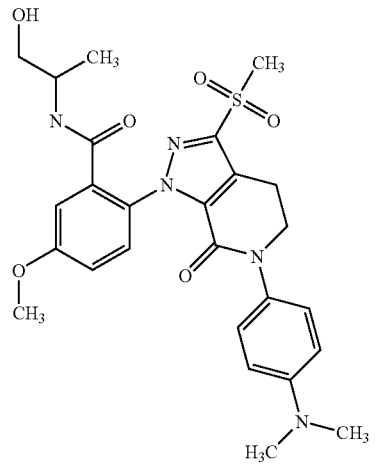
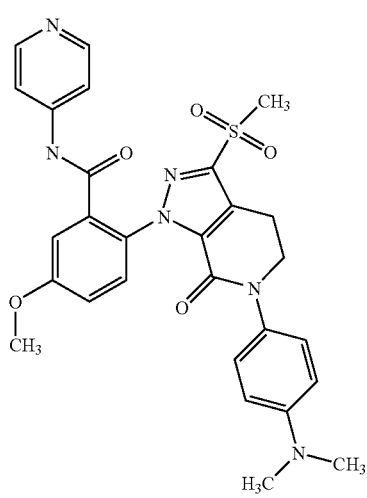
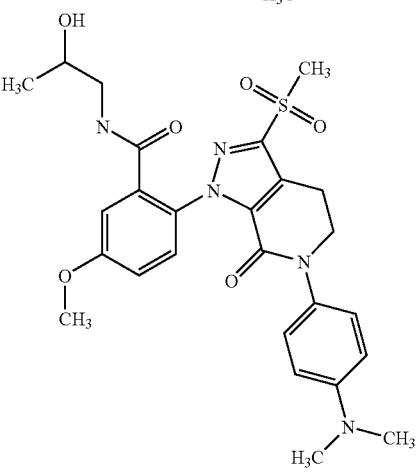
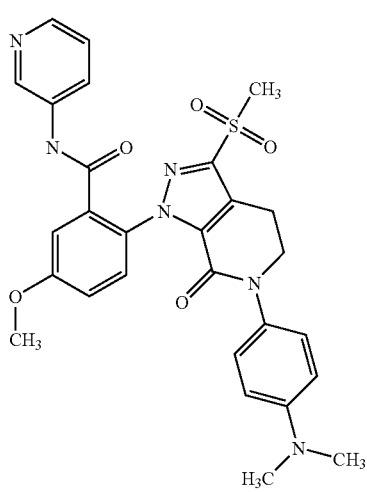
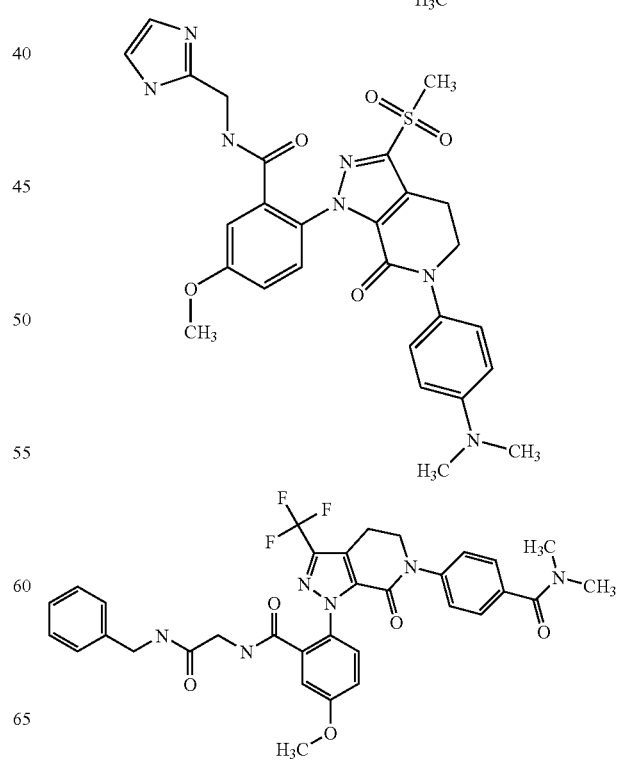

273
-continued
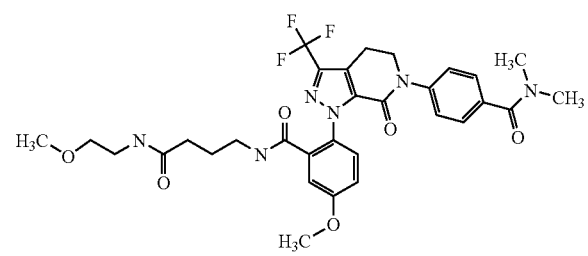
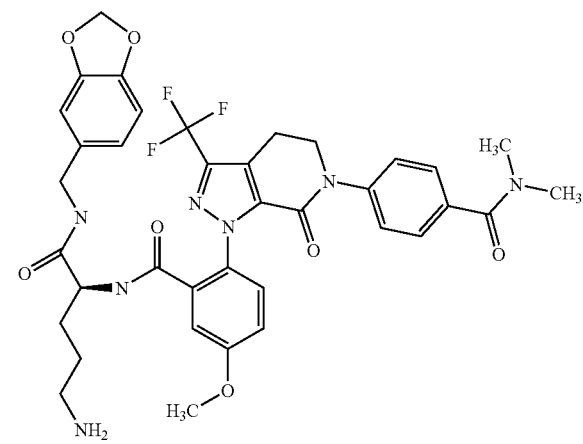
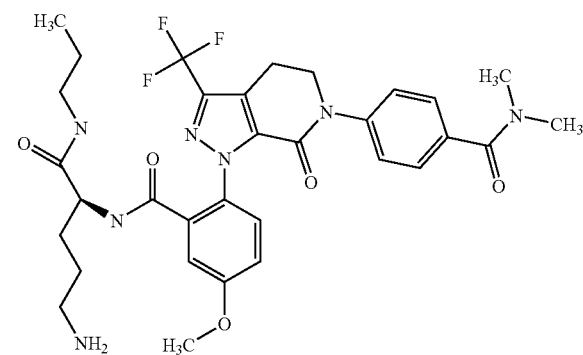
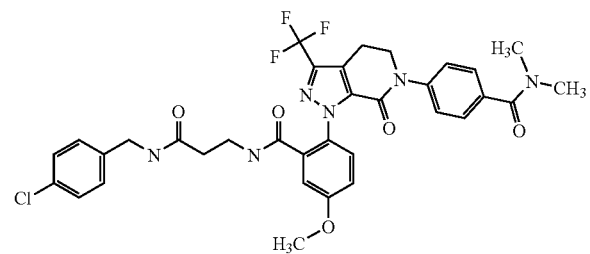
274
-continued
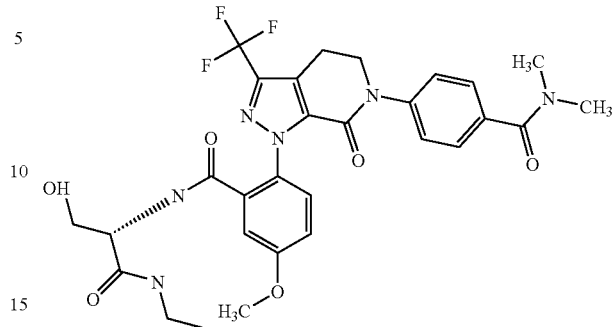
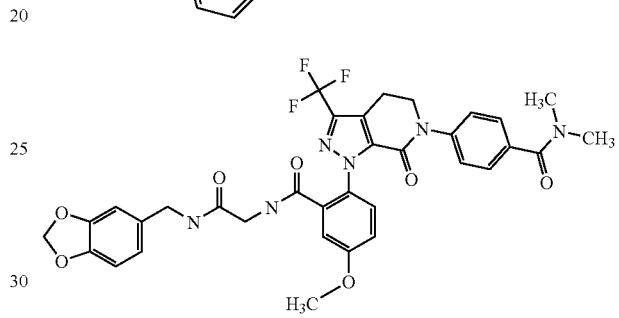
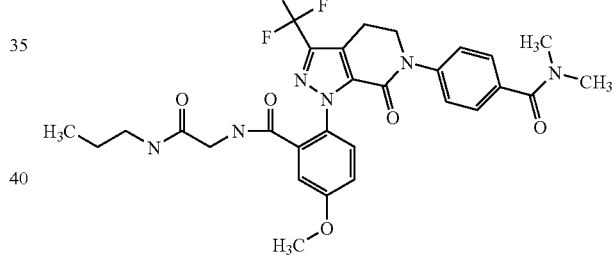
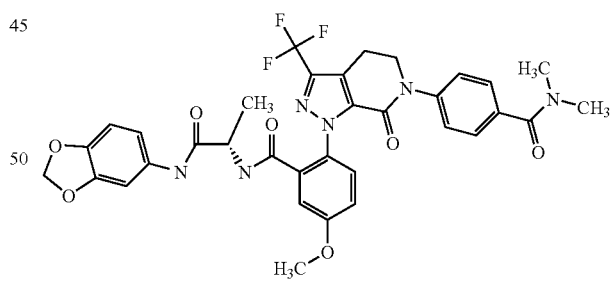
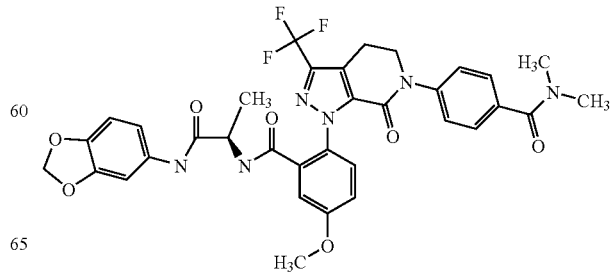

275 276
-continued -continued
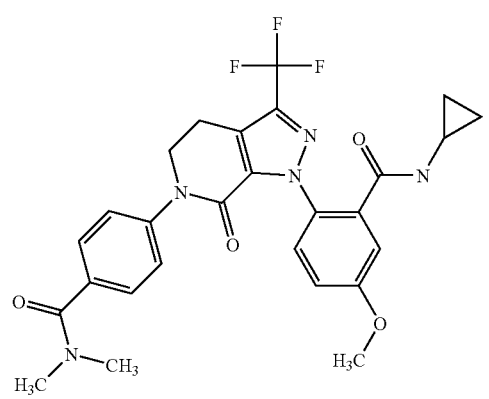
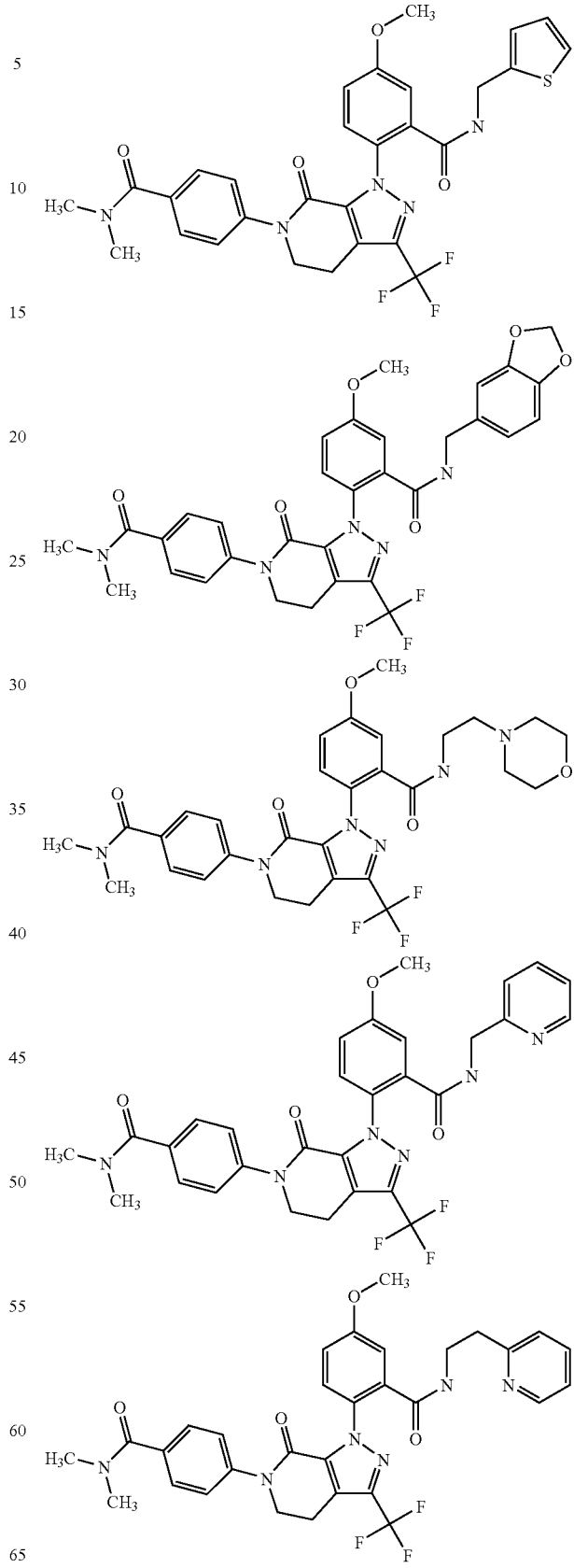

277
-continued
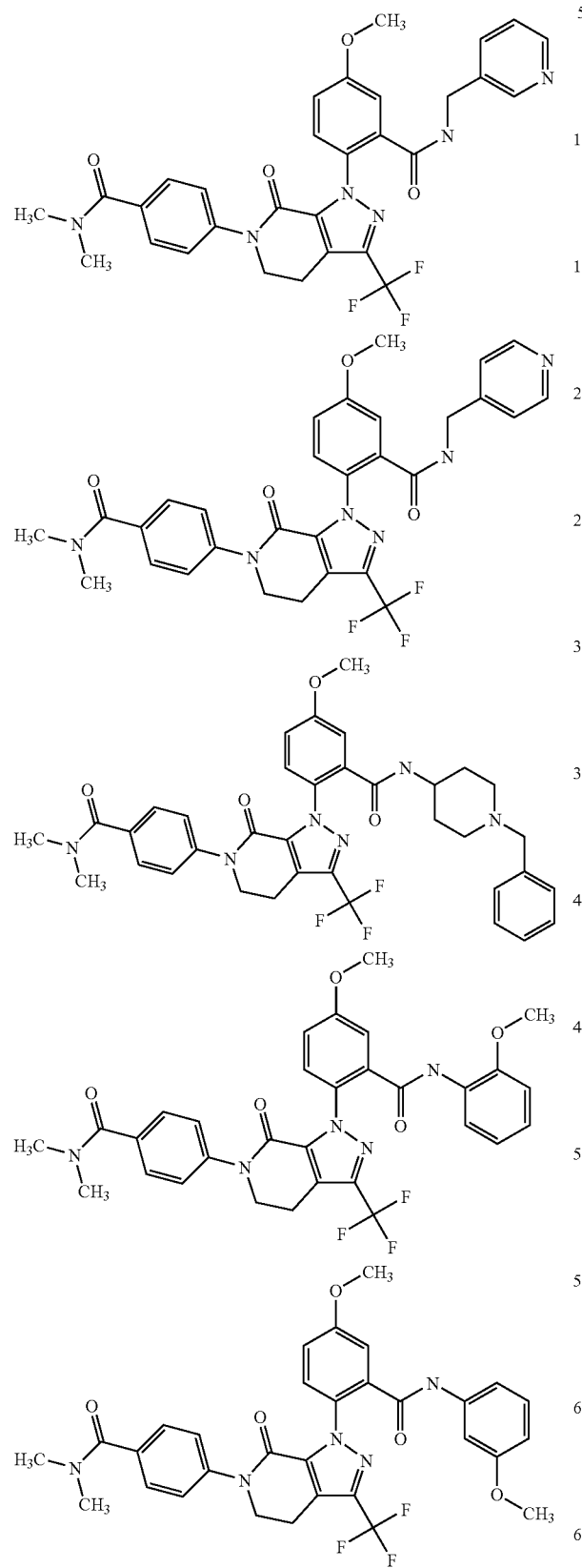
278
-continued
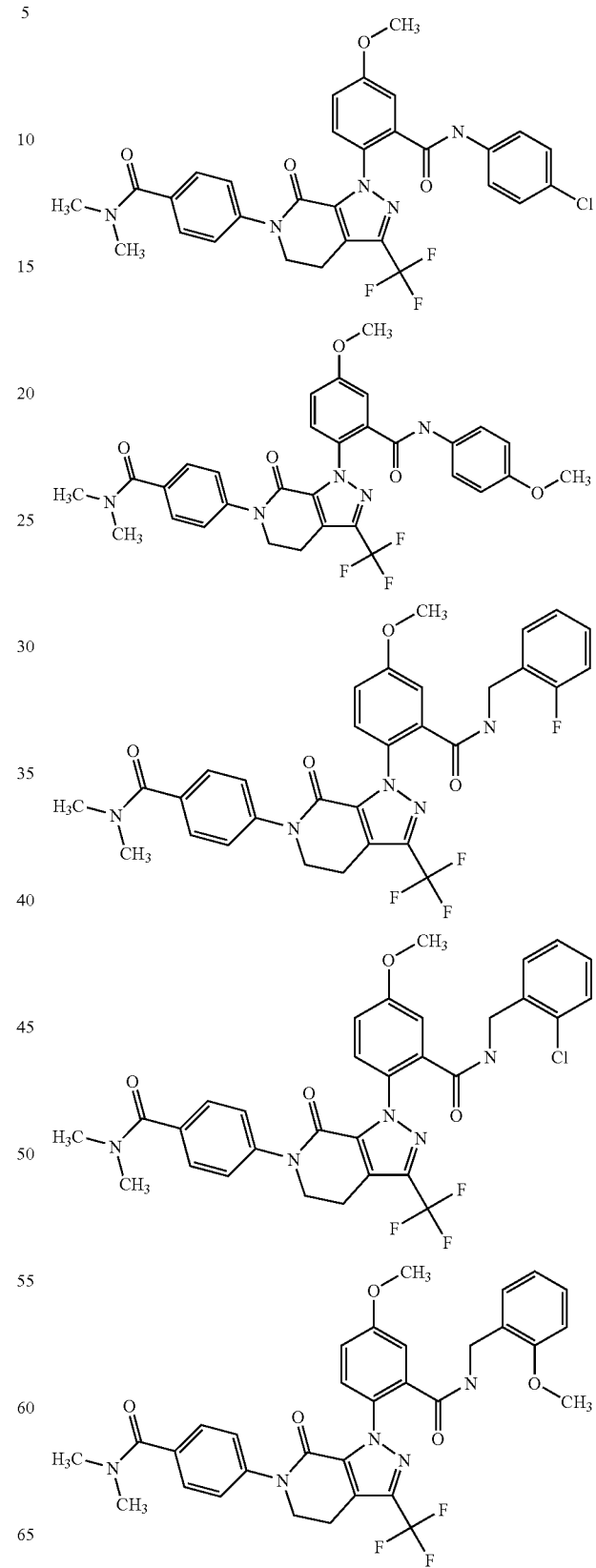

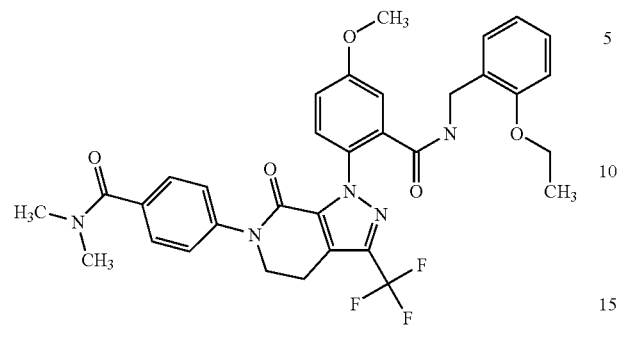
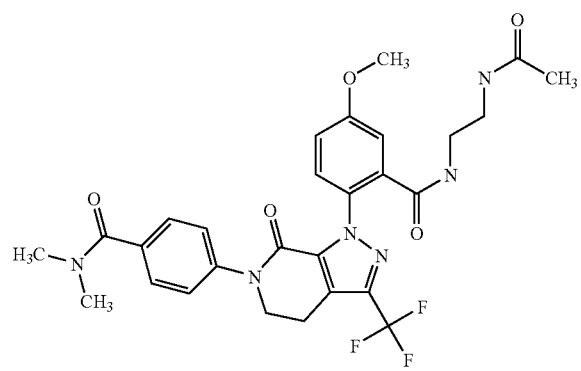
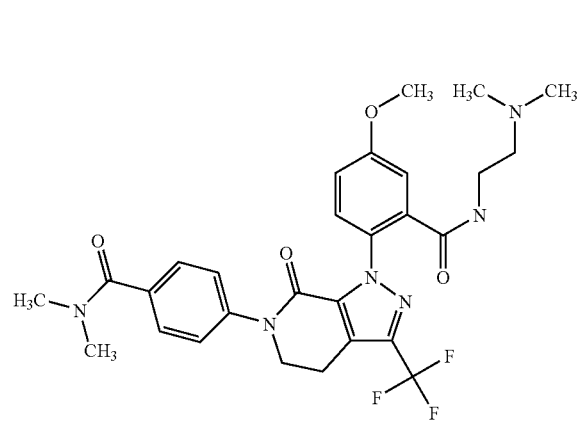
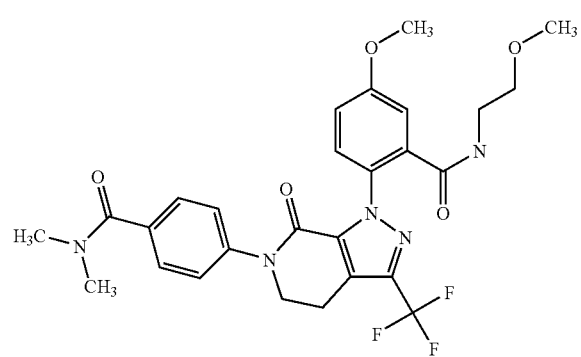
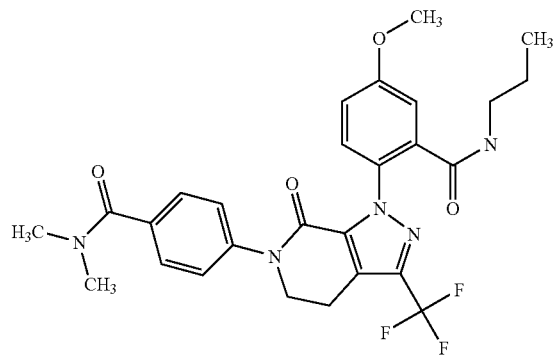
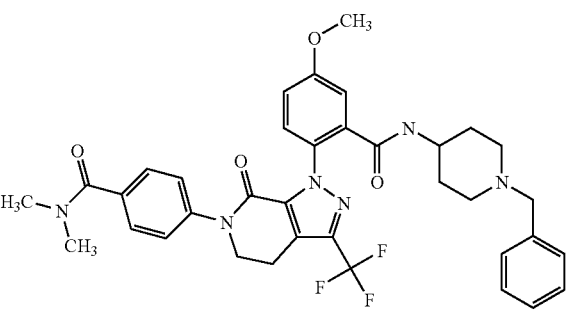
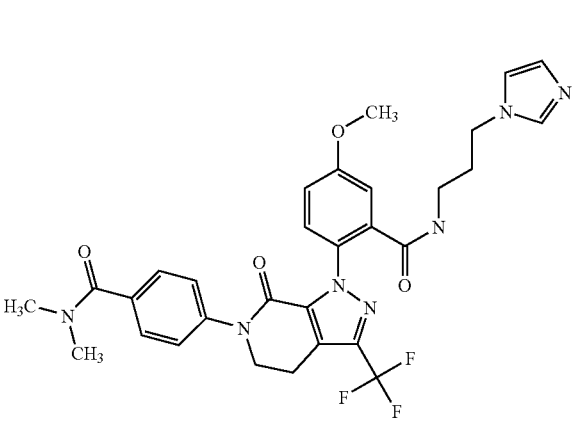
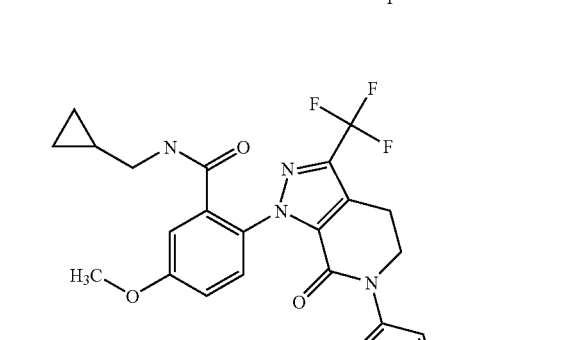

-continued
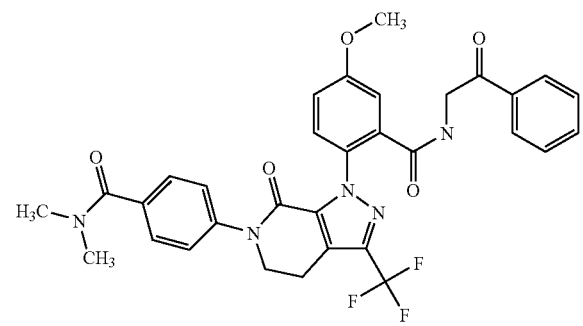
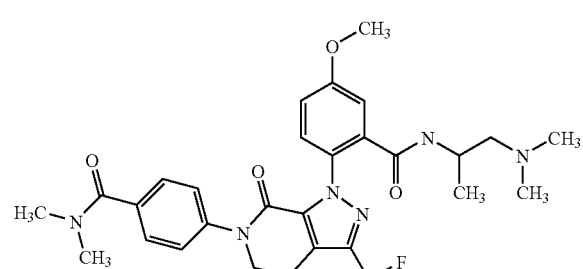
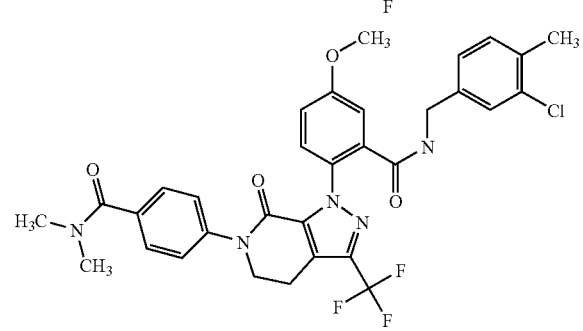
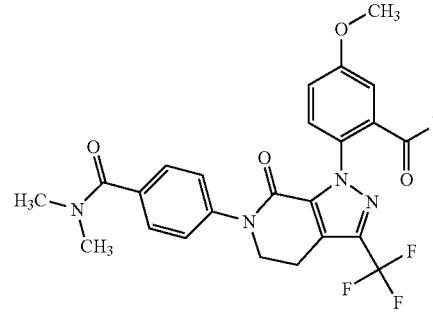
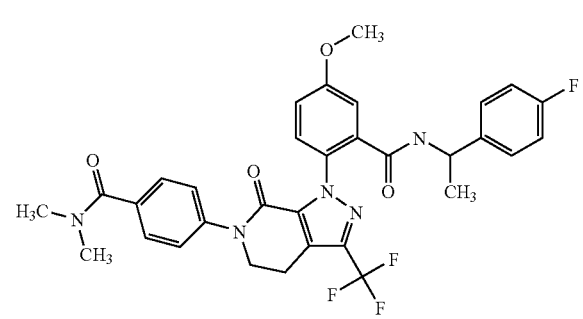
-continued
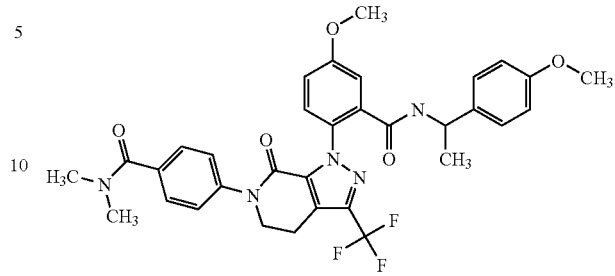
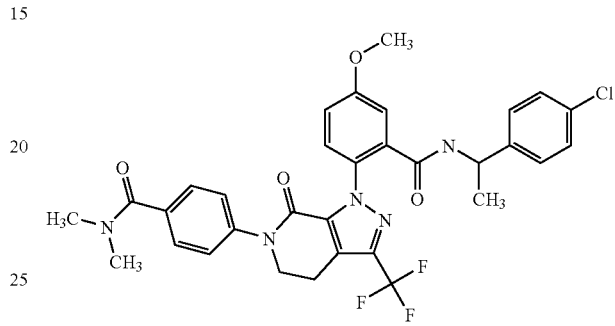
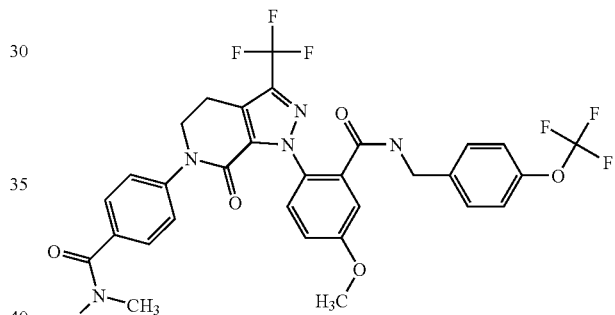
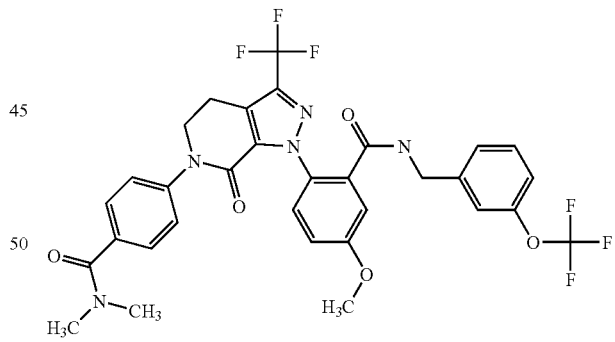
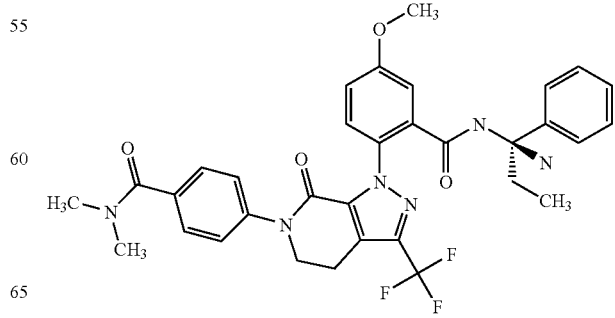

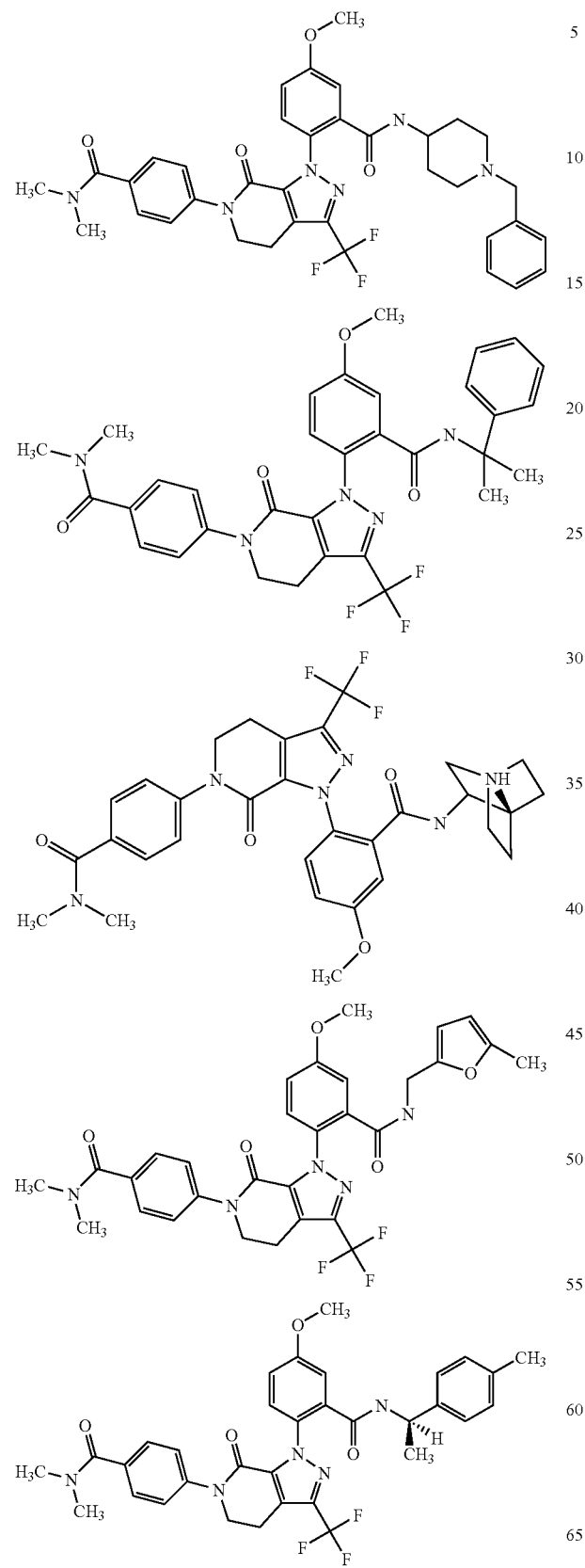
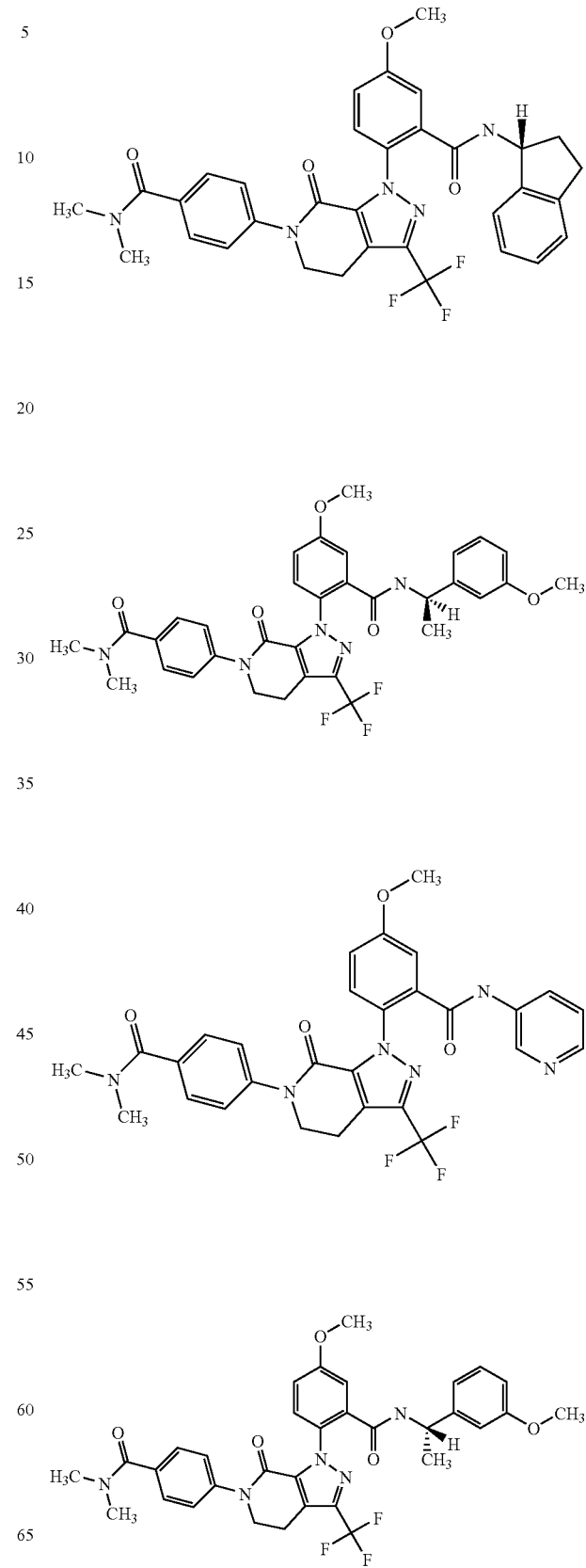

-continued
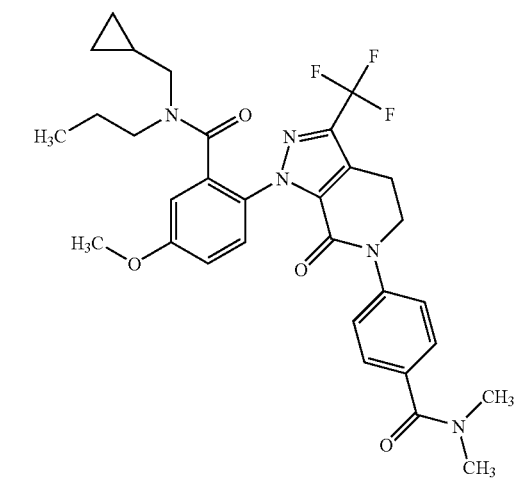
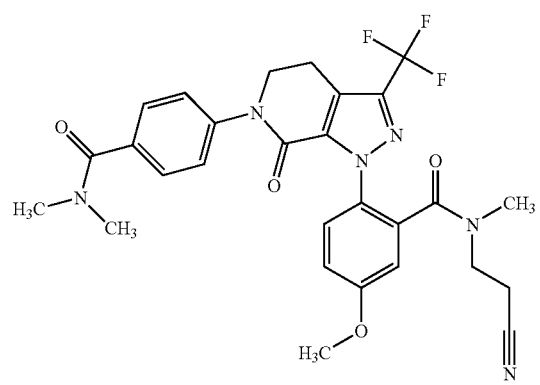
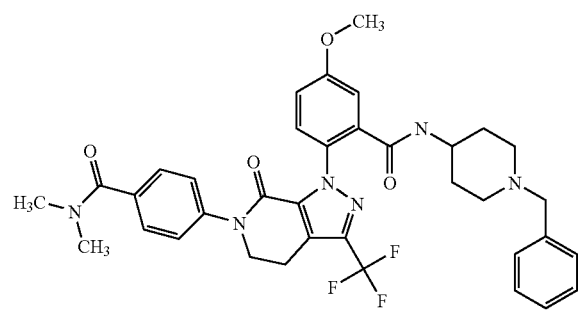
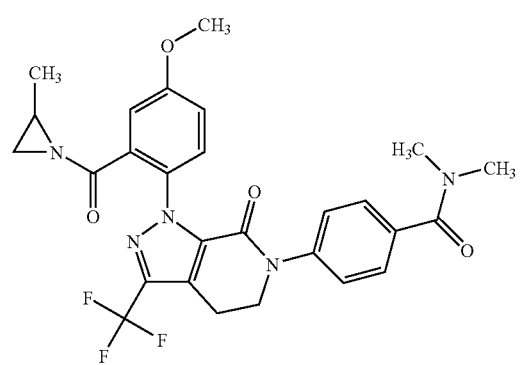
-continued
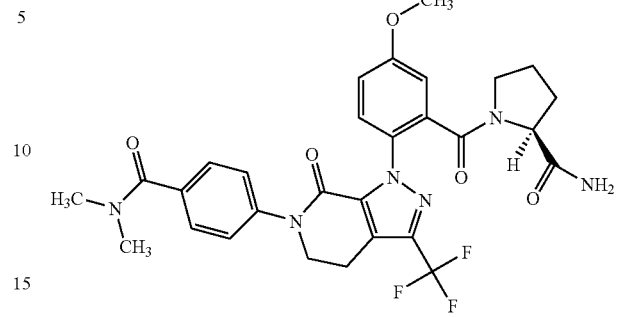
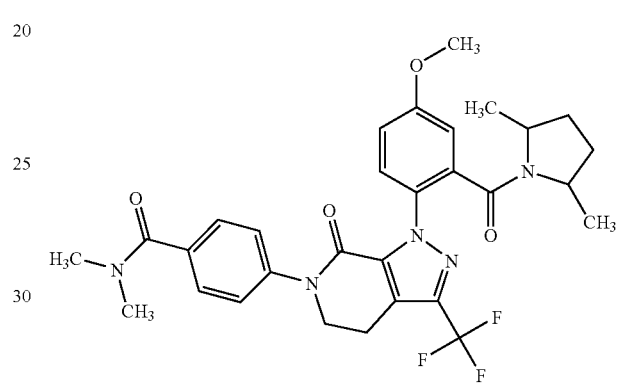
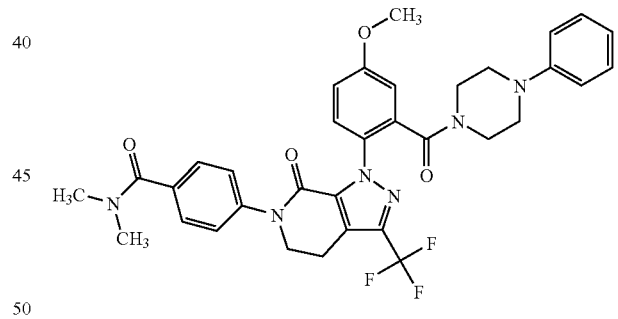
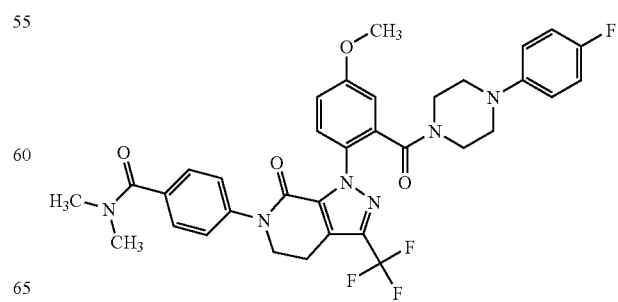

287
-continued
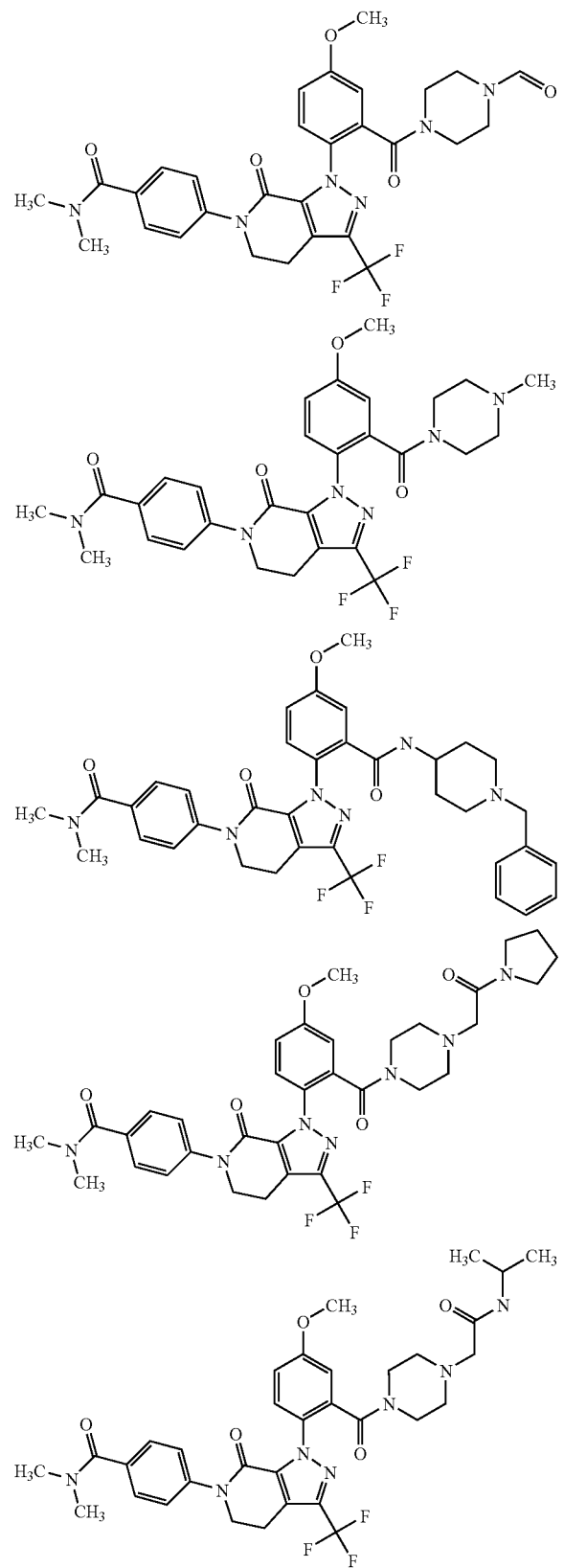
288
-continued
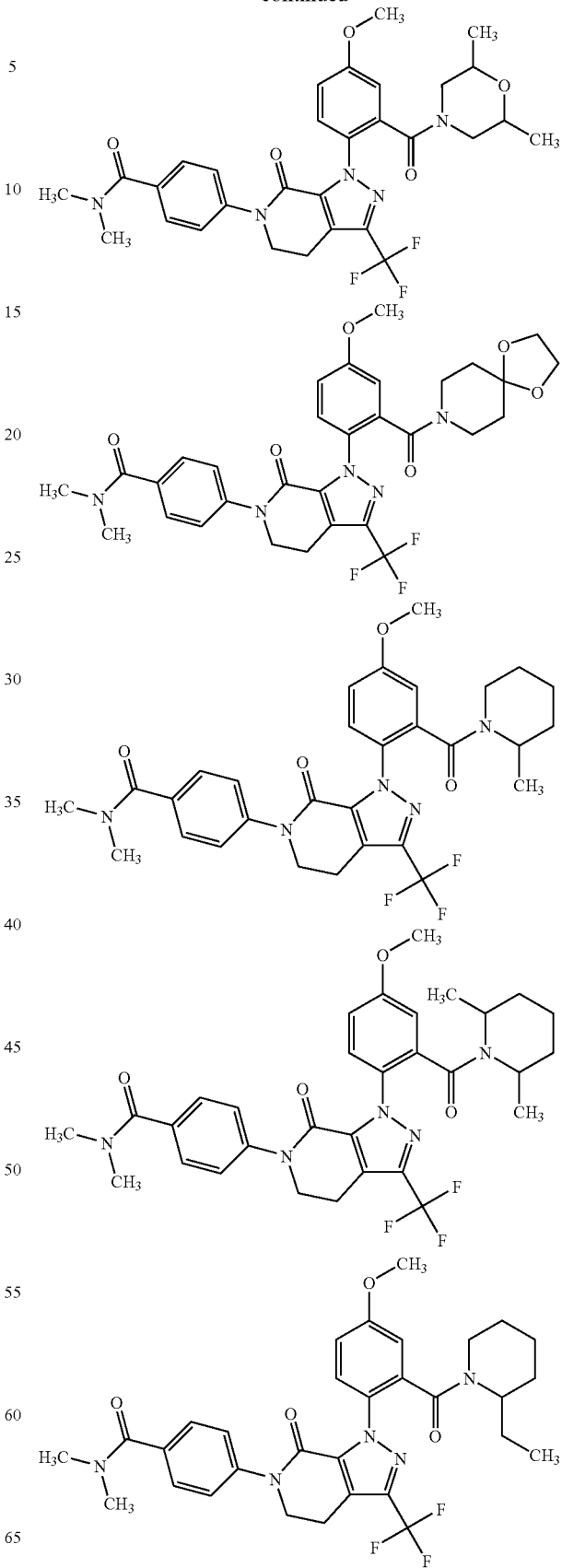

-continued
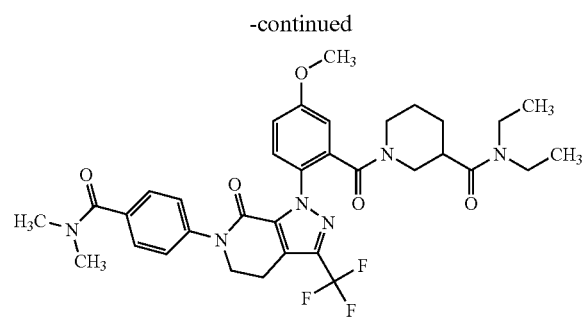
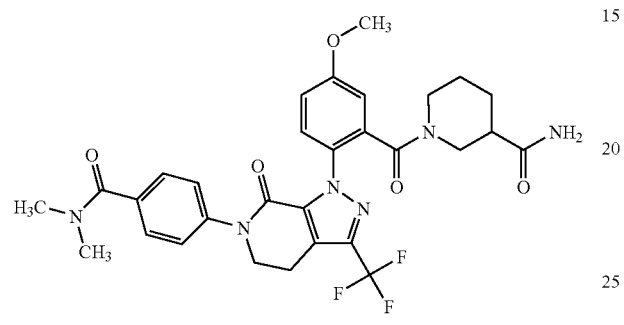
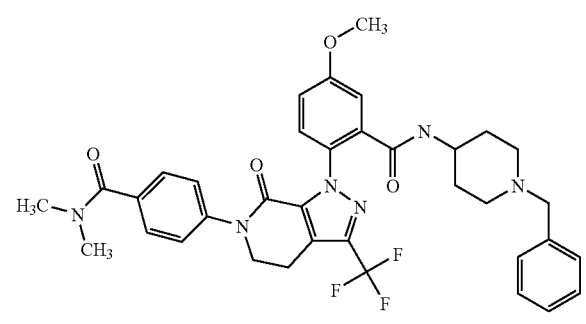
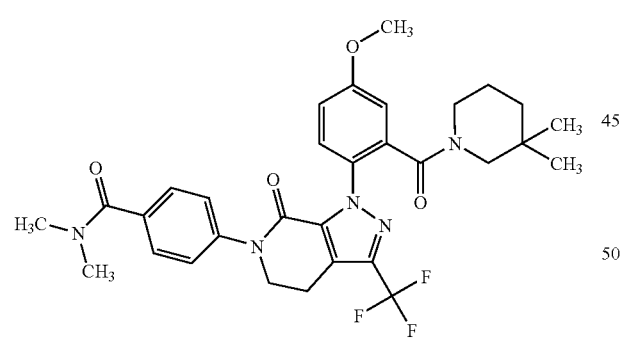
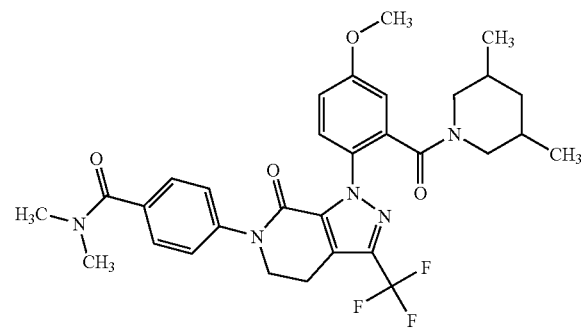
-continued
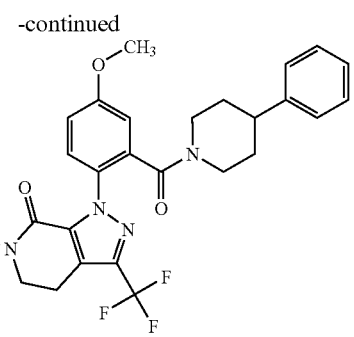
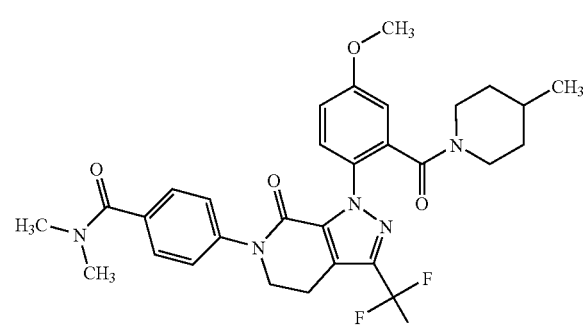
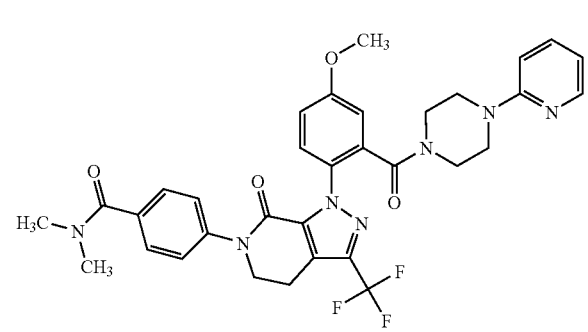
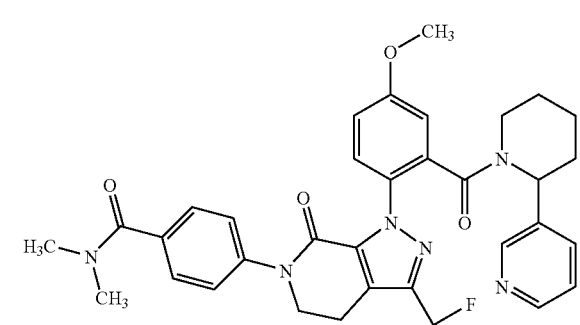
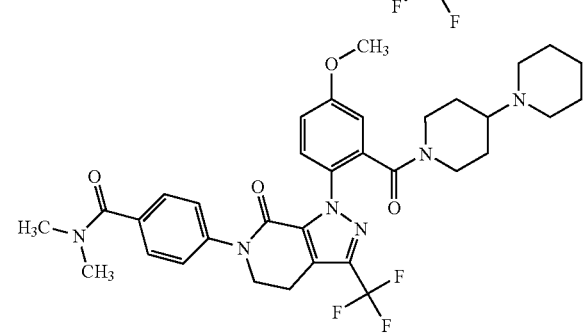

291
-continued
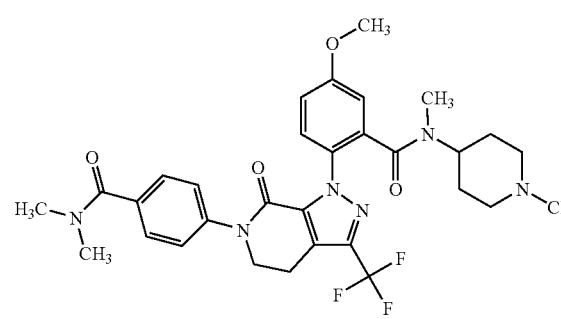
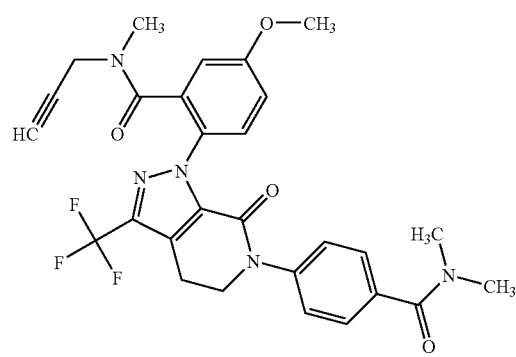
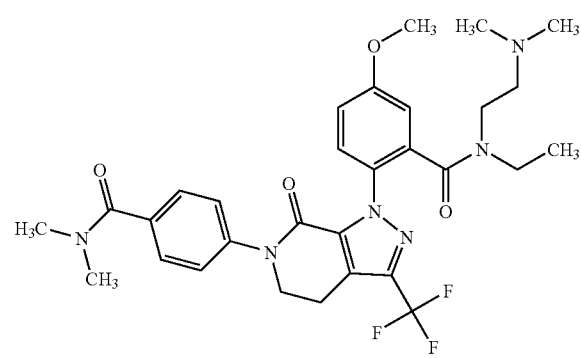
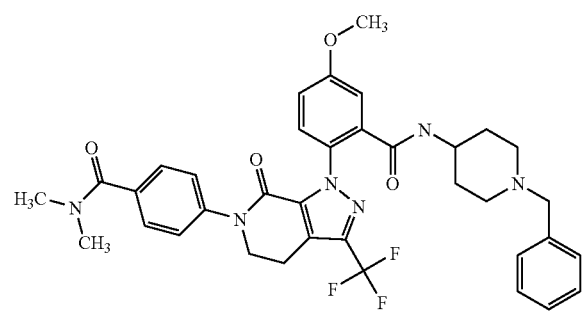
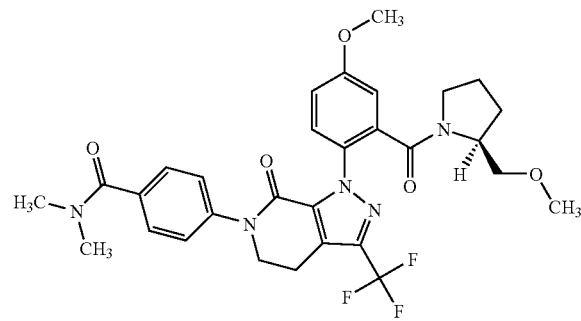
292
-continued
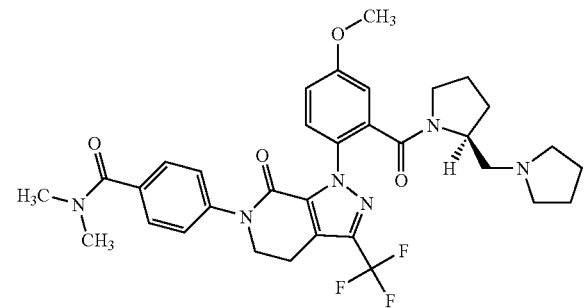
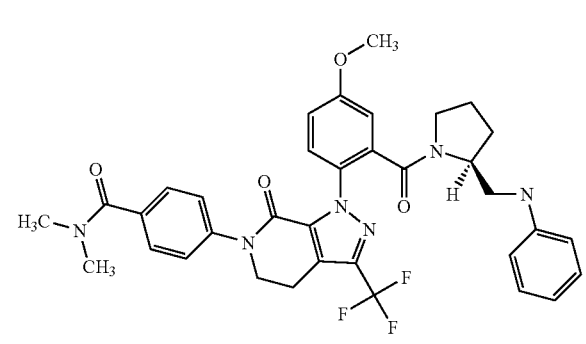
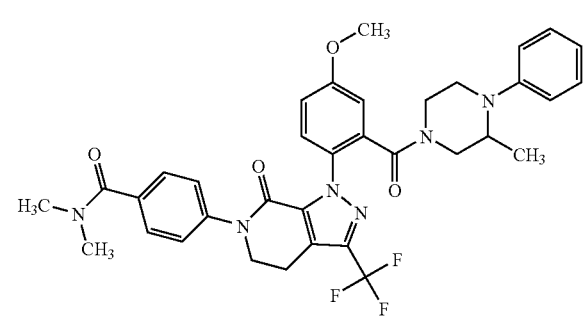
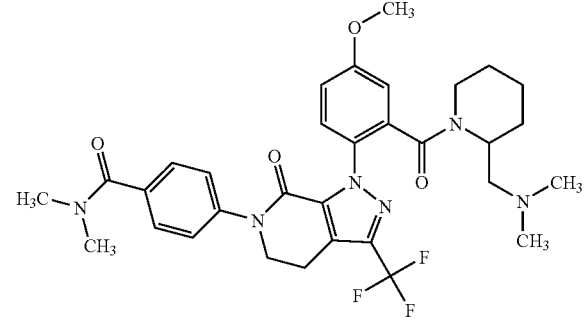
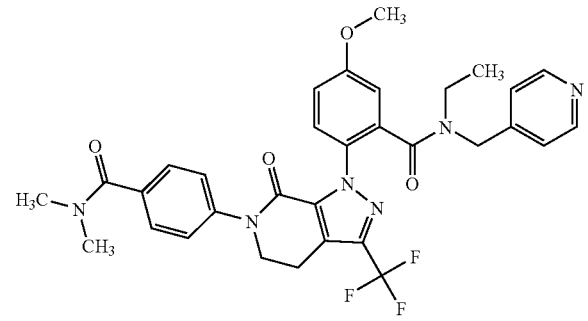

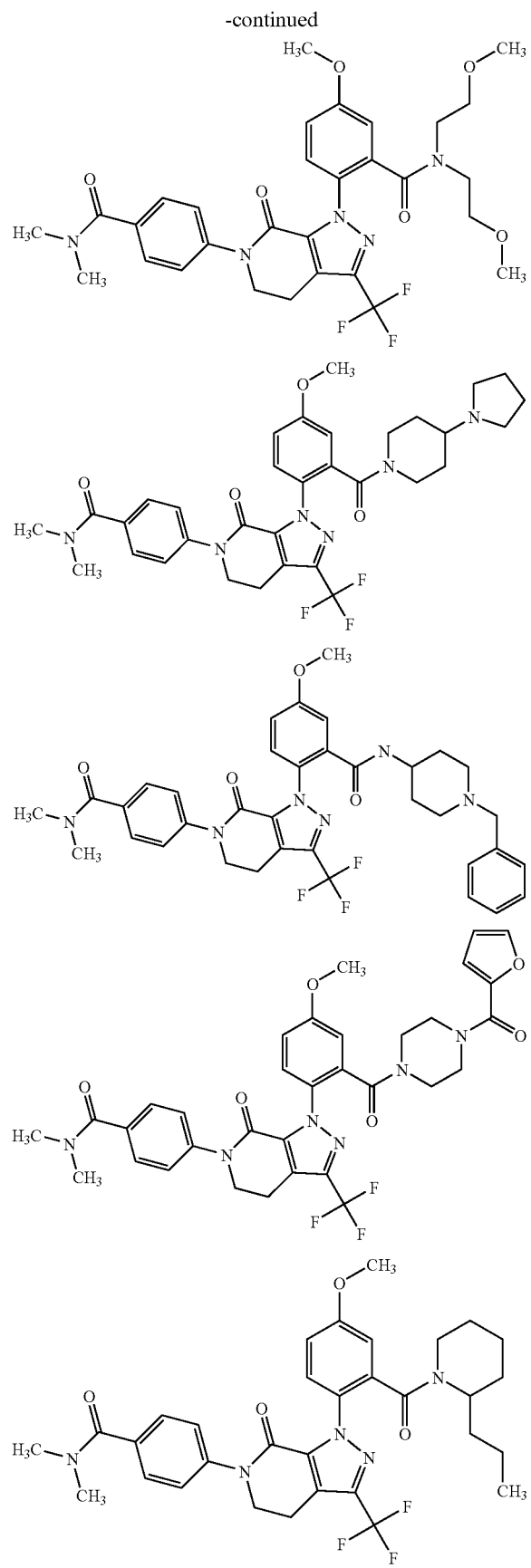
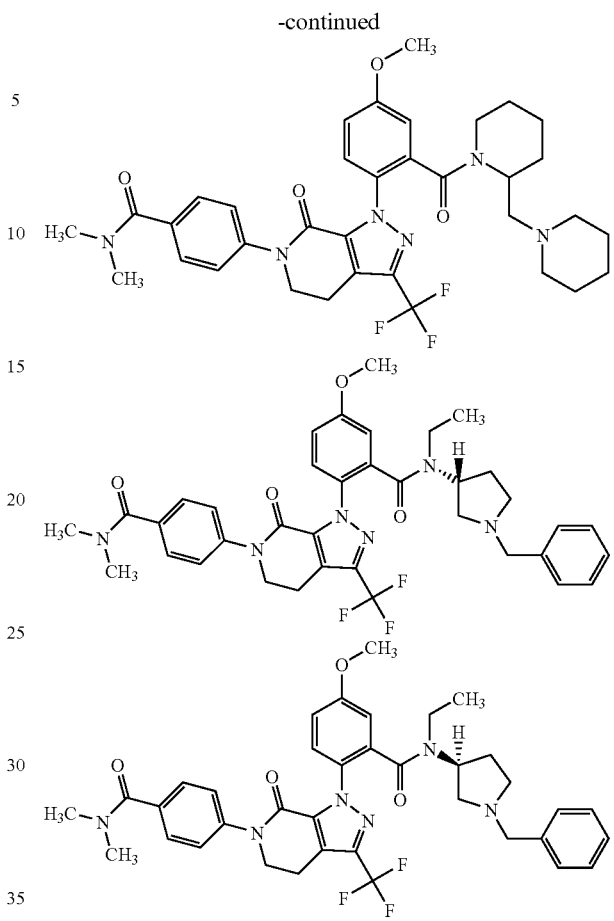

or a pharmaceutically acceptable salt form thereof.

2. A pharmaceutical composition, comprising: a pharmaceutically acceptable carrier and a therapeutically effective amount of a compound of claim 1 or a pharmaceutically acceptable salt form thereof.

3. A method for treating a thromboembolic disorder, comprising: administering to a patient in need thereof a therapeutically effective amount of a compound of claim 1 or a pharmaceutically acceptable salt form thereof.

4. A method according to claim 3, wherein the thromboembolic disorder is selected from the group consisting of arterial cardiovascular thromboembolic disorders, venous cardiovascular thromboembolic disorders, and thromboembolic disorders in the chambers of the heart.

5. A method according to claim 3, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *

UNITED STATES PATENT AND TRADEMARK OFFICE
CERTIFICATE OF CORRECTION

PATENT NO.       : 7,381,732 B2
APPLICATION NO.  : 11/256893
DATED            : June 3, 2008
INVENTOR(S)      : Patrick Y. S. Lam et al.

It is certified that error appears in the above-identified patent and that said Letters Patent is hereby corrected as shown below:

Title page Item [57], Abstract $P_4$-P-M-$M_4$I should read -- $P_4$-P-M-$M_4$I --

Signed and Sealed this

Twenty-eighth Day of April, 2009

JOHN DOLL
*Acting Director of the United States Patent and Trademark Office*